US012018001B2

(12) United States Patent
Hunt et al.

(10) Patent No.: US 12,018,001 B2
(45) Date of Patent: *Jun. 25, 2024

(54) PYRIMIDINE CYCLOHEXENYL GLUCOCORTICOID RECEPTOR MODULATORS

(71) Applicant: Corcept Therapeutics Incorporated, Menlo Park, CA (US)

(72) Inventors: Hazel Hunt, Storington (GB); Damien Francis Philippe Crepin, Nottingham (GB); Joseph Thomas Hill-Cousins, Nottingham (GB); Thomas Matthew Baker, Nottingham (GB); Lorna Duffy, Nottingham (GB)

(73) Assignee: Corcept Therapeutics Incorporated, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/056,227

(22) Filed: Nov. 16, 2022

(65) Prior Publication Data
US 2023/0183186 A1 Jun. 15, 2023

Related U.S. Application Data

(63) Continuation of application No. 15/734,525, filed as application No. PCT/US2019/035229 on Jun. 3, 2019, now Pat. No. 11,542,238.

(60) Provisional application No. 62/680,362, filed on Jun. 4, 2018.

(51) Int. Cl.
| | | |
|---|---|---|
| C07D 239/54 | (2006.01) | |
| A61K 31/50 | (2006.01) | |
| A61K 31/505 | (2006.01) | |
| A61K 31/513 | (2006.01) | |
| A61K 47/20 | (2006.01) | |
| A61P 1/16 | (2006.01) | |
| A61P 25/18 | (2006.01) | |
| A61P 35/00 | (2006.01) | |
| C07D 401/08 | (2006.01) | |
| C07D 401/10 | (2006.01) | |
| C07D 401/14 | (2006.01) | |
| C07D 403/08 | (2006.01) | |
| C07D 403/10 | (2006.01) | |
| C07D 405/08 | (2006.01) | |
| C07D 405/10 | (2006.01) | |
| C07D 417/04 | (2006.01) | |
| C07D 417/08 | (2006.01) | |
| C07D 471/04 | (2006.01) | |

(52) U.S. Cl.
CPC .............. *C07D 239/54* (2013.01); *A61P 1/16* (2018.01); *A61P 35/00* (2018.01); *C07D 401/08* (2013.01); *C07D 401/14* (2013.01); *C07D 403/08* (2013.01); *C07D 405/08* (2013.01); *C07D 417/08* (2013.01); *C07D 471/04* (2013.01)

(58) Field of Classification Search
CPC .. C07D 239/54; C07D 401/10; C07D 401/14; C07D 403/10; C07D 405/10; C07D 417/04; A61K 31/50; A61K 31/505; A61K 31/513; A61K 47/20; A61P 1/16; A61P 25/18; A61P 35/00
See application file for complete search history.

(56) References Cited

U.S. PATENT DOCUMENTS

| | | |
|---|---|---|
| 6,852,719 B2 | 2/2005 | Liu et al. |
| 7,576,076 B2 | 8/2009 | Clark et al. |
| 7,799,782 B2 | 9/2010 | Munson et al. |
| 8,173,664 B2 | 5/2012 | Clark et al. |
| 8,685,973 B2 | 4/2014 | Clark et al. |
| 8,906,917 B2 | 12/2014 | Clark et al. |
| 9,321,736 B2 | 4/2016 | Clark et al. |
| 9,622,979 B2 | 4/2017 | Bhavarisetti |
| 9,626,979 B2 | 4/2017 | Sung et al. |
| 10,238,659 B2 | 3/2019 | Belanoff et al. |
| 10,881,660 B2 | 1/2021 | Belanoff et al. |
| 11,542,238 B2 | 1/2023 | Hunt et al. |
| 11,548,856 B2 | 1/2023 | Hunt et al. |
| 11,760,731 B2 | 9/2023 | Hunt |
| 2010/0267643 A1 | 10/2010 | Baron |
| 2021/0238148 A1 | 8/2021 | Hunt et al. |
| 2021/0361651 A1 | 11/2021 | Chia et al. |
| 2021/0363112 A1 | 11/2021 | Hunt et al. |
| 2022/0220081 A1 | 7/2022 | Dener et al. |
| 2023/0212128 A1 | 7/2023 | Hunt |

FOREIGN PATENT DOCUMENTS

| | | |
|---|---|---|
| EP | 0037495 A1 | 10/1981 |
| EP | 0369627 A2 | 5/1990 |
| EP | 0722732 A1 | 7/1996 |
| EP | 2313212 B1 | 6/2012 |
| JP | H06128238 A | 5/1994 |
| JP | H1017555 A | 1/1998 |
| JP | 2000271618 A1 | 10/2000 |

(Continued)

OTHER PUBLICATIONS

International Search Report and Written Opinion issued in related International Patent Application No. PCT/US2019/035229 mailed on Oct. 1, 2019, 10 pages.

(Continued)

*Primary Examiner* — Bruck Kifle
(74) *Attorney, Agent, or Firm* — Mintz, Levin, Cohn, Ferris, Glovsky and Popeo, P.C.

(57) ABSTRACT

The present invention provides a class of pyrimidinedione cyclohexenyl compounds and methods of using these compounds as glucocorticoid receptor modulators.

14 Claims, 1 Drawing Sheet

(56) References Cited

FOREIGN PATENT DOCUMENTS

| WO | 0244120 | A1 | 6/2002 |
| WO | 03084935 | A2 | 10/2003 |
| WO | 2005105036 | A1 | 11/2005 |
| WO | 2009141414 | A1 | 11/2009 |
| WO | 2010052445 | A1 | 5/2010 |
| WO | 2011132094 | A2 | 10/2011 |
| WO | 2012129074 | A1 | 9/2012 |
| WO | 2016061195 | A1 | 4/2016 |
| WO | 2018236749 | A2 | 12/2018 |
| WO | 2019236487 | A1 | 12/2019 |
| WO | 2020190351 | A1 | 9/2020 |
| WO | 2021226258 | A1 | 11/2021 |
| WO | 2021226260 | A1 | 11/2021 |
| WO | 2022140293 | A1 | 6/2022 |

OTHER PUBLICATIONS

International Search Report and Written Opinion issued in related International Patent Application. No. PCT/US2005/023675 mailed on Dec. 13, 2005, 11 pages.

International Search Report and Written Opinion issued in related International Patent Application. No. PCT/US2012/029376 mailed on Jun. 27, 2012, 8 pages.

International Search Report and Written Opinion received for PCT Application No. PCT/US2021/030923 mailed on Aug. 18, 2021, 13 pages.

International Search Report and Written Opinion received for PCT Application No. PCT/US2021/030925 mailed on Aug. 20, 2021, 14 pages.

Bhuyan et al. (1998) "Studies on Uracils: Synthesis of Novel Uracil Analogues via 1,5- and 1,6-Intramolecular Cycloaddition Reactions", Journal of Chemical Research, Synopses, 9:502-503.

Bledsoe et al. (Jul. 12, 2002) "Crystal Structure of the Glucocorticoid Receptor Ligand Binding Domain Reveals a Novel Mode of Receptor Dimerization and Coactivator Recognition", Cell, 110(1):93-105.

Dorwald F. Zaragoza. (2005) "Side Reactions in Organic Synthesis: A Guide to Successful Synthesis Design", Wiley-VCH, 390 pages.

Fukazawa et al. (1998) "6-Amino-5-Methyluracil Derivatives and Their Use as Thymidine Phosphorylase Inhibitors and Neovascularization Inhibitors", XP002355358; Database CA 'Online'; Chemical Abstracts Service, Columbus, OH, US; Database Accession No. 1998:59356, 4 pages.

Hunt et al. (2012) "Discovery of a Novel Non-steroidal GR Antagonist With in Vivo Efficacy in the Olanzapine-induced Weight Gain Model in the Rat", Bioorganic & Medicinal Chemistry Letters, 22(24):7376-7380.

Koorneef et al. (2018) "Selective Glucocorticoid Receptor Modulation Prevents and Reverses Nonalcoholic Fatty Liver Disease In Male Mice", Endocrinology, 159(12):3925-3936.

Lee et al. (Apr. 2020) "Reversal Of Antipsychotic-induced Weight Gain In Rats With Miricorilant, A Selective Glucocorticoid Receptor (Gr) Modulator", American Psychiatric Association Annual Meeting, 1 Page.

Nguyen et al. (Sep. 1, 2017) "A Mixed Glucocorticoid/mineralocorticoid Receptor Modulator Dampens Endocrine and Hippocampal Stress Responsivity in Male Rats", Physiology & Behavior, 178:82-92.

Teutsch et al. (Nov. 1, 1991) "Design of Ligands for the Glucocorticoid and Progestin Receptors", Biochemical Society Transactions, 19(4):901-908.

Sester et al., "pH-Sensitive methacrylic acid-methyl methacrylate copolymer Eudragit L100 and dimethylaminoethyl methacrylate, butyl methacrylate, and methyl methacrylate tri-copolymer Eudragit E100", Polymers for Advanced Technologies 31(3): 440-450, 2020.

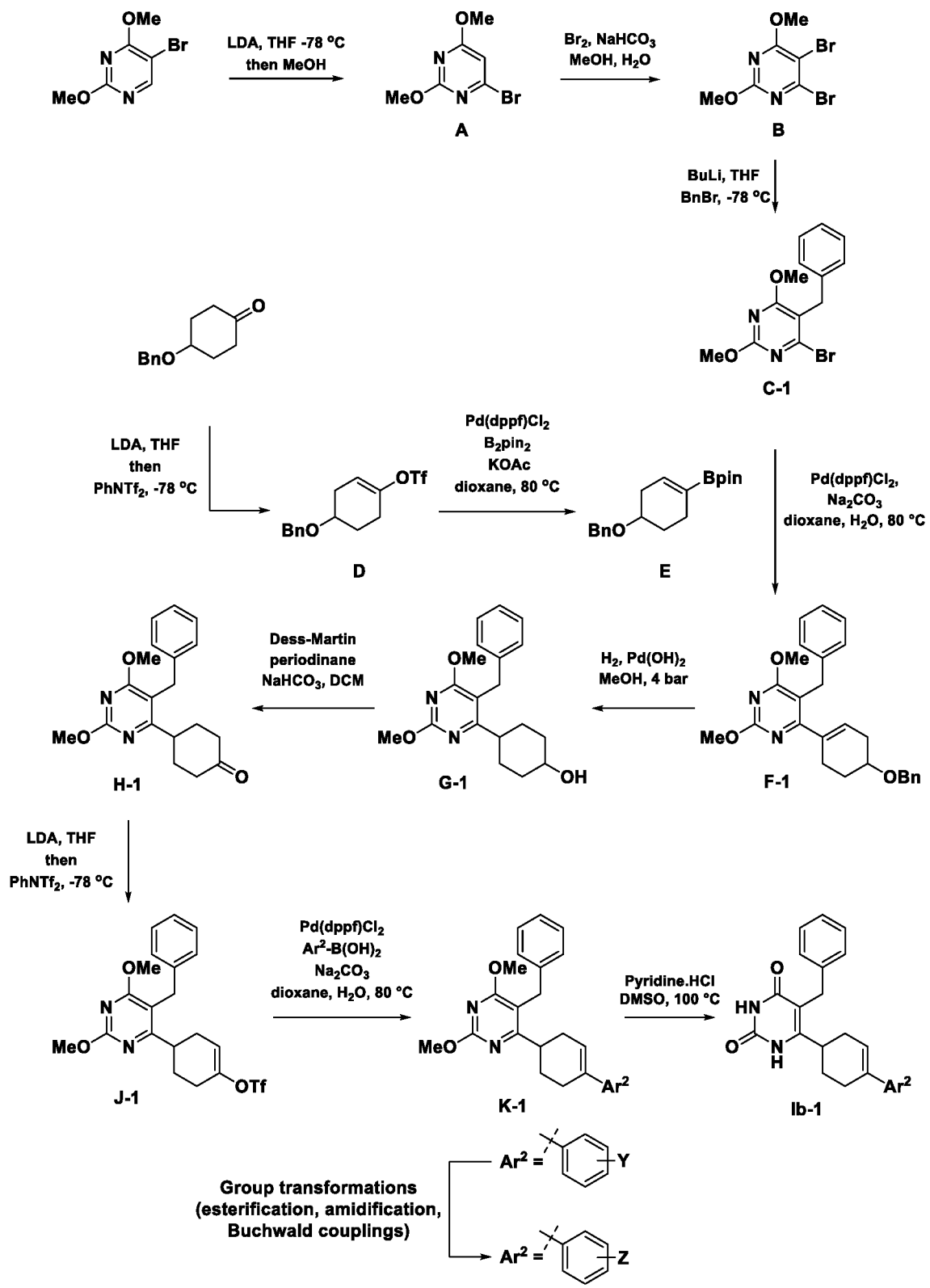

PYRIMIDINE CYCLOHEXENYL GLUCOCORTICOID RECEPTOR MODULATORS

CROSS-REFERENCES TO RELATED APPLICATIONS

This application is a continuation of U.S. application Ser. No. 15/734,525, filed Dec. 2, 2020, which is the U.S. National Stage Entry under § 371 of International Application No. PCT/US2019/035229, filed Jun. 3, 2019, which claims the benefit priority to U.S. Provisional Application No. 62/680,362, filed Jun. 4, 2018, each of which is herein incorporated by reference in its entirety for all purposes.

BACKGROUND OF THE INVENTION

In most species, including man, the physiological glucocorticoid is cortisol (hydrocortisone). In rodents, the physiological glucocorticoid is corticosterone. Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). In man, glucocorticoid receptors are present in two forms: a ligand-binding GR-alpha of 777 amino acids; and, a GR-beta isoform which lacks the 50 carboxy terminal residues. Since these residues include the ligand binding domain, GR-beta is unable to bind the natural ligand, and is constitutively localized in the nucleus.

The biologic effects of cortisol, including those caused by hypercortisolemia, can be modulated at the GR level using receptor modulators, such as agonists, partial agonists and antagonists. Several different classes of agents are able to block the physiologic effects of GR-agonist binding. These antagonists include compositions which, by binding to GR, block the ability of an agonist to effectively bind to and/or activate the GR. One such known GR antagonist, mifepristone, has been found to be an effective anti-glucocorticoid agent in humans (Bertagna (1984) J. Clin. Endocrinol. Metab. 59:25). Mifepristone binds to the GR with high affinity, with a dissociation constant $(K_d)$ of $10^{-9}$ M (Cadepond (1997) Annu. Rev. Med. 48:129).

Cortisol (and corticosterone) also binds to the mineralocorticoid receptor, MR. Cortisol has higher affinity for MR than it does for GR, and MR is usually considered to be fully occupied under normal physiological conditions. Under conditions of stress, cortisol concentrations are increased and GR becomes occupied. Aldosterone also binds to MR, and aldosterone and cortisol have similar affinity for MR. However, glucocorticoids circulate at roughly 100 times the level of mineralocorticoids. An enzyme (11-β hydroxysteroid dehydrogenase 1) exists in mineralocorticoid target tissues to prevent overstimulation by glucocorticoids.

When administered to subjects in need thereof, steroids can provide both intended therapeutic effects. as well as negative side effects. What is needed in the art are new compositions and methods for selectively modulating GR Surprisingly, the present invention meets these and other needs.

BRIEF SUMMARY OF THE INVENTION

In one aspect, the present invention provides a compound of formula I:

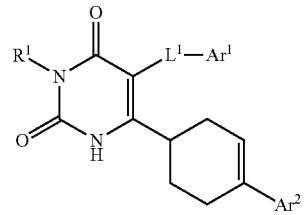

or a pharmaceutically acceptable salt thereof, or an isomer thereof,
wherein
$R^1$ is H or $C_{1-6}$ alkyl;
$L^1$ is $C_{1-4}$ alkylene;
$Ar^1$ is a $C_{6-12}$ aryl or 5-10 membered heteroaryl having 1-4 heteroatoms selected from N, O, and S, each of which is optionally substituted with 1-3 $R^a$ groups;
each $R^a$ is independently H, halogen, $C_{1-4}$ alkyl, $C_{1-4}$ alkoxy, $C_{1-4}$ haloalkyl, $C_{1-4}$ haloalkoxy, $—SO_2R^{a1}$, or $—NR^{a1}R^{a2}$;
$R^{a1}$ and $R^{a2}$ are each independently H or $C_{1-4}$ alkyl; or $R^{a1}$ and $R^{a2}$ when attached to a nitrogen atom are combined to form a 3-6 membered heterocycle having 1-2 heteroatoms selected from N, O, and S, which is optionally substituted with 1-2 $R^{a3}$;
each $R^{a3}$ is independently H, halogen, $C_{1-4}$ alkyl, or $C_{1-4}$ alkoxy;
$Ar^2$ is a $C_{6-12}$ aryl or 5-10 membered heteroaryl having 1-4 heteroatoms selected from N, O, and S, each of which is optionally substituted with 1-4 $R^b$ groups;
each $R^b$ is independently H, halogen, CN, hydroxy, $C_{1-4}$ alkyl, $C_{2-4}$ alkenyl, $C_{2-4}$ alkynyl, $C_{1-4}$ alkoxy, $C_{1-4}$ alkoxy-$C_{1-4}$ alkyl, $C_{1-4}$ hydroxyalkyl, $C_{1-4}$ haloalkyl, $C_{1-4}$haloalkoxy, $—OR^{b4}$, $—NR^{b1}R^{b2}$, $—C(O)R^{b1}$, $—C(O)OR^{b1}$, $—OC(O)R^{b1}$, $—C(O)NR^{b1}R^{b2}$, $—NR^{b1}C(O)R^{b2}$ $SO_2R^{b1}$, $—SO_2NR^{b1}R^{b2}$ or $C_{3-6}$ cycloalkyl;
alternatively, two $R^b$ groups on adjacent ring atoms can be combined to form a $C_{5-8}$ cycloalkyl or a 5-8 membered heterocycle having 1-2 heteroatoms selected from N, O, and S;
$R^{b1}$ and $R^{b2}$ are each independently H or $C_{1-4}$ alkyl; or $R^{b1}$ and $R^{b2}$ when attached to a nitrogen atom are combined to form a 3-6 membered heterocycle having 1-2 heteroatoms selected from N, O, and S, which is optionally substituted with 1-2 $R^{b3}$;
each $R^{b3}$ is independently H, halogen, $C_{1-4}$ alkyl, or $C_{1-4}$ alkoxy; and
each $R^{b4}$ is independently $C_{1-4}$ hydroxyalkyl, $C_{1-4}$ alkoxy-$C_{1-4}$ alkyl, $C_{3-6}$ cycloalkyl or $C_{3-6}$ cycloalkyl-$C_{1-4}$ alkyl.

In a second aspect, the present invention provides a pharmaceutical composition including one or more pharmaceutically acceptable excipients and the compound of formula I.

In a third aspect, the present invention provides a method of treating a disorder or condition through modulating a glucocorticoid receptor, the method including administering to a subject in need of such treatment, a therapeutically effective amount of the compound of formula I or a pharmaceutical composition of the compound of formula I, thereby treating the disorder or condition.

In a fourth aspect, the present invention provides a method of treating a disorder or condition through antagonizing a glucocorticoid receptor, the method including administering to a subject in need of such treatment, an effective amount of the compound of formula I or a pharmaceutical composition of the compound of formula I.

BRIEF DESCRIPTION OF THE DRAWINGS

FIG. 1 shows a method of preparing the compounds of the present invention.

DETAILED DESCRIPTION OF THE INVENTION

I. General

The present invention provides compounds capable of modulating a glucocorticoid and thereby providing beneficial therapeutic effects. The compounds include, but are not limited to, benzyl pyrimidinedione-cyclohexenyl-phenyls and benzyl pyrimidinedione-cyclohexenyl-pyridinyls. The present invention also provides methods of treating diseases and disorders by modulating a GR and/or a MR receptor with the compounds of the present invention.

II. Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Alkyl" refers to a straight or branched, saturated, aliphatic radical having the number of carbon atoms indicated (i.e., $C_{1-6}$ means one to six carbons). Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. $C_{1-6}$ alkyl includes, but is not limited to, methyl, ethyl, propyl, isopropyl, butyl, isobutyl, sec-butyl, tert-butyl, pentyl, isopentyl, hexyl, etc.

"Alkylene" refers to a straight or branched, saturated, aliphatic radical having the number of carbon atoms indicated (i.e., $C_{1-6}$ means one to six carbons), and linking at least two other groups, i.e., a divalent hydrocarbon radical. The two moieties linked to the alkylene can be linked to the same atom or different atoms of the alkylene group. For instance, a straight chain alkylene can be the bivalent radical of —(CH$_2$)$_n$—, where n is 1, 2, 3, 4, 5 or 6. Representative $C_{1-4}$ alkenylene groups include, but are not limited to, methylene, ethylene, propylene, isopropylene, butylene, isobutylene, and sec-butylene.

"Alkenyl" refers to a straight chain or branched hydrocarbon having at least 2 carbon atoms and at least one double bond and having the number of carbon atom indicated (i.e., $C_{2-6}$ means to two to six carbons). Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-5}$, $C_5$, $C_{5-6}$, and $C_6$. Alkenyl groups can have any suitable number of double bonds, including, but not limited to, 1, 2, 3, 4, 5 or more. Examples of $C_{2-4}$ alkenyl groups include, but are not limited to, vinyl (ethenyl), propenyl, isopropenyl, 1-butenyl, 2-butenyl, isobutenyl, or butadienyl.

"Alkynyl" refers to either a straight chain or branched hydrocarbon having at least 2 carbon atoms and at least one triple bond and having the number of carbon atom indicated (i.e., $C_{2-6}$ means to two to six carbons). Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of $C_{2-4}$ alkynyl groups include, but are not limited to, acetylenyl, propynyl, 1-butynyl, 2-butynyl, isobutynyl, sec-butynyl, or butadiynyl.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. $C_{1-4}$ Alkoxy groups include, for example, methoxy, ethoxy, propoxy, iso-propoxy, butoxy, 2-butoxy, iso-butoxy, sec-butoxy, or tert-butoxy.

"Hydroxyalkyl" or "alkylhydroxy" refers to an alkyl group, as defined above, where at least one of the hydrogen atoms is replaced with a hydroxy group. As for the alkyl group, hydroxyalkyl or alkylhydroxy groups can have any suitable number of carbon atoms, such as $C_{1-6}$. Exemplary $C_{1-4}$ hydroxyalkyl groups include, but are not limited to, hydroxymethyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), 1,2-dihydroxyethyl, and the like.

"Alkoxy-alkyl" refers to a radical having an alkyl component and an alkoxy component, where the alkyl component links the alkoxy component to the point of attachment. The alkyl component is as defined above, where the alkyl component is at least divalent, an alkylene, to link to the alkoxy component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The alkoxy component is as defined above. Examples of the alkoxy-alkyl group include, but are not limited to, 2-ethoxy-ethyl and methoxymethyl.

"Halogen" refers to fluorine, chlorine, bromine and iodine.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, fluoromethyl, 2,2,2-trifluoroethyl, etc. In some instances, the term "perfluoro" can be used to define a compound or radical where all the hydrogens are replaced with fluorine. For example, perfluoromethyl refers to 1,1,1-trifluoromethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Amino" refers to an —N(R)$_2$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), secondary (one R is hydrogen) or tertiary (each R is other than hydrogen).

"Alkylamine" refers to an alkyl group as defined within, having one or more amino groups. The amino groups can be primary, secondary or tertiary. The alkyl amine can be further substituted with a hydroxy group to form an amino-hydroxy group. Alkyl amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2]bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_3$-$C_8$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Cycloalkyl-alkyl" refers to a radical having an alkyl component and a cycloalkyl component, where the alkyl component links the cycloalkyl component to the point of attachment. The alkyl component is as defined above, where the alkyl component is at least divalent, an alkylene, to link to the cycloalkyl component and to the point of attachment. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined within. Exemplary cycloalkyl-alkyl groups include, but are not limited to, cyclopropylmethyl, cyclobutylmethyl, cyclopentylmethyl, or cyclohexylmethyl.

"Heterocycle" or "heterocycloalkyl" refers to a saturated ring system having from 3 to 12 ring members and from 1 to 4 heteroatoms of N, O and S. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative $C_{6-12}$ aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl.

"Heteroaryl" refers to a monocyclic or fused bicyclic or tricyclic aromatic ring assembly containing 5 to 16 ring atoms, where from 1 to 5 of the ring atoms are a heteroatom such as N, O or S. The heteroatoms can also be oxidized, such as, but not limited to, N-oxide, —S(O)— and —S(O)$_2$—. The nitrogen atom(s) can also be quaternized. Heteroaryl groups can include any number of ring atoms, such as, 5 to 6, 5 to 8, 6 to 8, 5 to 9, 5 to 10, 5 to 11, or 5 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 10 ring members and from 1 to 4 heteroatoms, from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Isomers" refers to compounds with the same chemical formula but which are structurally distinguishable. Certain compounds of the present invention possess asymmetric carbon atoms (optical centers) or double bonds; the racemates, diastereomers, geometric isomers and individual isomers are all intended to be encompassed within the scope of the present invention.

"Tautomer" refers to one of two or more structural isomers which exist in equilibrium and which are readily converted from one form to another. For example, compounds of the following formulae can exist in equilibrium:

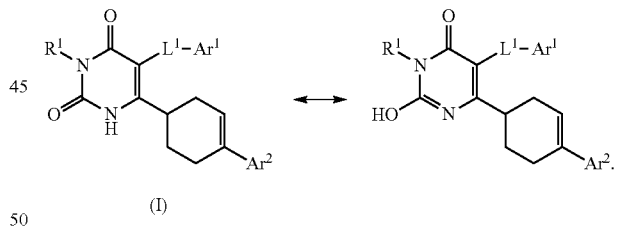

(I)

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier(s), diluent(s) or excipient(s) must be compatible with the other ingredients of the formulation and not deleterious to the recipient thereof.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, surfactants, coatings, sweeteners, flavors and colors. One of skill in the art will recognize that other pharmaceutical excipients are useful in the present invention.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Glucocorticoid receptor" ("GR") refers to a family of intracellular receptors which specifically bind to cortisol and/or cortisol analogs (e.g. dexamethasone). The glucocorticoid receptor is also referred to as the cortisol receptor. The term includes isoforms of GR, recombinant GR and mutated GR.

"Modulate" and "modulating" are used in accordance with its plain ordinary meaning and refer to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Modulator" refers to a composition that increases or decreases the level of a target molecule or the function of a target molecule or the physical state of the target of the molecule.

"Glucocorticoid receptor modulator" refers to any composition or compound which modulates the function of a glucocorticoid receptor (GR). The modulation can include partially or completely inhibiting (antagonizing) the binding of a GR agonist, such as cortisol, or cortisol analogs, synthetic or natural, to a GR. GR modulators of the present invention include compounds of formula I below.

"Antagonize' and "antagonizing" refer to blocking the binding of an agonist at a receptor molecule or to inhibiting the signal produced by a receptor-agonist. A receptor antagonist blocks or dampens agonist-mediated responses, such as gene expression.

"Antagonist" refers to a substance capable of detectably lowering expression or activity of a given gene or protein. The antagonist can inhibit expression or activity 10%, 20%, 30%, 40%, 50%, 60%, 70%, 80%, 90%, 100% or less in comparison to a control in the absence of the antagonist. In some embodiments, the inhibition is 1.5-fold, 2-fold, 3-fold, 4-fold, 5-fold, 10-fold, or more than the expression or activity in the absence of the antagonist.

"Inhibition", "inhibits" and "inhibitor" refer to a compound that prohibits or a method of prohibiting, a specific action or function.

"Disorder" or "condition" refers to a state of being or health status of a patient or subject capable of being treated with the glucocorticoid receptor modulators of the present invention. In some embodiments, examples of disorders or conditions include, but are not limited to, obesity, hypertension, depression, anxiety, and Cushing's Syndrome. In some embodiments, the disorders or conditions include nonalcoholic liver disease and/or nonalcoholic steatohepatitis. In some embodiments, the disorders or conditions include addiction disorders. In some embodiments, the disorders or conditions include cancer.

"Non-alcoholic fatty liver disease" ("NAFLD") refers to one of the types of fatty liver which occurs when fat is deposited (steatosis) in the liver due to causes other than excessive alcohol use. NAFLD is considered to cover a spectrum of disease activity. This spectrum begins as fatty accumulation in the liver (hepatic steatosis). Most people with NAFLD have few or no symptoms. Patients may complain of fatigue, malaise, and dull right-upper-quadrant abdominal discomfort. Mild jaundice may be noticed, although this is rare. More commonly NAFLD is diagnosed following abnormal liver function tests during routine blood tests. By definition, alcohol consumption of over 20 g/day (about 25 ml/day of net ethanol) excludes the condition.

"Non-alcoholic steatohepatitis" ("NASH") refers to the most extreme form of NAFLD. NAFLD can progress to become non-alcoholic steatohepatitis (NASH), a state in which steatosis is combined with inflammation and fibrosis (steatohepatitis). NASH is a progressive disease. Over a 10-year period, up to 20% of patients with NASH will develop cirrhosis of the liver, and 10% will suffer death related to liver disease.

"Cancer" refers to all types of cancer, neoplasm or malignant tumors found in mammals (e.g. humans), including leukemia, carcinomas and sarcomas.

"Patient" or "subject" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, horse, and other non-mammalian animals. In some embodiments, the patient is human.

"Therapeutically effective amount" refers to an amount of a compound or of a pharmaceutical composition useful for treating or ameliorating an identified disease or condition, or for exhibiting a detectable therapeutic or inhibitory effect. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

"A," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substitutent group, the compound is substituted with at least one substituent group, wherein each substituent group is optionally different.

III. Compounds

In one aspect, the present invention provides a compound of formula I:

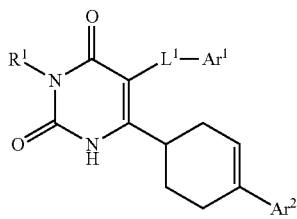

(I)

or a pharmaceutically acceptable salt thereof, or an isomer thereof,
wherein
$R^1$ is H or $C_{1-6}$ alkyl;
$L^1$ is $C_{1-4}$ alkylene;
$Ar^1$ is a $C_{6-12}$ aryl or 5-10 membered heteroaryl having 1-4 heteroatoms selected from N, O, and S, each of which is optionally substituted with 1-3 $R^a$ groups;
each $R^a$ is independently H, halogen, $C_{1-4}$ alkyl, $C_{1-4}$ alkoxy, $C_{1-4}$ haloalkyl, $C_{1-4}$ haloalkoxy, $-SO_2R^{a1}$, or $-NR^{a1}R^{a2}$;
$R^{a1}$ and $R^{a2}$ are each independently H or $C_{1-4}$ alkyl; or $R^{a1}$ and $R^{a2}$ when attached to a nitrogen atom are combined to form a 3-6 membered heterocycle having 1-2 heteroatoms selected from N, O, and S, which is optionally substituted with 1-2 $R^{a3}$;
each $R^{a3}$ is independently H, halogen, $C_{1-4}$ alkyl, or $C_{1-4}$ alkoxy;
$Ar^2$ is a $C_{6-12}$ aryl or 5-10 membered heteroaryl having 1-4 heteroatoms selected from N, O, and S, each of which is optionally substituted with 1-4 $R^b$ groups;
each $R^b$ is independently H, halogen, CN, hydroxy, $C_{1-4}$ alkyl, $C_{2-4}$ alkenyl, $C_{2-4}$ alkynyl, $C_{1-4}$ alkoxy, $C_{1-4}$ alkoxy-$C_{1-4}$ alkyl, $C_{1-4}$ hydroxyalkyl, $C_{1-4}$ haloalkyl, $C_{1-4}$haloalkoxy, $-OR^{b4}$, $-NR^{b1}R^{b2}$, $-C(O)R^{b1}$, $-C(O)OR^{b1}$, $-OC(O)R^{b1}$, $-C(O)NR^{b1}R^{b2}$, $-NR^{b1}C(O)R^{b2}$, $-SO_2R^{b1}$, $-SO_2NR^{b1}R^{b2}$ or $C_{3-6}$ cycloalkyl;
alternatively, two $R^b$ groups on adjacent ring atoms can be combined to form a $C_{5-8}$ cycloalkyl or a 5-8 membered heterocycle having 1-2 heteroatoms selected from N, O, and S;
$R^{b1}$ and $R^{b2}$ are each independently H or $C_{1-4}$ alkyl; or $R^{b1}$ and $R^{b2}$ when attached to a nitrogen atom are combined to form a 3-6 membered heterocycle having 1-2 heteroatoms selected from N, O, and S, which is optionally substituted with 1-2 $R^{b3}$;
each $R^{b3}$ is independently H, halogen, $C_{1-4}$ alkyl, or $C_{1-4}$ alkoxy; and
each $R^{b4}$ is independently $C_{1-4}$ hydroxyalkyl, $C_{1-4}$ alkoxy-$C_{1-4}$ alkyl, $C_{3-6}$ cycloalkyl or $C_{3-6}$ cycloalkyl-$C_{1-4}$ alkyl.

In some embodiments, the compound can be a compound of Formula I, or a pharmaceutically acceptable salt thereof, or an isomer thereof, wherein
$R^1$ is H or $C_{1-6}$ alkyl;
$L^1$ is $C_{1-4}$ alkylene;
$Ar^1$ is a $C_{6-12}$ aryl or 5-10 membered heteroaryl having 1-4 heteroatoms selected from N, O, and S, each of which is optionally substituted with 1-3 $R^a$ groups;
each $R^a$ is independently H, halogen, $C_{1-4}$ alkyl, $C_{1-4}$ alkoxy, $C_{1-4}$ haloalkyl, $C_{1-4}$ haloalkoxy, $-SO_2R^{a1}$, or $-NR^{a1}R^{a2}$;
$R^{a1}$ and $R^{a2}$ are each independently H or $C_{1-4}$ alkyl; or $R^{a1}$ and $R^{a2}$ when attached to a nitrogen atom are combined to form a 3-6 membered heterocycle having 1-2 heteroatoms selected from N, O, and S, which is optionally substituted with 1-2 $R^{a3}$;
each $R^{a3}$ is independently H, halogen, $C_{1-4}$ alkyl, or $C_{1-4}$ alkoxy;
$Ar^2$ is a $C_{6-12}$ aryl or 5-10 membered heteroaryl having 1-4 heteroatoms selected from N, O, and S, each of which is optionally substituted with 1-4 $R^b$ groups;
each $R^b$ is independently H, halogen, CN, hydroxy, $C_{1-4}$ alkyl, $C_{2-4}$ alkenyl, $C_{2-4}$ alkynyl, $C_{1-4}$ alkoxy, $C_{1-4}$ hydroxyalkyl, $C_{1-4}$ haloalkyl, $C_{1-4}$haloalkoxy, $-NR^{b1}R^{b2}$, $-C(O)R^{b1}$, $-C(O)OR^{b1}$, $-OC(O)R^{b1}$, $-C(O)NR^{b1}R^{b2}$, $-NR^{b1}C(O)R^{b2}$, $-SO_2R^{b1}$, or $-SO_2NR^{b1}R^{b2}$;
$R^{b1}$ and $R^{b2}$ are each independently H or $C_{1-4}$ alkyl; or $R^{b1}$ and $R^{b2}$ when attached to a nitrogen atom are combined to form a 3-6 membered heterocycle having 1-2 heteroatoms selected from N, O, and S, which is optionally substituted with 1-2 $R^{b3}$;
each $R^{b3}$ is independently H, halogen, $C_{1-4}$ alkyl, or $C_{1-4}$ alkoxy.

In some embodiments, $L^1$ is $C_{1-4}$ alkylene. The $C_{1-4}$ alkylene of $L^1$ can be methylene ($CH_2$), ethylene, propylene, isopropylene, butylene, isobutylene, or sec-butylene. In some embodiments, $L^1$ is $CH_2$.

In some embodiments, the compound of formula I is a compound of formula Ia:

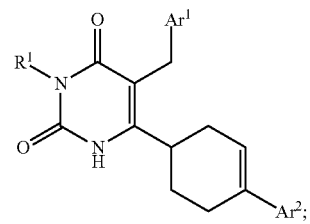

(Ia)

wherein $R^1$, $Ar^1$, and $Ar^2$ are as defined and described herein.

In some embodiments, $Ar^1$ is a $C_{6-12}$ aryl or 5-10 membered heteroaryl having 1-4 heteroatoms selected from N, O, and S, each of which is optionally substituted with 1-3 $R^a$ groups. In some embodiments, $Ar^1$ is a $C_{6-12}$ aryl optionally substituted with 1-3 $R^a$ groups. The $C_{6-12}$ aryl of $Ar^1$ can be phenyl, naphthyl and biphenyl. In some embodiments, $Ar^1$ is a phenyl optionally substituted with 1-3 $R^a$ groups.

In some embodiments, $Ar^1$ is a 5-10 membered heteroaryl having 1-4 heteroatoms selected from N, O, and S, which is optionally substituted with 1-3 $R^a$ groups. In some embodiments, $Ar^1$ is a 5-6 membered heteroaryl having 1-4 heteroatoms selected from N, O, and S, which is optionally substituted with 1-3 $R^a$ groups. In some embodiments, $Ar^1$ is a 5-6 membered heteroaryl having 1-3 heteroatoms selected from N, O, and S, which is optionally substituted with 1-3 $R^a$ groups. In some embodiments, $Ar^1$ is a 5-6 membered heteroaryl having 1-2 heteroatoms selected from N, O, and S, which is optionally substituted with 1-3 $R^a$ groups. In some embodiments, $Ar^1$ is a 5-6 membered heteroaryl having 1-2 heteroatoms selected from N and S, which is optionally substituted with 1-3 $R^a$ groups. The 5-6 membered heteroaryl having 1-2 heteroatoms selected from N, O, and S includes, but is not limited to, pyrrolyl, pyridinyl, imidazolyl, pyrazolyl, pyrazinyl, pyrimidinyl, pyridazinyl, thiophenyl, furanyl, thiazolyl, isothiazolyl, oxazolyl, and isoxazolyl. The 5-6 membered heteroaryl having 1-2 heteroatoms selected from N and S includes, but is not limited to, pyrrolyl, pyridinyl, imidazolyl, pyrazolyl, pyrazinyl, pyrimidinyl, pyridazinyl, thiophenyl, thiazolyl, and isothiazolyl. In some embodiments, $Ar^1$ is pyridinyl or thiazolyl, each of which is optionally substituted with 1-3 $R^a$ groups.

In some embodiments, $Ar^1$ is phenyl or a 5-6 membered heteroaryl having 1-4 heteroatoms selected from N, O, and S, each of which is optionally substituted with 1-3 $R^a$ groups. In some embodiments, $Ar^1$ is phenyl or a 5-6 membered heteroaryl having 1-3 heteroatoms selected from N, O, and S, each of which is optionally substituted with 1-3 $R^a$ groups. In some embodiments, $Ar^1$ is phenyl or a 5-6 membered heteroaryl having 1-2 heteroatoms selected from N, O, and S, each of which is optionally substituted with 1-3 $R^a$ groups. In some embodiments, $Ar^1$ is phenyl or a 5-6 membered heteroaryl having 1-2 heteroatoms selected from N and S, each of which is optionally substituted with 1-3 $R^a$ groups. In some embodiments, $Ar^1$ is phenyl, pyridinyl or thiazolyl, each of which is optionally substituted with 1-3 $R^a$ groups.

In some embodiments, $Ar^1$ is phenyl or 5-6 membered heteroaryl having 1-2 heteroatoms selected from N and S, each of which is optionally substituted with 1-2 $R^a$ groups. In some embodiments, $Ar^1$ is phenyl, pyridinyl, or thiazolyl, each of which is optionally substituted with 1-2 $R^a$ groups. In some embodiments, $Ar^1$ is phenyl, which is optionally substituted with 1-2 $R^a$ groups. In some embodiments, $Ar^1$ is pyridinyl, which is optionally substituted with 1-2 $R^a$ groups.

In some embodiments, each $R^a$ is independently H, halogen, CN, $C_{1-4}$ alkyl, $C_{1-4}$ alkoxy, $C_{1-4}$ haloalkyl, $C_{1-4}$haloalkoxy, $-SO_2R^{a1}$, or $-NR^{a1}R^{a2}$. $R^{a1}$ and $R^2$ are each independently H or $C_{1-4}$ alkyl; or $R^{a1}$ and $R^{a2}$ when attached to a nitrogen atom are combined to form a 3-6 membered heterocycle having 1-2 heteroatoms selected from N, O, and S, which is optionally substituted with 1-2 $R^{a3}$. Each $R^{a3}$ is independently H, halogen, $C_{1-4}$ alkyl, or $C_{1-4}$ alkoxy.

In some embodiments, each $R^a$ is independently H, halogen, CN, $C_{1-4}$ alkyl, $C_{1-4}$ alkoxy, $C_{1-4}$ haloalkyl, $C_{1-4}$haloalkoxy, or $-NR^{a1}R^{a2}$; wherein $R^{a1}$ and $R^{a2}$ are each independently H or $C_{1-4}$ alkyl. The $C_{1-4}$ alkyl of $R^a$ can be methyl, ethyl, propyl, isopropyl, butyl, or tert-butyl. The $C_{1-4}$ alkoxy of $R^a$ can be methoxy, ethoxy, propoxy, isopropoxy, or tert-butoxy. The $C_{1-4}$ haloalkyl of $R^a$ can be trifluoromethyl, fluoromethyl, or 2,2,2-trifluoroethyl. The $C_{1-4}$haloalkoxy of $R^a$ can be trifluoromethoxy or 2,2,2,-trifluoroethoxy.

In some embodiments, $R^{a1}$ and $R^{a2}$ are each independently H or $C_{1-4}$ alkyl. The $C_{1-4}$ alkyl of $R^{a1}$ or $R^{a2}$ can be methyl, ethyl, propyl, isopropyl, butyl, or tert-butyl. In some embodiments, $R^{a1}$ and $R^{a2}$ are each independently H, Me, or Et.

In some embodiments, $R^{a1}$ and $R^{a2}$ when attached to a nitrogen atom are combined to form a 3-6 membered heterocycle having 1-2 heteroatoms selected from N, O, and S, which is optionally substituted with 1-2 $R^{a3}$. The 3-6 membered heterocycle having 1-2 heteroatoms selected from N, O, and S includes, but is not limited to, aziridine, azetidine, pyrrolidine, piperidine, pyrazolidine, imidazolidine, piperazine, oxazolidine, isoxazolidine, thiazolidine, isothiazolidine, and morpholine.

In some embodiments, each $R^{a3}$ is independently H, F, Cl, Me, Et, or OMe. In some embodiments, each $R^{a3}$ is independently H, F, Me, or OMe. In some embodiments, each $R^{a3}$ is H.

In some embodiments, each $R^a$ is independently H, F, Cl, CN, Me, Et, OMe, OEt, $CF_3$, $OCF_3$, $NH_2$, NHMe, $N(Me)_2$, $N(Et)_2$, or pyrrolidin-1-yl. In some embodiments, each $R^a$ is independently H, F, Cl, CN, Me, Et, OMe, $CF_3$, $NH_2$, or $N(Me)_2$. In some embodiments, each $R^a$ is independently H, F, Cl, Me, OMe, or $CF_3$.

In some embodiments, each $R^a$ is independently H, halogen, $C_{1-4}$ haloalkyl, or $-NR^{a1}R^{a2}$; and $R^{a1}$ and $R^{a2}$ are combined to form a 3-6 membered heterocycle having 1-2 heteroatoms selected from N and O. In some embodiments, each $R^a$ is independently H, F, $CF_3$, or 1-pyrrolidinyl.

In some embodiments, $Ar^1$ is phenyl. In some embodiments, the compound of formula I or Ia is a compound of formula Ib:

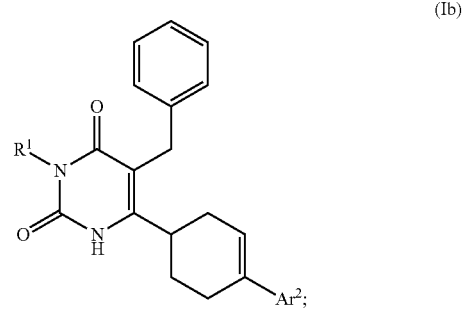

(Ib)

wherein $R^1$ and $Ar^2$ are as defined and described herein.

In some embodiments, $Ar^2$ is a $C_{6-12}$ aryl or 5-10 membered heteroaryl having 1-4 heteroatoms selected from N, O, and S, each of which is optionally substituted with 1-4 $R^b$ groups. In some embodiments, $Ar^2$ is a $C_{6-12}$ aryl optionally substituted with 1-4 $R^b$ groups. The $C_{6-12}$ aryl of $Ar^2$ can be phenyl, naphthyl and biphenyl. In some embodiments, $Ar^2$ is a phenyl optionally substituted with 1-4 $R^b$ groups.

In some embodiments, $Ar^2$ is a 5-10 membered heteroaryl having 1-4 heteroatoms selected from N, O, and S, which is optionally substituted with 1-4 $R^b$ groups. In some embodiments, $Ar^2$ is a 5-9 membered heteroaryl having 1-4 heteroatoms selected from N, O, and S, each of which is optionally substituted with 1-4 $R^b$ groups. In some embodiments, $Ar^2$ is a 5-6 membered heteroaryl having 1-4 heteroatoms selected from N, O, and S, which is optionally substituted with 1-4 $R^b$ groups. In some embodiments, $Ar^2$ is a 5-6 membered heteroaryl having 1-3 heteroatoms selected from N, O, and S, which is optionally substituted with 1-4 $R^b$ groups. In some embodiments, $Ar^2$ is a 5-6 membered heteroaryl having 1-2 heteroatoms selected from N, O, and S, which is optionally substituted with 1-4 $R^b$ groups. In some embodiments, $Ar^2$ is a 5-6 membered heteroaryl having 1-2 heteroatoms selected from N and S, which is optionally substituted with 1-4 $R^b$ groups. The 5-6 membered heteroaryl having 1-2 heteroatoms selected from N, O, and S includes, but is not limited to, pyrrolyl, pyridinyl, imidazolyl, pyrazolyl, pyrazinyl, pyrimidinyl, pyridazinyl, thiophenyl, furanyl, thiazolyl, isothiazolyl, oxazolyl, and isoxazolyl. The 5-6 membered heteroaryl having 1-2 heteroatoms selected from N and S includes, but is not limited to, pyrrolyl, pyridinyl, imidazolyl, pyrazolyl, pyrazinyl, pyrimidinyl, pyridazinyl, thiophenyl, thiazolyl, and isothiazolyl. In some embodiments, $Ar^2$ is pyridinyl, thiazolyl, or pyrazolyl, each of which is optionally substituted with 1-4 $R^b$ groups.

In some embodiments, Ar² is a phenyl or 5-10 membered heteroaryl having 1-4 heteroatoms selected from N, O, and S, each of which is optionally substituted with 1-4 R$^b$ groups. In some embodiments, Ar² is a phenyl or 5-9 membered heteroaryl having 1-4 heteroatoms selected from N, O, and S, each of which is optionally substituted with 1-4 R$^b$ groups. In some embodiments, Ar² is a phenyl or 5-9 membered heteroaryl having 1-3 heteroatoms selected from N and S, each of which is optionally substituted with 1-2 R$^b$ groups. In some embodiments, Ar² is phenyl or a 5-6 membered heteroaryl having 1-4 heteroatoms selected from N, O, and S, each of which is optionally substituted with 1-4 R$^b$ groups. In some embodiments, Ar² is phenyl or a 5-6 membered heteroaryl having 1-3 heteroatoms selected from N, O, and S, each of which is optionally substituted with 1-4 R$^b$ groups. In some embodiments, Ar² is phenyl or a 5-6 membered heteroaryl having 1-2 heteroatoms selected from N, O, and S, each of which is optionally substituted with 1-4 R$^b$ groups. In some embodiments, Ar² is phenyl or a 5-6 membered heteroaryl having 1-2 heteroatoms selected from N and S, each of which is optionally substituted with 1-4 R$^b$ groups. In some embodiments, Ar² is phenyl, pyridinyl, thiazolyl, or pyrazolyl, each of which is optionally substituted with 1-4 R$^b$ groups. In some embodiments, Ar² is phenyl or a 5-6 membered heteroaryl having 1-2 heteroatoms selected from N and S, each of which is optionally substituted with 1-2 R$^b$ groups. In some embodiments, Ar² is phenyl, pyridinyl, pyrimidinyl, thiazolyl, pyrazolyl, indazolyl, benzothiazolyl, benzopyrazolyl, or [1,2,4]triazolo[4,3-a]pyridinyl each of which is optionally substituted with 1-2 R$^b$ groups. In some embodiments, Ar² is

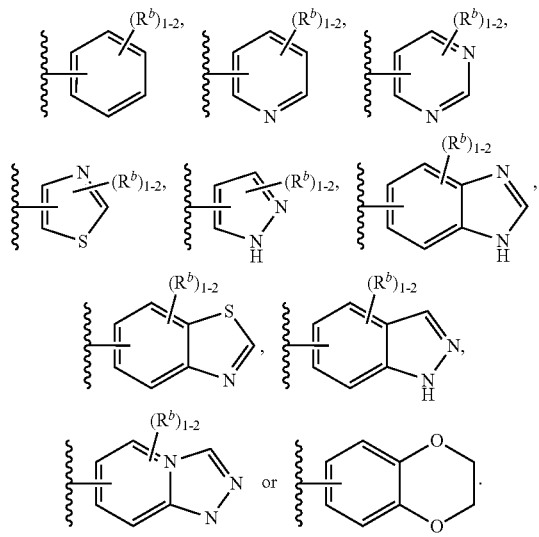

In some embodiments, Ar² is phenyl, pyridinyl, thiazolyl, or pyrazolyl, each of which is optionally substituted with 1-2 R$^b$ groups.

In some embodiments, Ar² is phenyl, which is optionally substituted with 1-2 R$^b$ groups. In some embodiments, the compound of formula I, Ia, or Ib is a compound of formula Ic:

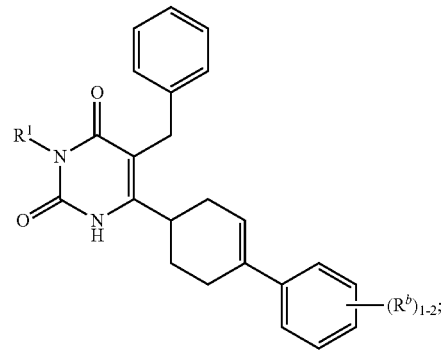

wherein R¹ and R$^b$ are as defined and described herein.

In some embodiments, Ar² is pyridinyl, which is optionally substituted with 1-2 R$^b$ groups. The pyridinyl can be, for example pyridin-2-yl, pyridin-3-yl, or pyridin-4-yl.

In some embodiments, Ar² is pyridin-3-yl, which is optionally substituted with 1-2 R$^b$ groups. In some embodiments, the compound of formula I, Ia, or Ib is a compound of formula Id:

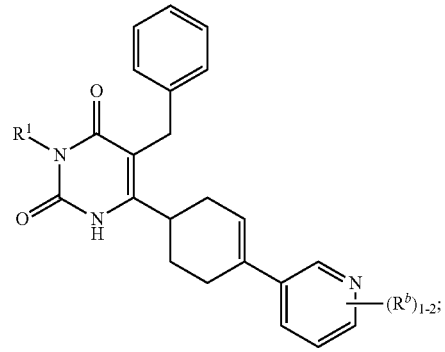

wherein R¹ and R$^b$ are as defined and described herein.

In some embodiments, Ar² is thiazolyl, which is optionally substituted with 1-2 R$^b$ groups. The thiazolyl can be, for example thiazol-2-yl, thiazol-4-yl, or thiazol-5-yl. In some embodiments, Ar² is thiazol-5-yl, which is optionally substituted with 1-2 R$^b$ groups.

In some embodiments, Ar² is pyrazolyl, which is optionally substituted with 1-2 R$^b$ groups. The pyrazolyl can be, for example pyrazol-1-yl, pyrazol-3-yl, pyrazol-4-yl, or pyrazol-5-yl. In some embodiments, Ar² is pyrazol-5-yl, which is optionally substituted with 1-2 R$^b$ groups.

In some embodiments, each R$^b$ is independently H, halogen, CN, $C_{1-4}$ alkyl, $C_{1-4}$ alkoxy, $C_{1-4}$ hydroxyalkyl, $C_{1-4}$ haloalkyl, $C_{1-4}$haloalkoxy, —OR$^{b4}$, —NR$^{b1}$R$^{b2}$, —C(O)NR$^{b1}$R$^{b2}$, —SO$_2$R$^{b1}$, —SO$_2$NR$^{b1}$R$^{b2}$, or $C_{3-6}$ cycloalkyl; R$^{b1}$ and R$^{b2}$ are each independently H or $C_{1-4}$ alkyl; or R$^{b1}$ and R$^{b2}$ when attached to a nitrogen atom are combined to form a 4-6 membered heterocycle having 1-2 nitrogen atoms, which is optionally substituted with 1-2 R$^{b3}$; each of R$^{b3}$ is independently H, halogen, $C_{1-4}$ alkyl, or $C_{1-4}$ alkoxy; and each R$^{b4}$ is independently $C_{1-4}$ hydroxyalkyl, $C_{3-6}$ cycloalkyl or $C_{3-6}$ cycloalkyl-$C_{1-4}$ alkyl. In some embodiments, each R$^b$ is independently H, halogen, CN, hydroxy, $C_{1-4}$ alkyl, $C_{2-4}$ alkenyl, $C_{2-4}$ alkynyl, $C_{1-4}$ alkoxy, $C_{1-4}$ hydroxyalkyl, $C_{1-4}$ haloalkyl, $C_{1-4}$haloalkoxy, —NR$^{b1}$R$^{b2}$, —C(O)R$^{b1}$, —C(O)OR$^{b1}$, —OC(O)R$^{b1}$, —C(O)NR$^{b1}$R$^{b2}$, NR$^{b1}$C(O)R$^{b2}$, —SO$_2$R$^{b1}$, or —SO$_2$NR$^{b1}$R$^{b2}$. R$^{b1}$ and R$^{b2}$ are each independently H or C$_{1-4}$ alkyl; or R$^{b1}$ and R$^{b2}$ when attached to a nitrogen atom are combined to form a 3-6 membered heterocycle having 1-2 nitrogen atoms, which is optionally substituted with 1-2 R$^{b3}$. Each of R$^{b3}$ is independently H, halogen, C$_{1-4}$ alkyl, or C$_{1-4}$ alkoxy.

In some embodiments, each R$^b$ is independently H, halogen, CN, C$_{1-4}$ alkyl, C$_{1-4}$ alkoxy, C$_{1-4}$ hydroxyalkyl, C$_{1-4}$ haloalkyl, C$_{1-4}$haloalkoxy, —NR$^{b1}$R$^{b2}$, —C(O)NR$^{b1}$R$^{b2}$, or —SO$_2$R$^{b1}$; wherein R$^{b1}$ and R$^{b2}$ are each independently H or C$_{1-4}$ alkyl; or R$^{b1}$ and R$^{b2}$ when attached to a nitrogen atom are combined to form a 4-6 membered heterocycle having 1-2 nitrogen atoms, which is optionally substituted with 1-2 R$^{b3}$; and each of R$^{b3}$ is independently H, halogen, C$_{1-4}$ alkyl, or C$_{1-4}$ alkoxy.

The C$_{1-4}$ alkyl of R$^b$ can be methyl, ethyl, propyl, isopropyl, butyl, or tert-butyl. The C$_{1-4}$ alkoxy of R$^b$ can be methoxy, ethoxy, propoxy, iso-propoxy, or tert-butoxy. The C$_{1-4}$ hydroxyalkyl of R$^b$ can be hydroxymethyl, hydroxyethyl (where the hydroxy is in the 1- or 2-position), hydroxypropyl (where the hydroxy is in the 1-, 2- or 3-position), or hydroxybutyl. The C$_{1-4}$ haloalkyl of R$^b$ can be trifluoromethyl, fluoromethyl, or 2,2,2-trifluoroethyl. The C$_{1-4}$haloalkoxy of R$^b$ can be trifluoromethoxy or 2,2,2,-trifluoroethoxy.

In some embodiments, R$^{b1}$ and R$^{b2}$ are each independently H or C$_{1-4}$ alkyl. The C$_{1-4}$ alkyl of R$^{b1}$ or R$^{b2}$ can be methyl, ethyl, propyl, isopropyl, butyl, or tert-butyl. In some embodiments, R$^{b1}$ and R$^{b2}$ are each independently H, Me, or Et.

In some embodiments, R$^{b1}$ and R$^{b2}$ when attached to a nitrogen atom are combined to form a 3-6 membered heterocycle having 1-2 nitrogen atoms, which is optionally substituted with 1-2 R$^{b3}$. The 3-6 membered heterocycle having 1-2 heteroatoms selected from N, O, and S includes, but is not limited to, aziridine, azetidine, pyrrolidine, piperidine, pyrazolidine, imidazolidine, piperazine, oxazolidine, isoxazolidine, thiazolidine, isothiazolidine, and morpholine.

In some embodiments, R$^{b1}$ and R$^{b2}$ when attached to a nitrogen atom are combined to form a 4-6 membered heterocycle having 1-2 nitrogen atoms, which is optionally substituted with 1-2 R$^{b3}$. The 4-6 membered heterocycle having 1-2 heteroatoms selected from N, O, and S includes, but is not limited to, azetidine, pyrrolidine, piperidine, pyrazolidine, imidazolidine, piperazine, oxazolidine, isoxazolidine, thiazolidine, isothiazolidine, and morpholine.

In some embodiments, each R$^{b3}$ is independently H, F, Cl, Me, Et, or OMe. In some embodiments, each R$^{b3}$ is independently H, F, Me, or OMe. In some embodiments, each R$^{b3}$ is H.

In some embodiments, each R$^b$ is independently H, halogen, CN, C$_{1-4}$ alkyl, C$_{1-4}$ alkoxy, C$_{1-4}$ hydroxyalkyl, C$_{1-4}$ haloalkyl, or C$_{1-4}$haloalkoxy.

In some embodiments, each R$^b$ is independently H, F, Cl, CN, Me, Et, nPr, iPr, nBu, iBu, sBu, tBu, OMe, OEt, OnPr, OiPr, CH$_2$F, CHF$_2$, CF$_3$, CH$_2$CF$_3$, OCH$_2$F, OCHF$_2$, OCF$_3$, OCH$_2$CF$_3$, —CH$_2$OH, —OCH$_2$CH$_2$OH, —O-cyclopropyl, —O-cyclobutyl, —O-cyclopentyl, —O-cyclohexyl, —O-cyclopropylmethyl, —O-cyclobutylmethyl, —O-cyclopentylmethyl, —O-cyclohexylmethyl, —NH$_2$, —NHMe, —NMe$_2$, —SO$_2$Me, —SO$_2$Et, —S(O)$_2$iPr, —S(O)$_2$NHMe, —S(O)$_2$NMe$_2$, 1-pyrrolidinyl, 1-piperidinyl, 1-piperazinyl, —C(O)-1-pyrrolidinyl, —C(O)-1-piperidinyl, —C(O)-1-piperazinyl, cyclopropyl, cyclobutyl, cyclopentyl or cyclohexyl, wherein each of 1-pyrrolidinyl, 1-piperidinyl, and 1-piperazinyl is optionally substituted with 1-2 R$^{b3}$; and each R$^{b3}$ is independently H, F, Me, or OMe. In some embodiments, each R$^b$ is independently H, F, Cl, CN, Me, Et, OMe, OEt, CF$_3$, CH$_2$CF$_3$, OCF$_3$, OCH$_2$CF$_3$, —CH$_2$OH, —SO$_2$Me, —SO$_2$Et, 1-pyrrolidinyl, 1-piperidinyl, 1-piperazinyl, —C(O)-1-pyrrolidinyl, —C(O)-1-piperidinyl, or —C(O)-1-piperazinyl; wherein each of 1-pyrrolidinyl, 1-piperidinyl, and 1-piperazinyl is optionally substituted with 1-2 R$^{b3}$; and each R$^{b3}$ is independently H, F, Me, or OMe.

In some embodiments, each R$^b$ is independently H, F, Cl, CN, Me, Et, iBu, OMe, OEt, OiPr, CF$_3$, OCHF$_2$, OCF$_3$, OCH$_2$CF$_3$, —CH$_2$OH, —OCH$_2$CH$_2$OH, —O-cyclopropyl, —O-cyclopropylmethyl, —NMe$_2$, —S(O)$_2$Me, —S(O)$_2$Et, —S(O)$_2$iPr, —S(O)$_2$NHMe, —S(O)$_2$NMe$_2$, 1-pyrrolidinyl, 1-piperidinyl, 4,4-difluoro-1-piperidinyl, 3,3-dimethyl-1-piperidinyl, 3-methyl-1-piperidinyl, 3-methoxy-1-piperidinyl, —C(O)-1-pyrrolidinyl, —C(O)-4-methyl-1-piperazinyl, or cyclopropyl. In some embodiments, each R$^b$ is independently H, F, Cl, CN, Me, OMe, CF$_3$, OCF$_3$, —CH$_2$OH, —SO$_2$Me, 1-pyrrolidinyl, 1-piperidinyl, 4,4-difluoro-1-piperidinyl, 3,3-dimethyl-1-piperidinyl, 3-methyl-1-piperidinyl, 3-methoxy-1-piperidinyl, —C(O)-1-pyrrolidinyl, or —C(O)-4-methyl-1-piperazinyl. In some embodiments, each R$^b$ is independently H, F, Cl, CN, Me, CF$_3$, OCF$_3$, or —CH$_2$OH.

In some embodiments, R$^1$ is H or C$_{1-6}$ alkyl. The C$_{1-6}$ alkyl of R$^1$ can be methyl, ethyl, propyl, isopropyl, butyl, isobutyl, sec-butyl, tert-butyl, pentyl, isopentyl, or hexyl. In some embodiments, R$^1$ is H, methyl, or ethyl. In some embodiments, R$^1$ is H.

In some embodiments wherein R$^1$ is H, the compound of formula I, Ia, or Ib is a compound of formula Ib-1:

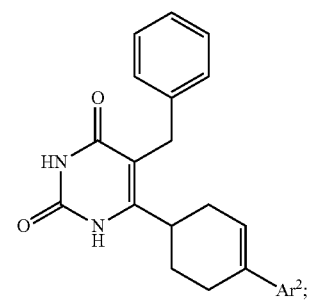

(Ib-1)

wherein Ar$^2$ is as defined and described herein.

In some embodiments of formula Ib-1, Ar$^2$ is phenyl or a 5-6 membered heteroaryl having 1-2 heteroatoms selected from N and S, each of which is optionally substituted with 1-2 R$^b$ groups.

In some embodiments of formula Ib-1, Ar$^2$ is phenyl, pyridinyl, thiazolyl, or pyrazolyl, each of which is optionally substituted with 1-2 R$^b$ groups.

In some embodiments of formula Ib-1, Ar$^2$ is phenyl, which is optionally substituted with 1-2 R$^b$ groups. In some embodiments, the compound of formula I, Ia, Ib, or Ib-1 is a compound of formula Ic-1:

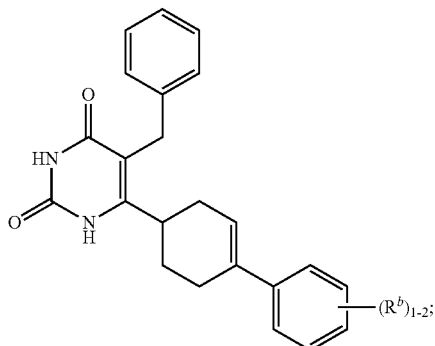

(Ic-1)

wherein $R^b$ is as defined and described herein.

In some embodiments of formula Ib-1, $Ar^2$ is pyridinyl, which is optionally substituted with 1-2 $R^a$ groups. The pyridinyl can be, for example pyridin-2-yl, pyridin-3-yl, or pyridin-4-yl.

In some embodiments of formula Ib-1, $Ar^2$ is pyridin-3-yl, which is optionally substituted with 1-2 $R^b$ groups. In some embodiments, the compound of formula I, Ia, Ib, or Ib-1 is a compound of formula Id-1:

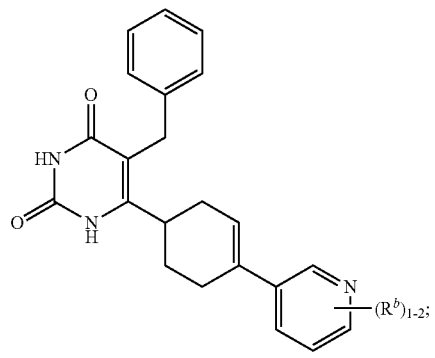

(Id-1)

wherein $R^b$ is as defined and described herein.

In some embodiments of formula Ib-1, $Ar^2$ is thiazolyl, which is optionally substituted with 1-2 $R^b$ groups. The thiazolyl can be, for example thiazol-2-yl, thiazol-4-yl, or thiazol-5-yl. In some embodiments of formula Ib-1, $Ar^2$ is thiazol-5-yl, which is optionally substituted with 1-2 $R^b$ groups.

In some embodiments of formula Ib-1, $Ar^2$ is pyrazolyl, which is optionally substituted with 1-2 $R^b$ groups. The pyrazolyl can be, for example pyrazol-1-yl, pyrazol-3-yl, pyrazol-4-yl, or pyrazol-5-yl. In some embodiments of formula Ib-1, $Ar^2$ is pyrazol-5-yl, which is optionally substituted with 1-2 $R^b$ groups.

In some embodiments of formula Ib-1, each $R^b$ is independently H, halogen, CN, $C_{1-4}$ alkyl, $C_{1-4}$ alkoxy, $C_{1-4}$ hydroxyalkyl, $C_{1-4}$ haloalkyl, $C_{1-4}$ haloalkoxy, $-NR^{b1}R^{b2}$, $-C(O)NR^{b1}R^{b2}$, or $-SO_2R^{b1}$; wherein $R^{b1}$ and $R^{b2}$ are each independently H or $C_{1-4}$ alkyl; or $R^{b1}$ and $R^{b2}$ when attached to a nitrogen atom are combined to form a 4-6 membered heterocycle having 1-2 nitrogen atoms, which is optionally substituted with 1-2 $R^{b3}$; and each of $R^{b3}$ is independently H, halogen, $C_{1-4}$ alkyl, or $C_{1-4}$ alkoxy.

In some embodiments, $R^{b1}$ and $R^{b2}$ are each independently H or $C_{1-4}$ alkyl. The $C_{1-4}$ alkyl of $R^{b1}$ or $R^{b2}$ can be methyl, ethyl, propyl, isopropyl, butyl, or tert-butyl. In some embodiments, $R^{b1}$ and $R^{b2}$ are each independently H, Me, or Et.

In some embodiments, $R^{b1}$ and $R^{b2}$ when attached to a nitrogen atom are combined to form a 4-6 membered heterocycle having 1-2 nitrogen atoms, which is optionally substituted with 1-2 $R^{b3}$. The 4-6 membered heterocycle having 1-2 heteroatoms selected from N, O, and S includes, but is not limited to, azetidine, pyrrolidine, piperidine, pyrazolidine, imidazolidine, piperazine, oxazolidine, isoxazolidine, thiazolidine, isothiazolidine, and morpholine.

In some embodiments, each $R^{b3}$ is independently H, F, Cl, Me, Et, or OMe. In some embodiments, each $R^{b3}$ is independently H, F, Me, or OMe. In some embodiments, each $R^{b3}$ is H.

In some embodiments of formula Ib-1, each $R^b$ is independently H, halogen, CN, $C_{1-4}$ alkyl, $C_{1-4}$ alkoxy, $C_{1-4}$ hydroxyalkyl, $C_{1-4}$ haloalkyl, or $C_{1-4}$ haloalkoxy.

In some embodiments of formula Ib-1, each $R^b$ is independently H, F, Cl, CN, Me, Et, OMe, OEt, $CF_3$, $CH_2CF_3$, $OCF_3$, $OCH_2CF_3$, $-CH_2OH$, $-SO_2Me$, $-SO_2Et$, 1-pyrrolidinyl, 1-piperidinyl, 1-piperazinyl, $-C(O)$-1-pyrrolidinyl, $-C(O)$-1-piperidinyl, or $-C(O)$-1-piperazinyl; wherein each of 1-pyrrolidinyl, 1-piperidinyl, and 1-piperazinyl is optionally substituted with 1-2 $R^{b3}$; and each $R^{b3}$ is independently H, F, Me, or OMe.

In some embodiments of formula Ib-1, each $R^b$ is independently H, F, Cl, CN, Me, OMe, $CF_3$, $OCF_3$, $-CH_2OH$, $-SO_2Me$, 1-pyrrolidinyl, 1-piperidinyl, 4,4-difluoro-1-piperidinyl, 3,3-dimethyl-1-piperidinyl, 3-methyl-1-piperidinyl, 3-methoxy-1-piperidinyl, $-C(O)$-1-pyrrolidinyl, or $-C(O)$-4-methyl-1-piperazinyl. In some embodiments of formula Ib-1, each $R^b$ is independently H, F, Cl, CN, Me, $CF_3$, $OCF_3$, or $-CH_2OH$.

In some embodiments, the compound of formula I is selected from the group consisting of:

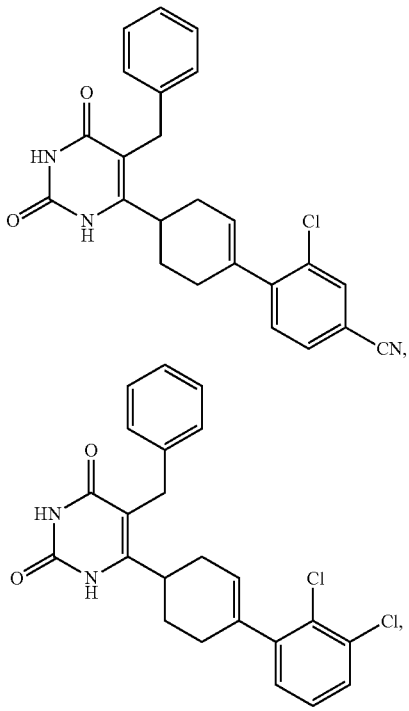

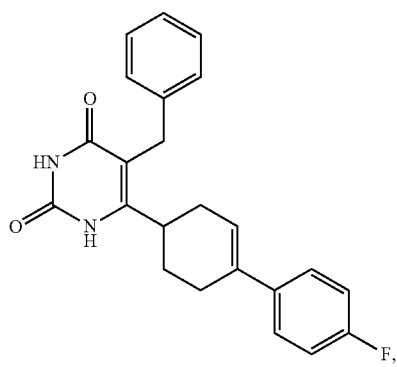
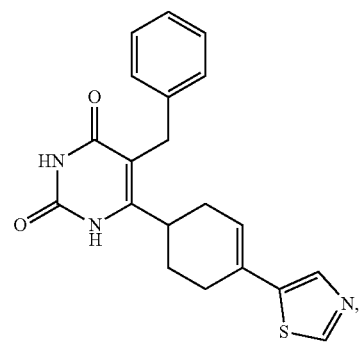
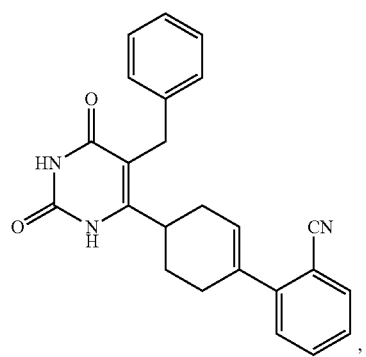
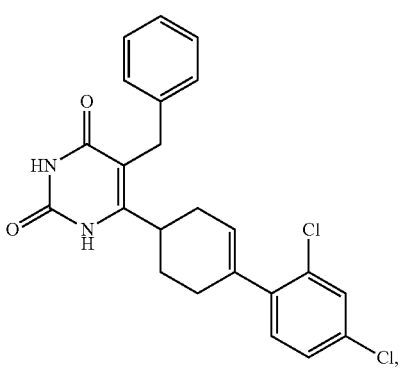
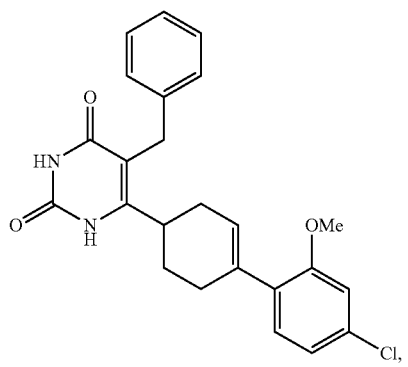
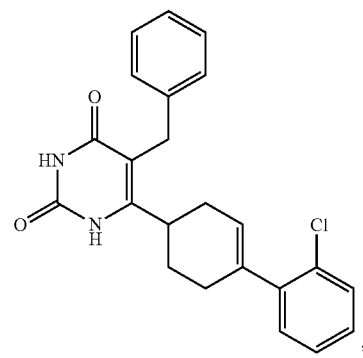
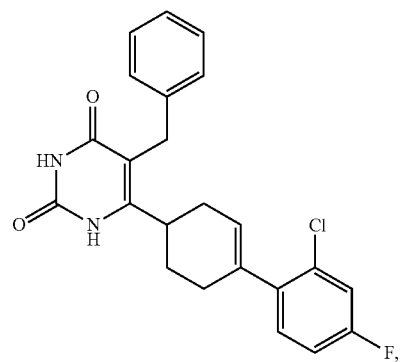
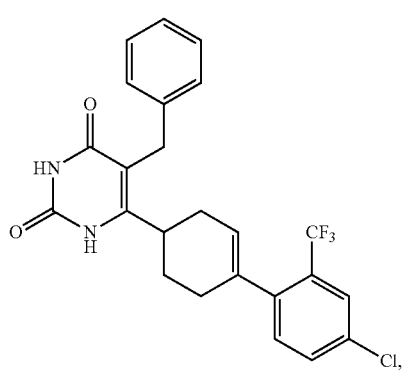

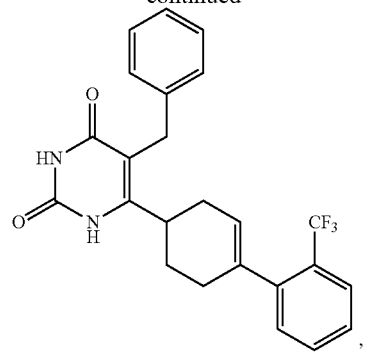
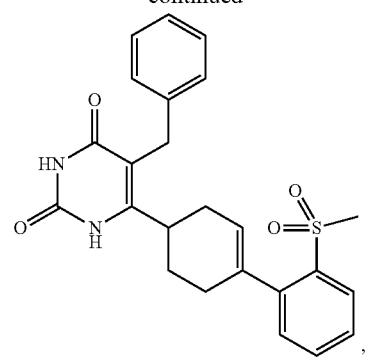
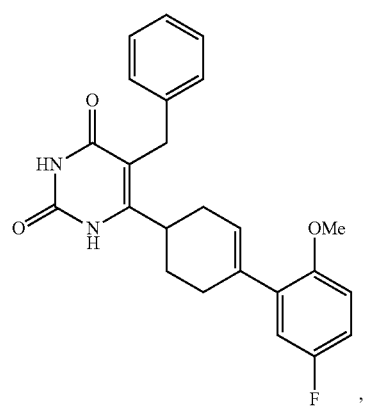
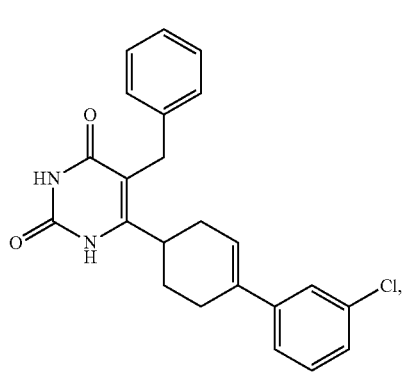
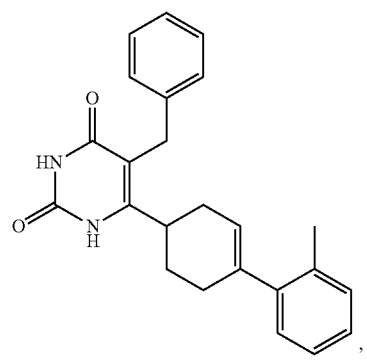
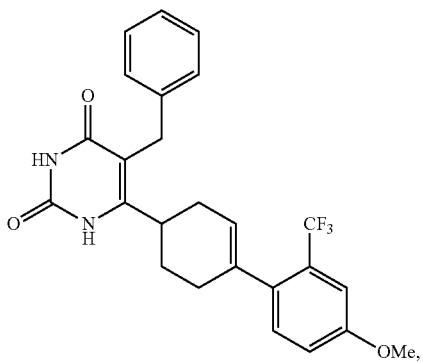
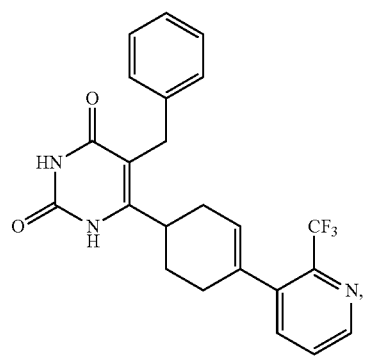
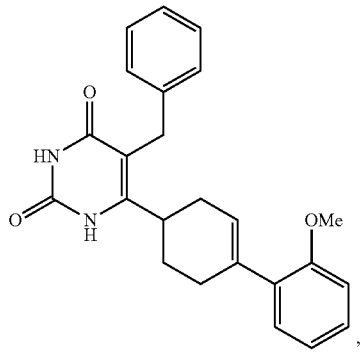

-continued
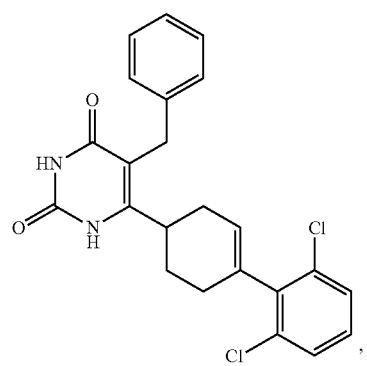
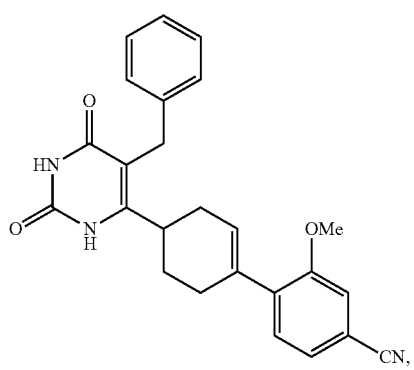
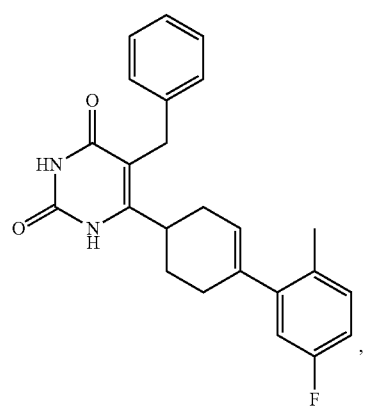
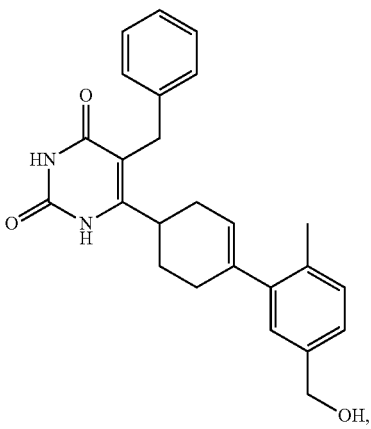
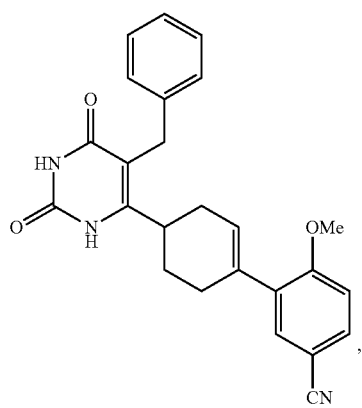
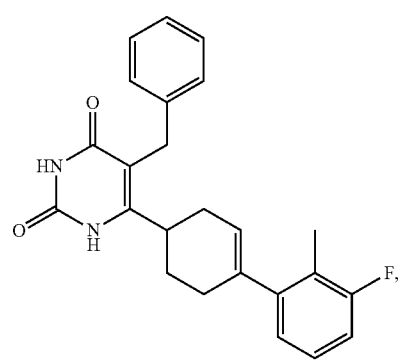
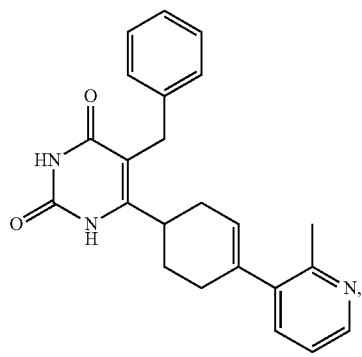
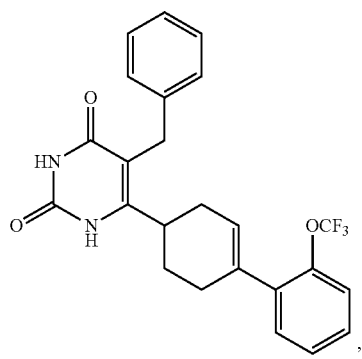

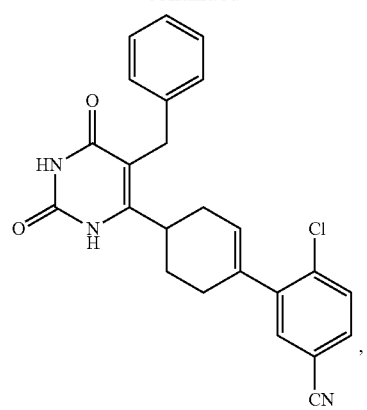
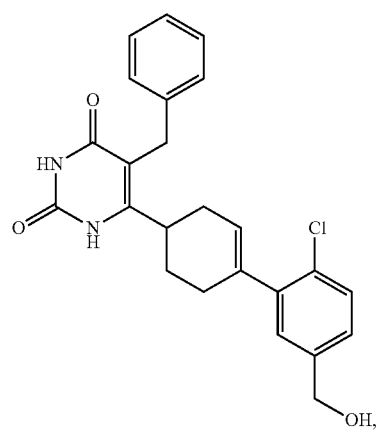
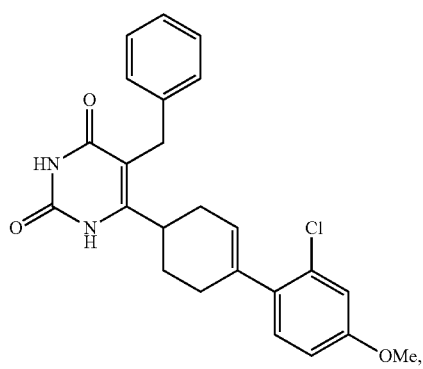
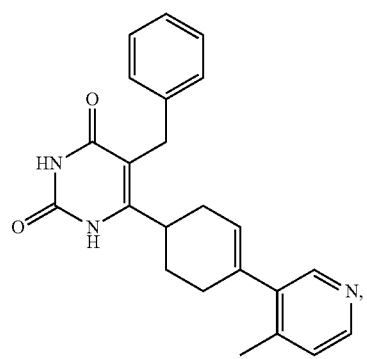
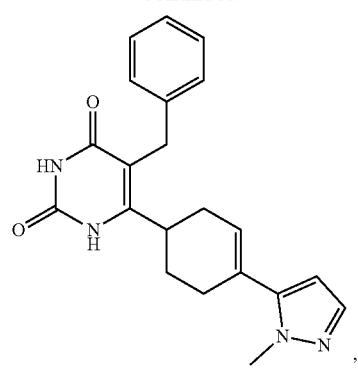
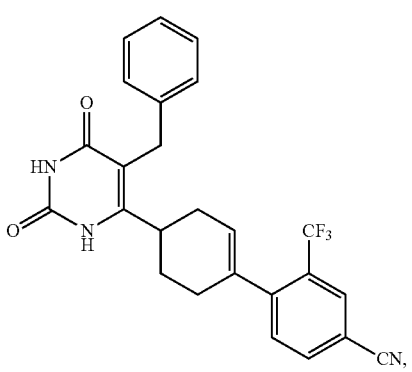
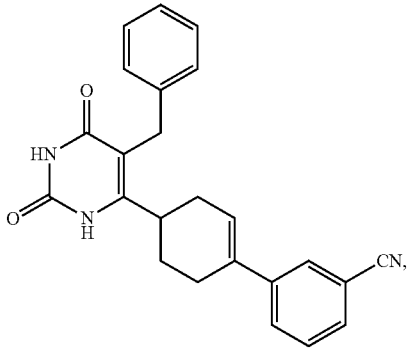
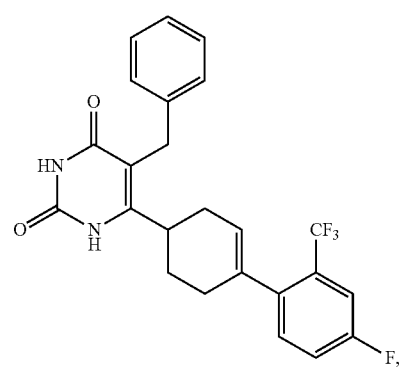

29
-continued
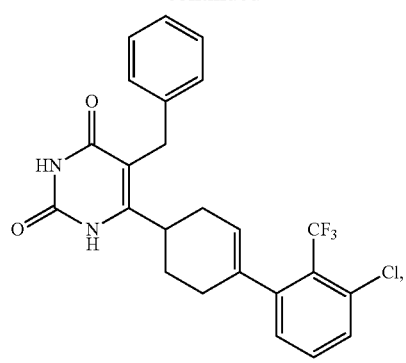
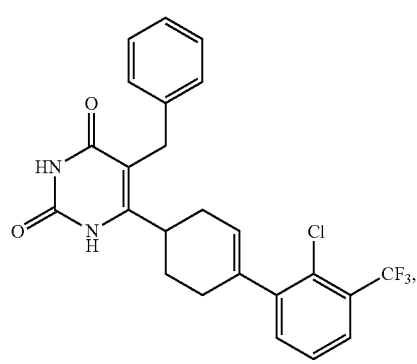
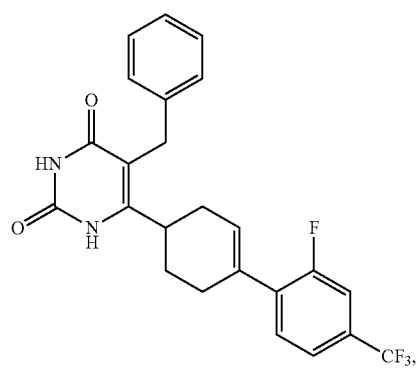
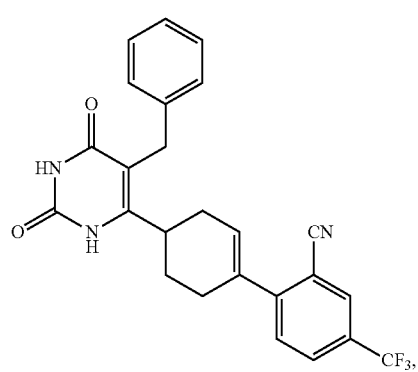
30
-continued
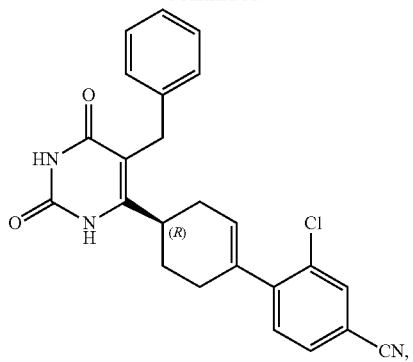
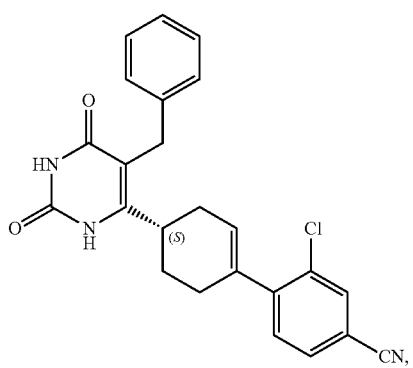
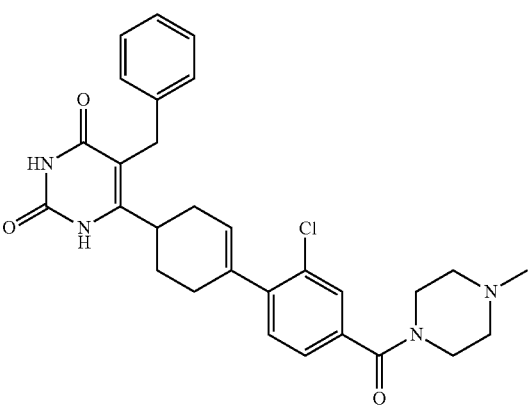
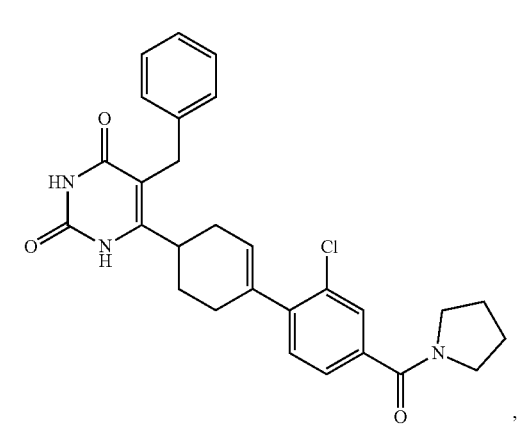

-continued
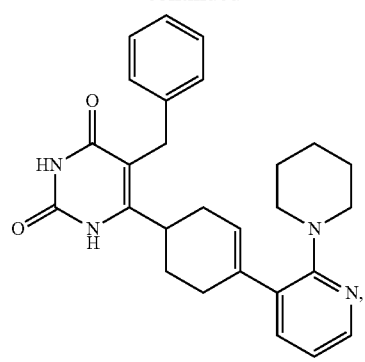
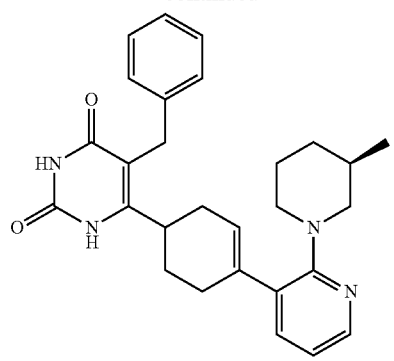
,
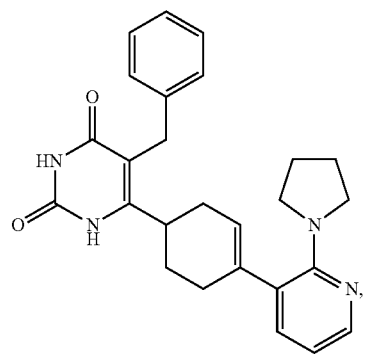
,
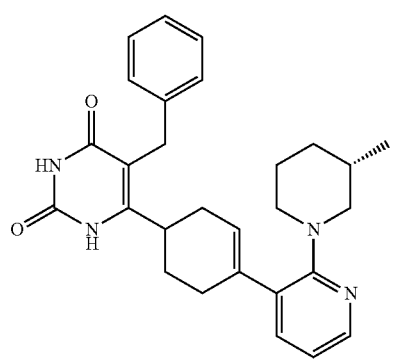
,
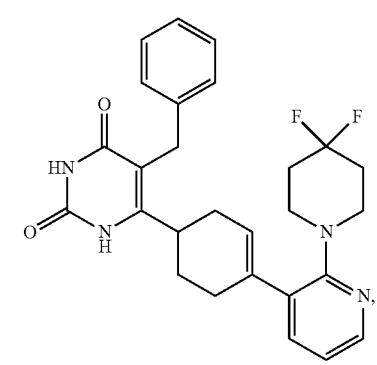
,
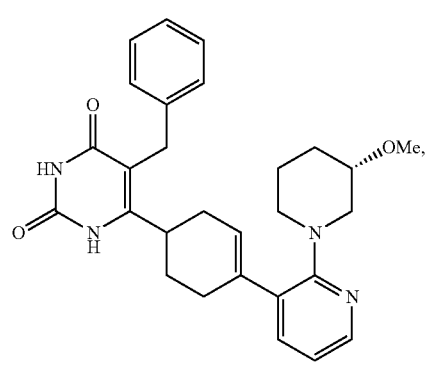
,
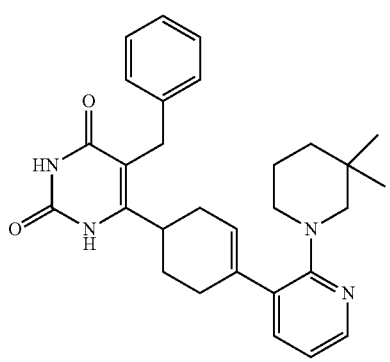
,
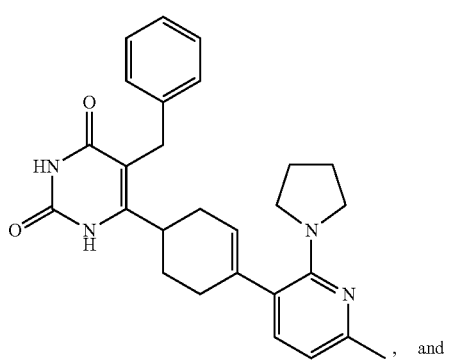
, and -continued
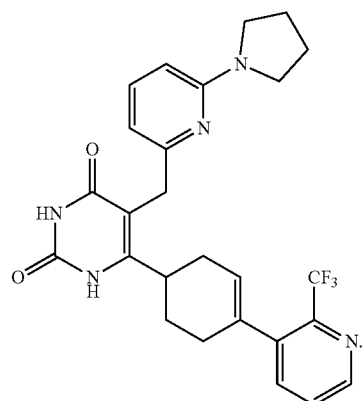
In some embodiments, the compound of formula I is selected from the group consisting of:
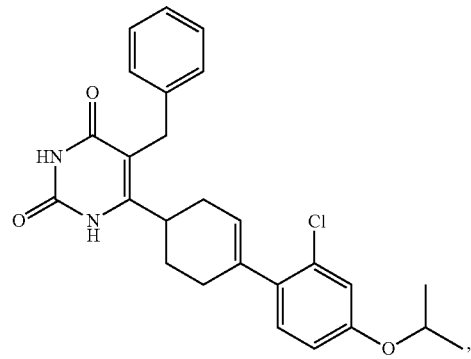
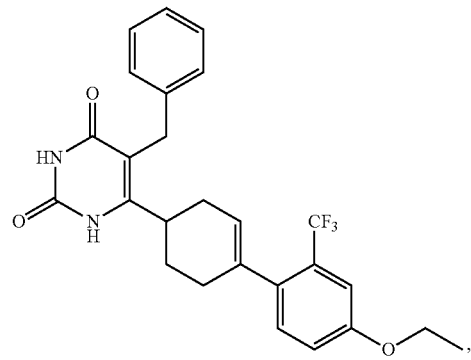
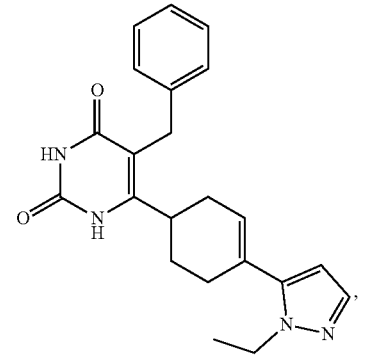
-continued
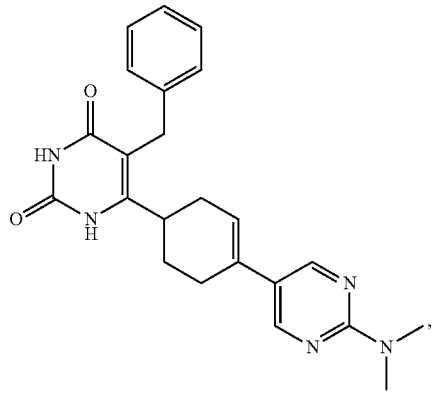
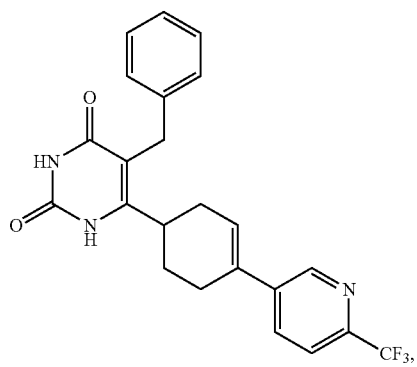
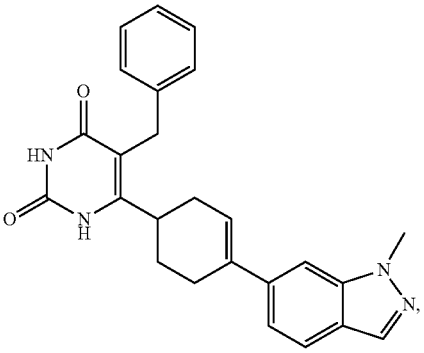
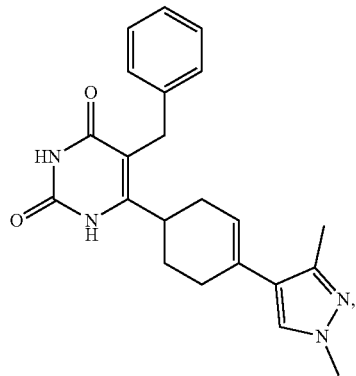

35
-continued
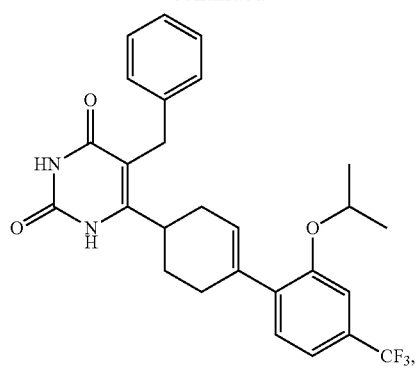
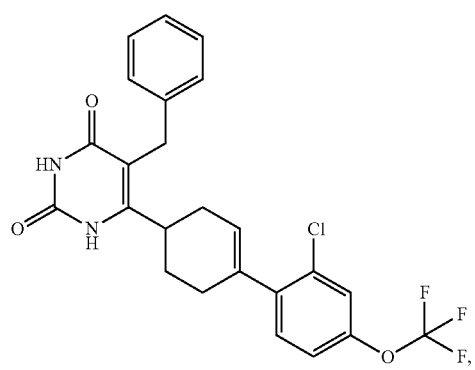
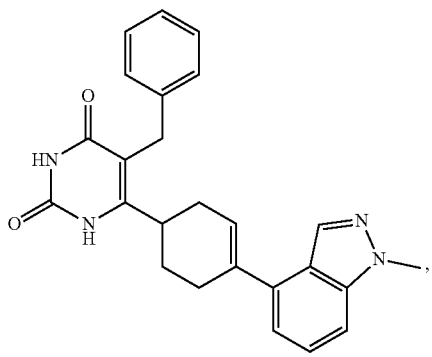
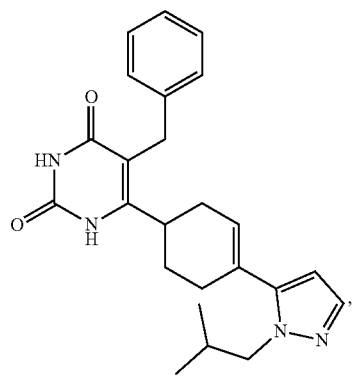
36
-continued
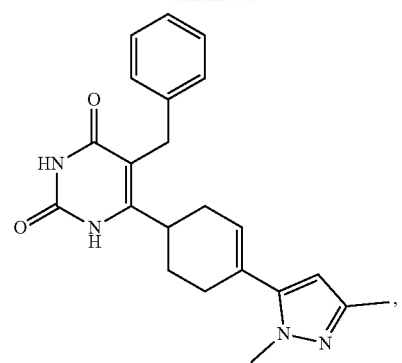
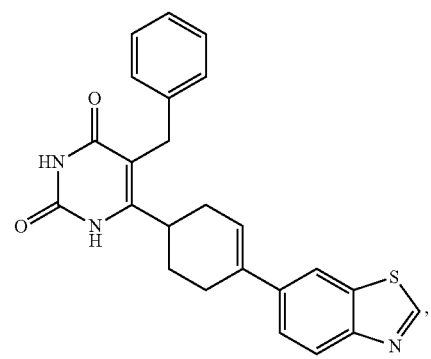
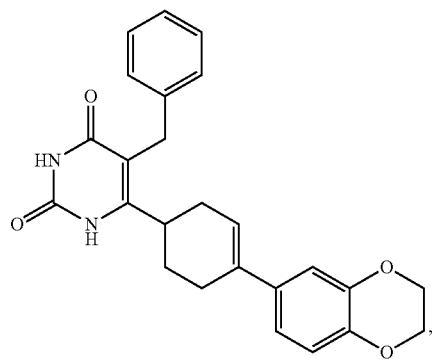
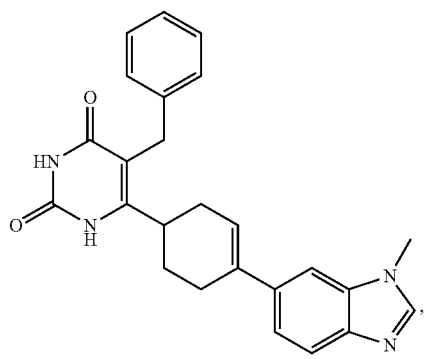

37
-continued
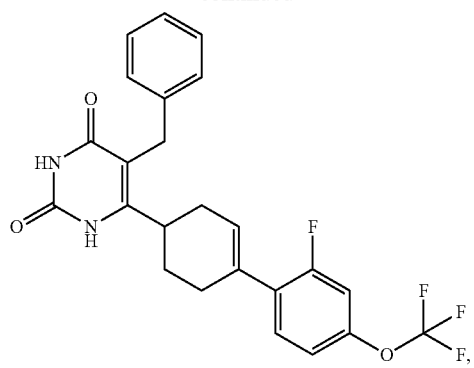
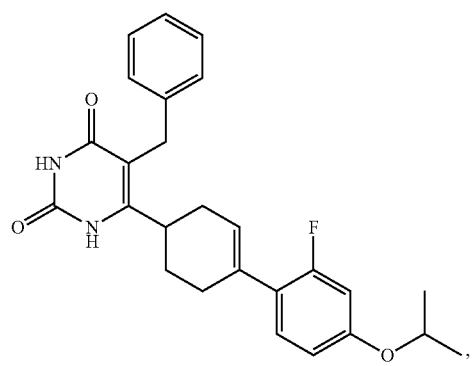
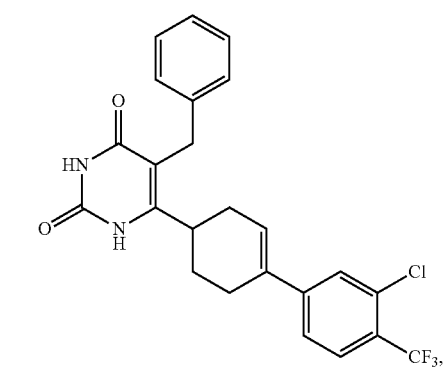
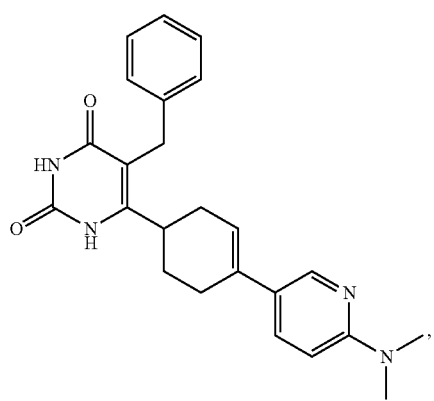
38
-continued
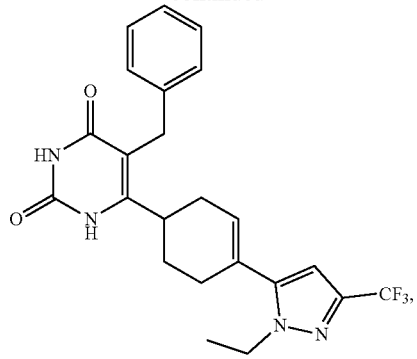
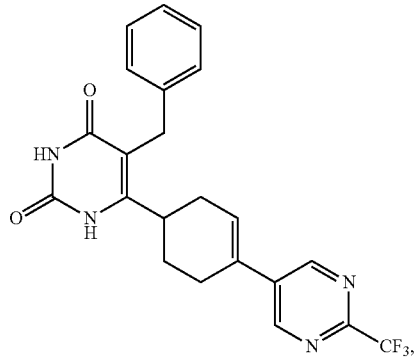
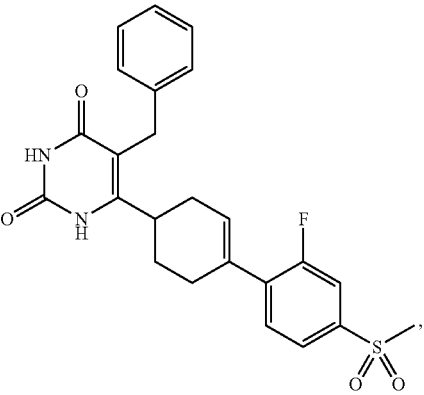
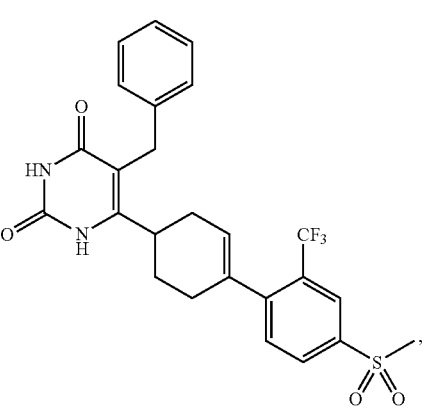

-continued
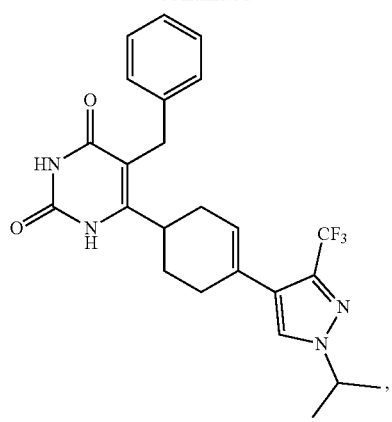
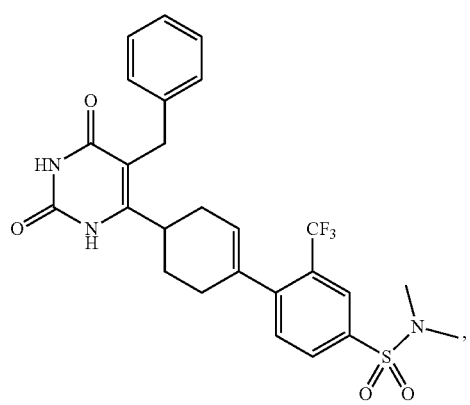
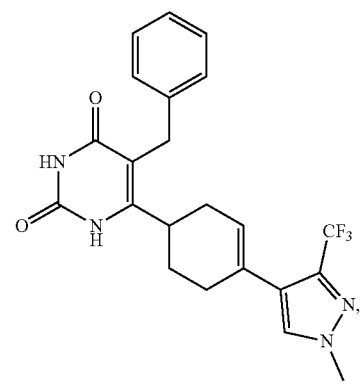
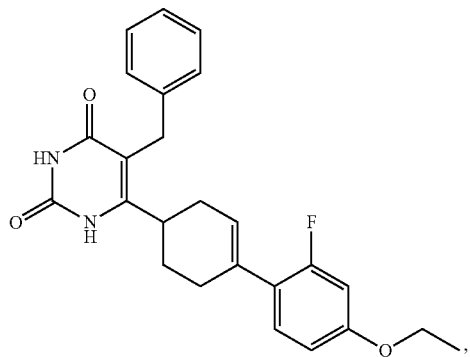
-continued
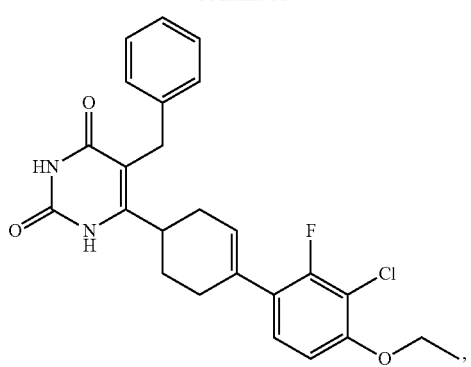
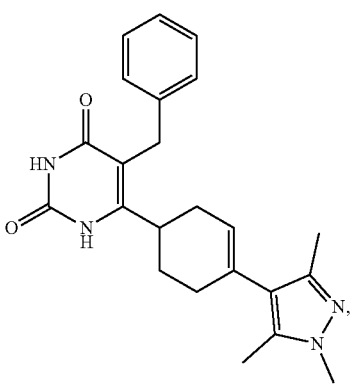
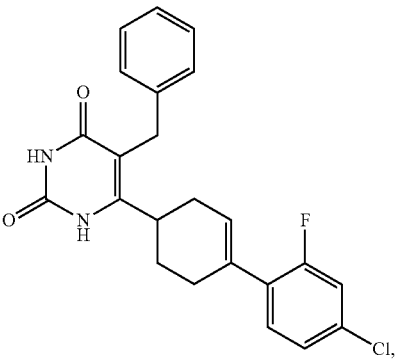
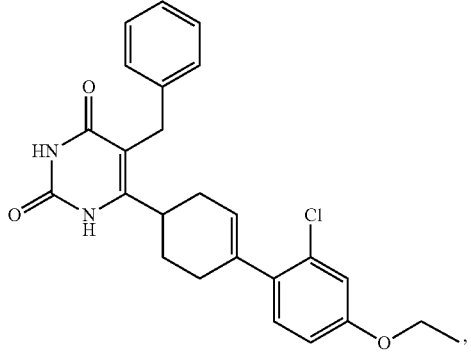

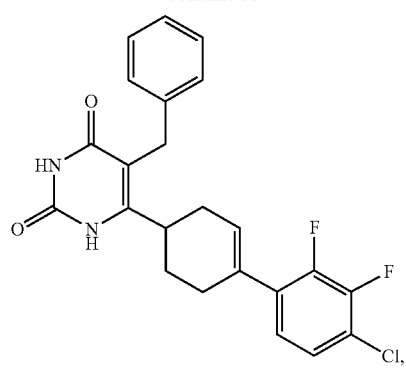
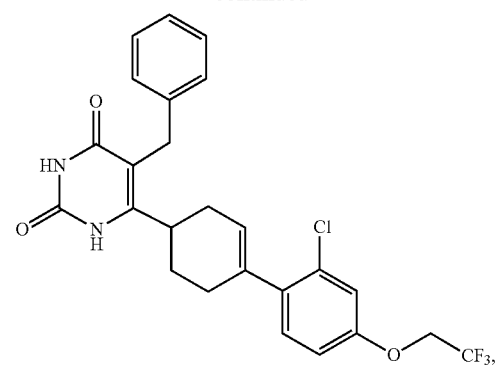
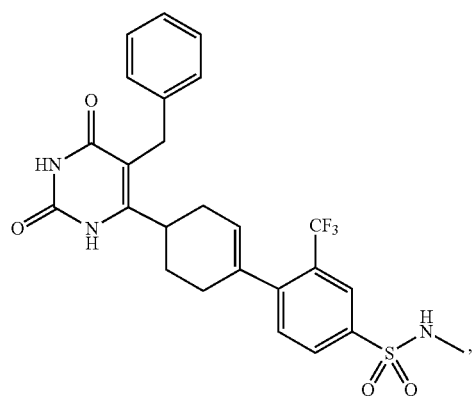
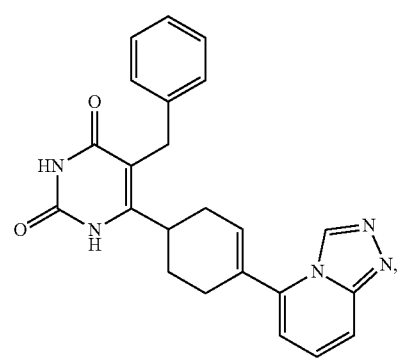
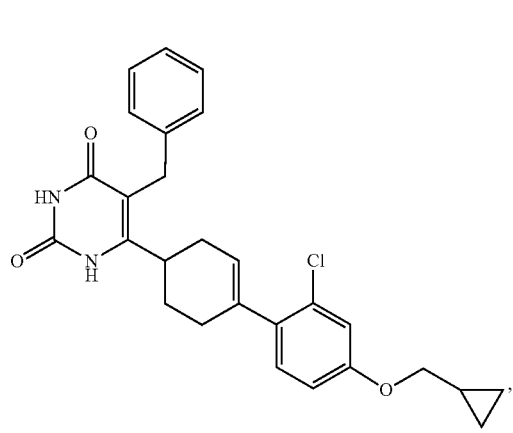
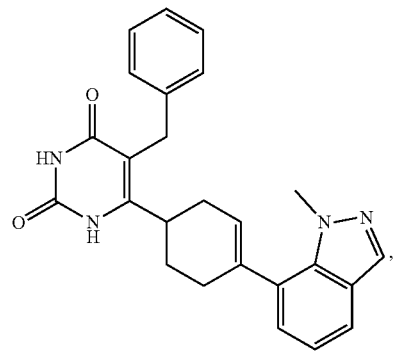
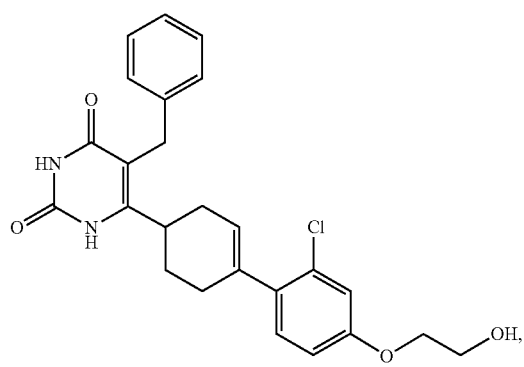
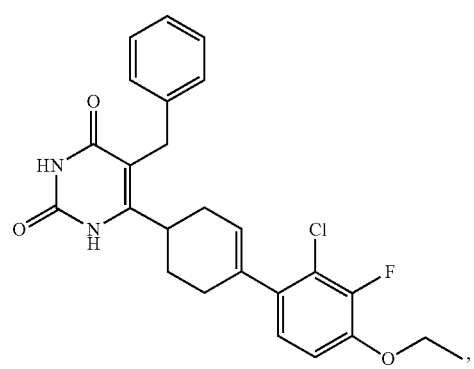

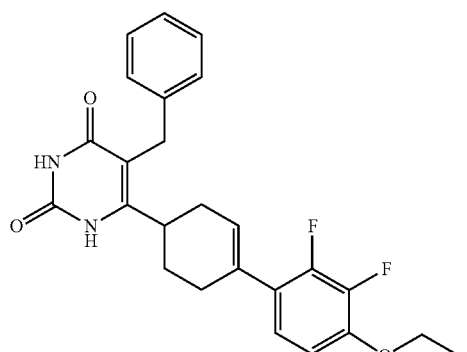
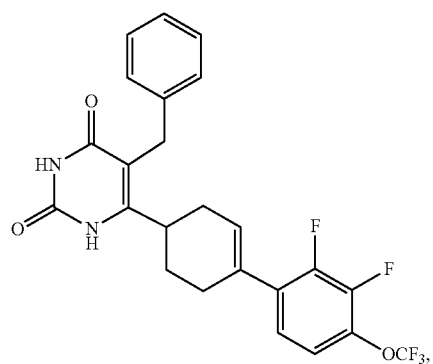
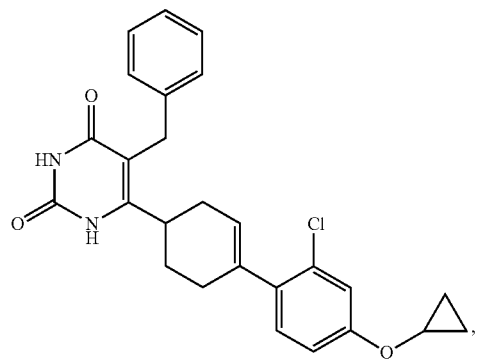
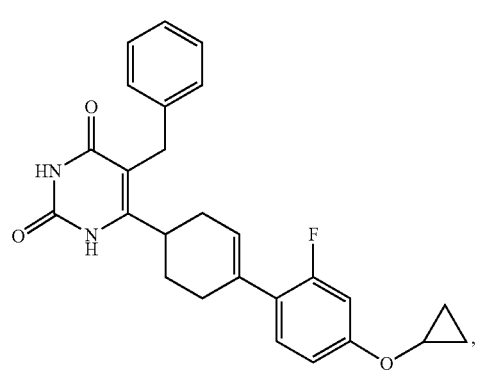
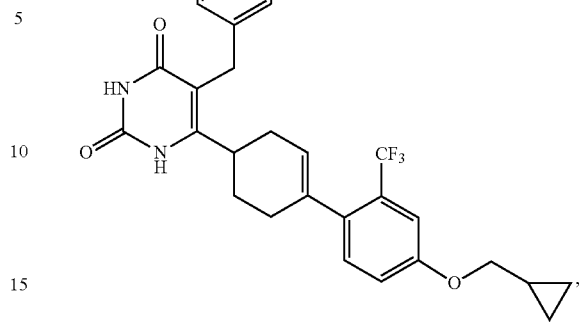
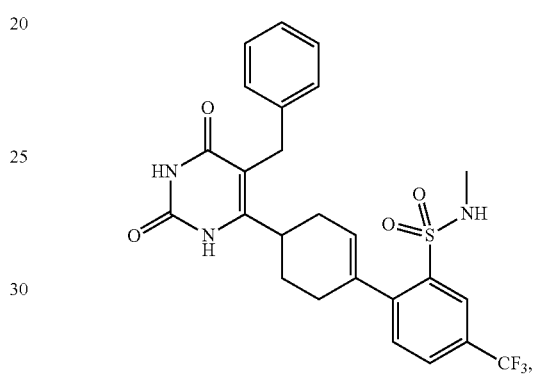
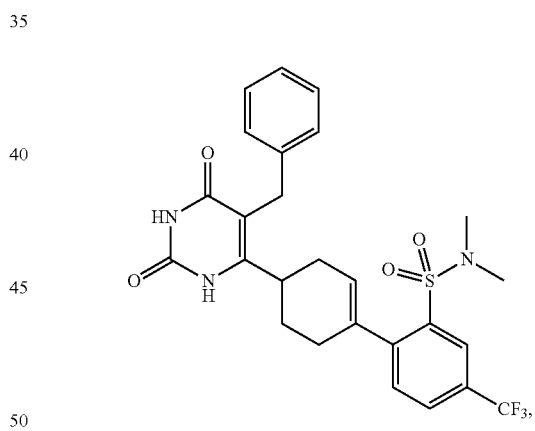
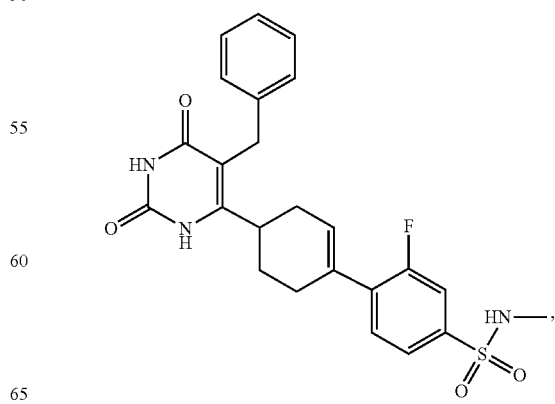

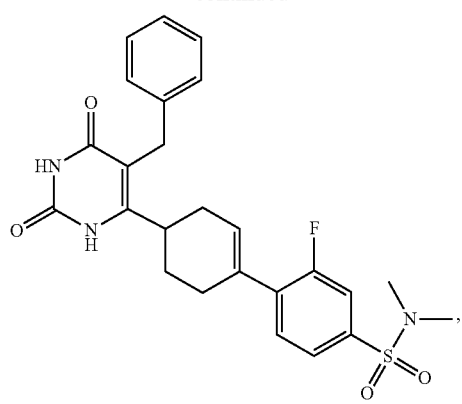
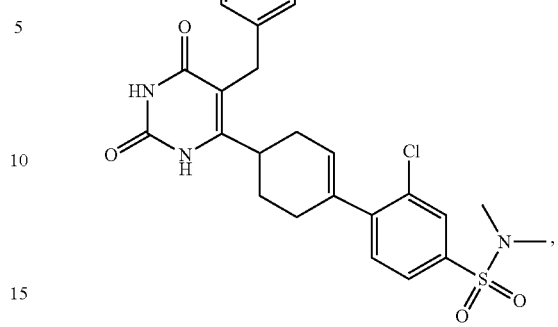
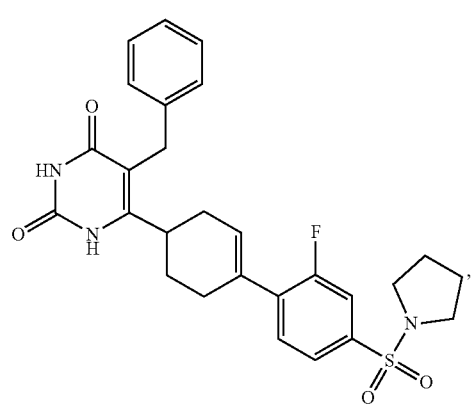
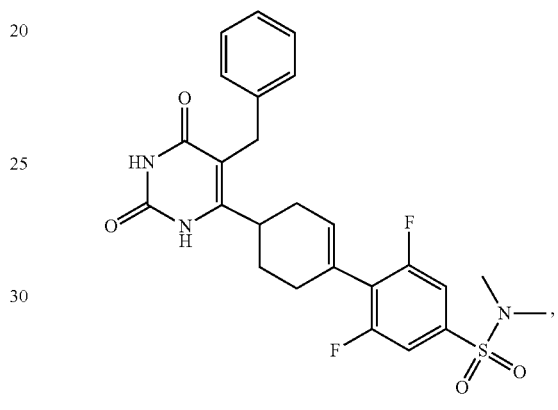
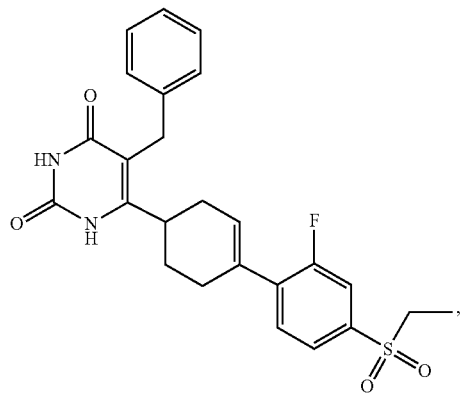
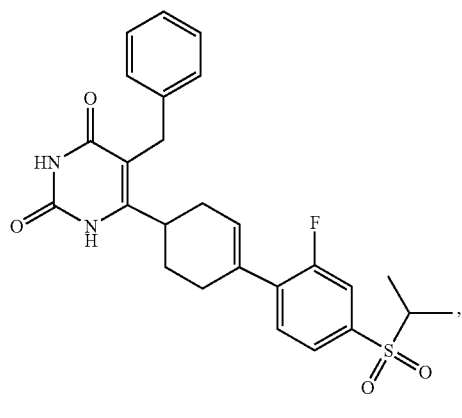

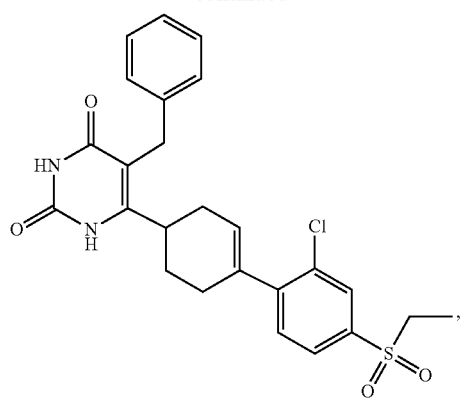
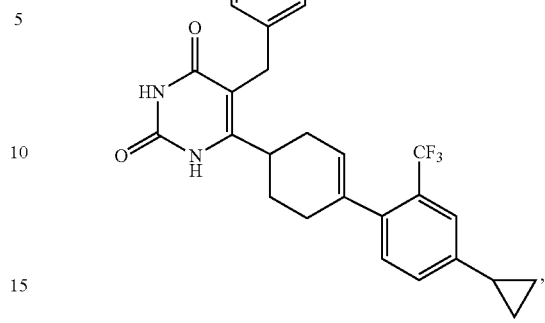
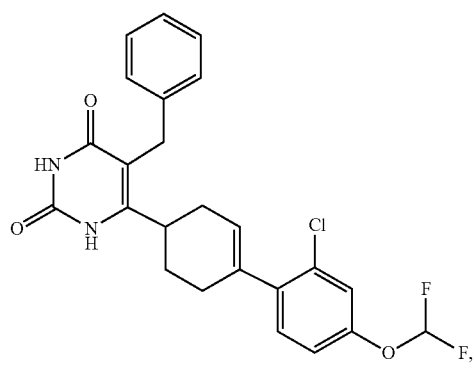
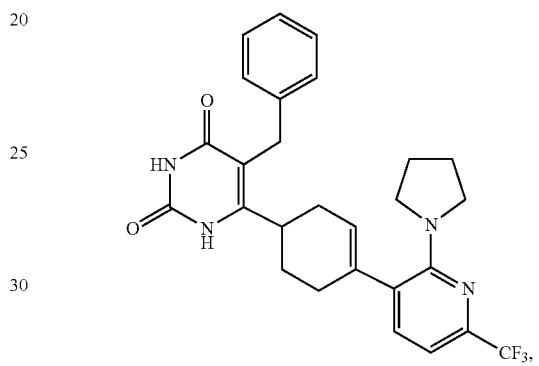
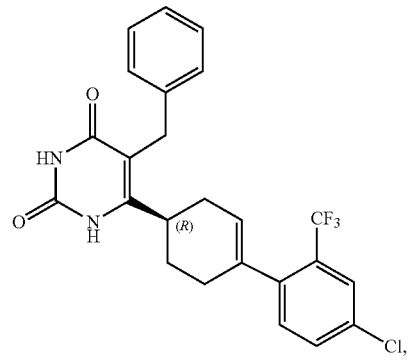
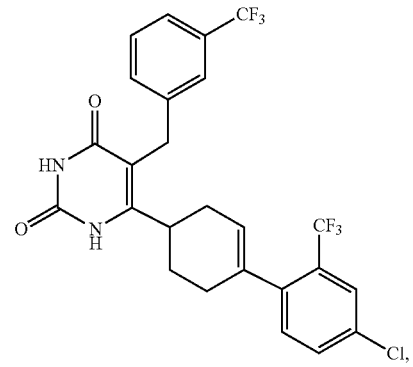
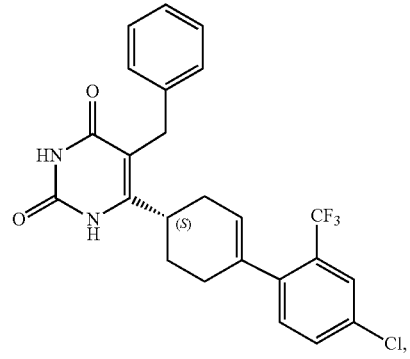
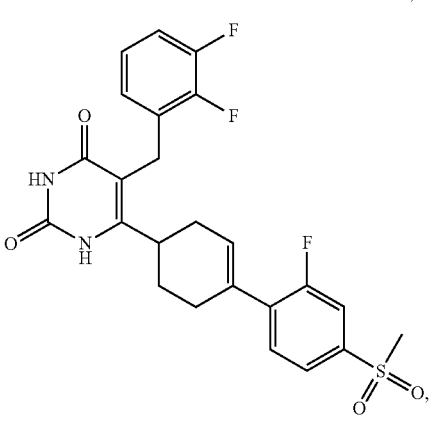

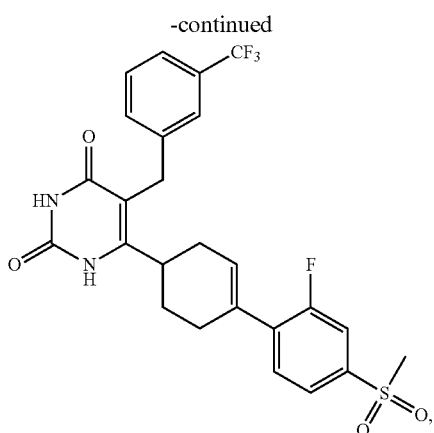
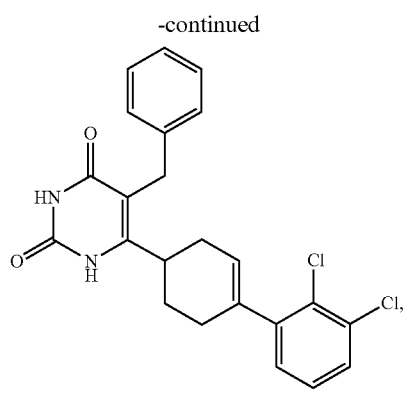
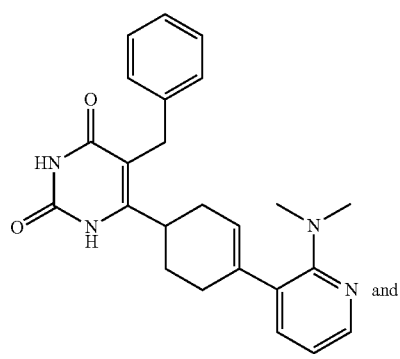
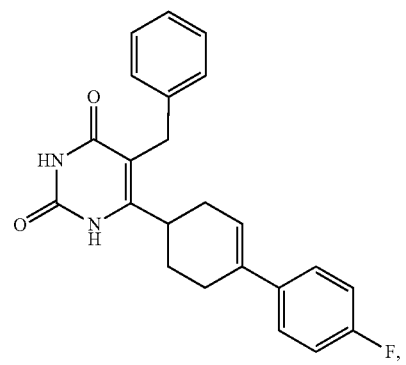
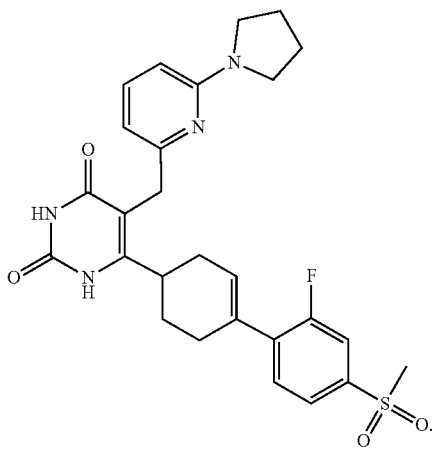
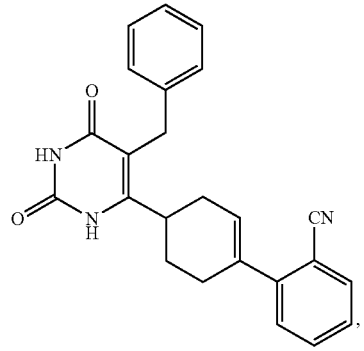
In some embodiments, the compound of formula I is selected from the group consisting of:
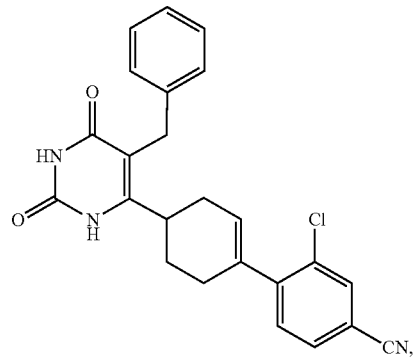
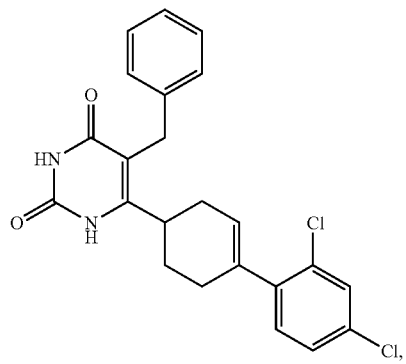

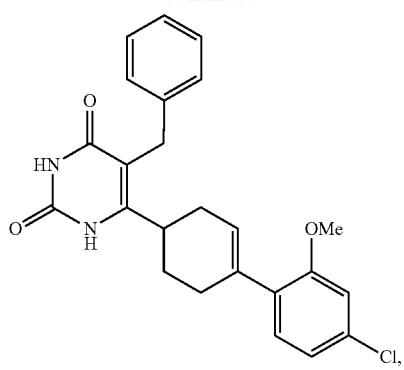
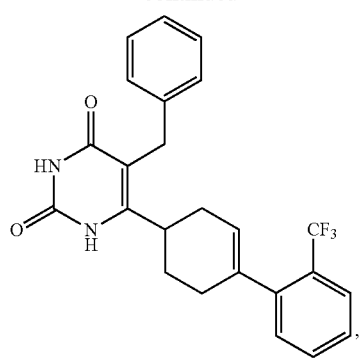
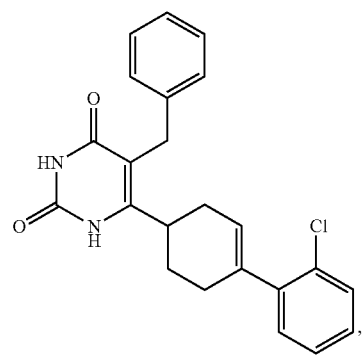
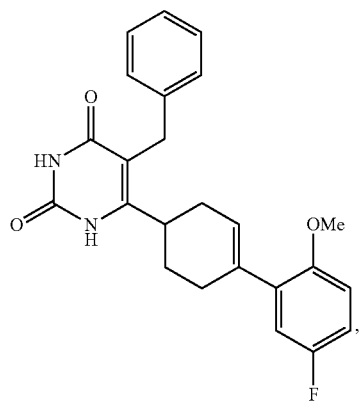
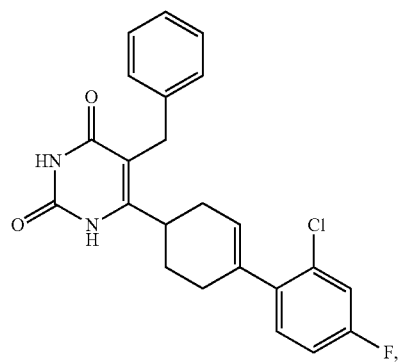
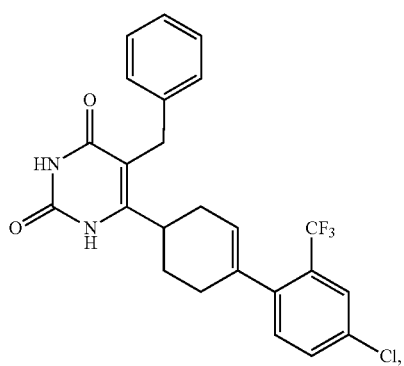
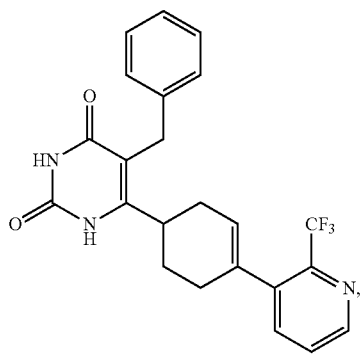

53
-continued
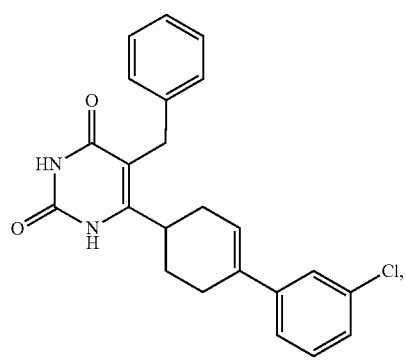
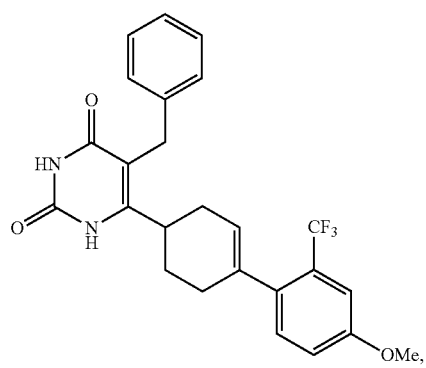
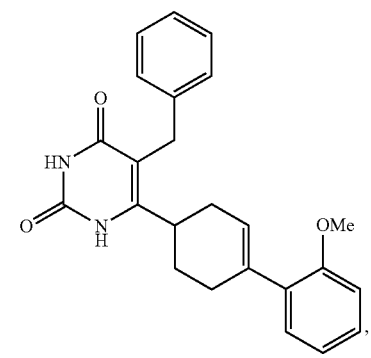
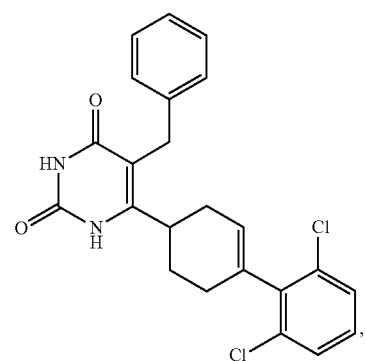
54
-continued
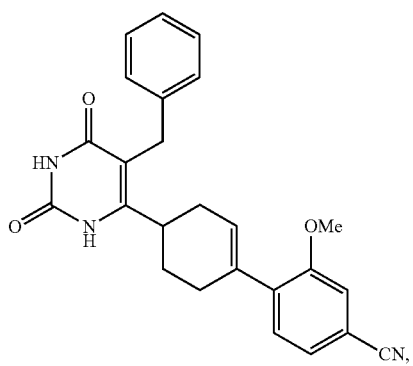
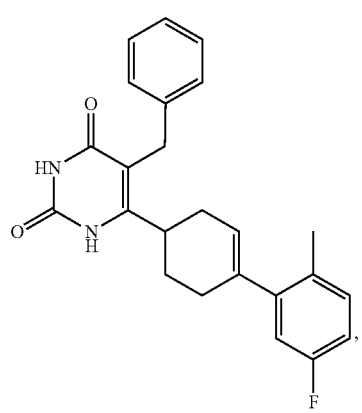
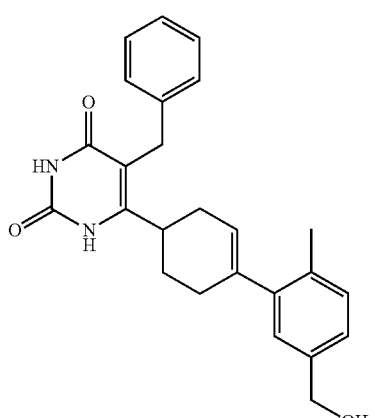
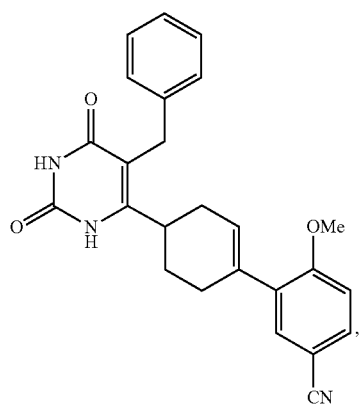

-continued

57
-continued
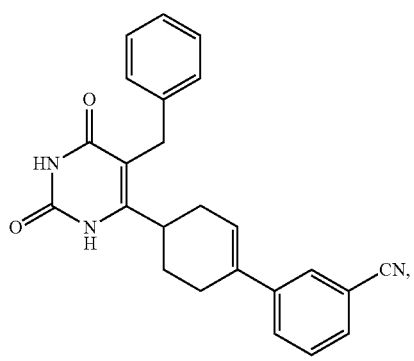
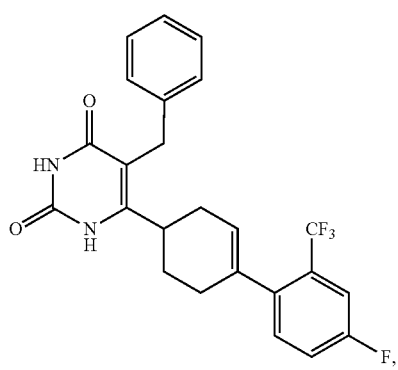
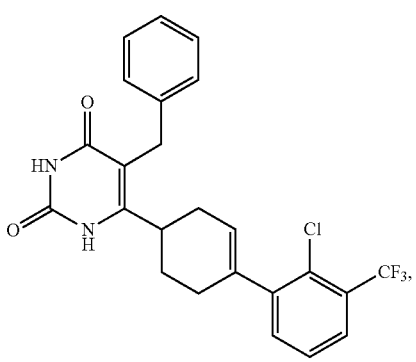
58
-continued
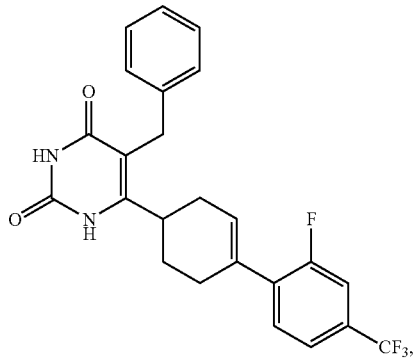
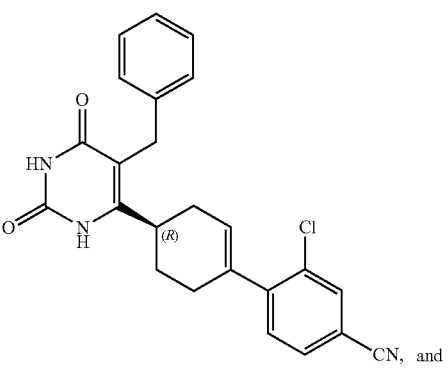
In some embodiments, the compound of formula I is selected form the group consisting of:

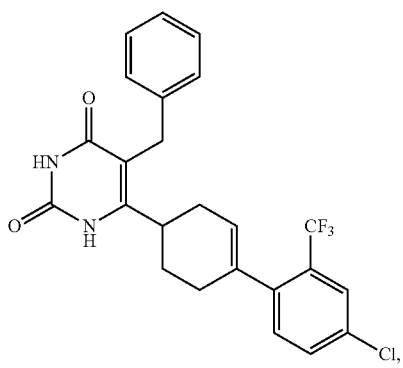

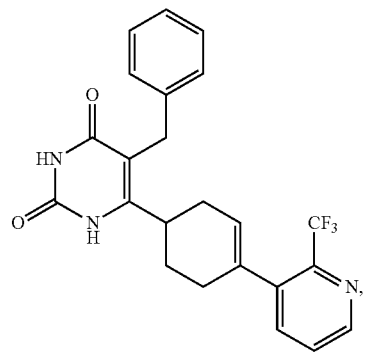

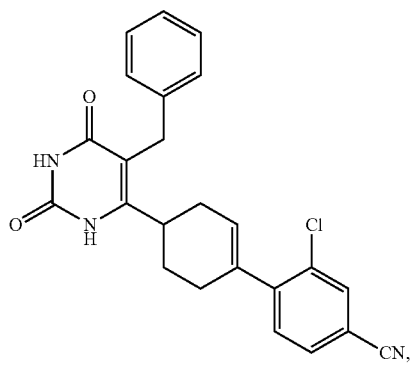

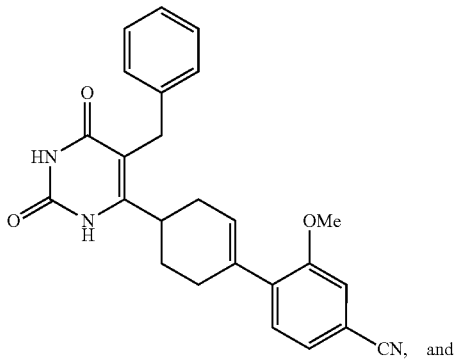

and

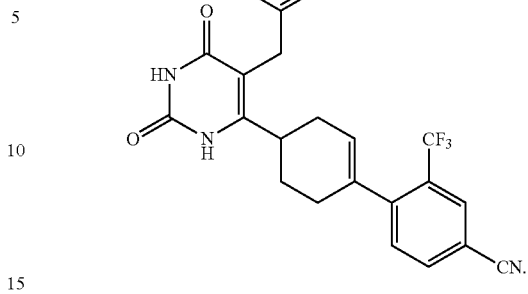

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

Other salts include acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts includes salts of the active compounds which are prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer refers to one of two or more structural isomers which exist in equilibrium and which are readily converted from one isomeric form to another. For example, compounds of the following formulae can exist in equilibrium:

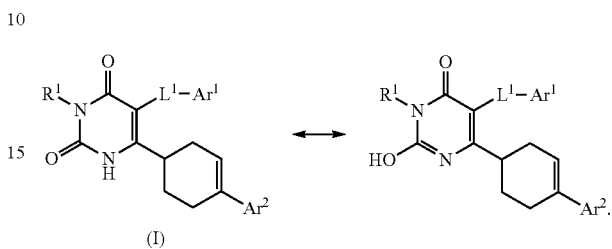

In some embodiments of formula I wherein $R^1$ is H, compounds of the following formulae can exist in equilibrium:

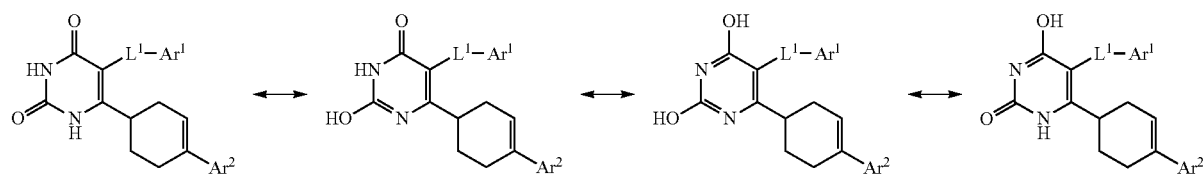

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of the present invention may also contain unnatural proportions of atomic isotopes at one or more of the atoms that constitute such compounds. For example, the compounds of the present invention may be labeled with radioactive or stable isotopes, such as for example deuterium ($^2$H), tritium ($^3$H), iodine-125 ($^{125}$I), fluorine-18 ($^{18}$F), nitrogen-15 ($^{15}$N), oxygen-17 ($^{17}$O), oxygen-18 ($^{18}$O), carbon-13 ($^{13}$C), or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

IV. Compositions

In a second aspect, the present invention provides a pharmaceutical composition including one or more pharmaceutically acceptable excipients and the compound of formula I. In some embodiments, the pharmaceutical composition includes one or more pharmaceutically acceptable excipients and the compound of formula Ib. In some embodiments, the pharmaceutical composition includes one or more pharmaceutically acceptable excipients and the compound of formula Ic. In some embodiments, the pharmaceutical composition includes one or more pharmaceutically acceptable excipients and the compound of formula Id.

The compounds of the present invention can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The compounds of formula I of this invention can also be administered by in intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995). Accordingly, the present invention also provides pharmaceutical compositions including one or more pharmaceutically acceptable carriers and/or excipients and either a compound of formula I, or a pharmaceutically acceptable salt of a compound of formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, surfacts, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA ("Remington's").

In powders, the carrier is a finely divided solid, which is in a mixture with the finely divided active component. In tablets, the active component is mixed with the carrier having the necessary binding properties and additional excipients as required in suitable proportions and compacted in the shape and size desired.

The powders, capsules and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other excepients, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers including, but not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of formula I mixed with a filler or binders such as lactose or starches, lubricants such as talc or magnesium stearate, and, optionally, stabilizers. In soft capsules, the compounds of formula I may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compound of formula I in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compounds of formula I of the invention can be delivered by transdermally, by a topical route, formulated as applicator sticks, solutions, suspensions, emulsions, gels, creams, ointments, pastes, jellies, paints, powders, and aerosols.

The compounds of formula I and compositions of the invention can also be delivered as microspheres for slow release in the body. For example, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

The pharmaceutical formulations of the compounds of formula I of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

The pharmaceutical formulations of the compounds of formula I of the invention can be provided as a salt and can be formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

In some embodiments, the formulations of the compounds of formula I of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

The dosage regimen also takes into consideration pharmacokinetics parameters well known in the art, i.e., the rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, GR and/or MR modulator and disease or condition treated.

Single or multiple administrations of the compound of formula I formulations can be administered depending on the dosage and frequency as required and tolerated by the patient. The formulations should provide a sufficient quantity of active agent to effectively treat the disease state. Thus, in one embodiment, the pharmaceutical formulations for oral administration of the compound of formula I is in a daily amount of between about 0.5 to about 30 mg per kilogram of body weight per day. In an alternative embodiment, dosages are from about 1 mg to about 20 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable the compound of formula I formulations will be known or apparent to those skilled in the art and are described in more detail in such publications as Remington's, supra. See also Nieman, In "Receptor Mediated Antisteroid Action," Agarwal, et al., eds., De Gruyter, New York (1987).

The compounds described herein can be used in combination with one another, with other active agents known to be useful in modulating a glucocorticoid receptor, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In some embodiments, the active agents can be formulated separately. In some embodiments, the active and/or adjunctive agents may be linked or conjugated to one another.

After a pharmaceutical composition including a compound of formula I of the invention has been formulated in one or more acceptable carriers, it can be placed in an appropriate container and labeled for treatment of an indicated condition. For administration of the compounds of formula I, such labeling would include, e.g., instructions concerning the amount, frequency and method of administration.

In some embodiments, the compositions of the present invention are useful for parenteral administration, such as intravenous (IV) administration or administration into a body cavity or lumen of an organ. The formulations for administration will commonly comprise a solution of the compositions of the present invention dissolved in one or more pharmaceutically acceptable carriers. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, tonicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In some embodiments, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

V. Methods

In a third aspect, the present invention provides a method of treating a disorder or condition through modulating a glucocorticoid receptor, the method including administering to a subject in need of such treatment, a therapeutically effective amount of the compound of formula I or a pharmaceutical composition of the compound of formula I, thereby treating the disorder or condition.

In a fourth aspect, the present invention provides a method of treating a disorder or condition through antagonizing a glucocorticoid receptor, the method including administering to a subject in need of such treatment, an effective amount of the compound of formula I or a pharmaceutical composition of the compound of formula I.

In some embodiments, the present invention provides methods of modulating glucocorticoid receptor activity using the techniques described herein. In an exemplary embodiment, the method includes contacting a GR with an effective amount of a compound of the present invention, such as the compound of formula I, and detecting a change in GR activity.

In an exemplary embodiment, the GR modulator is an antagonist of GR activity (also referred to herein as "a glucocorticoid receptor antagonist"). A glucocorticoid receptor antagonist, as used herein, refers to any composition or compound which partially or completely inhibits (antagonizes) the binding of a glucocorticoid receptor (GR) agonist (e.g. cortisol and synthetic or natural cortisol analog) to a GR thereby inhibiting any biological response associated with the binding of a GR to the agonist.

In some embodiments, the GR modulator is a specific glucocorticoid receptor antagonist. As used herein, a specific glucocorticoid receptor antagonist refers to a composition or compound which inhibits any biological response associated with the binding of a GR to an agonist by preferentially binding to the GR rather than another nuclear receptor (NR). In some embodiments, the specific glucocorticoid receptor antagonist binds preferentially to GR rather than the mineralocorticoid receptor (MR), aldosterone receptor (AR) or progesterone receptor (PR). In an exemplary embodiment, the specific glucocorticoid receptor antagonist binds preferentially to GR rather than the mineralocorticoid receptor (MR). In another exemplary embodiment, the specific glucocorticoid receptor antagonist binds preferentially to GR rather than the progesterone receptor (PR). In another exemplary embodiment, the specific glucocorticoid antagonist binds preferentially to GR rather than to the aldosterone receptor (AR).

In some embodiments, the specific glucocorticoid receptor antagonist binds to the GR with an association constant (Kd) that is at least 10-fold less than the Kd for any other NR. In some embodiments, the specific glucocorticoid receptor antagonist binds to the GR with an association constant (Kd) that is at least 100-fold less than the Kd for any other NR. In some embodiments, the specific glucocorticoid receptor antagonist binds to the GR with an association constant (Kd) that is at least 1000-fold less than the Kd for any other NR.

Examples of disorders or conditions suitable for use with present invention include, but are not limited to, obesity, diabetes, cardiovascular disease, hypertension, Syndrome X, depression, anxiety, glaucoma, human immunodeficiency virus (HIV) or acquired immunodeficiency syndrome (AIDS), neurodegeneration, Alzheimer's disease, Parkinson's disease, cognition enhancement, Cushing's Syndrome, Addison's Disease, osteoporosis, frailty, muscle frailty, inflammatory diseases, osteoarthritis, rheumatoid arthritis, asthma and rhinitis, adrenal function-related ailments, viral infection, immunodeficiency, immunomodulation, autoimmune diseases, allergies, defective wound healing, compulsive behavior, multi-drug resistance, addiction, psychosis, anorexia, cachexia, post-traumatic stress syndrome, post-surgical bone fracture, medical catabolism, major psychotic depression, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain, pain associated with gastroesophageal reflux disease, postpartum psychosis, postpartum depression, neurological disorders in premature infants, and migraine headaches. In some embodiments, the disorder or condition is major psychotic depression, stress disorders or antipsychotic induced weight gain.

In some embodiments, the disorder or condition is non-alcoholic fatty liver disease and/or nonalcoholic steatohepatitis. In some embodiments, the disorder or condition is nonalcoholic fatty liver disease. In some embodiments, the disorder or condition is nonalcoholic steatohepatitis.

Non-alcoholic fatty liver disease (NAFLD) is one of the types of fatty liver which occurs when fat is deposited (steatosis) in the liver due to causes other than excessive alcohol use. NAFLD is considered to cover a spectrum of disease activity. This spectrum begins as fatty accumulation in the liver (hepatic steatosis). Most people with NAFLD have few or no symptoms. Patients may complain of fatigue, malaise, and dull right-upper-quadrant abdominal discomfort. Mild jaundice may be noticed, although this is rare. More commonly NAFLD is diagnosed following abnormal liver function tests during routine blood tests. By definition, alcohol consumption of over 20 g/day (about 25 ml/day of net ethanol) excludes the condition.

NAFLD can progress to become non-alcoholic steatohepatitis (NASH), a state in which steatosis is combined with inflammation and fibrosis (steatohepatitis). NASH is a progressive disease. Over a 10-year period, up to 20% of patients with NASH will develop cirrhosis of the liver, and 10% will suffer death related to liver disease.

In some embodiments, the disorder or condition is an addiction disorder. Addictive disorders, such as substance abuse and dependence, are common disorders that involve the overuse of alcohol or drugs. Substance abuse, as a disorder, refers to the abuse of illegal substances or the abusive use of legal substances (e.g., alcohol). Substance dependence is an addictive disorder that describes continued use of drugs or alcohol, even when significant problems related to their use have developed. Signs include an increased tolerance that is, the need for increased amounts of the substance to attain the desired effect; withdrawal symptoms with decreased use; unsuccessful efforts to decrease use; increased time spent in activities to obtain the substance; withdrawal from social and recreational activities; and continued use of the substance even with awareness of the physical or psychological problems encountered by the extent of substance use. Chemical dependence is also an addictive disorder that describes the compulsive use of chemicals (usually drugs or alcohol) and the inability to stop using them despite all the problems caused by their use. The substances frequently abused, particularly by adolescents with addictive disorders, include, but are not limited to, alcohol, marijuana, hallucinogens, cocaine, amphetamines, opiates, anabolic steroids, inhalants, methamphetamine, or tobacco.

Carcinoma refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epidermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma villosum, meningioma, schwannoma, and ependymoma.

In some embodiments, the method includes administering one or more second agents (e.g. therapeutic agents). In some embodiments, the method includes administering one or more second agents (e.g. therapeutic agents) in a therapeutically effective amount. In some embodiments, the second agent is an agent known to be useful in modulating a glucocorticoid receptor. In some embodiments, the second agent is an agent for treating obesity, diabetes, cardiovascular disease, hypertension, Syndrome X, depression, anxiety, glaucoma, human immunodeficiency virus (HIV) or acquired immunodeficiency syndrome (AIDS), neurodegeneration, Alzheimer's disease, Parkinson's disease, cognition enhancement, Cushing's Syndrome, Addison's Disease, osteoporosis, frailty, muscle frailty, inflammatory diseases, osteoarthritis, rheumatoid arthritis, asthma and rhinitis, adrenal function-related ailments, viral infection, immunodeficiency, immunomodulation, autoimmune diseases, allergies, defective wound healing, compulsive behavior, multi-drug resistance, addiction, psychosis, anorexia, cachexia, post-traumatic stress syndrome, post-surgical bone fracture, medical catabolism, major psychotic depression, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain, pain associated with gastroesophageal reflux disease, postpartum psychosis, postpartum depression, neurological disorders in premature infants, or migraine headaches. In some embodiments, the second agent is an agent for treating major psychotic depression, stress disorders or antipsychotic induced weight gain. In some embodiments, the second agent is an agent for treating nonalcoholic fatty liver disease and/or nonalcoholic steatohepatitis. In some embodiments, the second agent is an agent for treating an addiction disorder. In some embodiments, the second agent is an agent for treating cancer. In some embodiments, the second agent is an anti-cancer agent. In some embodiments, the second agent is a chemotherapeutic.

Sarcoma generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

Melanoma refers to a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungual melanoma, or superficial spreading melanoma.

Carcinoma refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epidermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

In some embodiments, the method includes administering one or more second agents (e.g. therapeutic agents). In some embodiments, the method includes administering one or more second agents (e.g. therapeutic agents) in a therapeutically effective amount. In some embodiments, the second agent is an agent known to be useful in modulating a glucocorticoid and/or mineralocorticoid receptor. In some embodiments, the second agent is an agent for treating obesity, diabetes, cardiovascular disease, hypertension, Syndrome X, depression, anxiety, glaucoma, human immunodeficiency virus (HIV) or acquired immunodeficiency syndrome (AIDS), neurodegeneration, Alzheimer's disease, Parkinson's disease, cognition enhancement, Cushing's Syndrome, Addison's Disease, osteoporosis, frailty, muscle frailty, inflammatory diseases, osteoarthritis, rheumatoid arthritis, asthma and rhinitis, adrenal function-related ailments, viral infection, immunodeficiency, immunomodulation, autoimmune diseases, allergies, defective wound healing, compulsive behavior, multi-drug resistance, addiction, psychosis, anorexia, cachexia, post-traumatic stress syndrome, post-surgical bone fracture, medical catabolism, major psychotic depression, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain, pain associated with gastroesophageal reflux disease, postpartum psychosis, postpartum depression, neurological disorders in premature infants, or migraine headaches. In some embodiments, the second agent is an agent for treating major psychotic depression, stress disorders or antipsychotic induced weight gain. In some embodiments, the second agent is an agent for treating nonalcoholic fatty liver disease and/or nonalcoholic steatohepatitis. In some embodiments, the second agent is an agent for treating an addiction disorder. In some embodiments, the second agent is an agent for treating cancer. In some embodiments, the second agent is an anti-cancer agent. In some embodiments, the second agent is a chemotherapeutic.

VI. Combination Therapies

In accordance with the methods of the present invention, the compound of formula I or a pharmaceutical composition thereof can be co-administered in combination with other anti-cancer agents ("anticancer agent"). In some embodiments, the anti-cancer agent is a chemotherapeutic agent.

Chemotherapeutic agents suitable for use in combination with the compound of the invention include agents that have the property of killing cancer cells or inhibiting cancer cell growth, such as those disclosed in US Pat. Pub. No. 20150218274, and also http://chemocare.com/chemotherapy/what-is-chemotherapy/types-of-chemotherapy.aspx. These agents include, but are not limited to antimicrotubule agents (e.g., taxanes and *vinca* alkaloids), topoisomerase inhibitors and antimetabolites (e.g., nucleoside analogs acting as such, for example, Gemcitabine), mitotic inhibitors, alkylating agents, antimetabolites, anti-tumor antibiotics, mitotic inhibitors, anthracyclines, intercalating agents, agents capable of interfering with a signal transduction pathway, agents that promote apoptosis, proteosome inhibitors, and the like.

Alkylating agents are most active in the resting phase of the cell. These types of drugs are cell-cycle non-specific. Exemplary alkylating agents that can be used in combination with the compound of formula I or a pharmaceutical composition thereof include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednimustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoramide, TESPA and TSPA, Thioplex®); Cyclophosphamide (Endoxan®, Cytoxan®, Neosar®, Procytox®, Revimmune®); and Bendamustine HCl (Treanda®).

Antitumor antibiotics are chemo agents obtained from natural products produced by species of the soil fungus *Streptomyces*. These drugs act during multiple phases of the cell cycle and are considered cell-cycle specific. There are several types of antitumor antibiotics, including but are not limited to Anthracyclines (e.g., Doxorubicin, Daunorubicin, Epirubicin, Mitoxantrone, and Idarubicin), Chromomycins (e.g., Dactinomycin and Plicamycin), Mitomycin and Bleomycin.

Antimetabolites are types of chemotherapy treatments that are cell-cycle specific. When the cells incorporate these antimetabolite substances into the cellular metabolism, they are unable to divide. These class of chemotherapy agents include folic acid antagonists such as Methotrexate; pyrimidine antagonists such as 5-Fluorouracil, Floxuridine, Cytarabine, Capecitabine, and Gemcitabine; purine antagonists such as 6-Mercaptopurine and 6-Thioguanine; Adenosine deaminase inhibitors such as Cladribine, Fludarabine, Nelarabine and Pentostatin.

Exemplary anthracyclines that can be used in combination with the compound of the invention include, e.g., doxorubicin (Adriamycin® and Rubex®); Bleomycin (Lenoxane®); Daunorubicin (daunorubicin hydrochloride, daunomycin, and rubidomycin hydrochloride, Cerubidine®); Daunorubicin liposomal (daunorubicin citrate liposome, DaunoXome®); Mitoxantrone (DHAD, Novantrone®); Epirubicin (Ellence); Idarubicin (Idamycin®, Idamycin PFS®); Mitomycin C (Mutamycin®); Geldanamycin; Herbimycin; Ravidomycin; and Desacetylravidomycin.

Antimicrotubule agents include vinca alkaloids and taxanes. Exemplary vinca alkaloids that can be used in combination with the SGRM of the invention include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®). Exemplary taxanes that can be used in combination with the SGRM of the invention include, but are not limited to paclitaxel and docetaxel. Non-limiting examples of paclitaxel agents include nanoparticle albumin-bound paclitaxel (ABRAXANE, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., Biopolymers (2007) 87:225-230), and glucose-conjugated paclitaxel (e.g., 2'-paclitaxel methyl 2-glucopyranosyl succinate, see Liu et al., Bioorganic & Medicinal Chemistry Letters (2007) 17:617-620).

Exemplary proteosome inhibitors that can be used in combination with the compound of the invention, include, but are not limited to, Bortezomib (Velcade®); Carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(−2R)-2-methyl-2-oxiranyl]-2-oxo-1-(phenylmethyl)ethyl]-L-serinamide (ONX-0912).

In some embodiments, the chemotherapeutic agent is selected from the group consisting of chlorambucil, cyclophosphamide, ifosfamide, melphalan, streptozocin, carmustine, lomustine, bendamustine, uramustine, estramustine, carmustine, nimustine, ranimustine, mannosulfan busulfan, dacarbazine, temozolomide, thiotepa, altretamine, 5-fluorouracil (5-FU), 6-mercaptopurine (6-MP), capecitabine, cytarabine, floxuridine, fludarabine, gemcitabine, hydroxyurea, methotrexate, pemetrexed, daunorubicin, doxorubicin, epirubicin, idarubicin, SN-38, ARC, NPC, camptothecin, topotecan, 9-nitrocamptothecin, 9-aminocamptothecin, rubifen, gimatecan, diflomotecan, BN80927, DX-895 If, MAG-CPT, amsacrine, etoposide, etoposide phosphate, teniposide, doxorubicin, paclitaxel, docetaxel, gemcitabine, accatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephalomannine, gemcitabine, Irinotecan, albumin-bound paclitaxel, Oxaliplatin, Capecitabine, Cisplatin, docetaxel, irinotecan liposome, and etoposide, and combinations thereof.

In certain embodiments, the chemotherapeutic agent is administered at a dose and a schedule that may be guided by doses and schedules approved by the U.S. Food and Drug Administration (FDA) or other regulatory body, subject to empirical optimization. In some cases, the chemotherapeutic agent is administered at a dose of about 100 to 1000 mg, e.g., about 200 mg to 800 mg, about 300 mg to 700 mg, or about 400 mg to 600 mg, e.g., about 200 mg, 300 mg, 400 mg, 500 mg, 600 mg, or 700 mg. The dosing schedule can vary from, e.g. every week, every five days, every four days, every other day to daily, twice, or three times a day. In one embodiment, the chemotherapeutic agent is administered at an oral dose or an intravenous dose from about 100 mg to 600 mg daily, e.g., about 100 mg, 200 mg, 260 mg, 300 mg, 400 mg, or 600 mg daily, every other day or every four days for the whole or a portion of the treatment period. In some embodiments, the chemotherapeutic agent is a taxane and can be used at any standard dose, for example those taxane doses approved by the FDA, in accordance with the methods of the invention. In various embodiments, the taxane is nab-paclitaxel, which is administered at a dose ranging from 80 mg to 125 mg per square meter of body-surface area as an intravenous infusion over 30 minutes on days 1, 8, and 15 of every 28-day cycle.

In still further embodiments, more than one chemotherapeutic agent may be administered simultaneously, or sequentially in any order during the entire or portions of the treatment period. The two agents may be administered following the same or different dosing regimens.

Various combinations with the compound of the invention and a chemotherapeutic agent (or a combination of such agents and compounds) may be employed to reduce the tumor load in the patient. By "combination therapy" or "in combination with", it is not intended to imply that the therapeutic agents must be administered at the same time and/or formulated for delivery together, although these methods of delivery are within the scope described herein. The compound of the invention and the chemotherapeutic agent can be administered following the same or different dosing regimen. In some embodiments, the compound of formula I or a pharmaceutical composition thereof and the chemotherapeutic agent is administered sequentially in any order during the entire or portions of the treatment period. In some embodiments, the compound of the invention and the anticancer agent is administered simultaneously or approximately simultaneously (e.g., within about 1, 5, 10, 15, 20, or 30 minutes of each other). Non-limiting examples of combination therapies are as follows, with administration of the compound of the invention and the chemo agent for example, the compound of the invention is "A" and the anticancer agent or compound, given as part of an chemo therapy regime, is "B":

A/B/AB/A/BB/B/AA/A/BA/B/BB/A/AA/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the therapeutic compounds or agents to a patient will follow general protocols for the administration of such compounds, taking into account the toxicity, if any, of the therapy. Surgical intervention may also be applied in combination with the described therapy.

The methods of the invention can be combined with other means of treatment such as surgery, radiation, targeted therapy, immunotherapy, use of growth factor inhibitors, or anti-angiogenesis factors.

VII. Examples

General Methods

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated or under pressure in a gas autoclave (bomb).

Column chromatography was performed on pre-packed silica (230-400 mesh, 40-63 μm) cartridges using the amount indicated. Strong cation exchange (SCX) was purchased from Supelco and treated with 1 M hydrochloric acid prior to use. Unless stated otherwise the reaction mixture to be purified was first diluted with methanol (MeOH) and made acidic with a few drops of acetic acid (AcOH). This solution was loaded directly onto the SCX and washed with MeOH. The desired material was then eluted by washing with 1% ammonia ($NH_3$) in MeOH.

Preparative RP-HPLC was performed using UV detection at 215 and 254 nm with either Method A or Method B. Method A: a Waters X-Select Prep-C18, 5 μm, 19×50 mm column eluting with a water-acetonitrile ($H_2O$-MeCN) gradient containing 0.1% v/v formic acid over 10 min. Method B: a Waters X-Bridge Prep-C18, 5 μm, 19×50 mm column eluting with a $H_2O$-MeCN gradient containing 0.1% ammonium bicarbonate over 10 min.

Analytical Methods

Reverse Phase High Performance Liquid Chromatography

Method 1: Waters XSelect CSH C18 2.5 μm (4.6×30 mm) at 40° C.; flow rate 2.5-4.5 mL min$^{-1}$ eluted with a $H_2O$-MeCN gradient containing 0.1% v/v formic acid over 4 min employing UV detection at 254 and 215 nm. Gradient information: 0-3.00 min, ramped from 95% $H_2O$-5% MeCN to 5% $H_2O$-95% MeCN; 3.00-3.01 min, held at 5% $H_2O$-95% MeCN, flow rate increased to 4.5 mL min$^{-1}$; 3.01-3.50 min, held at 5% $H_2O$-95% MeCN; 3.50-3.60 min, returned to 95% $H_2O$-5% MeCN, flow rate reduced to 3.50 mL min$^{-1}$; 3.60-3.90 min, held at 95% $H_2O$-5% MeCN; 3.90-4.00 min, held at 95% $H_2O$-5% MeCN, flow rate reduced to 2.5 mL min$^{-1}$.

Method 2: Waters XBridge BEH C18, 2.5 μm (4.6×30 mm) at 40° C.; flow rate 2.5-4.5 mL min$^{-1}$ eluted with a $H_2O$-MeCN gradient containing 10 mM ammonium bicarbonate over 4 min employing UV detection at 254 nm. Gradient information: 0-3.00 min, ramped from 95% $H_2O$-5% MeCN to 5% $H_2O$-95% MeCN; 3.00-3.01 min, held at 5% $H_2O$-95% MeCN, flow rate increased to 4.5 mL min$^{-1}$; 3.01-3.50 min, held at 5% $H_2O$-95% MeCN; 3.50-3.60 min, returned to 95% $H_2O$-5% MeCN, flow rate reduced to 3.50 mL min$^{-1}$; 3.60-3.90 min, held at 95% $H_2O$-5% MeCN; 3.90-4.00 min, held at 95% $H_2O$-5% MeCN, flow rate reduced to 2.5 mL min$^{-1}$.

Method 3: Waters XSelect UPLC C18 1.7 μm (2.1×30 mm) at 40° C.; flow rate 0.7 mL·min$^{-1}$ eluted with a H₂O-MeCN gradient containing 0.1% v/v formic acid over 3 min employing PDA detection between 210 and 400 nm. Gradient information: 0-0.11 min, 95% H₂O-5% MeCN, 0.11-2.15 min ramped from 95% H₂O-5% MeCN to 5% H₂O-95% MeCN; 2.15-2.49 min, held at 5% H₂O-95% MeCN, 2.49-2.56 min, ramped down from 5% H₂O-95% MeCN to 95% H₂O-5% MeCN, 2.56-3.00 min, 95% H₂O-5% MeCN.

Method 4: Waters XSelect UPLC C18 1.7 μm (2.1×30 mm) at 40° C.; flow rate 0.7 mL·min⁻¹ eluted with a H₂O-MeCN gradient containing 0.1% v/v formic acid over 3 min employing PDA detection between 210 and 400 nm. Gradient information: 0-0.08 min, 95% H₂O-5% MeCN, 0.08-0.70 min ramped from 95% H₂O-5% MeCN to 5% H₂O-95% MeCN; 0.7-0.8 min, held at 5% H₂O-95% MeCN, 0.8-0.9 min, ramped down from 5% H₂O-95% MeCN to 95% H₂O-5% MeCN, 0.9-1.00 min, 95% H₂O-5% MeCN.

LCMS Methods

Method A: experiments were performed using a Waters Platform LC quadrupole mass spectrometer with positive and negative ion electrospray and ELS/Diode array detection using a Phenomenex Luna 3 micron C18 (2) 30×4.6 mm column and a 2 mL/minute flow rate. The solvent system was a 95% water containing 0.1% formic acid (solvent A) and a 5% acetonitrile containing 0.1% formic acid (solvent B) for the first 50 seconds followed by a gradient up to 5% solvent A and 95% solvent B over the next 4 minutes. The final solvent system was held constant for a further 1 minute.

Method B: experiments were performed using a Waters Micromass ZQ2000 quadrupole mass spectrometer with a positive and negative ion electrospray and ELS/Diode array detection using a Higgins Clipeus 5 micron C18 100×3.0 mm column and a 1 mL/minute flow rate. The initial solvent system was 95% water containing 0.1% formic acid (solvent A) and a 5% acetonitrile containing 0.1% formic acid (solvent B) for the first minute followed by a gradient up to 5% solvent A and 95% solvent B over the next 8 minutes. The final solvent system was held constant for a further 5 minutes.

Method C: experiments were performed using a Waters ZMD quadrupole mass spectrometer with positive and negative ion electrospray and ELS/Diode array detection using a Phenomenex Luna 3 micron C18 (2) 30×4.6 mm column and a 2 mL/minute flow rate. The solvent system was a 95% water containing 0.1% formic acid (solvent A) and a 5% acetonitrile containing 0.1% formic acid (solvent B) for the first 50 seconds followed by a gradient up to 5% solvent A and 95% solvent B over the next 4 minutes. The final solvent system was held constant for a further 1 minute.

Method D: experiments were performed using a Waters Micromass ZQ2000 quadrupole mass spectrometer linked to a Waters Acquity UPLC system with a PDA UV detector using an Acquity UPLC BEH C18 1.7 micron 100×2.1 mm, maintained at 40° C. The spectrometer has an electrospray source operating in positive and negative ion mode. The initial solvent system was 95% water containing 0.1% formic acid (solvent A) and a 5% acetonitrile containing 0.1% formic acid (solvent B) for 0.4 minutes followed by a gradient up to 5% solvent A and 95% solvent B over the next 6.4 minutes.

Method E: experiments were performed using a Waters Quattro Micro triple quadrupole mass spectrometer linked to a Hewlett Packard HP1100 LC system with a positive and negative ion electrospray and ELS/Diode array detection using a Higgins Clipeus 5 micron C18 100×3.0 mm column and a 1 mL/minute flow rate. The initial solvent system was 85% water containing 0.1% formic acid (solvent A) and 15% acetonitrile containing 0.1% formic acid (solvent B) for the first minute followed by a gradient up to 5% solvent A and 95% solvent B over the next 13 minutes. The solvent system was held constant for a further 7 minutes before returning to the initial solvent conditions.

¹H NMR Spectra were recorded using a Bruker 400 MHz Avance III spectrometer fitted with a BBFO 5 mm probe, or a Bruker 500 MHz Avance III HD spectrometer equipped with a Bruker 5 mm SmartProbe™. Spectra were measured at 298 K, unless indicated otherwise, and were referenced relative to the solvent resonance. The chemical shifts are reported in parts per million. Data were acquired using Bruker TopSpin software.

General Synthetic Methods

The compounds of the present invention can be prepared by a variety of methods known in the art.

One synthetic route to compounds of Formula Ia-1 involves the key intermediate ketone H. One route for obtaining a ketone of formula H is depicted in Scheme 1. Although Scheme 1 includes specific reagents, it will be obvious to one skilled in the art that alternative reagents or solvents could be used to achieve the synthesis. It will also be obvious to one skilled in the art that protecting groups other than benzyl would be suitable for the protection of the hydroxyl group in the starting material, 4-hydroxycyclohexanone. Protecting groups other than methyl can also be used for the protection of the two hydroxyl groups in the pyrimidine.

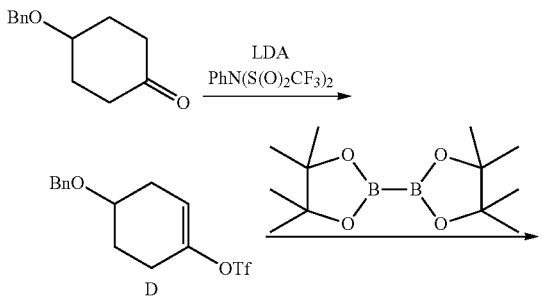

Scheme 1. Synthesis of ketone H

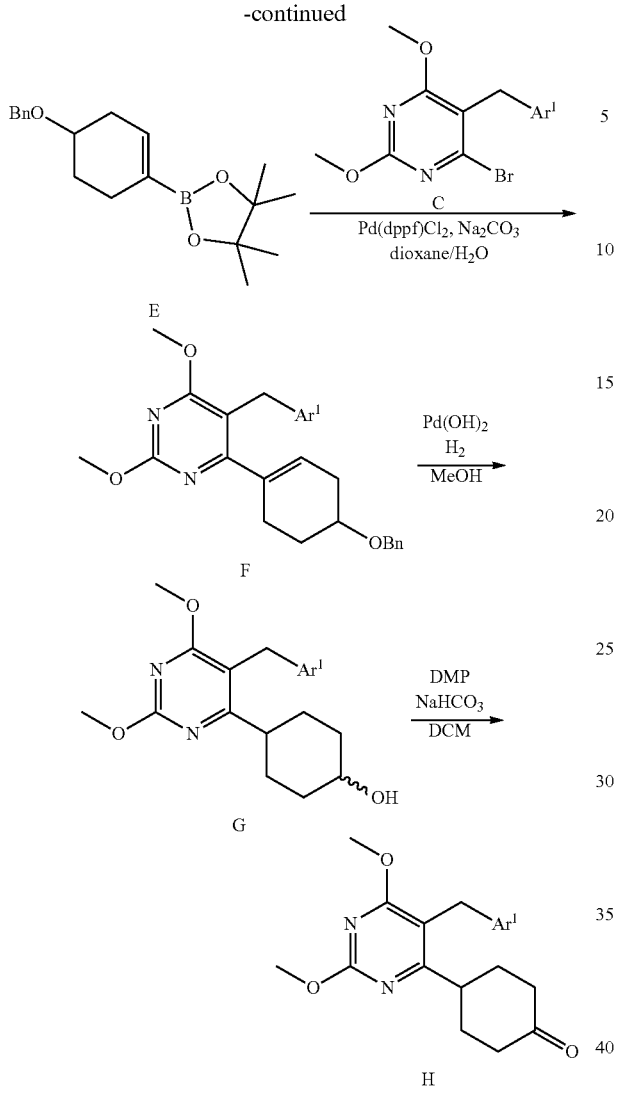

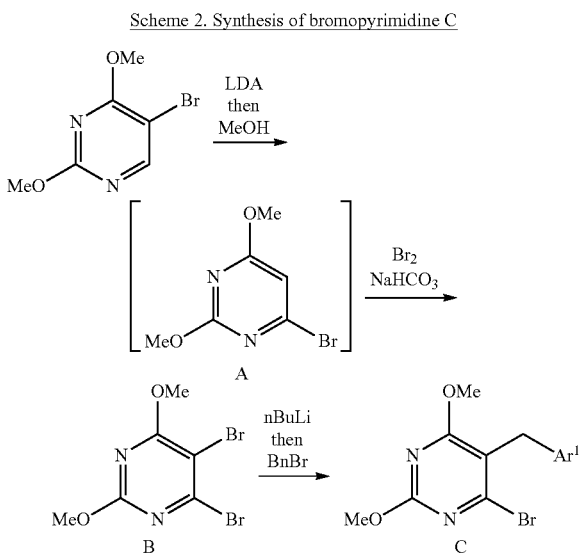

Scheme 2. Synthesis of bromopyrimidine C dine (C) can be accomplished under any suitable conditions, by employing an appropriate palladium catalyst, such as [1,1'-bis(diphenylphosphino)ferrocene]dichloropalladium (II) in the presence of a base (e.g., sodium carbonate) in a suitable solvent (e.g., aqueous dioxane) at an appropriate temperature (e.g., 80° C.). Conversion of the coupled product (F) to ketone (H) is accomplished by reduction of the cyclohexene to the corresponding cyclohexane, and removal of the benzyl protecting group followed by oxidation of the alcohol to the ketone. Conveniently, the removal of the benzyl protecting group and the reduction of the carbon-carbon double bond can be accomplished in a single reaction under hydrogenation conditions. Hydrogenation is carried out in the presence of a suitable catalyst, for example Pearlman's catalyst in a suitable solvent (e.g., methanol) at an appropriate temperature (e.g., room temperature). Oxidation of the resultant alcohol (G) can be achieved using any suitable oxidizing agent known to those skilled in the art, for example Dess-Martins periodinane in the presence of a base (e.g., sodium hydrogen carbonate) in a solvent (e.g., dichloromethane) at a temperature (e.g., room temperature).

Bromopyrimidine of formula C can be prepared by any feasible method evident to one skilled in the art. One suitable approach involves bromination of bromo-dimethoxypyrimidine followed by reaction with an appropriate arylmethylhalide in the presence of base (e.g., n-butyl-lithium) in a suitable solvent (e.g., tetrahydrofuran) at a temperature (e.g., −78° C.). This approach is summarized in Scheme 2.

A suitably protected 4-hydroxycyclohexanone can be converted into an appropriate coupling partner such as a triflate (D). This conversion can be accomplished by the use of a suitable base (e.g., LDA), and an appropriate reagent (e.g., phenyl bistriflimide). The reaction can be conducted in any suitable solvent (e.g., tetrahydrofuran), at an appropriate temperature (e.g., −78° C.). Coupling of the cyclohexene derivative with the desired pyrimidine group can be accomplished by converting the vinyl triflate (D) into a vinyl boronate (E) followed by reaction of the vinyl boronate (E) with an appropriate bromopyrimidine (C) under palladium catalysis. Conversion of the vinyl triflate (D) to a vinyl boronate (E) can be achieved by the use of a suitable boron reagent, such as bis(pinacolato)diboron, in the presence of a palladium catalyst such as [1,1'-bis(diphenylphosphino)ferrocene]dichloropalladium (II). The reaction is conducted in a suitable solvent (e.g., dioxane) at an appropriate temperature (e.g., 80° C.). It will be evident to one skilled in the art that alternative boron reagents, palladium catalysts, solvents and temperatures could also be employed for the conversion. Reaction of the vinyl boronate (E) with the bromopyrimi- Ketone H can be converted into compounds of formula Ia-1 in several ways. One suitable approach is to convert ketone H into a vinyl triflate (J) and couple the vinyl triflate (J) with an appropriate aryl boronic acid, as described in Scheme 3. The aryl boronic acid may be prepared in situ from an appropriate arylbromide (V)) as shown in Scheme 3.

Scheme 3. Conversion of ketone H to compounds of formula Ia-1

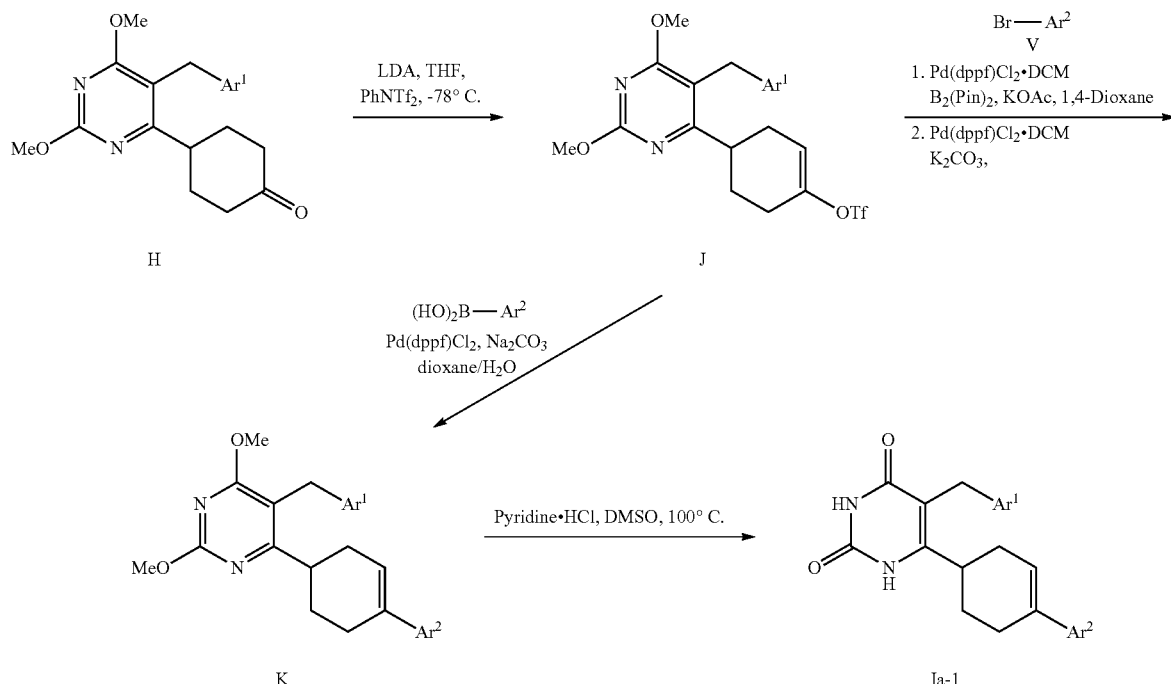

The conversion of ketone H into the vinyl triflate (J) can be carried out using any suitable conditions known to those skilled in the art, such as by reaction with a suitable base (e.g., lithium diisopropylamine), and a suitable triflating agent (e.g., phenyl bistriflimide) in a suitable solvent (e.g., tetrahydrofuran) at a low temperature (e.g., −78° C.). Coupling of the vinyl triflate with an aryl boronic acid can be conducted in the presence of a suitable palladium catalyst, for example [1,1'-bis(diphenyl-phosphino)ferrocene]dichloropalladium (II) in the presence of a base (e.g., sodium carbonate) in a solvent (e.g., aqueous dioxane) at an appropriate temperature (e.g., 80° C.). The final step in the preparation of compounds of formula Ia-1 involves the removal of the protecting groups to liberate the pyrimidinedione structure. The deprotection can be carried out using any suitable method known to those skilled in the art, for example by the use of pyridine hydrochloride in a suitable solvent (e.g., dimethylsulfoxide) at an elevated temperature (e.g., 100° C.). The aryl boronic acid is either commercially available, or can be readily prepared using standard procedures known to those shilled in the art.

An alternative method for the conversion of ketone H into compounds of formula Ia-1 involves reaction with a suitable aryl-metal reagent, such as an aryl-lithium reagent followed by elimination of the resultant alcohol to provide the desired cyclohexene. The addition of the aryl-metal reagent can be achieved using any methods known to those skilled in the art, for example by treating an aryl halide with a suitable base (e.g., butyllithium) in an appropriate solvent (e.g., tetrahydrofuran) at a low temperature (e.g., −78° C.). Removal of the methyl protecting groups provides compounds of formula Ia-1 as described previously. This approach is depicted in Scheme 4.

Scheme 4. Alternative approach from ketone H

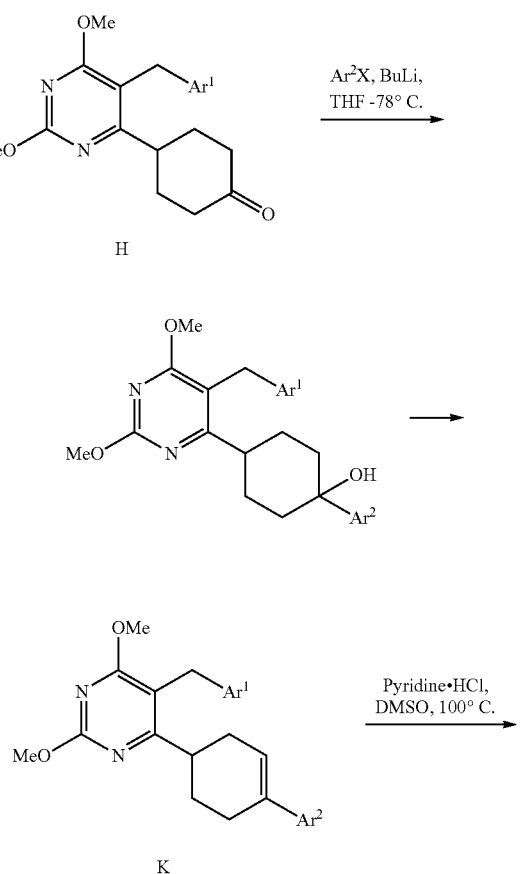

-continued

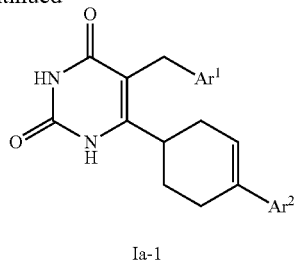

Ia-1

An alternative synthesis of compounds of formula Ia-1 is summarized in Scheme 5.

In this route, a suitable substituted aryl cyclohexene of formula Q is reacted with Meldrum's acid in the presence of a suitable coupling agent, for example EDC and a suitable base (e.g., dimethylaminopyridine) in an appropriate solvent (e.g., ethanol) at a temperature (e.g., room temperature). The resulting keto-ester (R) can then be alkylated with an appropriate arylmethylhalide in the presence of a base (e.g., sodium hydride) in a suitable solvent (e.g., tetrahydrofuran) at a temperature (e.g., 0° C.). Cyclization of the resulting substituted keto-ester (S) can be accomplished by any standard conditions know to those skilled in the art, such as reaction with thioguanidine to provide a thiopyrimidine (T). Cyclisation can be accomplished in an appropriate solvent (e.g., ethanol) in the presence of a base (e.g., sodium

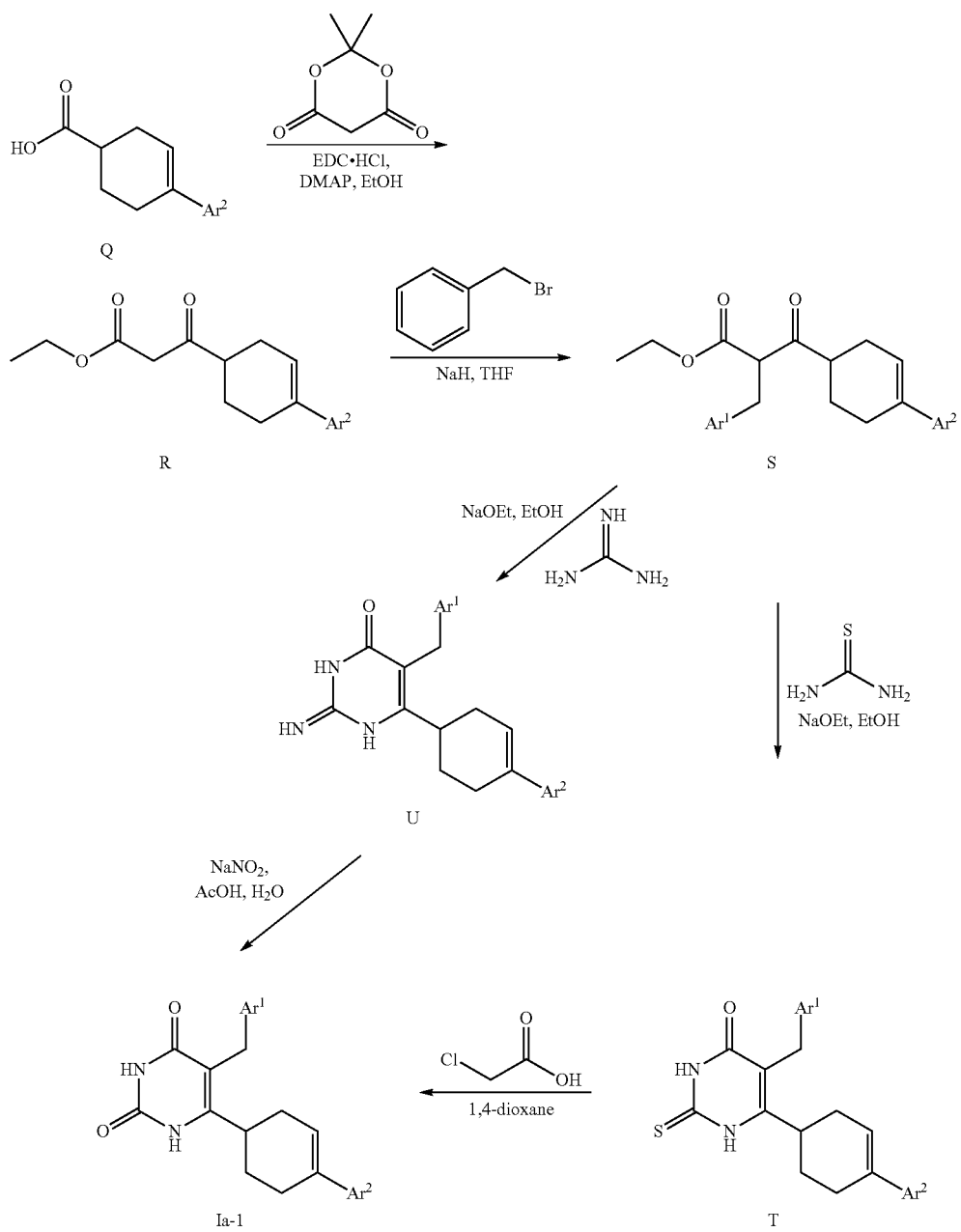

ethoxide) at a suitable temperature (e.g., room temperature). Conversion of the thiocarbonyl to the desired carbonyl can be readily achieved, for example by the use of chloroacetic acid in dioxane. Alternatively, the substituted keto-ester (S) could be cyclized with guanidine to form the corresponding guanidine-pyrimidine (U) and the desired pyrimidinedione could be obtained by reaction of the guanidine-pyrimidine with sodium nitrite in a suitable solvent (e.g., aqueous acetic acid) at an elevated temperature (e.g., 70° C.).

The aryl cyclohexene of formula Q can be obtained by any suitable method known to those skilled in the art.

Scheme 6. Synthesis of aryl cyclohexene 4

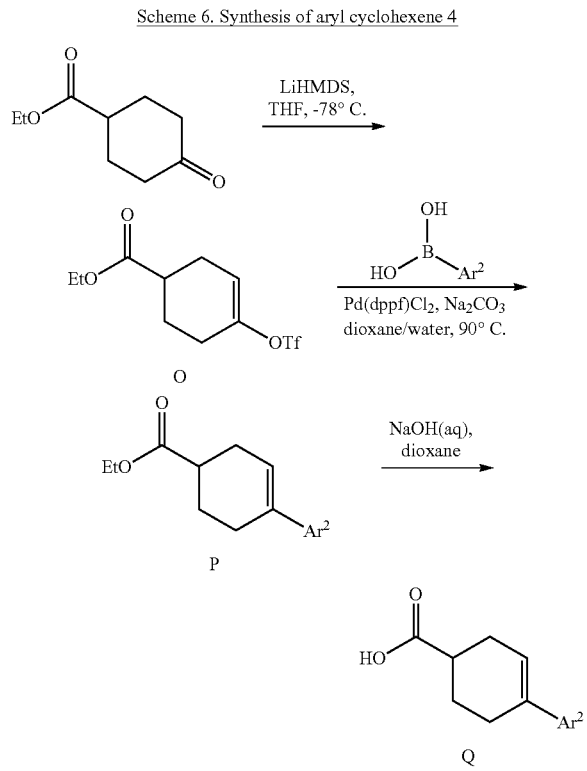

One suitable method, shown in Scheme 6, involves starting with a suitable ester of 4-cyclohexanone carboxylic acid and converting the ketone into a suitable coupling partner such as a vinyl triflate (O). This transformation can be performed using any suitable method known to one skilled in the art, for example by the use of a triflating agent (e.g., phenylbistriflimide) in the presence of a suitable base (e.g., lithium bis(trimethylsilyl)amide) in an appropriate solvent (e.g., tetrahydrofuran) at low temperature (e.g., −78° C.). The resultant vinyl triflate (O) can be coupled with an aryl boronic acid by the use of a palladium catalyst such as [1,1'-bis(diphenylphosphino)ferrocene]dichloropalladium (II) in the presence of a base (e.g., sodium carbonate) in a suitable solvent (e.g., aqueous dioxane) at an elevated temperature (e.g., 90° C.). Hydrolysis of the ester can be achieved under any standard conditions, for example the use of sodium hydroxide in aqueous dioxane.

For example, compounds of formula Ib-1 can be prepared by the above general methods, as detailed in FIG. 1.

Example 1: 4'-(5-benzyl-2,6-dioxo-1,2,3,6-tetrahydropyrimidin-4-yl)-2-chloro-2',3',4',5'-tetrahydro-[1,1'-biphenyl]-4-carbonitrile Intermediate A: 4-Bromo-2,6-dimethoxypyrimidine

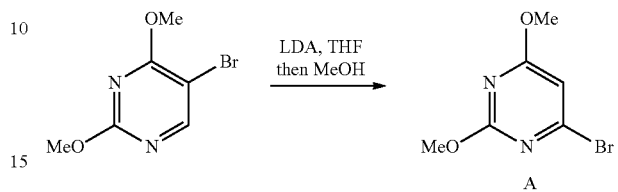

To a stirred solution of LDA (2.0 M in THF/heptane/ethylbenzene) (25.8 mL, 51.5 mmol) in tetrahydrofuran (THF) (50 mL) at −78° C. was added a solution of 5-bromo-2,4-dimethoxypyrimidine (10.3 g, 46.8 mmol) in THF (50 mL) dropwise. The mixture was stirred at −78° C. for 15 minutes. MeOH (10 mL) was added, the cooling bath was removed and the mixture stirred for 30 minutes. The reaction was quenched by addition of saturated Ammonium chloride ($NH_4Cl$) solution (100 mL) and the mixture extracted with ethyl acetate (EtOAc) (3×40 mL). The organic extracts were combined and then dried over magnesium sulfate ($MgSO_4$), filtered and concentrated in vacuo to afford the title compound 4-bromo-2,6-dimethoxypyrimidine as an orange solid. The crude product was used directly in the next step.

Intermediate B: 4,5-Dibromo-2,6-dimethoxypyrimidine

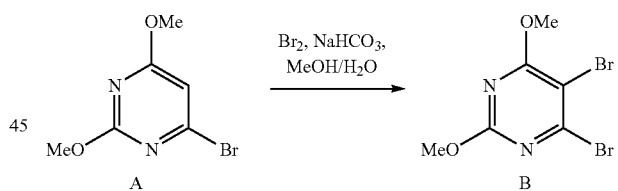

To a suspension of 4-bromo-2,6-dimethoxypyrimidine (Intermediate A) (10.3 g, 46.8 mmol) and sodium hydrogen carbonate ($NaHCO_3$) (5.51 g, 65.6 mmol) in MeOH/$H_2O$ (1:1, 120 mL) at room temperature was added bromine (4.34 mL, 84.2 mmol). The reaction mixture was stirred at room temperature for 1.5 hours. The mixture was diluted with dichloromethane (DCM) (100 mL) and the layers were separated. The aqueous phase was extracted with DCM (2×30 mL). The organic extracts were combined, filtered through a phase separator cartridge and concentrated in vacuo. The crude product was purified by chromatography on silica gel (220 g, 0-10% EtOAc in isohexane, gradient elution) to afford the title compound 4,5-dibromo-2,6-dimethoxypyrimidine (8.48 g, 60%) as a pale orange solid. Analytical data: $R^t$ 2.24 min (Method 1); m/z 297/299/301 $(M+H)^+$ $(ES^+)$.

Intermediate C-1: 5-Benzyl-4-bromo-2,6-dimethoxypyrimidine

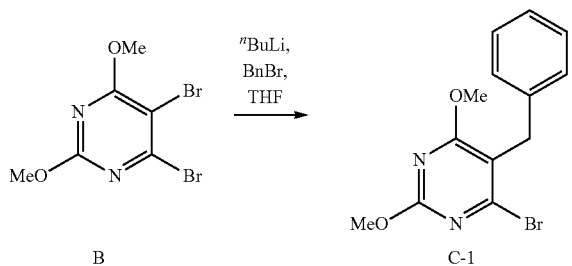

To a solution of 4,5-dibromo-2,6-dimethoxypyrimidine (Intermediate B) (8.48 g, 28.5 mmol) in dry THF (100 mL) at −78° C. was added n-butyllithium (2.5 M in hexanes) (12.5 mL, 31.3 mmol) dropwise. The reaction mixture was stirred at −78° C. for 10 minutes and then benzyl bromide (10.2 mL, 85.0 mmol) was added. The reaction mixture was warmed to room temperature over 1 hour and then quenched by addition of saturated $NH_4Cl$ solution (50 mL). The mixture was extracted with EtOAc (3×30 mL). The organic extracts were combined and then dried over $MgSO_4$, filtered and concentrated in vacuo. The crude product was purified by chromatography on silica gel (220 g column, 0-5% THF in isohexane, gradient elution) to afford the title compound 5-benzyl-4-bromo-2,6-dimethoxypyrimidine (7.70 g, 78%) as a pale yellow oil. Analytical date: $R^t$ 2.63 min (Method 1); m/z 309/311 $(M+H)^+$ $(ES^+)$.

Intermediate D: 4-(Benzyloxy)cyclohex-1-en-1-yl Trifluoromethanesulfonate

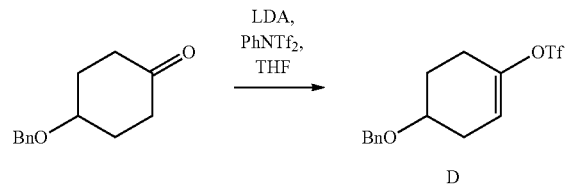

To a stirred solution of LDA (2.0 M in THF/heptane/ethylbenzene) (36.6 mL, 73.2 mmol) in THF (60 mL) at −78° C. was added 4-(benzyloxy)cyclohexanone (13.6 g, 66.6 mmol) dropwise over 15 minutes. The resulting solution was stirred at −78° C. for 1 hour before the addition of a solution of 1,1,1-trifluoro-N-phenyl-N-((trifluoromethyl)sulfonyl)methanesulfonamide (25.0 g, 69.9 mmol) in THF (60 mL) dropwise over 30 minutes. The reaction was stirred at −78° C. for 1 hour, then allowed to slowly warm to room temperature overnight. The mixture was partitioned between EtOAc (100 mL) and water/saturated brine (1:1, 100 mL). The layers were separated and the aqueous extracted with EtOAc (3×50 mL). The organic extracts were combined and then dried over $MgSO_4$, filtered and concentrated in vacuo. The crude product was purified by chromatography on silica gel (330 g, 0-10% EtOAc in isohexane, gradient elution) to afford the title compound 4-(benzyloxy)cyclohex-1-en-1-yl trifluoromethanesulfonate (14.8 g, 59%) as a pale yellow oil. Analytical data: $^1$H NMR (400 MHz, DMSO-$d_6$) δ: 7.38-7.22 (5H, m), 5.79 (1H, t), 4.54 (1H, d), 4.51 (1H, d), 3.72 (1H, m), 2.54-2.38 (2H, m), 2.38-2.18 (2H, m), 1.96-1.81 (2H, m).

Intermediate E: 2-(4-(Benzyloxy)cyclohex-1-en-1-yl)-4,4,5,5-tetramethyl-1,3,2-dioxaborolane

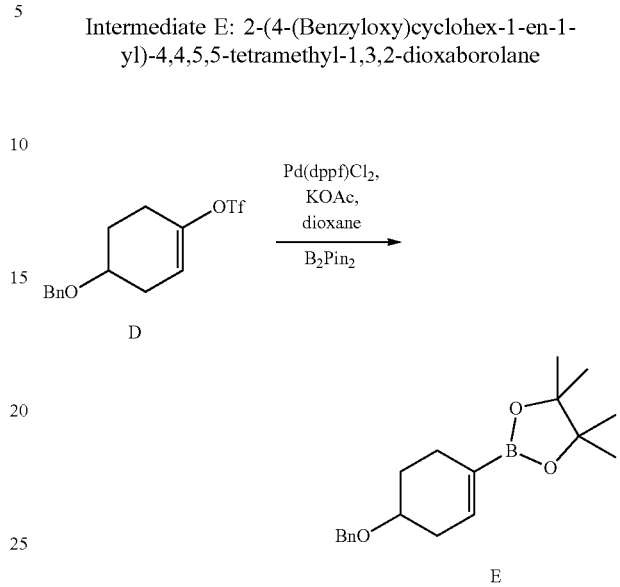

A suspension of 4-(benzyloxy)cyclohex-1-en-1-yl trifluoromethanesulfonate (Intermediate D) (14.8 g, 43.9 mmol), 4,4,4',4',5,5,5',5'-octamethyl-2,2'-bi(1,3,2-dioxaborolane) (12.3 g, 48.2 mmol) and potassium acetate (KOAc) (12.9 g, 132 mmol) in dioxane (100 mL) was degassed by bubbling $N_2$ through the mixture for 5 min. 1,1'-Bis(diphenylphosphino)ferrocene-palladium (II) dichloride dichloromethane complex (3.58 g, 4.39 mmol) was added and the mixture was heated at 80° C. for 4 hours. After cooling to room temperature, the mixture was filtered through celite, washing with EtOAc (150 mL), and the filtrate concentrated in vacuo. The crude product was purified by chromatography on silica gel (330 g, 0-10% EtOAc in isohexane, gradient elution) to afford the title compound 2-(4-(benzyloxy)cyclohex-1-en-1-yl)-4,4,5,5-tetramethyl-1,3,2-dioxaborolane (6.88 g, 47%) as a pale yellow solid. Analytical data: $^1$H NMR (400 MHz, DMSO-$d_6$) δ: 7.39-7.17 (5H, m), 6.34 (1H, m), 4.52 (1H, d), 4.49 (1H, d), 3.60 (1H, m), 2.44 (1H, m), 2.17 (1H, m), 2.10-1.95 (2H, m), 1.85 (1H, m), 1.51 (1H, m), 1.18 (12H, s).

Intermediate F-1: 5-Benzyl-4-(4-(benzyloxy)cyclohex-1-en-1-yl)-2,6-dimethoxypyrimidine

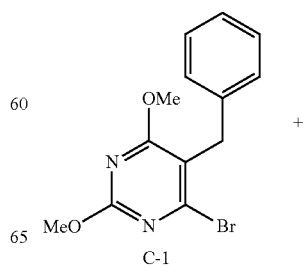

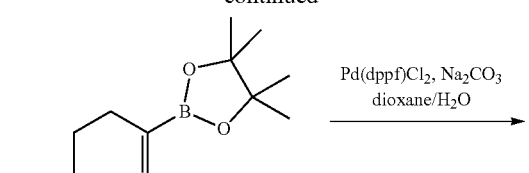

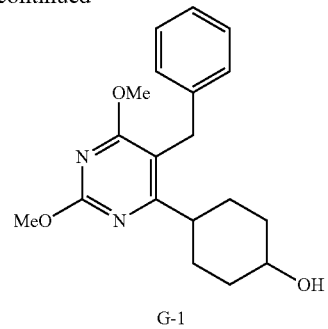

G-1

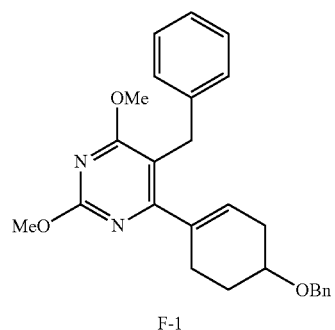

F-1

To a suspension of 5-benzyl-4-(4-(benzyloxy)cyclohex-1-en-1-yl)-2,6-dimethoxypyrimidine (Intermediate F-1) (6.79 g, 16.3 mmol) in MeOH (60 mL) was added 20% palladium hydroxide on carbon (Pd(OH)$_2$/C) (1.15 g, 1.63 mmol) and the mixture was hydrogenated with H$_2$ gas at 4 bar for 20 hours. The mixture was filtered through celite, washing with MeOH (60 mL), and the filtrate concentrated in vacuo. The crude product was purified by chromatography on silica gel (80 g, 0-50% EtOAc in isohexane, gradient elution) to afford the title compound 4-(5-benzyl-2,6-dimethoxypyrimidin-4-yl)cyclohexanol (~3:1 mixture of diastereoisomers) (5.01 g, 82%) as a white solid. Analytical data: R$^t$ 2.20 min and 2.28 min (Method 1); m/z 329 (M+H)$^+$ (ES$^+$).

To a suspension of 5-benzyl-4-bromo-2,6-dimethoxypyrimidine (Intermediate C-1) (6.52 g, 21.1 mmol) and 2-(4-(benzyloxy)cyclohex-1-en-1-yl)-4,4,5,5-tetramethyl-1,3,2-dioxaborolane (Intermediate E) (6.63 g, 21.1 mmol) in dioxane (100 mL) was added a solution of Na$_2$CO$_3$ (4.92 g, 46.4 mmol) in water (20 mL). The mixture was degassed by bubbling N$_2$ through the mixture for 5 minutes. 1,1'-Bis(diphenylphosphino)ferrocene-palladium (II) dichloride dichloromethane complex (0.862 g, 1.06 mmol) was added and the mixture was heated at 80° C. for 6 hours. The reaction was cooled to room temperature and partitioned between saturated NH$_4$Cl solution (100 mL) and EtOAc (100 mL). The layers were separated and the aqueous phase was extracted with EtOAc (2×50 mL). The organic extracts were combined and then dried over MgSO$_4$, filtered and concentrated in vacuo. The crude product was purified by chromatography on silica gel (120 g, 0-30% EtOAc in isohexane, gradient elution) to afford the title compound 5-benzyl-4-(4-(benzyloxy)cyclohex-1-en-1-yl)-2,6-dimethoxypyrimidine (6.79 g, 64%) as a colourless oil. Analytical data: R$^t$ 2.99 min (Method 1); m/z 417 (M+H)$^+$ (ES$^+$).

Intermediate H: 4-(5-Benzyl-2,6-dimethoxypyrimidin-4-yl)cyclohexanone

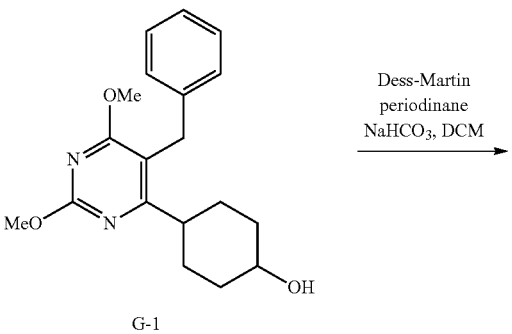

G-1

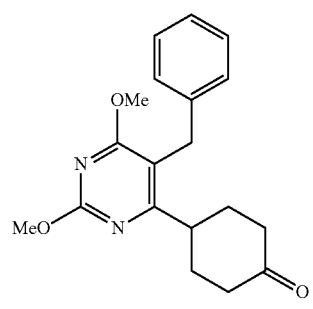

H-1

Intermediate G-1: 4-(5-Benzyl-2,6-dimethoxypyrimidin-4-yl)cyclohexanol

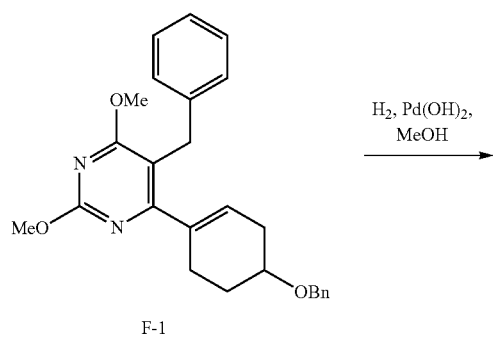

F-1

To a solution of 4-(5-benzyl-2,6-dimethoxypyrimidin-4-yl)cyclohexanol (Intermediate G-1) (5.00 g, 15.2 mmol) in dichloromethane (DCM) (100 mL) at room temperature was added NaHCO$_3$ (1.41 g, 16.8 mmol) then Dess-Martin periodinane (7.10 g, 16.8 mmol). The reaction mixture was stirred at room temperature for 25 minutes and then water (100 mL) was added. The layers were separated and the aqueous phase was extracted with DCM (2×30 mL). The organic extracts were combined and then dried over MgSO₄, filtered and concentrated in vacuo. The crude product was purified by chromatography on silica gel (80 g, 0-30% EtOAc in isohexane, gradient elution) to afford the title compound 4-(5-benzyl-2,6-dimethoxypyrimidin-4-yl)cyclohexanone (3.95 g, 79%) as a thick colourless oil, which solidified on standing. Analytical data: $R^r$ 2.34 min (Method 1); m/z 327 (M+H)⁺ (ES⁺).

Intermediate J-1: 4-(5-Benzyl-2,6-dimethoxypyrimidin-4-yl)cyclohex-1-en-1-yl trifluoromethanesulfonate Intermediate K-1a: 4'-(5-Benzyl-2,6-dimethoxypyrimidin-4-yl)-2-chloro-2',3',4',5'-tetrahydro-[1,1'-biphenyl]-4-carbonitrile

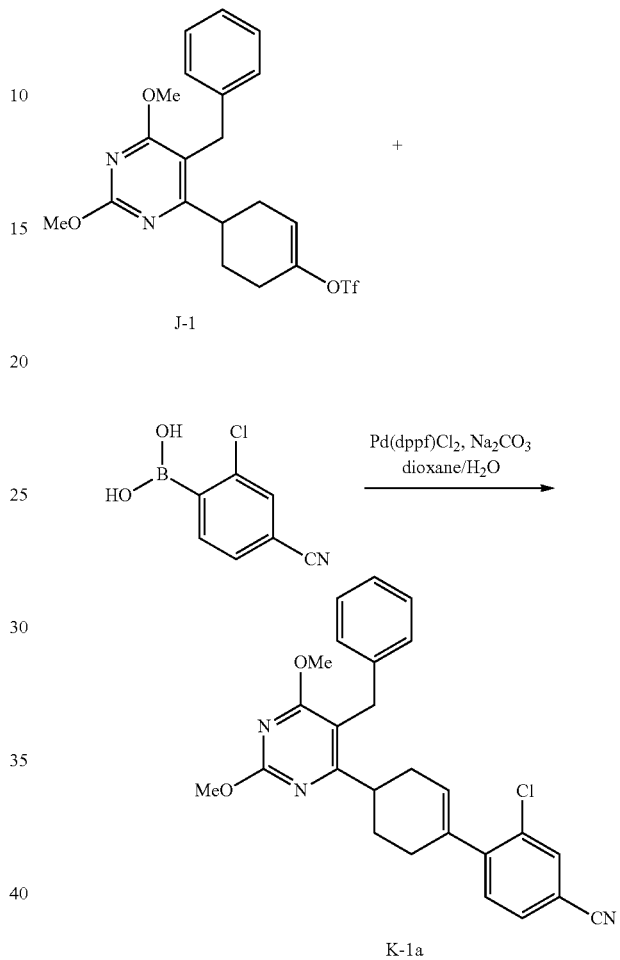

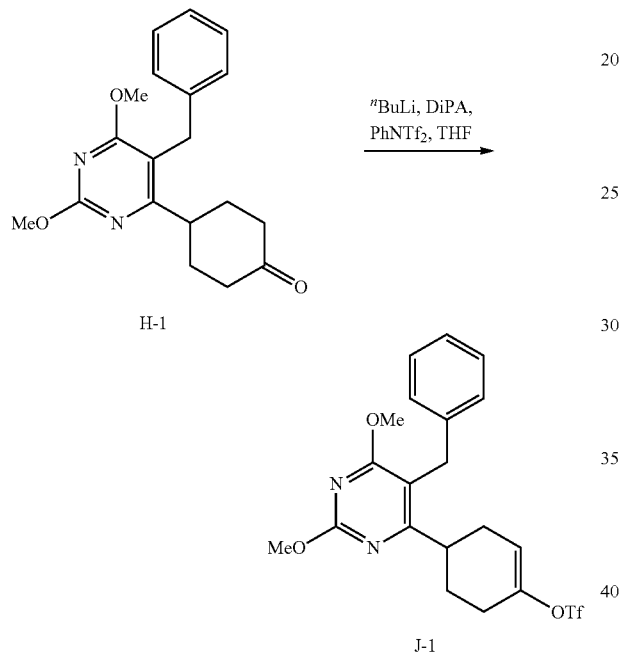

To a stirred solution of diisopropylamine (1.30 mL, 9.10 mmol) in THF (20 mL) at −78° C. was added a solution of n-butyllithium (2.5 M in hexanes) (3.64 mL, 9.10 mmol) dropwise. The reaction was stirred for 15 minutes before the dropwise addition of a solution of 4-(5-benzyl-2,6-dimethoxypyrimidin-4-yl)cyclohexanone (Intermediate H-1) (2.70 g, 8.27 mmol) in THF (20 mL). The resulting solution was stirred at −78° C. for 1 hour before the addition of a solution of 1,1,1-trifluoro-N-phenyl-N-((trifluoromethyl)sulfonyl)methanesulfonamide (3.10 g, 8.69 mmol) in THF (20 mL) dropwise. The reaction was stirred at −78° C. for 1 hour, then allowed to slowly warm to room temperature overnight. The mixture was partitioned between EtOAc (60 mL) and water (60 mL). The layers were separated and the aqueous phase was extracted with EtOAc (3×30 mL). The organic extracts were combined, washed with brine (50 mL) and then dried over MgSO₄, filtered and concentrated in vacuo. The crude product was purified by chromatography on silica gel (80 g, 0-20% EtOAc in isohexane, gradient elution) to afford the title compound 4-(5-benzyl-2,6-dimethoxypyrimidin-4-yl)cyclohex-1-en-1-yl trifluoromethanesulfonate (3.93 g, quant.) as a thick colorless gum. Analytical data: $R^r$ 3.10 min (Method 1); m/z 459 (M+H)⁺ (ES⁺).

To a suspension of 4-(5-benzyl-2,6-dimethoxypyrimidin-4-yl)cyclohex-1-en-1-yl trifluoromethanesulfonate (Intermediate J-1) (0.111 g, 0.242 mmol) and (2-chloro-4-cyanophenyl)boronic acid (44 mg, 0.24 mmol) in dioxane (3 mL) was added a solution of Na₂CO₃ (56 mg, 0.53 mmol) in water (0.5 mL). The mixture was degassed by bubbling N₂ through the mixture for 5 minutes. 1,1'-Bis(diphenylphosphino)ferrocene-palladium (II) dichloride dichloromethane complex (20 mg, 0.024 mmol) was added and the mixture was heated at 80° C. for 45 minutes. The reaction was cooled to room temperature and partitioned between saturated NH₄Cl solution (10 mL) and EtOAc (10 mL). The layers were separated and the aqueous phase was extracted with EtOAc (2×10 mL). The organic extracts were combined and then dried over MgSO₄, filtered and concentrated in vacuo. The crude product was purified by chromatography on silica gel (4 g, 0-10% EtOAc in isohexane, gradient elution) to afford the title compound 4'-(5-benzyl-2,6-dimethoxypyrimidin-4-yl)-2-chloro-2',3',4',5'-tetrahydro-[1,1'-biphenyl]-4-carbonitrile (88 mg, 73%) as a thick colorless gum. Analytical data: $R^r$ 3.17 min (Method 1); m/z 446 (M+H)⁺ (ES⁺).

4'-(5-Benzyl-2,6-dioxo-1,2,3,6-tetrahydropyrimidin-4-yl)-2-chloro-2',3',4',5'-tetrahydro-[1,1'-biphenyl]-4-carbonitrile

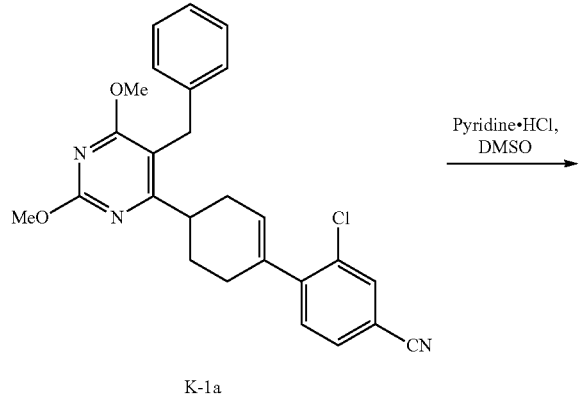

K-1a

Pyridine·HCl, DMSO
→

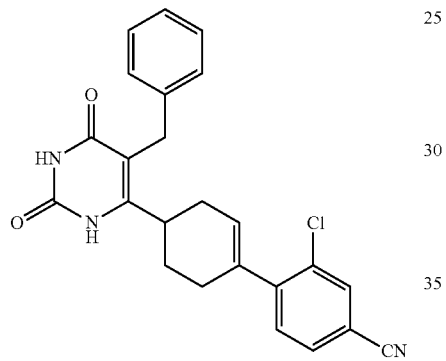

A solution of 4'-(5-benzyl-2,6-dimethoxypyrimidin-4-yl)-2-chloro-2',3',4',5'-tetrahydro-[1,1'-biphenyl]-4-carbonitrile (Intermediate K-1a) (0.080 g, 0.18 mmol) and pyridine hydrochloride (0.207 g, 1.79 mmol) in dimethylsulfoxide (DMSO) (0.5 mL) was heated at 100° C. for 30 minutes. After cooling to room temperature, the mixture was partitioned between DCM (5 mL) and water (5 mL). The layers were separated and the aqueous phase was extracted with DCM (3×5 mL). The organic extracts were combined, filtered through a phase separator cartridge and concentrated in vacuo. The crude product was purified by chromatography on silica gel (4 g, 0-100% EtOAc in isohexane, gradient elution) to afford the title compound 4'-(5-benzyl-2,6-dioxo-1,2,3,6-tetrahydropyrimidin-4-yl)-2-chloro-2',3',4',5'-tetrahydro-[1,1'-biphenyl]-4-carbonitrile (0.044 g, 58%) as a white solid. Analytical data: $R^t$ 2.33 min (Method 1); m/z 418 (M+H)$^+$ (ES$^+$); $^1$H NMR (400 MHz, DMSO-$d_6$) δ: 11.12 (1H, s), 10.53 (1H, s), 8.03 (1H, d), 7.79 (1H, dd), 7.41 (1H, d), 7.31-7.20 (2H, m), 7.20-7.08 (3H, m), 5.70 (1H, m), 3.79 (1H, d), 3.69 (1H, d), 3.02 (1H, m), 2.48 (1H, m), 2.30 (1H, m), 2.18 (1H, m), 2.11-1.87 (2H, m), 1.49 (1H, m).

Example 2 to Example 38: 4-substituted 5-benzyl-6-(cyclohex-3-en-1-yl)pyrimidine-2,4(1H,3H)-diones The following compounds as shown in Table 1 were prepared by similar methods to those as described in Example 1.

TABLE 1

| Example 2 to Example 38 | | |
|---|---|---|
| EXAMPLE | STRUCTURE | ANALYTICAL DATA |
| 2 | ![structure] 5-Benzyl-6-(2',3'-dichloro-2,3,4,5-tetrahydro-[1,1'biphenyl]-4-yl)pyrimidine-2,4(1H,3H)-dione | $R^t$ 2.62 min (Method 1); m/z 427 (M + H)$^+$ (ES$^+$) |

TABLE 1-continued

Example 2 to Example 38

| EXAMPLE | STRUCTURE | ANALYTICAL DATA |
| --- | --- | --- |
| 3 | 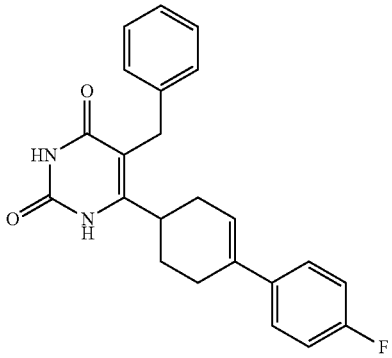<br>5-Benzyl-6-(4'-fluoro-2,3,4,5-tetrahydro-[1,1'-biphenyl]-4-yl)pyrimidine-2,4(1H,3H)-dione | $R^t$ 2.37 min (Method 1);<br>m/z 377 $(M + H)^+$ $(ES^+)$ |
| 4 | 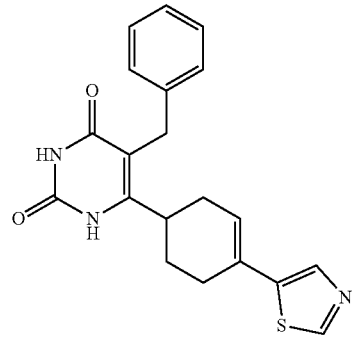<br>5-Benzyl-6-(4-(thiazol-5-yl)cyclohex-3-en-1-yl)pyrimidine-2,4(1H,3H)-dione | $R^t$ 1.82 min (Method 1);<br>m/z 366 $(M + H)^+$ $(ES^+)$ |
| 5 | 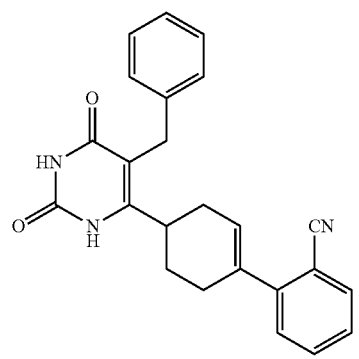<br>4'-(5-Benzyl-2,6-dioxo-1,2,3,6-tetrahydropyrimidin-4-yl)-2',3',4',5'-tetrahydro-[1,1'-biphenyl]-2-carbonitrile | $R^t$ 2.18 min (Method 1);<br>m/z 384 $(M + H)^+$ $(ES^+)$ |

TABLE 1-continued

Example 2 to Example 38

| EXAMPLE | STRUCTURE | ANALYTICAL DATA |
| --- | --- | --- |
| 6 | 5-Benzyl-6-(2′,4′-dichloro-2,3,4,5-tetrahydro-[1,1′-biphenyl]-4-yl)pyrimidine-2,4(1H,3H)-dione | $R^t$ 2.71 min (Method 1); m/z 427 (M + H)$^+$ (ES$^+$) |
| 7 | 5-Benzyl-6-(4′-chloro-2′-methoxy-2,3,4,5-tetrahydro-[1,1′-biphenyl]-4-yl)pyrimidine-2,4(1H,3H)-dione | $R^t$ 2.54 min (Method 1); m/z 423 (M + H)$^+$ (ES$^+$) |
| 8 | 5-Benzyl-6-(2′-chloro-2,3,4,5-tetrahydro-[1,1′-biphenyl]-4-yl)pyrimidine-2,4(1H,3H)-dione | $R^t$ 2.46 min (Method 1); m/z 393 (M + H)$^+$ (ES$^+$) |

TABLE 1-continued

Example 2 to Example 38

| EXAMPLE | STRUCTURE | ANALYTICAL DATA |
|---|---|---|
| 9 | 5-Benzyl-6-(2'-chloro-4'-fluoro-2,3,4,5-tetrahydro-[1,1'-biphenyl]-4-yl)pyrimidine-2,4(1H,3H)-dione | $R^t$ 2.52 min (Method 1); m/z 411 (M + H)$^+$ (ES$^+$) |
| 10 | 5-Benzyl-6-(4'-chloro-2'-(trifluoromethyl)-2,3,4,5-tetrahydro-[1,1'-biphenyl]-4-yl)pyrimidine-2,4(1H,3H)-dione | $R^t$ 2.73 min (Method 1); m/z 461 (M + H)$^+$ (ES$^+$) |
| 11 | 5-Benzyl-6-(2'-(trifluoromethyl)-2,3,4,5-tetrahydro-[1,1'-biphenyl]-4-yl)pyrimidine-2,4(1H,3H)-dione | $R^t$ 2.52 min (Method 1); m/z 427 (M + H)$^+$ (ES$^+$) |

TABLE 1-continued

Example 2 to Example 38

| EXAMPLE | STRUCTURE | ANALYTICAL DATA |
|---------|-----------|-----------------|
| 12 | 5-Benzyl-6-(5'-fluoro-2'-methoxy-2,3,4,5-tetrahydro-[1,1'-biphenyl]-4-yl)pyrimidine-2,4(1H,3H)-dione | $R^t$ 2.36 min (Method 1); m/z 407 (M + H)$^+$ (ES$^+$) |
| 13 | 5-Benzyl-6-(2'-methyl-2,3,4,5-tetrahydro-[1,1'-biphenyl]-4-yl)pyrimidine-2,4(1H,3H)-dione | $R^t$ 2.46 min (Method 1); m/z 373 (M + H)$^+$ (ES$^+$) |
| 14 | 5-Benzyl-6-(4-(2-(trifluoromethyl)pyridin-3-yl)cyclohex-3-en-1-yl)pyrimidine-2,4(1H,3H)-dione | $R^t$ 2.10 min (Method 1); m/z 428 (M + H)$^+$ (ES$^+$) |

TABLE 1-continued

Example 2 to Example 38

| EXAMPLE | STRUCTURE | ANALYTICAL DATA |
|---|---|---|
| 15 | 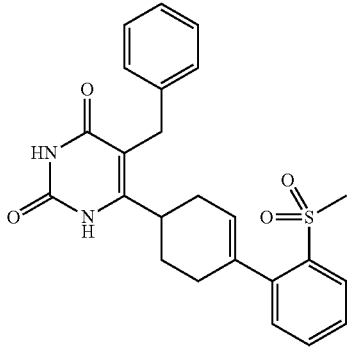<br>5-Benzyl-6-(2'-(methylsulfonyl)-2,3,4,5-tetrahydro-[1,1'-biphenyl]-4-yl)pyrimidine-2,4(1H,3H)-dione | $R^t$ 2.01 min (Method 1);<br>m/z 437 $(M + H)^+$ $(ES^+)$ |
| 16 | 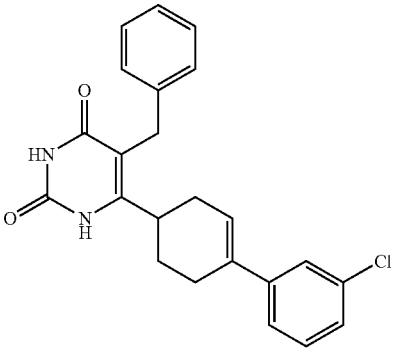<br>5-Benzyl-6-(3'-chloro-2,3,4,5-tetrahydro-[1,1'-biphenyl]-4-yl)pyrimidine-2,4(1H,3H)-dione | $R^t$ 2.52 min (Method 1);<br>m/z 393 $(M + H)^+$ $(ES^+)$ |
| 17 | 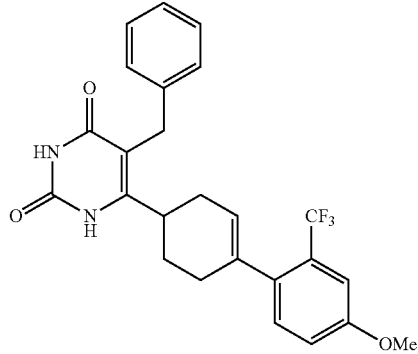<br>5-Benzyl-6-(4'-methoxy-2'-(trifluoromethyl-2,3,4,5-tetrahydro-[1,1'-biphenyl]-4-yl)pyrimidine-2,4(1H,3H)-dione | $R^t$ 2.53 min (Method 1);<br>m/z 457 $(M + H)^+$ $(ES^+)$ |

TABLE 1-continued

Example 2 to Example 38

| EXAMPLE | STRUCTURE | ANALYTICAL DATA |
|---|---|---|
| 18 | 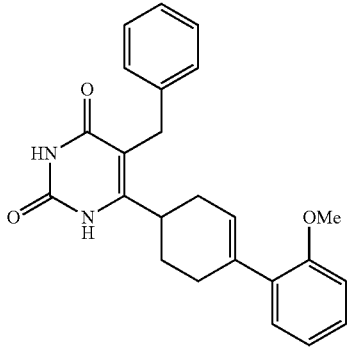<br>5-Benzyl-6-(2'-methoxy-2,3,4,5-tetrahydro-[1,1'-biphenyl]-4-yl)pyrimidine-2,4(1H,3H)-dione | $R^t$ 2.34 min (Method 1);<br>m/z 389 $(M + H)^+$ $(ES^+)$ |
| 19 | 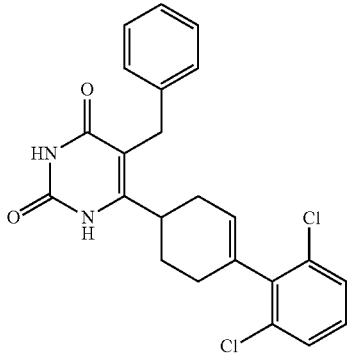<br>5-Benzyl-6-(2',6'-dichloro-2,3,4,5-tetrahydro-[1,1'-biphenyl]-4-yl)pyrimidine-2,4(1H,3H)-dione | $R^t$ 2.59 min (Method 1);<br>m/z 427 $(M + H)^+$ $(ES^+)$ |
| 20 | 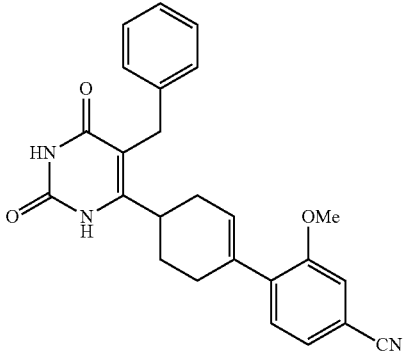<br>4'-(5-Benzyl-2,6-dioxo-1,2,3,6-tetrahydropyrimidin-4-yl)-2-methoxy-2',3',4',5'-tetrahydro-[1,1'-biphenyl]-4-carbonitrile | $R^t$ 2.22 min (Method 1);<br>m/z 414 $(M + H)^+$ $(ES^+)$ |

TABLE 1-continued

Example 2 to Example 38

| EXAMPLE | STRUCTURE | ANALYTICAL DATA |
|---|---|---|
| 21 | 5-Benzyl-6-(5'-fluoro-2'-methyl-2,3,4,5-tetrahydro-[1,1'-biphenyl]-4-yl)pyrimidine-2,4(1H,3H)-dione | $R^t$ 2.49 min (Method 1); m/z 391 (M + H)$^+$ (ES$^+$) |
| 22 | 5-Benzyl-6-(5'-(hydroxymethyl)-2'-methyl-2,3,4,5-tetrahydro-[1,1'-biphenyl]-4-yl)pyrimidine-2,4(1H,3H)-dione | $R^t$ 2.02 min (Method 1); m/z 403 (M + H)$^+$ (ES$^+$) |
| 23 | 4'-(5-Benzyl-2,6-dioxo-1,2,3,6-tetrahydropyrimidin-4-yl)-6-methoxy-2',3',4',5'-tetrahydro-[1,1'-biphenyl]-3-carbonitrile | $R^t$ 2.19 min (Method 1); m/z 414 (M + H)$^+$ (ES$^+$) |

TABLE 1-continued

Example 2 to Example 38

| EXAMPLE | STRUCTURE | ANALYTICAL DATA |
|---|---|---|
| 24 | 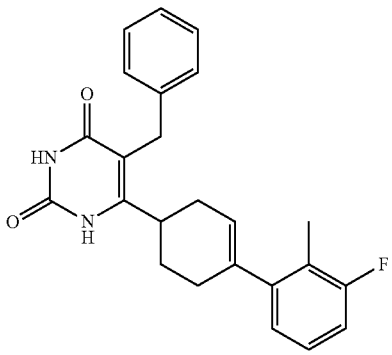

5-Benzyl-6-(3'-fluoro-2'-methyl-2,3,4,5-tetrahydro-[1,1'-biphenyl]-4-yl)pyrimidine-2,4(1H,3H)-dione | $R^t$ 2.49 min (Method 1); m/z 391 $(M + H)^+$ $(ES^+)$ |
| 25 | 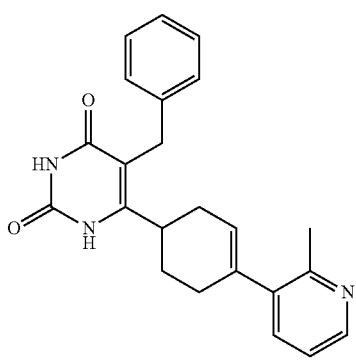

5-Benzyl-6-(4-(2-methylpyridin-3-yl)cyclohex-3-en-1-yl)pyrimidine-2,4(1H,3H)-dione | $R^t$ 1.16 min (Method 1); m/z 374 $(M + H)^+$ $(ES^+)$ |
| 26 | 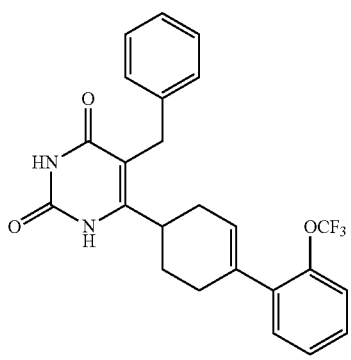

5-benzyl-6-(2'-(trifluoromethoxy)-2,3,4,5-tetrahydro-[1,1'-biphenyl]-4-yl)pyrimidine-2,4(1H,3H)-dione | $R^t$ 2.56 min (Method 1); m/z 443 $(M + H)^+$ $(ES^+)$ |

TABLE 1-continued

Example 2 to Example 38

| EXAMPLE | STRUCTURE | ANALYTICAL DATA |
|---|---|---|
| 27 | 4'-(5-Benzyl-2,6-dioxo-1,2,3,6-tetrahydropyrimidin-4-yl)-6-chloro-2',3',4',5'-tetrahydro-[1,1'-biphenyl]-3-carbonitrile | $R^t$ 2.33 min (Method 1); m/z 418 (M + H)$^+$ (ES$^+$) |
| 28 | 5-Benzyl-6-(2'-chloro-5'-(hydroxymethyl)-2,3,4,5-tetrahydro-[1,1'-biphenyl]-4-yl)pyrimidine-2,4(1H,3H)-dione | $R^t$ 2.07 min (Method 1); m/z 423 (M + H)$^+$ (ES$^+$) |
| 29 | 5-Benzyl-6-(2'-chloro-4'-methoxy-2,3,4,5-tetrahydro-[1,1'-biphenyl]-4-yl)pyrimidine-2,4(1H,3H)-dione | $R^t$ 2.47 min (Method 1); m/z 423 (M + H)$^+$ (ES$^+$) |

TABLE 1-continued

Example 2 to Example 38

| EXAMPLE | STRUCTURE | ANALYTICAL DATA |
|---|---|---|
| 30 | 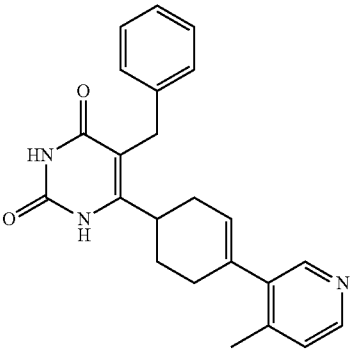<br>5-Benzyl-6-(4-(4-methylpyridin-3-yl)cyclohex-3-en-1-yl)pyrimidine-2,4(1H,3H)-dione | $R^t$ 1.20 min (Method 1);<br>m/z 374 (M + H)$^+$ (ES$^+$) |
| 31 | 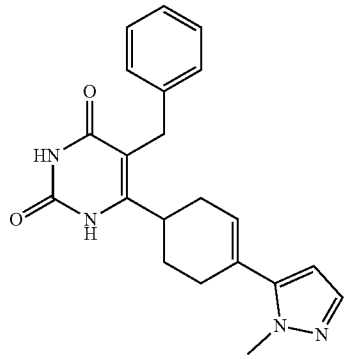<br>5-Benzyl-6-(4-(1-methyl-1H-pyrazol-5-yl)cyclohex-3-en-1-yl)pyrimidine-2,4(1H,3H)-dione | $R^t$ 1.76 min (Method 1);<br>m/z 363 (M + H)$^+$ (ES$^+$) |
| 32 | 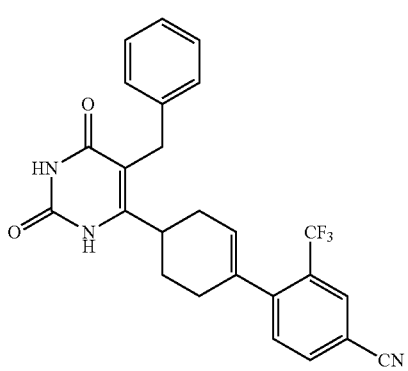<br>4′-(5-Benzyl-2,6-dioxo-1,2,3,6-tetrahydropyrimidin-4-yl)-2-(trifluoromethyl)-2′,3′,4′,5′-tetrahydro-[1,1′-biphenyl]-4-carbonitrile | $R^t$ 2.39 min (Method 1);<br>m/z 452 (M + H)$^+$ (ES$^+$) |

TABLE 1-continued

Example 2 to Example 38

| EXAMPLE | STRUCTURE | ANALYTICAL DATA |
|---|---|---|
| 33 | 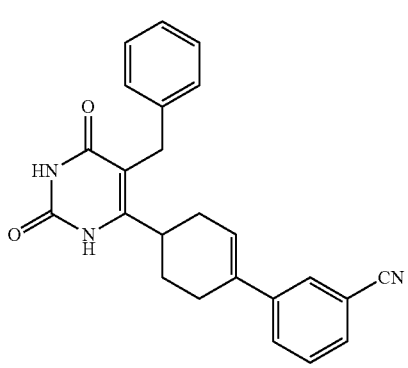<br>4'-(5-Benzyl-2,6-dioxo-1,2,3,6-tetrahydropyrimidin-4-yl)-2',3',4',5'-tetrahydro-[1,1'-biphenyl]-3-carbonitrile | $R^t$ 2.16 min (Method 1);<br>m/z 384 (M + H)$^+$ (ES$^+$) |
| 34 | 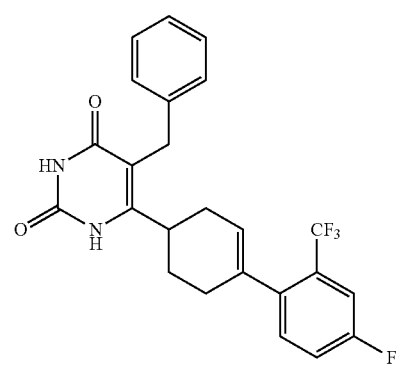<br>5-benzyl-6-(4'-fluoro-2'-(trifluoromethyl)-2,3,4,5-tetrahydro-[1,1'-biphenyl]-4-yl)pyrimidine-2,4(1H,3H)-dione | $R^t$ 1.67 min (Method 3);<br>m/z 445 (M + H)$^+$ (ES$^+$) |
| 35 | 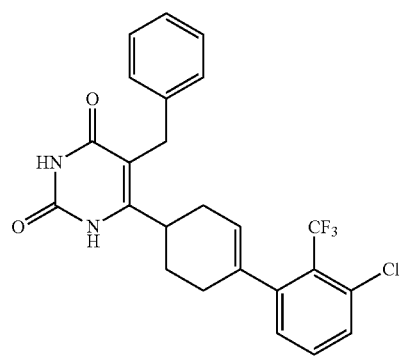<br>5-benzyl-6-(3'-chloro-2'-(trifluoromethyl)-2,3,4,5-tetrahydro-[1,1'-biphenyl]-4-yl)pyrimidine-2,4(1H,3H)-dione | $R^t$ 1.72 min (Method 3);<br>m/z 461 (M + H)$^+$ (ES$^+$) |

TABLE 1-continued

Example 2 to Example 38

| EXAMPLE | STRUCTURE | ANALYTICAL DATA |
|---|---|---|
| 36 | 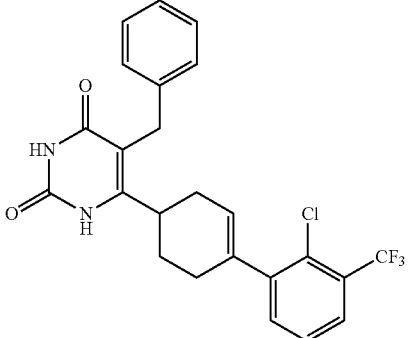<br>5-benzyl-6-(2′-chloro-3′-(trifluoromethyl)-2,3,4,5-tetrahydro-[1,1′-biphenyl]-4-yl)pyrimidine-2,4(1H,3H)-dione | $R^t$ 1.71 min (Method 3); m/z 461 (M + H)$^+$ (ES$^+$) |
| 37 | 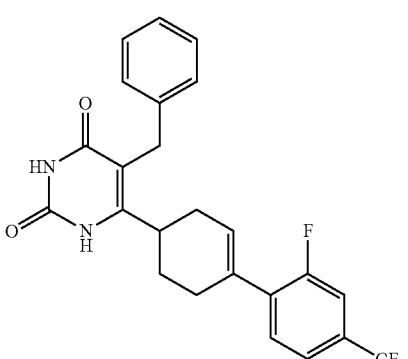<br>5-benzyl-6-(2′-fluoro-4′-(trifluoromethyl)-2,3,4,5-tetrahydro-[1,1′-biphenyl]-4-yl)pyrimidine-2,4(1H,3H)-dione | $R^t$ 1.70 min (Method 3); m/z 445 (M + H)$^+$ (ES$^+$) |
| 38 | 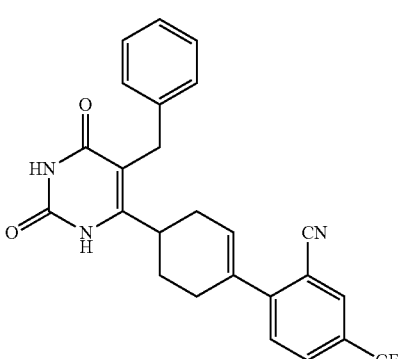<br>4′-(5-benzyl-2,6-dioxo-1,2,3,6-tetrahydropyrimidin-4-yl)-4-(trifluoromethyl)-2′,3′,4′,5′-tetrahydro-[1,1′-biphenyl]-2-carbonitrile | $R^t$ 1.59 min (Method 3); m/z 452 (M + H)$^+$ (ES$^+$) |

Example 39: (R)-4'-(5-Benzyl-2,6-dioxo-1,2,3,6-tetrahydropyrimidin-4-yl)-2-chloro-2',3',4',5'-tetrahydro-[1,1'-biphenyl]-4-carbonitrile Example 40: (S)-4'-(5-Benzyl-2,6-dioxo-1,2,3,6-tetrahydropyrimidin-4-yl)-2-chloro-2',3',4',5'-tetrahydro-[1,1'-biphenyl]-4-carbonitrile

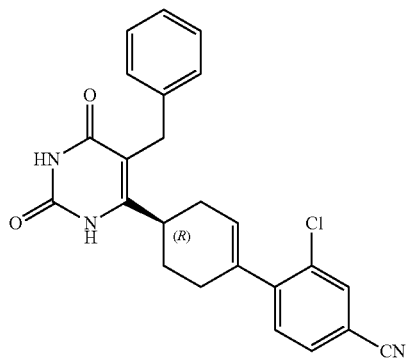

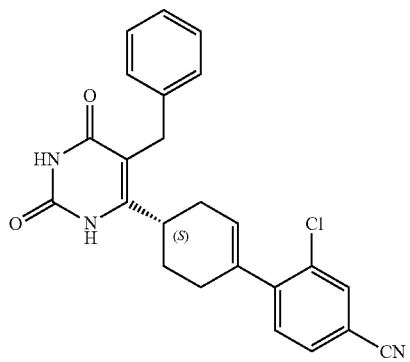

The compound of Example 1 (22 mg, 0.053 mmol) was dissolved to a concentration of 5 mg/mL in DCM and was then purified by Supercritical fluid chromatography (SFC) chiral separation (Lux C3 (4.6 mm×250 mm, 5 um), 40° C., 4 mL/min, 25:75 MeOH:CO$_2$). Combined fractions were then concentrated in vacuo to give (R)-4'-(5-Benzyl-2,6-dioxo-1,2,3,6-tetrahydropyrimidin-4-yl)-2-chloro-2',3',4',5'-tetrahydro-[1,1'-biphenyl]-4-carbonitrile (6 mg, 0.014 mmol) as a white solid and (S)-4'-(5-Benzyl-2,6-dioxo-1,2,3,6-tetrahydropyrimidin-4-yl)-2-chloro-2',3',4',5'-tetrahydro-[1,1'-biphenyl]-4-carbonitrile (6 mg, 0.014 mmol) as a white solid. Analytical data: R$^t$ 2.31 min (Method 1); m/z 418 (M+H)$^+$ (ES$^+$); and R$^t$ 2.32 min (Method 1); m/z 418 (M+H)$^+$ (ES$^+$). Stereochemistry was assigned arbitrarily.

Example 41: 5-Benzyl-6-(2'-chloro-4'-(4-methylpiperazine-1-carbonyl)-2,3,4,5-tetrahydro-[1,1'-biphenyl]-4-yl)pyrimidine-2,4(1H,3H)-dione Intermediate K-1b: 4'-(5-benzyl-2,6-dimethoxypyrimidin-4-yl)-2-chloro-2',3',4',5'-tetrahydro-[1,1'-biphenyl]-4-carboxylic Acid

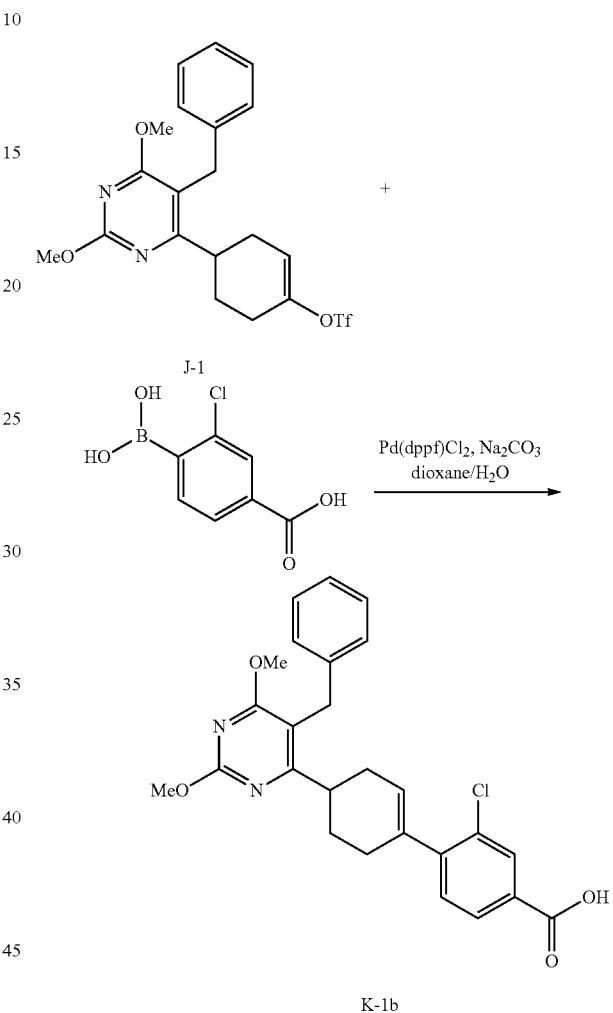

K-1b

To a suspension of 4-(5-benzyl-2,6-dimethoxypyrimidin-4-yl)cyclohex-1-en-1-yl trifluoromethanesulfonate (Intermediate J-1) (0.165 g, 0.360 mmol) and 4-borono-3-chlorobenzoic acid (0.079 g, 0.396 mmol) in dioxane (3 mL) was added a solution of sodium carbonate (0.084 g, 0.792 mmol) in water (0.5 mL). The mixture was degassed with bubbling N$_2$ for 5 minutes. 1,1'-Bis(diphenylphosphino)ferrocene-palladium(II)dichloride dichloromethane complex (Pd(dppf)Cl$_2$) (29 mg, 0.036 mmol) was added and the mixture was heated at 80° C. for 1 hour 15 minutes. The reaction was cooled to room temperature and partitioned between aqueous NH$_4$Cl solution (10 ml) and EtOAc (10 ml). The layers were separated and the aqueous layer was extracted with EtOAc (2×10 mL). The organic extracts were combined, dried over MgSO$_4$ and concentrated in vacuo. The crude product was purified by chromatography on silica gel (4 g column, 0-50% EtOAc/isohexane) to afford the title compound 4'-(5-benzyl-2,6-dimethoxypyrimidin-4-yl)-2- chloro-2',3',4',5'-tetrahydro-[1,1'-biphenyl]-4-carboxylic acid (0.117 g, 0.239 mmol, 66.4% yield) as a white solid. Analytical data: R$^t$ 3.17 min (Method 1); m/z 465 (M+H)$^+$ (ES$^+$).

Intermediate K-1c: (4'-(5-benzyl-2,6-dimethoxypyrimidin-4-yl)-2-chloro-2',3',4',5'-tetrahydro-[1,1'-biphenyl]-4-yl)(4-methylpiperazin-1-yl)methanone

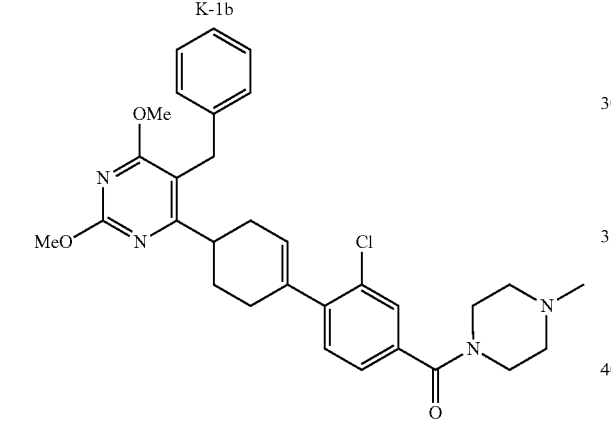

122

5-Benzyl-6-(2'-chloro-4'-(4-methylpiperazine-1-carbonyl)-2,3,4,5-tetrahydro-[1,1'-biphenyl]-4-yl)pyrimidine-2,4(1H,3H)-dione

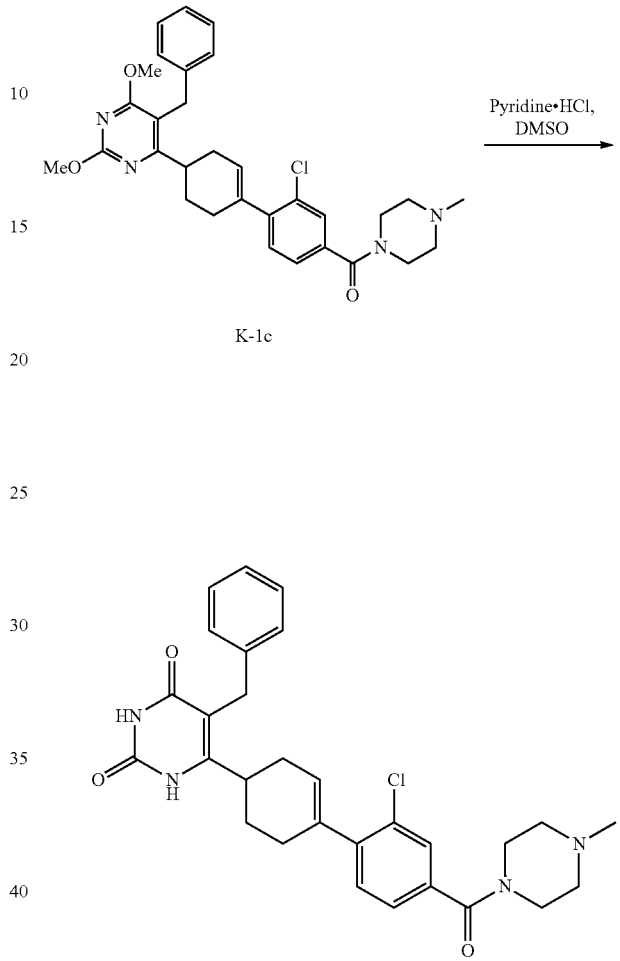

To a solution of 4'-(5-benzyl-2,6-dimethoxypyrimidin-4-yl)-2-chloro-2',3',4',5'-tetrahydro-[1,1'-biphenyl]-4-carboxylic acid (Intermediate K-1b) (0.113 g, 0.243 mmol) and hexafluorophosphate azabenzotriazole tetramethyl uronium (HATU) (0.102 g, 0.267 mmol) in dimethylformamide (DMF) (1 mL) was added 1-methylpiperazine (0.030 ml, 0.267 mmol) followed by diisopropylethylamine (0.127 ml, 0.729 mmol). The mixture was stirred at room temperature for 16 hours. The mixture was concentrated in vacuo and the residues partitioned between EtOAc (10 mL) and water/saturated NaHCO$_3$ solution (1:1, 10 mL). The layers were separated and the aqueous phase was extracted with EtOAc (3×5 mL). The organic extracts were combined and then dried over MgSO$_4$, filtered and concentrated in vacuo. The crude product was purified by chromatography on silica gel (4 g column, 0-10% (0.7 M Ammonia/MeOH)/DCM) to afford the title compound (4'-(5-benzyl-2,6-dimethoxypyrimidin-4-yl)-2-chloro-2',3',4',5'-tetrahydro-[1,1'-biphenyl]-4-yl)(4-methylpiperazin-1-yl)methanone (0.130 g, 0.235 mmol, 97% yield) as a thick yellow gum. Analytical data: R$^t$ 1.94 min (Method 1); m/z 547 (M+H)$^+$ (ES$^+$).

A solution of (4'-(5-benzyl-2,6-dimethoxypyrimidin-4-yl)-2-chloro-2',3',4',5'-tetrahydro-[1,1'-biphenyl]-4-yl)(4-methylpiperazin-1-yl)methanone (Intermediate K-1c) (0.121 g, 0.221 mmol) and pyridine hydrochloride (0.256 g, 2.212 mmol) in DMSO (0.5 mL) was heated at 100° C. for 30 minutes. After cooling to room temperature the mixture was diluted with 1 M hydrochloric acid (HCl) (10 mL) and filtered through an SCX column, washing with MeOH (20 mL). The filtrate was discarded before the column was washed with 0.7 M NH$_3$ in MeOH (30 mL). The filtrate was concentrated in vacuo and the residue triturated with t-butyl methyl ether (TBME) to afford the title compound 5-benzyl-6-(2'-chloro-4'-(4-methylpiperazine-1-carbonyl)-2,3,4,5-tetrahydro-[1,1'-biphenyl]-4-yl)pyrimidine-2,4(1H,3H)-dione (0.031 g, 0.058 mmol, 26.2% yield) as an off-white solid. Analytical data: R$^t$ 1.36 min (Method 1); m/z 519 (M+H)$^+$ (ES$^+$); $^1$H NMR (400 MHz, DMSO-d$_6$) δ: 9.30 (1H, br. s), 7.41 (1H, dd), 7.27 (2H, d), 7.24-7.12 (4H, m), 7.08 (1H, m), 5.67 (1H, m), 3.72 (1H, d), 3.66-3.50 (2H, m), 2.79 (1H, m), 2.41-2.20 (6H, m), 2.19 (3H, s), 2.13 (1H, m), 1.93-1.72 (2H, m), 1.39 (1H, m) (NH not visible and 3 aliphatic protons appear under DMSO signal).

Example 42: 5-Benzyl-6-(2'-chloro-4'-(pyrrolidine-1-carbonyl)-2,3,4,5-tetrahydro-[1,1'-biphenyl]-4-yl)pyrimidine-2,4(1H,3H)-dione

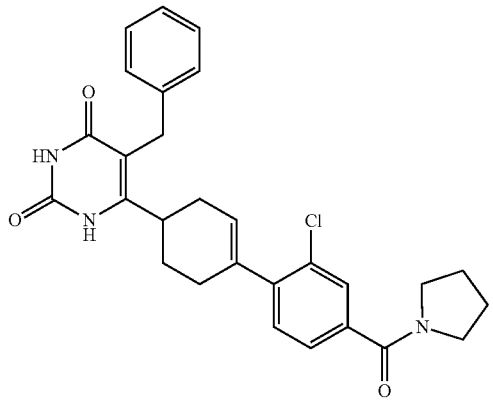 [SMILES: O=C(c1ccc(C2=CCC(c3[nH]c(=O)[nH]c(=O)c3Cc3ccccc3)CC2)c(Cl)c1)N1CCCC1]

The above compound was prepared from Intermediate K-2 with pyrrolidine according to the procedures as described in Example 41. Analytical data: $R^t$ 2.13 min (Method 1); m/z 490 (M+H)$^+$ (ES$^+$).

Example 43: 5-Benzyl-6-(4-(2-(piperidin-1-yl)pyridin-3-yl)cyclohex-3-en-1-yl)pyrimidine-2,4(1H,3H)-dione

Intermediate K-1d: 5-benzyl-4-(4-(2-chloropyridin-3-yl)cyclohex-3-en-1-yl)-2,6-dimethoxypyrimidine

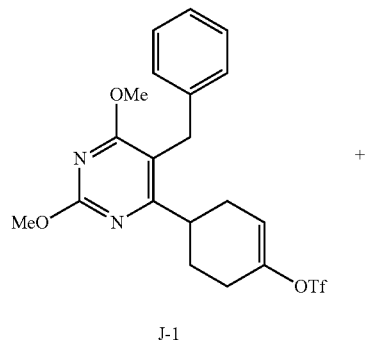

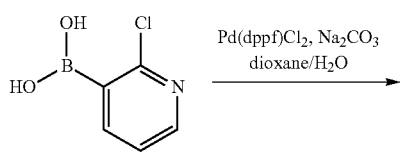

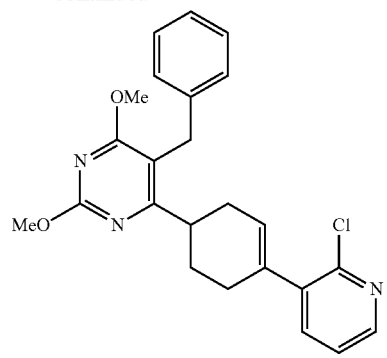

To a suspension of 4-(5-benzyl-2,6-dimethoxypyrimidin-4-yl)cyclohex-1-en-1-yl trifluoromethanesulfonate (Intermediate J-1) (0.15 g, 0.325 mmol) and (2-chloropyridin-3-yl)boronic acid (0.051 g, 0.325 mmol) in dioxane (3 mL) was added a solution of sodium carbonate (0.076 g, 0.715 mmol) in water (0.5 mL). The mixture was degassed with bubbling $N_2$ for 5 minutes. Pd(dppf)Cl$_2$ (27 mg, 0.033 mmol) was added and the mixture was heated at 80° C. for 1 hour. The reaction was cooled to room temperature and partitioned between aqueous NH$_4$Cl solution (10 ml) and EtOAc (10 ml). The layers were separated and the aqueous extracted phase was with EtOAc (2×10 mL). The organic extracts were combined, dried over MgSO$_4$, filtered and concentrated in vacuo. The crude product was purified by chromatography on silica gel (4 g column, 0-30% EtOAc/isohexane) to afford the title compound 5-benzyl-4-(4-(2-chloropyridin-3-yl)cyclohex-3-en-1-yl)-2,6-dimethoxypyrimidine (95 mg, 0.218 mmol, 67.2% yield) as a thick colorless gum. Analytical data: $R^t$ 3.02 min (Method 1); m/z 422 (M+H)$^+$ (ES$^+$).

Intermediate K-1e: 5-benzyl-2,4-dimethoxy-6-(4-(2-(piperidin-1-yl)pyridin-3-yl)cyclohex-3-en-1-yl)pyrimidine

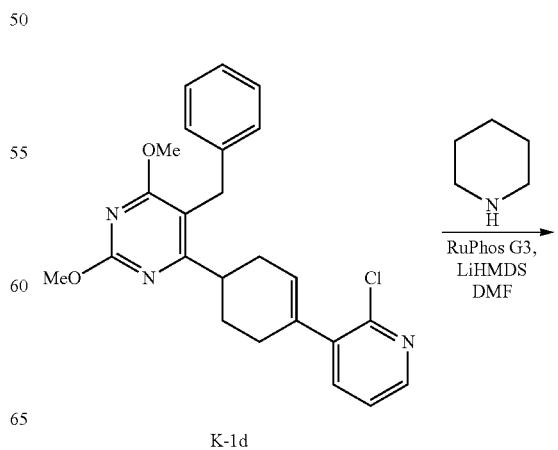

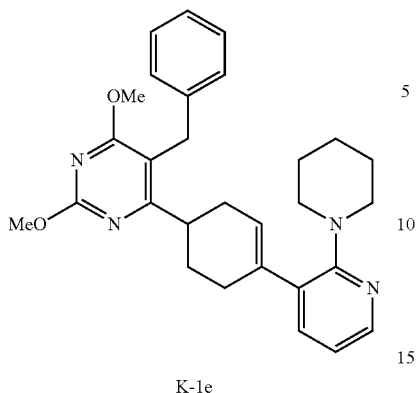

K-1e

A solution of 5-benzyl-4-(4-(2-chloropyridin-3-yl)cyclohex-3-en-1-yl)-2,6-dimethoxypyrimidine (Intermediate K-1d) (60 mg, 0.142 mmol), piperidine (12.11 mg, 0.142 mmol), Ruphos G3 (11.89 mg, 0.014 mmol) in DMF (2.5 ml) was degassed with bubbling $N_2$ for 5 min. Lithium bis(trimethylsilyl)amide (LiHMDS) (1 M in THF) (427 µl, 0.427 mmol) was added and the reaction mixture was stirred at room temperature for 30 minutes. Water (5 ml) and EtOAc (25 ml) were added. The layers were separated and the organic layer was washed with brine (4×5 ml), dried over $MgSO_4$, filtered and concentrated in vacuo. The crude product was purified by chromatography on silica gel (12 g column, 0 to 100% EtOAc in isohexane) to afford the title compound 5-benzyl-2,4-dimethoxy-6-(4-(2-(piperidin-1-yl)pyridin-3-yl)cyclohex-3-en-1-yl)pyrimidine (47 mg, 0.099 mmol, 69.5% yield) as a white solid. Analytical data: $R^t$ 1.47 min (Method 3); m/z 472 (M+H)$^+$ (ES$^+$).

5-benzyl-6-(4-(2-(piperidin-1-yl)pyridin-3-yl)cyclohex-3-en-1-yl)pyrimidine-2,4(1H,3H)-dione

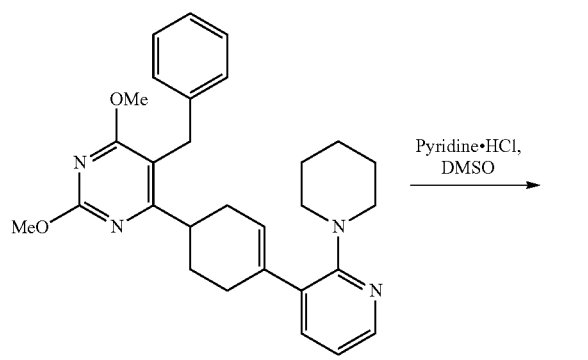

A solution of 5-benzyl-2,4-dimethoxy-6-(4-(2-(piperidin-1-yl)pyridin-3-yl)cyclohex-3-en-1-yl)pyrimidine (Intermediate K-1e) (35 mg, 0.074 mmol) and pyridine hydrochloride (86 mg, 0.744 mmol) in DMSO (0.5 ml) was heated at 100° C. for 1 hour. After cooling to room temperature, the mixture was partitioned between DCM (10 ml) and water (5 ml). The layers were separated and the aqueous phase was extracted with DCM (3×10 ml). The organic extracts were combined, filtered through a phase separator and concentrated in vacuo. The crude product was purified by chromatography on silica gel (12 g column, 0-100% EtOAc/isohexane) to afford the product. The product was repurified by chromatography on silica gel (12 g column, 0 to 100% EtOAc in isohexane) to afford 5-benzyl-6-(4-(2-(piperidin-1-yl)pyridin-3-yl)cyclohex-3-en-1-yl)pyrimidine-2,4(1H,3H)-dione (14 mg, 0.030 mmol, 40.8% yield) as a white solid. Analytical data: $R^t$ 0.89 min (Method 3); m/z 444 (M+H)$^+$ (ES$^+$); $^1$H NMR (400 MHz, DMSO-$d_6$) δ: 11.11 (s, 1H), 10.59 (s, 1H), 8.06 (dd, 1H), 7.31-7.23 (m, 3H), 7.18-7.11 (m, 3H), 6.81 (dd, 1H), 5.75 (d, 1H), 3.78 (d, 1H), 3.69 (d, 1H), 3.21-3.08 (m, 4H), 3.01-2.89 (m, 2H), 2.22-2.10 (m, 1H), 2.07-1.92 (m, 2H), 1.60-1.43 (m, 8H).

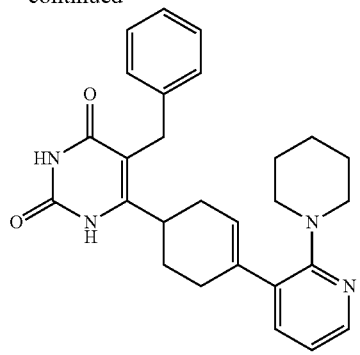

Example 44 to Example 50 and Example 113: 2-substituted 5-benzyl-6-(4-(pyridin-3-yl)cyclohex-3-en-1-yl)pyrimidine-2,4(1H,3H)-diones The following compounds as shown in Table 2 were prepared by similar methods to those described in Example 43.

TABLE 2

Example 44 to Example 50 and Example 113

| EXAMPLE | STRUCTURE | ANALYTICAL DATA |
|---|---|---|
| 44 | 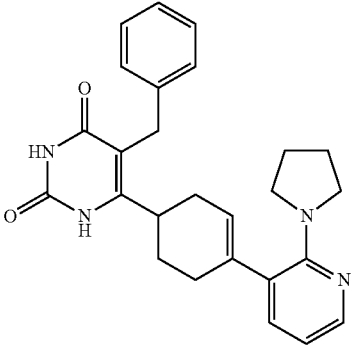<br>5-Benzyl-6-(4-(2-(pyrrolidin-1-yl)pyridin-3-yl)cyclohex-3-en-1-yl)pyrimidine-2,4(1H,3H)-dione | R$^t$ 1.29 min (Method 1); m/z 429 (M + H)$^+$ (ES$^+$) |
| 45 | 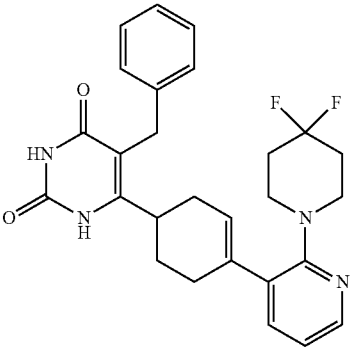<br>5-benzyl-6-(4-(2-(4,4-difluoropiperidin-1-yl)pyridin-3-yl)cyclohex-3-en-1-yl)pyrimidine-2,4(1H,3H)-dione | R$^t$ 1.95 min (Method 1); m/z 479 (M + H)$^+$ (ES$^+$) |
| 46 | 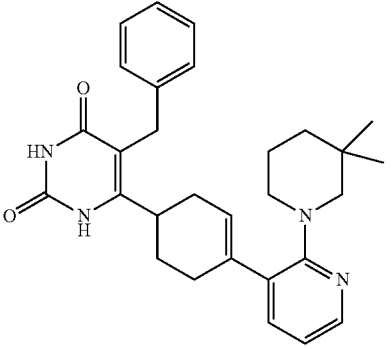<br>5-benzyl-6-(4-(2-(3,3-dimethylpiperidin-1-yl)pyridin-3-yl)cyclohex-3-en-1-yl)pyrimidine-2,4(1H,3H)-dione | R$^t$ 1.69 min (Method 1); m/z 471 (M + H)$^+$ (ES$^+$) |

TABLE 2-continued

Example 44 to Example 50 and Example 113

| EXAMPLE | STRUCTURE | ANALYTICAL DATA |
|---------|-----------|-----------------|
| 47 | 5-benzyl-6-(4-(2-((R)-3-methylpiperidin-1-yl)pyridin-3-yl)cyclohex-3-en-1-yl)pyrimidine-2,4(1H,3H)-dione | $R^t$ 1.61 min (Method 1); m/z 457 (M + H)$^+$ (ES$^+$) |
| 48 | 5-benzyl-6-(4-(2-((S)-3-methylpiperidin-1-yl)pyridin-3-yl)cyclohex-3-en-1-yl)pyrimidine-2,4(1H,3H)-dione | $R^t$ 1.60 min (Method 1); m/z 457 (M + H)$^+$ (ES$^+$) |
| 49 | 5-benzyl-6-(4-(2-((S)-3-methoxypiperidin-1-yl)pyridin-3-yl)cyclohex-3-en-1-yl)pyrimidine-2,4(1H,3H)-dione | $R^t$ 1.48 min (Method 1); m/z 473 (M + H)$^+$ (ES$^+$) |

TABLE 2-continued

Example 44 to Example 50 and Example 113

| EXAMPLE | STRUCTURE | ANALYTICAL DATA |
|---|---|---|
| 50 | 5-benzyl-6-(4-(6-methyl-2-(pyrrolidin-1-yl)pyridin-3-yl)cyclohex-3-en-1-yl)pyrimidine-2,4(1H,3H)-dione | $R^t$ 1.38 min (Method 1); m/z 443 (M + H)$^+$ (ES$^+$) |
| 113 | 5-benzyl-6-(4-(2-(pyrrolidin-1-yl)-6-(trifluoromethyl)pyridin-3-yl)cyclohex-3-en-1-yl)pyrimidine-2,4(1H,3H)-dione | $R^t$ 1.83 min (Method 3); m/z 497 (M + H)$^+$ (ES$^+$) |

Example 51: 5-((6-(Pyrrolidin-1-yl)pyridin-2-yl)methyl)-6-(4-(2-(trifluoromethyl)pyridin-3-yl)cyclohex-3-en-1-yl)pyrimidine-2,4(1H,3H)-dione, formic acid Intermediate O: Ethyl 4-(((trifluoromethyl)sulfonyl)oxy)cyclohex-3-enecarboxylate

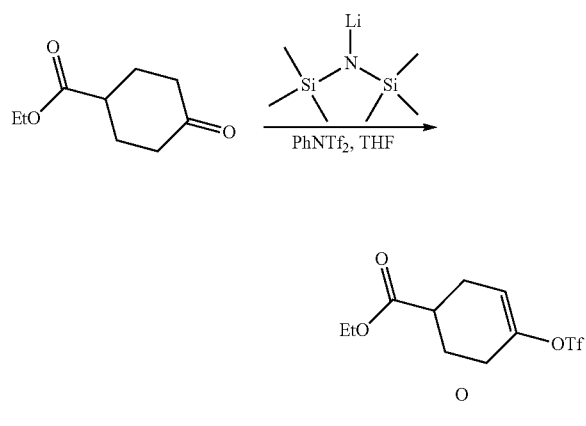

To a solution of LiHMDS (1.0 M in THF) (12.93 ml, 12.93 mmol) in THF (30 mL) at −78° C. was added dropwise ethyl 4-oxocyclohexanecarboxylate (1.873 ml, 11.75 mmol). The reaction mixture was stirred for 30 minutes and then 1,1,1-trifluoro-N-phenyl-N-((trifluoromethyl)sulfonyl)methanesulfonamide (4.62 g, 12.93 mmol) was added and the reaction mixture was warmed to room temperature and stirred overnight. The solvent was evaporated and the residue was partitioned between EtOAc (50 mL) and NaHCO$_3$ solution (50 mL) and the phases were separated. The aqueous phase was extracted with EtOAc (20 mL×2) and the combined organic phases were washed with brine (50 mL), dried over MgSO$_4$, filtered and concentrated in vacuo. The crude product was purified by chromatography on the Companion (80 g column, 0-20% EtOAc/isohexane) (Grace companion using ELSD detection) affording ethyl 4-(((trifluoromethyl)sulfonyl)oxy)cyclohex-3-enecarboxylate (1.74 g, 5.58 mmol, 47.5% yield) as a colourless oil. Analytical data: $^1$H NMR (400 MHz, DMSO-d6) δ: 5.69-5.71 (m, 1H), 4.09 (q, 2H), 2.49-2.56 (m, 1H), 2.31-2.41 (m, 4H), 2.04-2.10 (m, 1H), 1.81-1.90 (m, 1H), 1.20 (t, 3H).

Intermediate P-1: Ethyl 4-(2-(trifluoromethyl)pyridin-3-yl)cyclohex-3-enecarboxylate

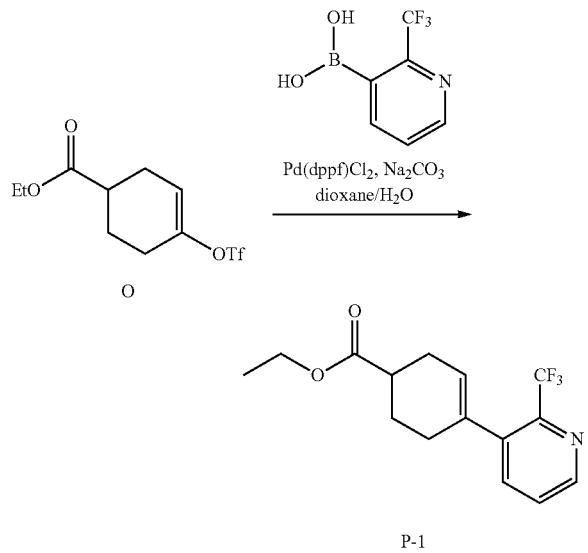

To a suspension of ethyl 4-(((trifluoromethyl)sulfonyl) oxy)cyclohex-3-enecarboxylate (Intermediate O) (800 mg, 2.65 mmol) and (2-(trifluoromethyl)pyridin-3-yl)boronic acid (505 mg, 2.65 mmol) in dioxane (20 mL) was added a solution of sodium carbonate (617 mg, 5.82 mmol) in water (3 mL). The mixture was degassed with bubbling $N_2$ for 5 minutes. 1,1'-bis(diphenylphosphino)ferrocene-palladium (II)dichloride dichloromethane complex (216 mg, 0.265 mmol) was added and the mixture was heated at 80° C. for 1 hour. The reaction was cooled to room temperature and reduced to half its initial volume in vacuo. The residue was partitioned between aq. $NH_4Cl$ solution (20 ml) and EtOAc (20 ml). The biphasic mixture was filtered through celite and the layers separated. The aqueous layer was extracted with EtOAc (2×10 mL) and the organic extracts were combined, dried over $MgSO_4$, filtered and concentrated in vacuo. The crude product was purified by chromatography on silica gel (24 g column, 0-50% EtOAc/isohexane) to afford ethyl 4-(2-(trifluoromethyl)pyridin-3-yl)cyclohex-3-enecarboxylate (536 mg, 1.737 mmol, 65.6% yield) as a yellow oil. Analytical data: $R^t$ 2.43 min (Method 1); m/z 300 (M+H)$^+$ (ES$^+$); 1H NMR (400 MHz, DMSO-d6) δ: 8.65 (d, 1H), 7.82 (d, 1H), 7.68 (dd, 1H), 5.60 (s, 1H), 4.11 (qd, 2H), 2.61-2.68 (m, 1H), 2.20-2.42 (m, 4H), 2.00-2.07 (m, 1H), 1.72-1.71 (m, 1H), 1.21 (t, 3H).

Intermediate Q-1: 4-(2-(trifluoromethyl)pyridin-3-yl)cyclohex-3-enecarboxylic Acid

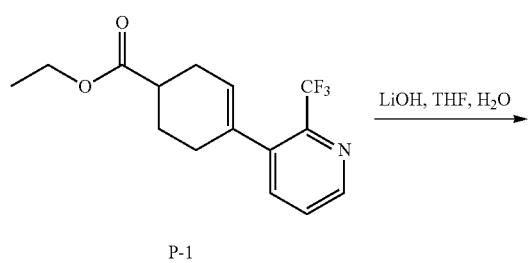

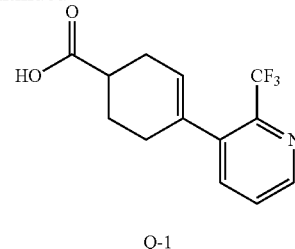

To a stirred solution of ethyl 4-(2-(trifluoromethyl)pyridin-3-yl)cyclohex-3-enecarboxylate (Intermediate P-1) (536 mg, 1.791 mmol) in THF (8 ml) was added lithium hydroxide (LiOH) (5M aqueous) (2 ml, 10.00 mmol). MeOH (2 ml) and water (2 ml) were added and stirring continued for 3 hours. The reaction was concentrated in vacuo and dried completely in a desiccator at 40° C. overnight. The residue was acidified with 1 M HCl forming a cloudy, oily suspension. The aqueous phase was extracted with EtOAc (2×20 ml) and the combined organics dried via hydrophobic frit and concentrated in vacuo to afford 4-(2-(trifluoromethyl) pyridin-3-yl)cyclohex-3-enecarboxylic acid (456 mg, 1.664 mmol, 93% yield) as a white solid. Analytical data: $R^t$ 1.88 min (Method 1); m/z 272 (M+H)$^+$ (ES$^+$).

Intermediate R-1: Ethyl 3-oxo-3-(4-(2-(trifluoromethyl)pyridin-3-yl)cyclohex-3-en-1-yl)propanoate

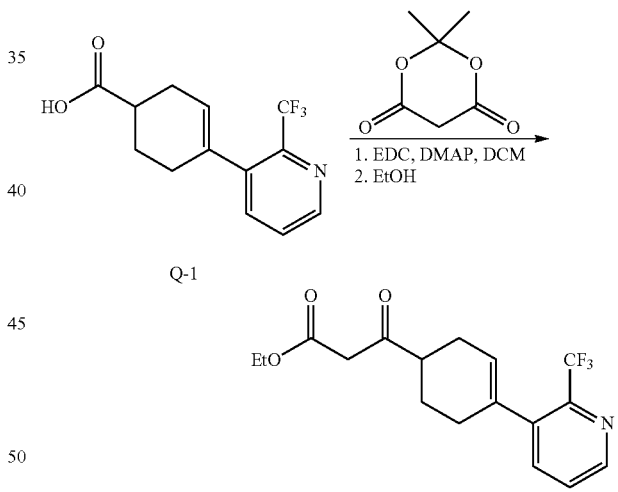

To a solution of 4-(2-(trifluoromethyl)pyridin-3-yl)cyclohex-3-enecarboxylic acid (Intermediate Q-1) (456 mg, 1.681 mmol), 2,2-dimethyl-1,3-dioxane-4,6-dione (Meldrum's acid) (267 mg, 1.849 mmol) and dimethylaminopyridine (DMAP) (226 mg, 1.849 mmol) in DCM (4 mL) at room temperature was added 1-ethyl-3(3-dimethylaminopropyl) carbodiimide (EDC) (387 mg, 2.017 mmol). The reaction mixture was stirred at room temperature for 1 hour. 1 M HCl (6 mL) was added and the phases were separated. The aqueous phase was extracted with DCM (2×4 mL) and the combined organic phases were washed with water (5 mL), brine (5 mL), filtered through a phase separator and concentrated in vacuo. The residue was dissolved in ethanol (EtOH) (5 mL), heated to 80° C. and stirred for 1.5 hour. The solvent was removed in vacuo. The crude product was purified by chromatography on silica gel (12 g column, 0-50% EtOAc/isohexane) to afford ethyl 3-oxo-3-(4-(2-(trifluoromethyl)pyridin-3-yl)cyclohex-3-en-1-yl)propanoate (492 mg, 1.297 mmol, 77% yield) as a colourless oil. Analytical data: R$^r$ 2.27 min (Method 1); m/z 342 (M+H)$^+$ (ES$^+$). 1H NMR (400 MHz, DMSO-d6) δ: 8.66 (d, 1H), 7.82 (d, 1H), 7.69 (dd, 1H), 5.60-5.64 (m, 1H), 4.12 (q, 2H), 3.76 (dd, 2H), 2.78-2.87 (m, 1H), 2.30-2.41 (m, 2H), 2.18-2.28 (m, 2H), 2.05-2.12 (m, 1H), 1.55-1.65 (m, 1H), 1.20 (t, 3H).

Intermediate S-1: Ethyl 3-oxo-2-((6-(pyrrolidin-1-yl)pyridin-2-yl)methyl)-3-(4-(2-(trifluoromethyl)pyridin-3-yl)cyclohex-3-en-1-yl)propanoate Intermediate T-1: 5-((6-(pyrrolidin-1-yl)pyridin-2-yl)methyl)-2-thioxo-6-(4-(2-(trifluoromethyl)pyridin-3-yl)cyclohex-3-en-1-yl)-2,3-dihydropyrimidin-4(1H)-one

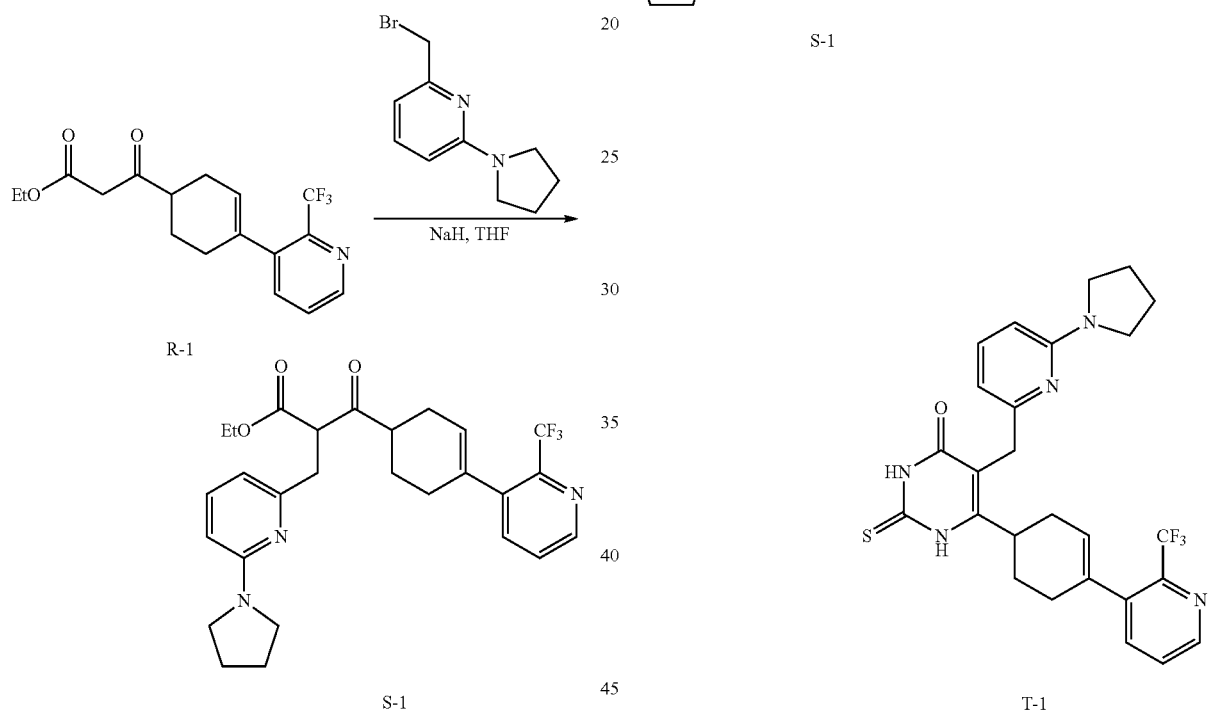

To a suspension of sodium hydride (60.5 mg, 1.514 mmol) in THF (10 mL) at 0° C. was added a solution of ethyl 3-oxo-3-(4-(2-(trifluoromethyl)pyridin-3-yl)cyclohex-3-en-1-yl)propanoate (Intermediate R-1) (492 mg, 1.441 mmol) in THF (3 mL) dropwise. The mixture was warmed to room temperature and stirred for 30 minutes. A solution of 2-(bromomethyl)-6-(pyrrolidin-1-yl)pyridine (365 mg, 1.514 mmol) was added and the mixture was heated at 60° C. for 2.5 hours. After cooling to room temperature, the reaction was quenched by addition of saturated NH$_4$Cl solution (3 mL) and extracted with EtOAc (3×3 mL). The organic extracts were combined and then dried over MgSO$_4$, filtered and concentrated in vacuo. The crude product was purified by chromatography on the Companion (24 g column, 0-30% EtOAc/isohexane) to afford ethyl 3-oxo-2-((6-(pyrrolidin-1-yl)pyridin-2-yl)methyl)-3-(4-(2-(trifluoromethyl)pyridin-3-yl)cyclohex-3-en-1-yl)propanoate (649 mg, 1.152 mmol, 80% yield) as a clear pale yellow oil. Analytical data: R$^r$ 1.79 min (Method 1); m/z 502 (M+H)$^+$ (ES$^+$).

To a stirred solution of thiourea (576 mg, 7.57 mmol) in EtOH (7 ml) was added sodium (161 mg, 6.99 mmol) and the mixture heated at reflux for 1 hour. The reaction was cooled to 0° C. and a solution of ethyl 3-oxo-2-((6-(pyrrolidin-1-yl)pyridin-2-yl)methyl)-3-(4-(2-(trifluoromethyl)pyridin-3-yl)cyclohex-3-en-1-yl)propanoate (Intermediate S-1) (649 mg, 1.165 mmol) in EtOH (3 ml) added dropwise. The resulting mixture was heated at reflux for 1.5 hours. The reaction was cooled to room temperature and the solvent removed in vacuo. The residue was partitioned between EtOAc (2×25 mL) and NH$_4$Cl (20 mL) solution. The organic phase was dried via hydrophobic frit and concentrated in vacuo. The crude product was purified by chromatography on the Companion (40 g column, 0-100% EtOAc/isohexane) to afford 5-((6-(pyrrolidin-1-yl)pyridin-2-yl)methyl)-2-thioxo-6-(4-(2-(trifluoromethyl)pyridin-3-yl)cyclohex-3-en-1-yl)-2,3-dihydropyrimidin-4(1H)-one (230 mg, 0.439 mmol, 37.7% yield) as a white solid. Analytical data: R$^r$ 1.45 min (Method 1); m/z 514 (M+H)$^+$ (ES$^+$).

5-((6-(Pyrrolidin-1-yl)pyridin-2-yl)methyl)-6-(4-(2-(trifluoromethyl)pyridin-3-yl)cyclohex-3-en-1-yl) pyrimidine-2,4(1H,3H)-dione, Formic Acid Salt

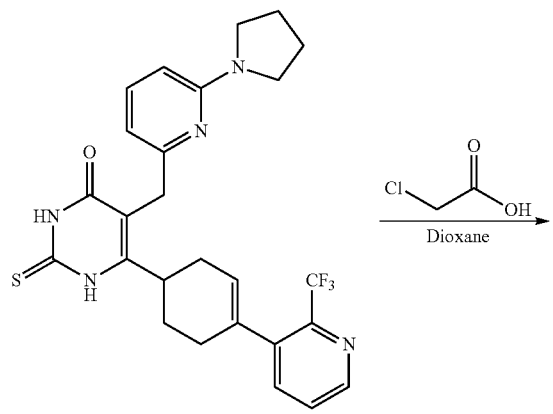

T-1

To a stirred solution of 5-((6-(pyrrolidin-1-yl)pyridin-2-yl)methyl)-2-thioxo-6-(4-(2-(trifluoromethyl)pyridin-3-yl)cyclohex-3-en-1-yl)-2,3-dihydropyrimidin-4(1H)-one (230 mg, 0.448 mmol) in dioxane (10 ml) was added a solution of 2-chloroacetic acid (423 mg, 4.48 mmol) in water (2.5 ml) and the mixture stirred at 100° C. over the weekend. The reaction was cooled to room temperature and partitioned between NaHCO$_3$ (20 mL) solution and DCM (2×15 mL). The organic phase was dried via hydrophobic frit and concentrated in vacuo affording a red foam. The crude product was purified by preparative HPLC (Waters, Acidic (0.1% Formic acid), Acidic, Waters X-Select Prep-C18, 5 µm, 19×50 mm column, 10-40% MeCN in Water) to afford 5-((6-(pyrrolidin-1-yl)pyridin-2-yl)methyl)-6-(4-(2-(trifluoromethyl)pyridin-3-yl)cyclohex-3-en-1-yl)pyrimidine-2,4 (1H,3H)-dione, formic acid salt (100 mg, 0.180 mmol, 40.3% yield) as a pale yellow solid. Analytical data: R$^t$ 1.33 min (Method 1); m/z 498 (M+H)$^+$ (ES$^+$). $^1$H NMR in DMSO-d6 1648-66-1 was consistent with product structure at 98% purity. $^1$H NMR (400 MHz, DMSO-d$_6$) δ: 11.06 (s, 1H), 10.52 (s, 1H), 8.66 (d, 1H), 8.18 (s, 1H), 7.78 (d, 1H), 7.69 (dd, 1H), 7.35 (t, 1H), 6.38 (d, 1H), 6.21 (d, 1H), 5.59 (d, 1H), 3.66 (s, 2H), 3.26-3.38 (m, 5H), 2.43-2.46 (m, 1H), 2.29-2.35 (m, 1H), 2.04-2.20 (m, 3H), 1.85-1.90 (m, 4H), 1.61-1.64 (m, 1H). Example 51 appears to be a partial formate salt.

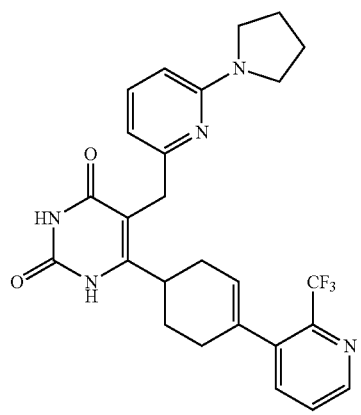

Example 52 to Example 84: 4-substituted 5-benzyl-6-(cyclohex-3-en-1-yl)pyrimidine-2,4(1H,3H)-diones The following compounds as shown in Table 3 were prepared by similar methods to those as described in Example 1.

TABLE 3

Example 52 to Example 84

| EXAMPLE | STRUCTURE | ANALYTICAL DATA |
|---|---|---|
| 52 | 5-benzyl-6-(2'-chloro-4'-isopropoxy-2,3,4,5-tetrahydro-[1,1'-biphenyl]-4-yl)pyrimidine-2,4(1H,3H)-dione | R$^t$ 1.77 min (Method 3); m/z 451 (M + H)$^+$ (ES$^+$) |

TABLE 3-continued

Example 52 to Example 84

| EXAMPLE | STRUCTURE | ANALYTICAL DATA |
|---|---|---|
| 53 | 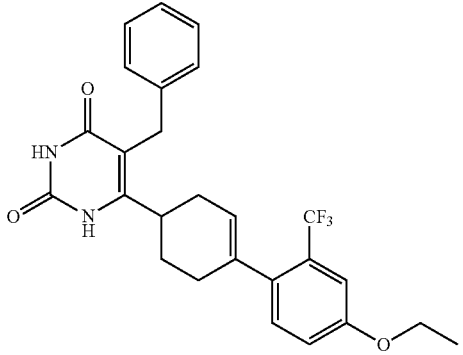  5-benzyl-6-(4'-ethoxy-2'-(trifluoromethyl)-2,3,4,5-tetrahydro-[1,1'-biphenyl]-4-yl)pyrimidine-2,4(1H,3H)-dione | $R^t$ 1.76 min (Method 3); m/z 471 (M + H)$^+$ (ES$^+$) |
| 54 | 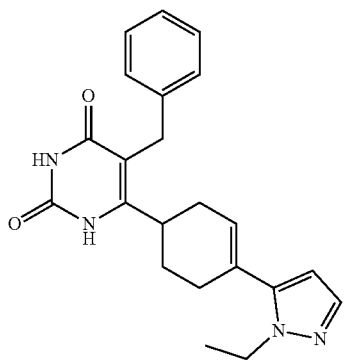  5-benzyl-6-(4-(1-ethyl-1H-pyrazol-5-yl)-cyclohex-3-en-1-yl)pyrimidine-2,4(1H,3H)-dione | $R^t$ 1.15 min (Method 3); m/z 377 (M + H)$^+$ (ES$^+$) |
| 55 | 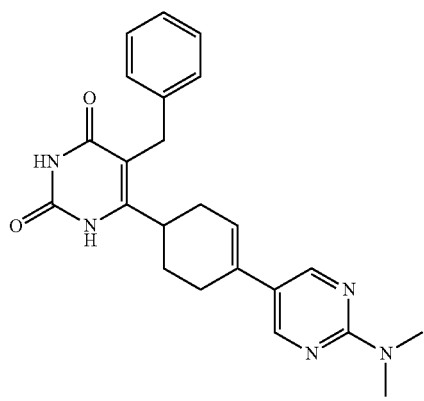  5-benzyl-6-(4-(2-(dimethylamino)pyrimidin-5-yl)-cyclohex-3-en-1-yl)pyrimidine-2,4(1H,3H)-dione | $R^t$ 1.75 min (Method 1); m/z 404 (MH)$^+$ (ES$^+$) |

TABLE 3-continued

Example 52 to Example 84

| EXAMPLE | STRUCTURE | ANALYTICAL DATA |
|---|---|---|
| 56 | 5-benzyl-6-(4-(2-(trifluoromethyl)pyridin-3-yl)-cyclohex-3-en-1-yl)pyrimidine-2,4(1H,3H)-dione | $R^t$ 2.19 min (Method 3); m/z 428 (M + H)$^+$ (ES$^+$) |
| 57 | 5-benzyl-6-(4-(1-methyl-1H-indazol-6-yl)cyclohex-3-en-1-yl)pyrimidine-2,4(1H,3H)-dione | $R^t$ 1.36 min (Method 3); m/z 413 (M + H)$^+$ (ES$^+$) |
| 58 | 5-benzyl-6-(4-(1,3-dimethyl-1H-pyrazol-4-yl)cyclohex-3-en-1-yl)pyrimidine-2,4(1H,3H)-dione | $R^t$ 1.11 min (Method 3); m/z 377 (M + H)$^+$ (ES$^+$) |

TABLE 3-continued

Example 52 to Example 84

| EXAMPLE | STRUCTURE | ANALYTICAL DATA |
|---|---|---|
| 59 | 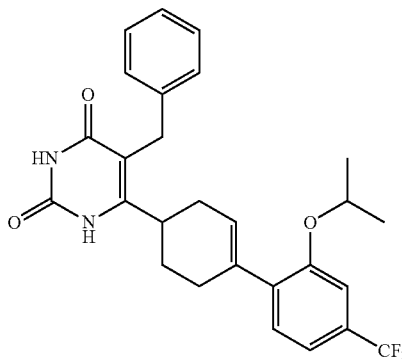<br>5-benzyl-6-(2'-isopropoxy-4'-(trifluoromethyl)-2,3,4,5-tetrahydro-[1,1'-biphenyl]-4-yl)pyrimidine-2,4(1H,3H)-dione | $R^t$ 1.82 min (Method 3);<br>m/z 485 (M + H)$^+$ (ES$^+$) |
| 60 | 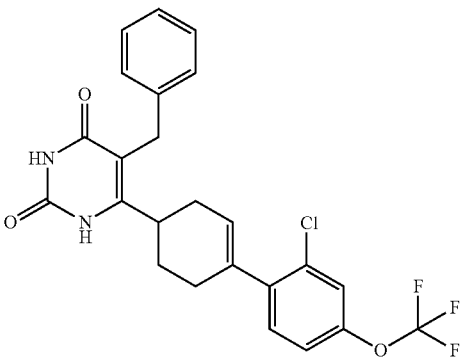<br>5-benzyl-6-(2'-chloro-4'-(trifluoromethyl)-2,3,4,5-tetrahydro-[1,1'-biphenyl]-4-yl)pyrimidine-2,4(1H,3H)-dione | $R^t$ 1.80 min (Method 3);<br>m/z 477 (M + H)$^+$ (ES$^+$) |
| 61 | 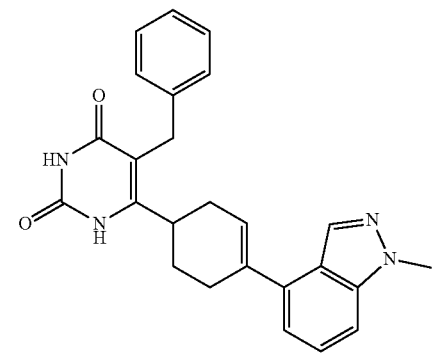<br>5-benzyl-6-(4-(1-methyl-1H-indazol-4-yl)cyclohex-3-en-1-yl)pyrimidine-2,4(1H,3H)-dione | $R^t$ 1.36 min (Method 3);<br>m/z 413 (M + H)$^+$ (ES$^+$) |

TABLE 3-continued

Example 52 to Example 84

| EXAMPLE | STRUCTURE | ANALYTICAL DATA |
| --- | --- | --- |
| 62 | 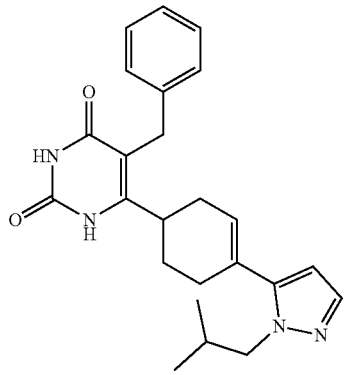<br>5-benzyl-6-(4-(1-isobutyl-1H-pyrazol-5-yl)<br>cyclohex-3-en-1-yl)pyrimidine-2,4(1H,3H)-dione | $R^t$ 1.32 min (Method 3);<br>m/z 405 (M + H)$^+$ (ES$^+$) |
| 63 | 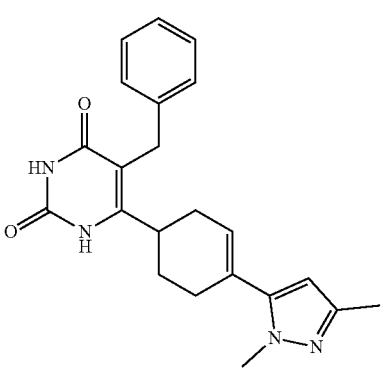<br>5-benzyl-6-(4-(1,3-dimethyl-1H-pyrazol-5-yl)<br>cyclohex-3-en-1-yl)pyrimidine-2,4(1H,3H)-dione | $R^t$ 1.13 min (Method 3);<br>m/z 377 (M + H)$^+$ (ES$^+$) |
| 64 | 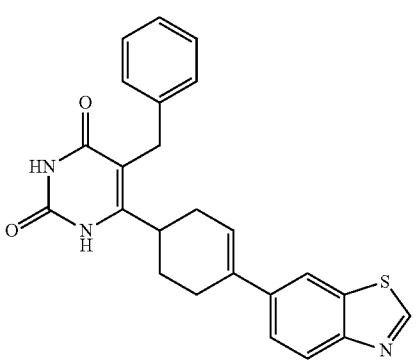<br>6-(4-(benzo[d]thiazol-6-yl)<br>cyclohex-3-en-1-yl)-5-benzylpyrimidine-<br>2,4(1H,3H)-dione | $R^t$ 1.36 min (Method 3);<br>m/z 416 (M + H)$^+$ (ES$^+$) |

TABLE 3-continued

Example 52 to Example 84

| EXAMPLE | STRUCTURE | ANALYTICAL DATA |
| --- | --- | --- |
| 65 | 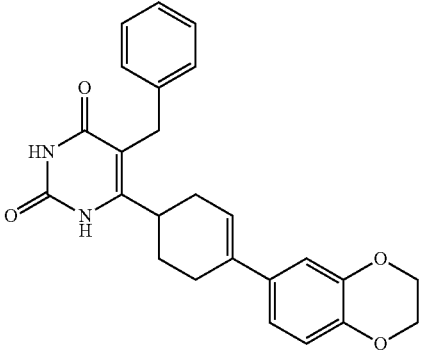<br>5-benzyl-6-(4-(2,3-dihydrobenzo[b][1,4]dioxin-6-yl)cyclohex-3-en-1-yl)pyrimidine-2,4(1H,3H)-dione | $R^t$ 1.43 min (Method 3); m/z 417 (M + H)$^+$ (ES$^+$) |
| 66 | 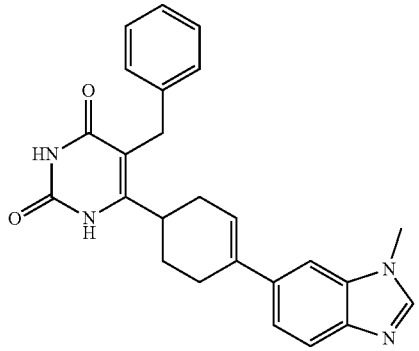<br>5-benzyl-6-(4-(1-methyl-1H-benzo[d]imidazol-6-yl)cyclohex-3-en-1-yl)pyrimidine-2,4(1H,3H)-dione | $R^t$ 0.80 min (Method 3); m/z 413 (M + H)$^+$ (ES$^+$) |
| 67 | 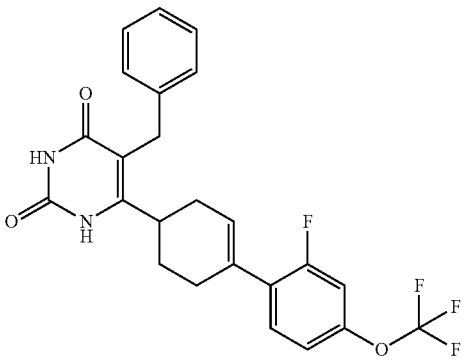<br>5-benzyl-6-(2'-fluoro-4'-(trifluoromethoxy)-2,3,4,5-tetrahydro-[1,1'-biphenyl]-4-yl)pyrimidine-2,4(1H,3H)-dione | $R^t$ 1.72 min (Method 3); m/z 461 (M + H)$^+$ (ES$^+$) |

TABLE 3-continued

Example 52 to Example 84

| EXAMPLE | STRUCTURE | ANALYTICAL DATA |
| --- | --- | --- |
| 68 | 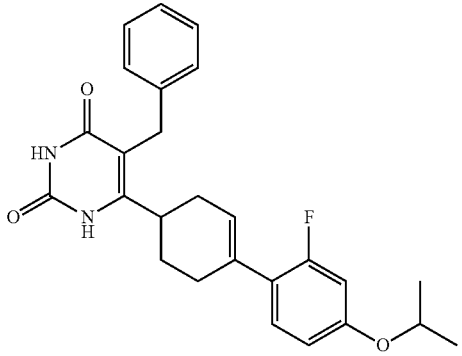<br>5-benzyl-6-(2'-fluoro-4'-isopropoxy-2,3,4,5-tetrahydro-[1,1'-biphenyl]-4-yl)pyrimidine-2,4(1H,3H)-dione | $R^t$ 2.37 min (Method 1); m/z 435 (M + H)$^+$ (ES$^+$) |
| 69 | 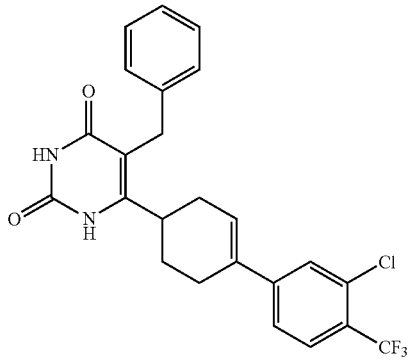<br>5-benzyl-6-(3'-chloro-4'-(trifluoromethyl)-2,3,4,5-tetrahydro-[1,1'-biphenyl]-4-yl)pyrimidine-2,4(1H,3H)-dione | $R^t$ 2.64 min (Method 1); m/z 461 (M + H)$^+$ (ES$^+$) |
| 70 | 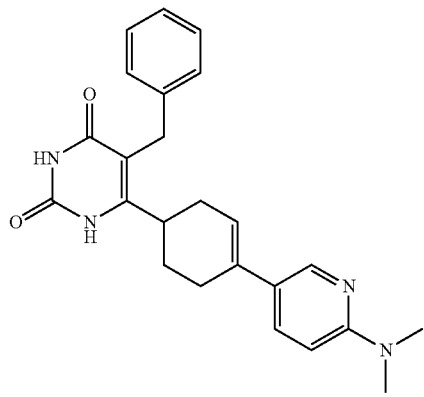<br>5-benzyl-6-(4-(6-(dimethylamino)pyridin-3-yl)cyclohex-3-en-1-yl)pyrimidine-2,4(1H,3H)-dione | $R^t$ 1.20 min (Method 1); m/z 403 (M + H)$^+$ (ES$^+$) |

TABLE 3-continued

Example 52 to Example 84

| EXAMPLE | STRUCTURE | ANALYTICAL DATA |
|---|---|---|
| 71 | 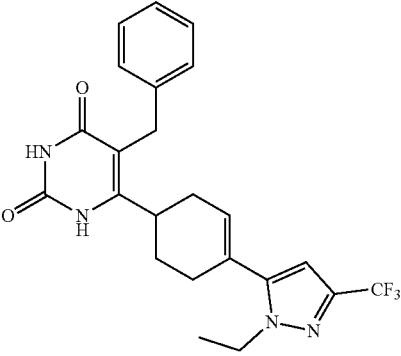<br>5-benzyl-6-(4-(1-ethyl-3-(trifluoromethyl)-1H-pyrazol-5-yl)cyclohex-3-en-1-yl)pyrimidine-2,4(1H,3H)-dione | $R^t$ 1.49 min (Method 3);<br>m/z 445 (M + H)$^+$ (ES$^+$) |
| 72 | 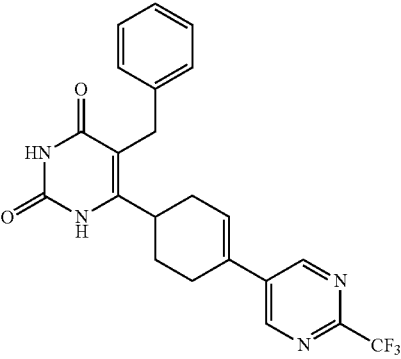<br>5-benzyl-6-(4-(2-(trifluoromethyl)pyrimidin-5-yl)cyclohex-3-en-1-yl)pyrimidine-2,4(1H,3H)-dione | $R^t$ 1.37 min (Method 3);<br>m/z 429 (M + H)$^+$ (ES$^+$) |
| 73 | 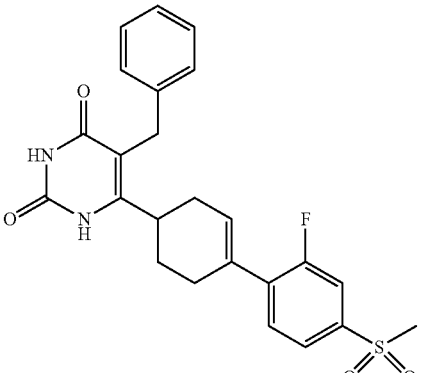<br>5-benzyl-6-(2'-fluoro-4'-(methylsulfonyl)-2,3,4,5-tetrahydro-[1,1'-biphenyl]-4-yl)pyrimidine-2,4(1H,3H)-dione | $R^t$ 1.27 min (Method 3);<br>m/z 455 (M + H)$^+$ (ES$^+$) |

TABLE 3-continued

Example 52 to Example 84

| EXAMPLE | STRUCTURE | ANALYTICAL DATA |
|---|---|---|
| 74 | 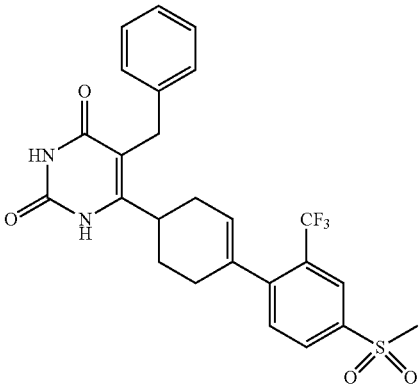<br>5-benzyl-6-(4'-(methylsulfonyl)-2'-(trifluoromethyl)-2,3,4,5-tetrahydro-[1,1'-biphenyl]-4-yl)pyrimidine-2,4(1H,3H)-dione | R' 1.36 min (Method 3);<br>m/z 505 (M + H)+ (ES+) |
| 75 | 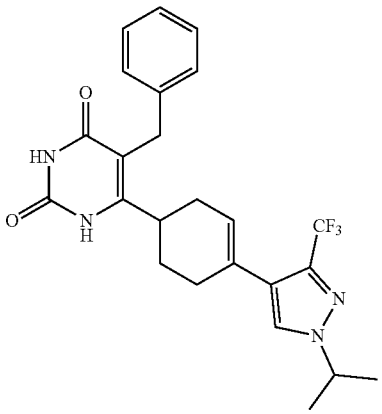<br>5-benzyl-6-(4-(1-isopropyl-3-(trifluoromethyl)-1H-pyrazol-4-yl)cyclohex-3-en-1-yl)pyrimidine-2,4(1H,3H)-dione | R' 1.54 min (Method 3);<br>m/z 459 (M + H)+ (ES+) |
| 76 | 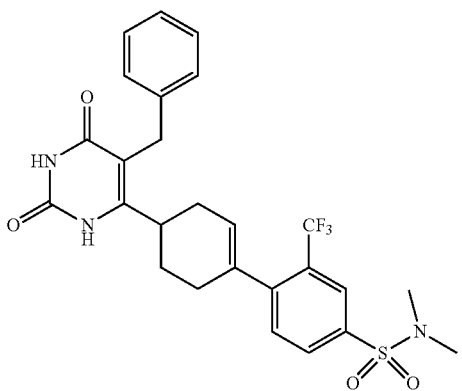<br>4'-(5-benzyl-2,6-dioxo-1,2,3,6-tetrahydropyrimidin-4-yl)-N,N-dimethyl-2-(trifluoromethyl)-2',3',4',5'-tetrahydro-[1,1'-biphenyl]-4-sulfonamide | R' 1.82 min (Method 3);<br>m/z 467 (M + H)+ (ES+) |

TABLE 3-continued

Example 52 to Example 84

| EXAMPLE | STRUCTURE | ANALYTICAL DATA |
| --- | --- | --- |
| 77 | 5-benzyl-6-(4-(1-methyl-3-(trifluoromethyl)-1H-pyrazol-4-yl)cyclohex-3-en-1-yl)pyrimidine-2,4(1H,3H)-dione | R$^t$ 1.36 min (Method 3); m/z 431 (M + H)$^+$ (ES$^+$) |
| 78 | 5-benzyl-6-(4'-ethoxy-2'-fluoro-2,3,4,5-tetrahydro-[1,1'-biphenyl]-4-yl)pyrimidine-2,4(1H,3H)-dione | R$^t$ 1.63 min (Method 3); m/z 421 (M + H)$^+$ (ES$^+$) |
| 79 | 5-benzyl-6-(3'-chloro-4'-ethoxy-2'-fluoro-2,3,4,5-tetrahydro-[1,1'-biphenyl]-4-yl)pyrimidine-2,4(1H,3H)-dione | R$^t$ 1.70 min (Method 3); m/z 455 (M + H)$^+$ (ES$^+$) |

TABLE 3-continued

Example 52 to Example 84

| EXAMPLE | STRUCTURE | ANALYTICAL DATA |
|---|---|---|
| 80 | 5-benzyl-6-(4-(1,3,5-trimethyl-1H-pyrazol-4-yl)cyclohex-3-en-1-yl)pyrimidine-2,4(1H,3H)-dione | R$^t$ 1.06 min (Method 3); m/z 391 (M + H)$^+$ (ES$^+$) |
| 81 | 5-benzyl-6-(4'-chloro-2'-fluoro-2,3,4,5-tetrahydro-[1,1'-biphenyl]-4-yl)pyrimidine-2,4(1H,3H)-dione | R$^t$ 1.68 min (Method 3); m/z 411 (M + H)$^+$ (ES$^+$) |
| 82 | 5-benzyl-6-(2'-chloro-4'-ethoxy-2,3,4,5-tetrahydro-[1,1'-biphenyl]-4-yl)pyrimidine-2,4(1H,3H)-dione | R$^t$ 1.71 min (Method 3); m/z 437 (M + H)$^+$ (ES$^+$) |

TABLE 3-continued

Example 52 to Example 84

| EXAMPLE | STRUCTURE | ANALYTICAL DATA |
| --- | --- | --- |
| 83 | 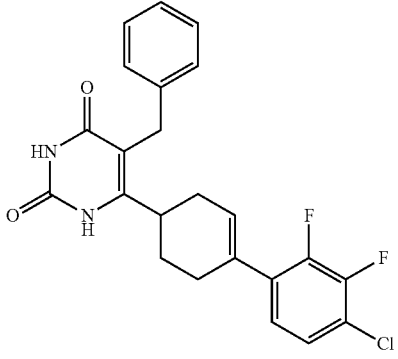<br>5-benzyl-6-(4'-chloro-2',3'-difluoro-2,3,4,5-tetrahydro-[1,1'-biphenyl]-4-yl)pyrimidine-2,4(1H,3H)-dione | $R^t$ 1.70 min (Method 3); m/z 429 (M + H)$^+$ (ES$^+$) |
| 84 | 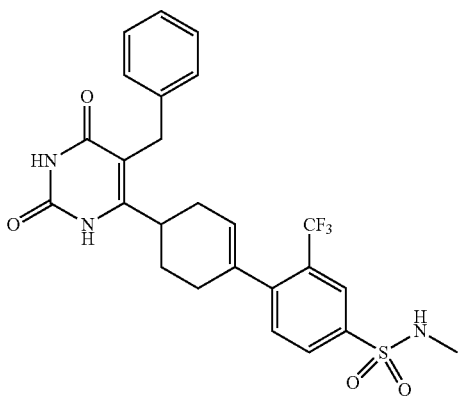<br>4'-(5-benzyl-2,6-dioxo-1,2,3,6-tetrahydropyrimidin-4-yl)-N-methyl-2-(trifluoromethyl)-2',3',4',5'-tetrahydro-[1,1'-biphenyl]-4-sulfonamide | $R^t$ 1.38 min (Method 3); m/z 520 (M + H)$^+$ (ES$^+$) |
| 118 | 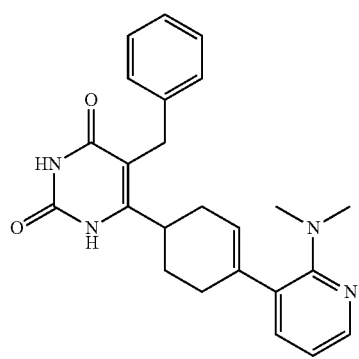<br>5-benzyl-6-(4-(2-(dimethylamino)pyridin-3-yl)cyclohex-3-en-1-yl)pyrimidine-2,4(1H,3H)-dione | $R^t$ 1.27 min (Method 1); m/z 403 (M + H)$^+$ (ES$^+$) |

Example 85: 5-benzyl-6-(2'-chloro-4'-(cyclopropyl-methoxy)-2,3,4,5-tetrahydro-[1,1'-biphenyl]-4-yl)pyrimidine-2,4(1H,3H)-dione Intermediate V-1: 1-bromo-4-(cyclopropylmethoxy)-2-(trifluoromethyl)benzene

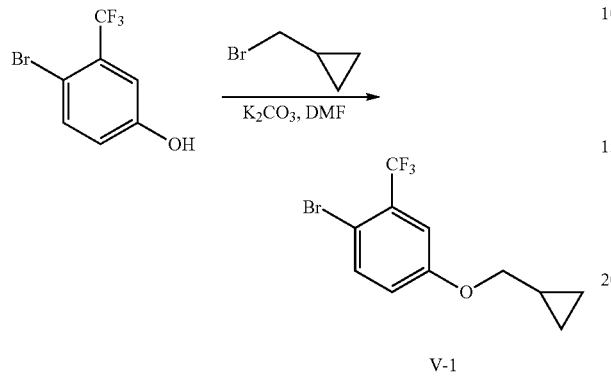

To a solution of 4-bromo-3-(trifluoromethyl)phenol (500 mg, 2.075 mmol) in DMF (2 mL) was added $K_2CO_3$ (860 mg, 6.22 mmol) and (bromomethyl)cyclopropane (402 µl, 4.15 mmol) and the mixture was warmed to 50° C. overnight. The reaction was cooled to room temperature and then partitioned between EtOAc (2×25 mL) and water (25 mL), the organics were washed with NaOH (2 M, 2×10 mL), brine (2*10 mL), dried over $MgSO_4$ and then concentrated in vacuo to give the crude product. The crude product was purified by chromatography on silica gel (40 g cartridge, 0-50% EtOAc/isohexane) to afford 1-bromo-4-(cyclopropylmethoxy)-2-(trifluoromethyl)benzene (0.357 g, 1.198 mmol, 57.7% yield) as a clear oil. Analytical data: $R^t$ 2.86 min (Method 1); no mass observed.

Intermediate V-2: 1-bromo-2-chloro-4-cyclopropoxybenzene

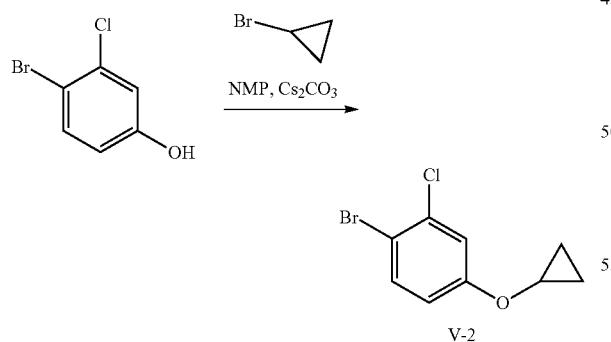

To a solution of 4-bromo-3-chlorophenol (250 mg, 1.205 mmol) in NMP (5 mL) was added cesium carbonate (1178 mg, 3.62 mmol) and bromocyclopropane (729 mg, 6.03 mmol) and the reaction was heated to 150° C. overnight. The reaction was cooled, partitioned between $NaHCO_3$ (2×25 mL) and EtOAc (2×25 mL), the organics were then washed with brine (2×10 mL), dried over $MgSO_4$ and concentrated in vacuo to give the crude product The crude product was purified by chromatography on silica gel (12 g cartridge, 0-50% EtOAc/isohexane) to afford 1-bromo-2-chloro-4-cyclopropoxybenzene (208 mg, 0.815 mmol, 67.6% yield) as a clear oil. Analytical data: $R^t$ 1.82 min (Method 3); no mass observed.

Intermediate V-3: 2-bromo-N,N-dimethyl-5-(trifluoromethyl)benzenesulfonamide

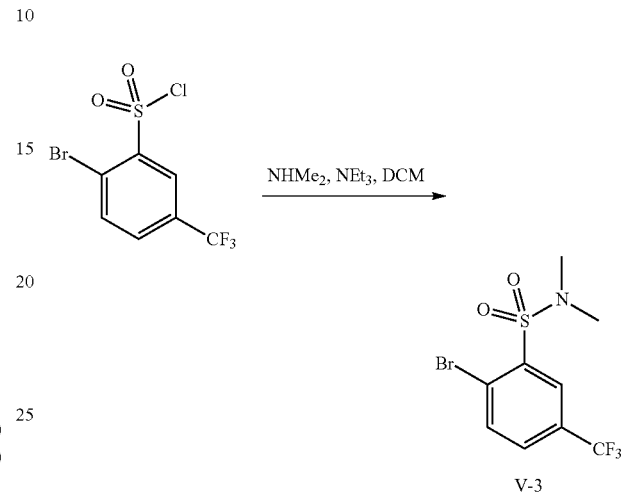

To a solution of 2-bromo-5-(trifluoromethyl)benzene-1-sulfonyl chloride (400 mg, 1.236 mmol) in DCM (6 mL) was added triethylamine (862 µl, 6.18 mmol) and dimethylamine (2 M in THF) (1236 µl, 2.473 mmol). The resultant yellow solution was stirred at room temperature for 18 hours. The reaction mixture was quenched with a saturated solution of $NaHCO_3$ (10 mL), passed through a hydrophobic frit and extracted with DCM (2×10 mL). The organic layers were combined and concentrated in vacuo. The crude product was purified by chromatography on silica gel (40 g cartridge, 0-50% EtOAc/isohexane) to afford 2-bromo-N,N-dimethyl-5-(trifluoromethyl)benzenesulfonamide (400 mg, 1.183 mmol, 96% yield) as a yellow solid. Analytical data: $R^t$ 1.50 min (Method 3); no mass observed.

Intermediate V-4: 4-bromo-3-chloro-N,N-dimethylbenzenesulfonamide

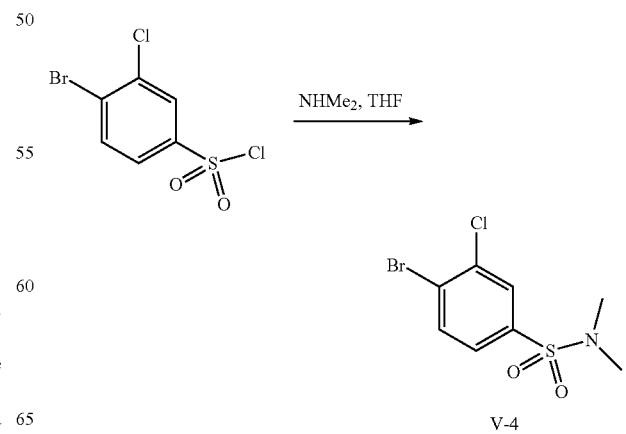

4-bromo-3-chlorobenzene-1-sulfonyl chloride (200 mg, 0.690 mmol) was dissolved in a solution of dimethylamine (2 M in THF) (2 mL, 4.00 mmol) and stirred at rt for 3 h. The mixture was diluted with DCM (20 mL) and extracted with water (3×10 mL) and brine (10 mL). The organic phase was dried by passing through a hydrophobic frit then concentrated in vacuo. The crude product was purified by chromatography on silica gel (12 g cartridge, 0-50% EtOAc/isohexane) to afford 4-bromo-3-chloro-N,N-dimethylbenzenesulfonamide (182 mg, 0.610 mmol, 88% yield) as a colourless crystalline solid. Analytical data: $R^t$ 1.44 min (Method 3); no mass observed.

Intermediate V-5: 4-bromo-3,5-difluoro-N,N-dimethylbenzenesulfonamide

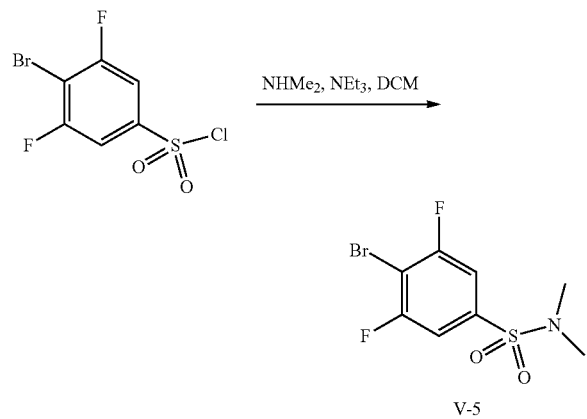

To a solution of 4-bromo-3,5-difluorobenzene-1-sulfonyl chloride (500 mg, 1.715 mmol) in DCM (6 mL) were added triethylamine (1195 μl, 8.58 mmol) and dimethylamine (2 M in THF) (1715 μl, 3.43 mmol). The resultant yellow solution was stirred at RT for 16 h. The reaction mixtures were quenched with a saturated solution of NaHCO₃ (10 mL), passed through a hydrophobic frit and extracted with DCM (2×10 mL). The organic layers were combined and the solvent was removed under reduced pressure to afford a yellow residue. The crude products were purified by chromatography on silica gel (80 g cartridge, 0-50% EtOAc/isohexane) to afford 4-bromo-3,5-difluoro-N,N-dimethylbenzenesulfonamide (420 mg, 1.374 mmol, 80% yield) as a flocculent white solid. Analytical data: $R^t$ 1.42 min (Method 3); no mass observed.

Intermediate V-6: 2-bromo-5-(ethylsulfonyl)-1,3-difluorobenzene

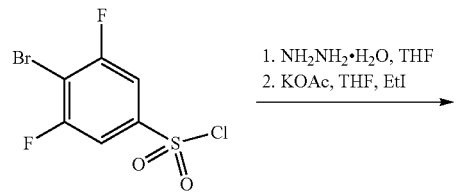

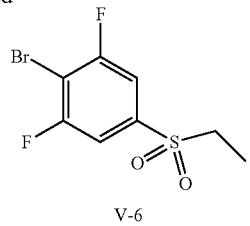

To a solution of 4-bromo-3,5-difluorobenzene-1-sulfonyl chloride (250 mg, 0.858 mmol) in THF (5 mL) at 0° C. was added a 35 wt % solution of hydrazine (389 μl, 4.29 mmol) in water. The resultant cloudy solution was stirred at room temperature for 16 hours. The mixture was diluted with EtOAc (20 mL) and washed with water (3×5 mL). The combined organics were dried by passing through a hydrophobic frit and concentrated in vacuo to give crude 4-bromo-3,5-difluorobenzenesulfonohydrazide as a white solid. Half the solid was dissolved in EtOH (10 mL) and potassium acetate (673 mg, 6.86 mmol) and iodoethane (345 μl, 4.29 mmol) were added. The colourless reaction mixture was heated to reflux for 16 hours. The mixture was cooled to room temperature and absorbed onto silica gel. The crude product was purified by chromatography on silica gel (24 g cartridge, 0-50% EtOAc/isohexane) to afford 2-bromo-5-(ethylsulfonyl)-1,3-difluorobenzene (100 mg, 0.345 mmol, 40.2% yield) as a white solid. Analytical data: $R^t$ 1.30 min (Method 3); no mass observed.

Intermediate K-1f: 5-benzyl-4-(2'-chloro-4'-(cyclopropylmethoxy)-2,3,4,5-tetrahydro-[1,1'-biphenyl]-4-yl)-2,6-dimethoxypyrimidine

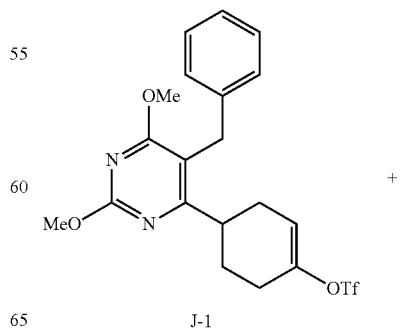

166

5-benzyl-6-(2'-chloro-4'-(cyclopropylmethoxy)-2,3,4,5-tetrahydro-[1,1'-biphenyl]-4-yl)pyrimidine-2,4(1H,3H)-dione

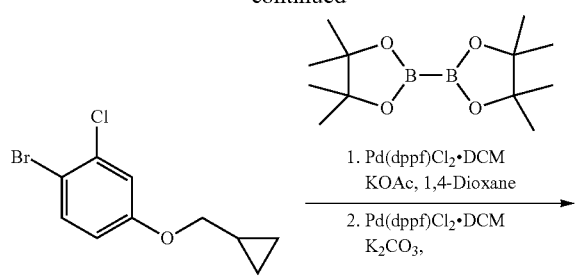

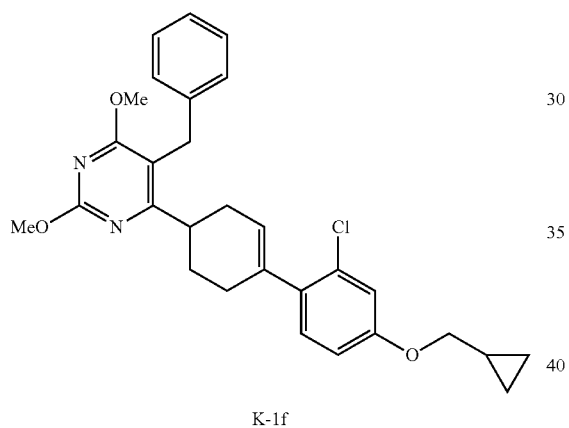

K-1f

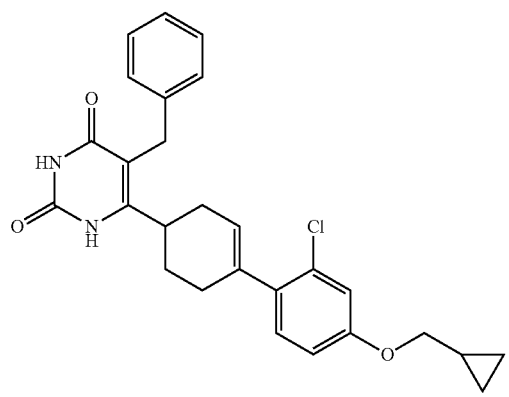

1-bromo-2-chloro-4-(cyclopropylmethoxy)benzene (0.03 g, 0.108 mmol), bis(pinacolato)diboron (0.03 g, 0.118 mmol), potassium acetate (0.03 g, 0.306 mmol), and Pd(dppf)Cl$_2$·DCM (0.005 g, 6.12 μmol) were suspended in 1,4-dioxane (3 mL). The mixture was evacuated and backfilled with nitrogen (3×) then heated to 90° C. overnight. The mixture was cooled to room temperature. A solution of 4-(5-benzyl-2,6-dimethoxypyrimidin-4-yl)cyclohex-1-en-1-yl trifluoromethanesulfonate (Intermediate J-1) (0.035 g, 0.076 mmol) in dioxane (1 mL) and a solution of K$_2$CO$_3$ (0.045 g, 0.326 mmol) in water (0.5 mL) was then added followed by a second portion of Pd(dppf)Cl$_2$·DCM (0.005 g, 6.12 μmol). The mixture was evacuated and backfilled with nitrogen (3×) then heated to 90° C. (bath temperature) for 1 hour. After cooling to room temperature, the mixture was absorbed directly onto silica gel and purified by chromatography on silica gel (12 g cartridge, 0-30% EtOAc/isohexane) to afford 5-benzyl-4-(2'-chloro-4'-(cyclopropylmethoxy)-2,3,4,5-tetrahydro-[1,1'-biphenyl]-4-yl)-2,6-dimethoxypyrimidine (11 mg, 0.022 mmol, 29.3% yield) as a colourless oil. Analytical data: R$^t$ 2.34 min (Method 3); m/z 492 (M+H)$^+$ (ES$^+$).

To a stirred solution of 5-benzyl-4-(2'-chloro-4'-(cyclopropylmethoxy)-2,3,4,5-tetrahydro-[1,1'-biphenyl]-4-yl)-2,6-dimethoxypyrimidine (Intermediate K-1f) (10 mg, 0.020 mmol) in DMSO (1 mL) was added pyridine hydrochloride (30 mg, 0.260 mmol) and the reaction was heated to 100° C. for 2 hours. Water (10 mL) was added and the mixture was stirred for 15 minutes. The resulting precipitate was isolated by filtration and dried overnight in vacuo to give 5-benzyl-6-(2'-chloro-4'-(cyclopropylmethoxy)-2,3,4,5-tetrahydro-[1,1'-biphenyl]-4-yl)pyrimidine-2,4(1H,3H)-dione (5.8 mg, 0.012 mmol, 59.1% yield) as an off white solid. Analytical data: R$^t$ 1.77 min (Method 3); m/z 463 (M+H)$^+$ (ES$^+$). $^1$H NMR (500 MHz, DMSO-d$_6$) δ: 11.12 (s, 1H), 10.49 (s, 1H), 7.32-7.23 (m, 2H), 7.20-7.14 (m, 3H), 7.10 (d, J=8.5 Hz, 1H), 6.97 (d, J=2.6 Hz, 1H), 6.86 (dd, J=8.5, 2.6 Hz, 1H), 5.58-5.54 (m, 1H), 3.82 (d, J=7.1 Hz, 2H), 3.77 (d, J=15.7 Hz, 1H), 3.69 (d, J=15.7 Hz, 1H), 3.06-2.89 (m, 1H), 2.48-2.40 (m, 1H), 2.29-2.13 (m, 2H), 2.10-1.90 (m, 2H), 1.51-1.43 (m, 1H), 1.29-1.15 (m, 1H), 0.60-0.54 (m, 2H), 0.35-0.29 (m, 2H).

The following compounds as shown in Table 4 were prepared by similar methods to those described in Example 85.

TABLE 4

Example 86 to Example 108

| EXAMPLE | STRUCTURE | ANALYTICAL DATA |
| --- | --- | --- |
| 86 | 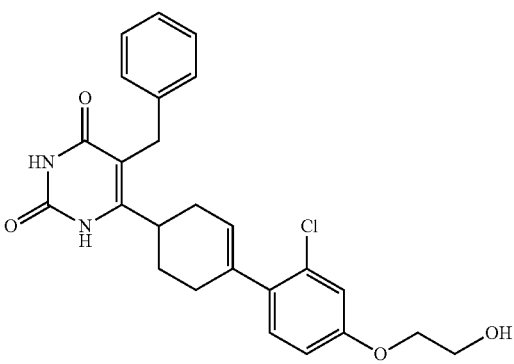 5-benzyl-6-(2'-chloro-4'-(2-hydroxyethoxy)-2,3,4,5-tetrahydro-[1,1'-biphenyl]-4-yl)pyrimidine-2,4(1H,3H)-dione | $R^t$ 1.27 min (Method 3); m/z 453 (M + H)$^+$ (ES$^+$) |
| 87 | 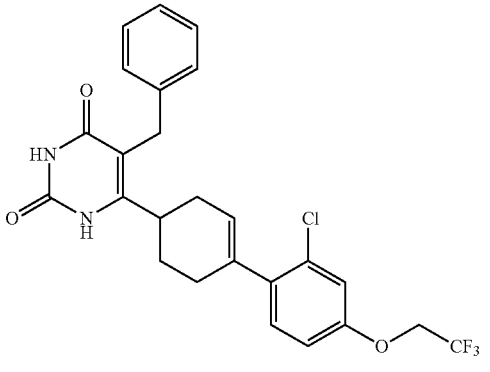 5-benzyl-6-(2'-chloro-4'-(2,2,2-trifluoroethoxy)-2,3,4,5-tetrahydro-[1,1'-biphenyl]-4-yl)pyrimidine-2,4(1H,3H)-dione | $R^t$ 1.69 min (Method 3); m/z 491 (M + H)$^+$ (ES$^+$) |
| 88 | 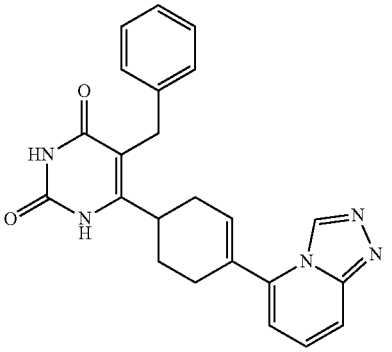 6-(4-([1,2,4]triazolo[4,3-a]pyridin-5-yl)cyclohex-3-en-1-yl)-5-benzylprimidine-2,4(1H,3H)-dione | $R^t$ 0.95 min (Method 3); m/z 400 (M + H)$^+$ (ES$^+$) |

TABLE 4-continued

Example 86 to Example 108

| EXAMPLE | STRUCTURE | ANALYTICAL DATA |
| --- | --- | --- |
| 89 | 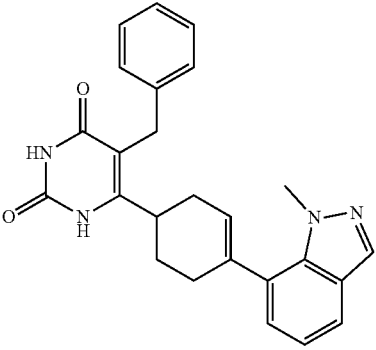

5-benzyl-6-(4-(1-methyl-1H-indazol-7-yl)cyclohex-3-en-1-yl)pyrimidine-2,4(1H,3H)-dione | R$^t$ 1.41 min (Method 3); m/z 413 (M + H)$^+$ (ES$^+$) |
| 90 | 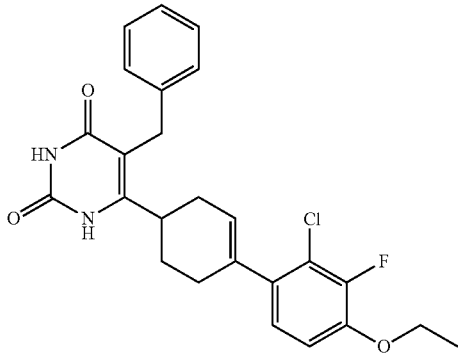

5-benzyl-6-(2'-chloro-4'-ethoxy-3'-fluoro-2,3,4,5-tetrahydro-[1,1'-biphenyl]-4-yl)pyrimidine-2,4(1H,3H)-dione | R$^t$ 1.66 min (Method 3); m/z 455 (M + H)$^+$ (ES$^+$) |
| 91 | 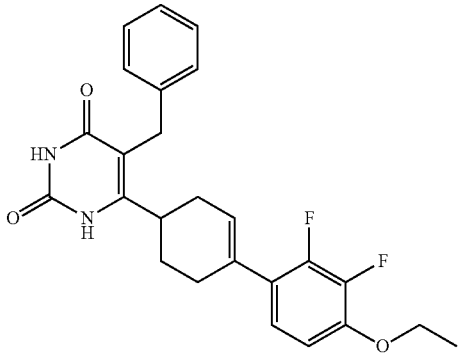

5-benzyl-6-(4'-ethoxy-2',3'-difluoro-2,3,4,5-tetrahydro-[1,1'-biphenyl]-4-yl)pyrimidine-2,4(1H,3H)-dione | R$^t$ 1.61 min (Method 3); m/z 439 (M + H)$^+$ (ES$^+$) |

TABLE 4-continued

Example 86 to Example 108

| EXAMPLE | STRUCTURE | ANALYTICAL DATA |
|---|---|---|
| 92 | 5-benzyl-6-(2',3'-difluoro-4'-(trifluoromethoxy)-2,3,4,5-tetrahydro-[1,1'-biphenyl]-4-yl)pyrimidine-2,4(1H,3H)-dione | R' 1.73 min (Method 3); m/z 479 (M + H)+ (ES+) |
| 93 | 5-benzyl-6-(2'-chloro-4'-cyclopropoxy-2,3,4,5-tetrahydro-[1,1'-biphenyl]-4-yl)pyrimidine-2,4(1H,3H)-dione | R' 1.74 min (Method 3); m/z 449 (M + H)+ (ES+) |
| 94 | 5-benzyl-6-(4'-cyclopropoxy-2'-fluoro-2,3,4,5-tetrahydro-[1,1'-biphenyl]-4-yl)pyrimidine-2,4(1H,3H)-dione | R' 1.83 min (Method 3); m/z 433 (M + H)+ (ES+) |

TABLE 4-continued

Example 86 to Example 108

| EXAMPLE | STRUCTURE | ANALYTICAL DATA |
|---|---|---|
| 95 | 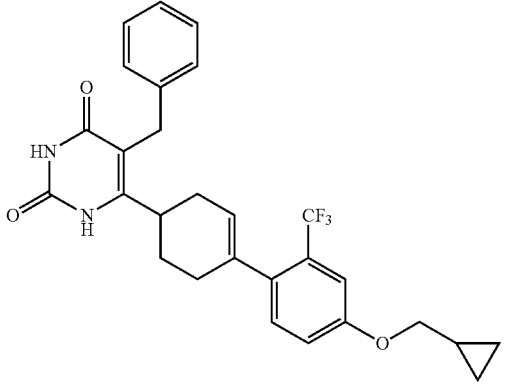<br>5-benzyl-6-(4'-(cyclopropylmethoxy)-2'-(trifluoromethyl)-2,3,4,5-tetrahydro-[1,1'-biphenyl]-4-yl)pyrimidine-2,4(1H,3H)-dione | R$^t$ 2.75 min (Method 1);<br>m/z 497 (M + H)$^+$ (ES$^+$) |
| 96 | 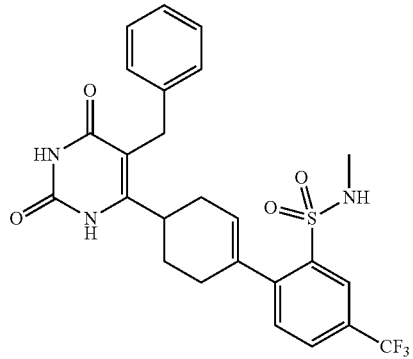<br>4'-(5-benzyl-2,6-dioxo-1,2,3,6-tetrahydropyrimidin-4-yl)-N-methyl-2-(trifluoromethyl)-2',3',4',5'-tetrahydro-[1,1'-biphenyl]-4-sulfonamide | R$^t$ 1.56 min (Method 3);<br>m/z 520 (M + H)$^+$ (ES$^+$) |
| 97 | 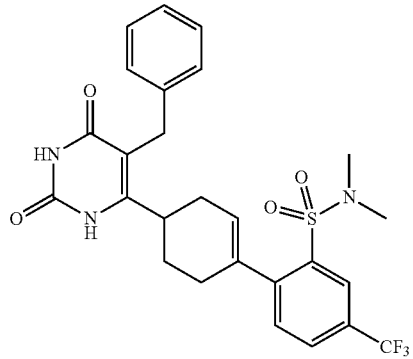<br>4'-(5-benzyl-2,6-dioxo-1,2,3,6-tetrahydropyrimidin-4-yl)-N,N-dimethyl-4-(trifluoromethyl)-2',3',4',5'-tetrahydro-[1,1'-biphenyl]-2-sulfonamide | R$^t$ 1.59 min (Method 3);<br>m/z 534 (M + H)$^+$ (ES$^+$) |

TABLE 4-continued

Example 86 to Example 108

| EXAMPLE | STRUCTURE | ANALYTICAL DATA |
|---|---|---|
| 98 | 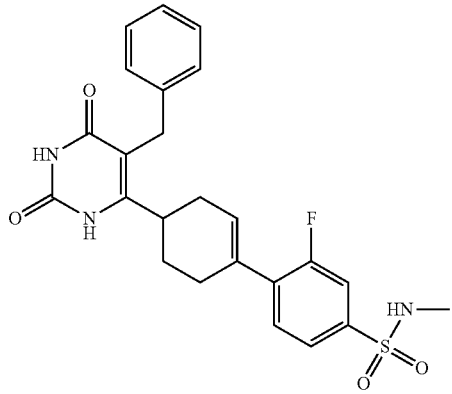<br>4'-(5-benzyl-2,6-dioxo-1,2,3,6-tetrahydropyrimidin-4-yl)-2-fluoro-N-methyl-2',3',4',5'-tetrahydro-[1,1'-biphenyl]-4-sulfonamide | $R^t$ 1.28 min (Method 3); m/z 470 (M + H)$^+$ (ES$^+$) |
| 99 | 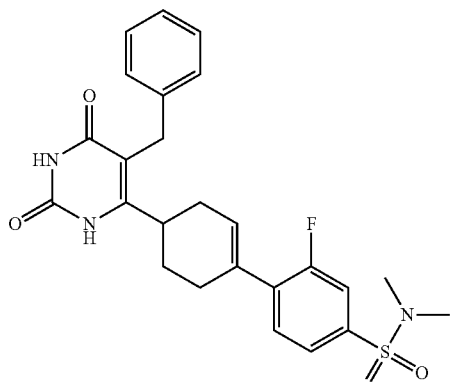<br>4'-(5-benzyl-2,6-dioxo-1,2,3,6-tetrahydropyrimidin-4-yl)-2-fluoro-N,N-dimethyl-2',3',4',5'-tetrahydro-[1,1'-biphenyl]-4-sulfonamide | $R^t$ 1.41 min (Method 3); m/z 484 (M + H)$^+$ (ES$^+$) |
| 100 | 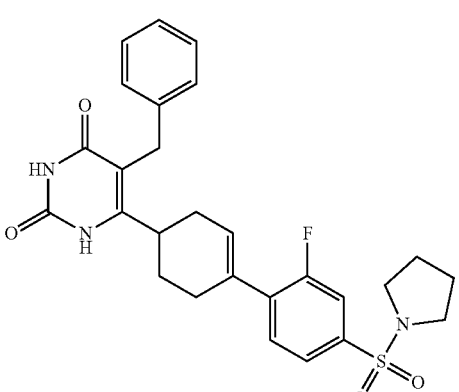<br>5-benzyl-6-(2'-fluoro-4'-(pyrrolidin-1-ylsulfonyl)-2,3,4,5-tetrahydro-[1,1'-biphenyl]-4-yl)pyrimidine-2,4(1H,3H)-dione | $R^t$ 1.47 min (Method 3); m/z 510 (M + H)$^+$ (ES$^+$) |

TABLE 4-continued

Example 86 to Example 108

| EXAMPLE | STRUCTURE | ANALYTICAL DATA |
|---|---|---|
| 101 | 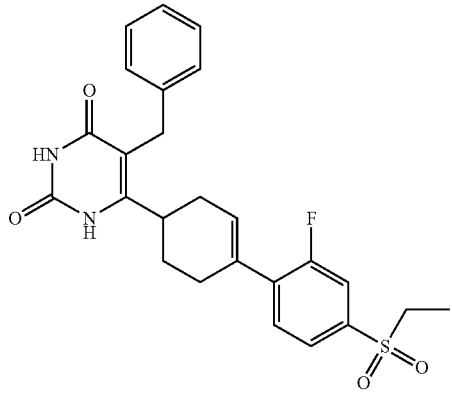<br>5-benzyl-6-(4'-(ethylsulfonyl)-2'-fluoro-2,3,4,5-tetrahydro-[1,1'-biphenyl]-4-yl)pyrimidine-2,4(1H,3H)-dione | $R^t$ 1.33 min (Method 3); m/z 469 (M + H)$^+$ (ES$^+$) |
| 102 | 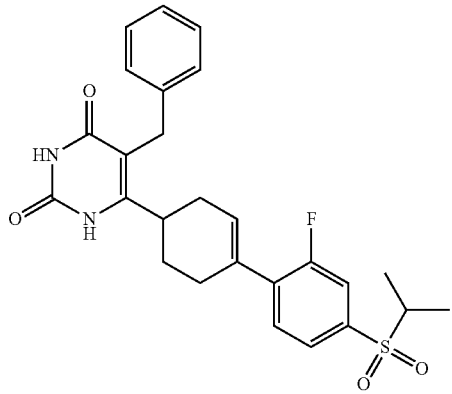<br>5-benzyl-6-(2'-fluoro-4'-(isopropylsulfonyl)-2,3,4,5-tetrahydro-[1,1'-biphenyl]-4-yl)pyrimidine-2,4(1H,3H)-dione | $R^t$ 1.40 min (Method 3); m/z 483 (M + H)$^+$ (ES$^+$) |
| 103 | 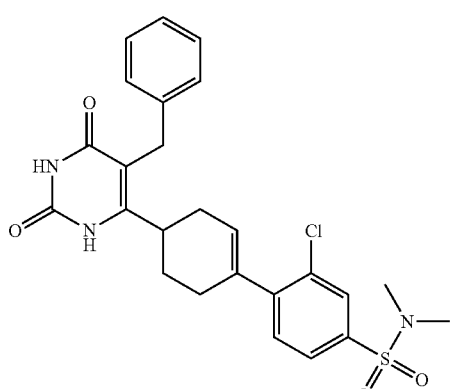<br>4'-(5-benzyl-2,6-dioxo-1,2,3,6-tetrahydropyrimidin-4-yl)-2-chloro-N,N-dimethyl-2',3',4',5'-tetrahydro-[1,1'-biphenyl]-4-sulfonamide | $R^t$ 1.47 min (Method 3); m/z 501 (M + H)$^+$ (ES$^+$) |

TABLE 4-continued

Example 86 to Example 108

| EXAMPLE | STRUCTURE | ANALYTICAL DATA |
| --- | --- | --- |
| 104 | 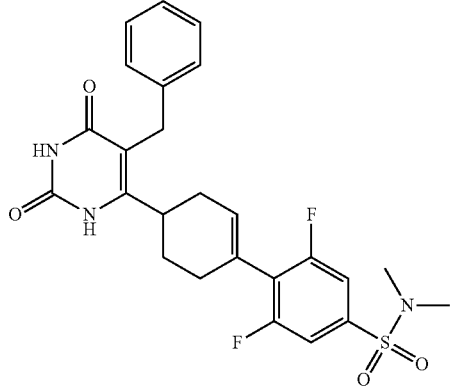<br>4'-(5-benzyl-2,6-dioxo-1,2,3,6-tetrahydropyrimidin-4-yl)-2,6-difluoro-N,N-dimethyl-2',3',4',5'-tetrahydro-[1,1'-biphenyl]-4-sulfonamide | $R^t$ 1.45 min (Method 3); m/z 502 (M + H)$^+$ (ES$^+$) |
| 105 | 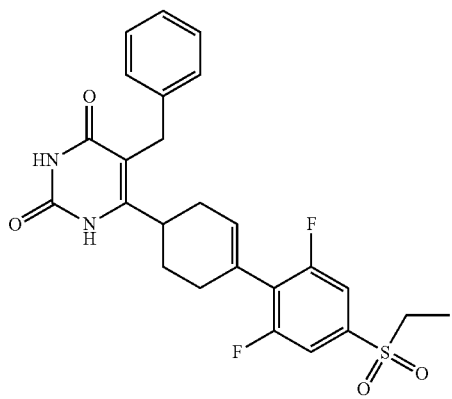<br>5-benzyl-6-(4'-(ethylsulfonyl)-2',6'-difluoro-2,3,4,5-tetrahydro-[1,1'-biphenyl]-4-yl)pyrimidine-2,4(1H,3H)-dione | $R^t$ 1.36 min (Method 3); m/z 487 (M + H)$^+$ (ES$^+$) |
| 106 | 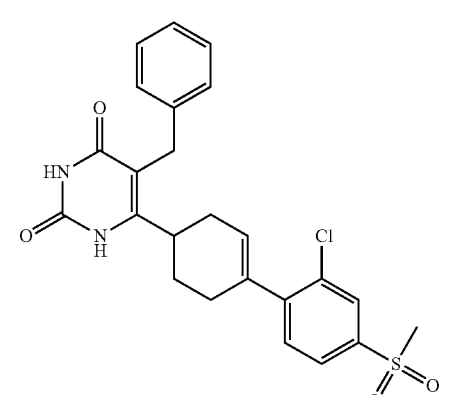<br>5-benzyl-6-(2'-chloro-4'-(methylsulfonyl)-2,3,4,5-tetrahydro-[1,1'-biphenyl]-4-yl)pyrimidine-2,4(1H,3H)-dione | $R^t$ 1.32 min (Method 3); m/z 471 (M + H)$^+$ (ES$^+$) |

TABLE 4-continued
| Example 86 to Example 108 |||
| --- | --- | --- |
| EXAMPLE | STRUCTURE | ANALYTICAL DATA |
| 107 | 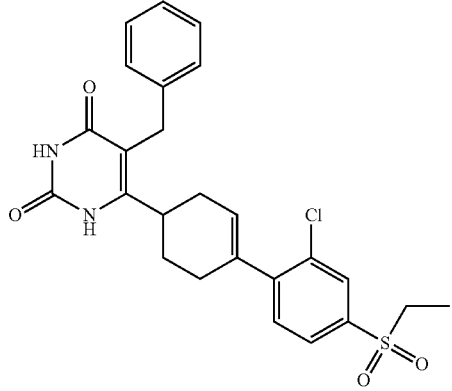<br>5-benzyl-6-(2'-chloro-4'-(ethylsulfonyl)-2,3,4,5-tetrahydro-[1,1'-biphenyl]-4-yl)pyrimidine-2,4(1H,3H)-dione | $R^t$ 1.38 min (Method 3); m/z 485 (M + H)$^+$ (ES$^+$) |
| 108 | 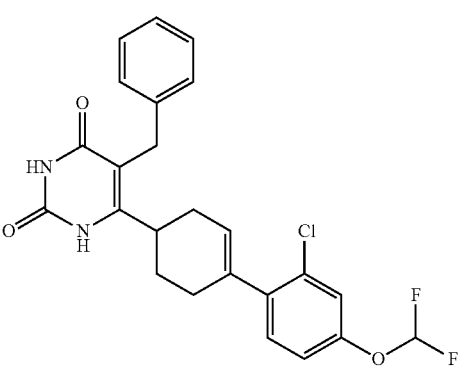<br>5-benzyl-6-(2'-chloro-4'-(difluoromethoxy)-2,3,4,5-tetrahydro-[1,1'-biphenyl]-4-yl)pyrimidine-2,4(1H,3H)-dione | $R^t$ 1.64 min (Method 3); m/z 459 (M + H)$^+$ (ES$^+$) |

Example 109: (R)-5-benzyl-6-(4'-chloro-2'-(trifluoromethyl)-2,3,4,5-tetrahydro-[1,1'-biphenyl]-4-yl)pyrimidine-2,4(1H,3H)-dione Example 110: (S)-5-benzyl-6-(?4'-chloro-2'-(trifluoromethyl)-2,3,4,5-tetrahydro-[1,1'-biphenyl]-4-yl)pyrimidine-2,4(1H,3H)-dione

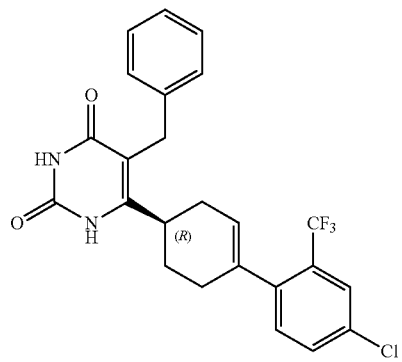

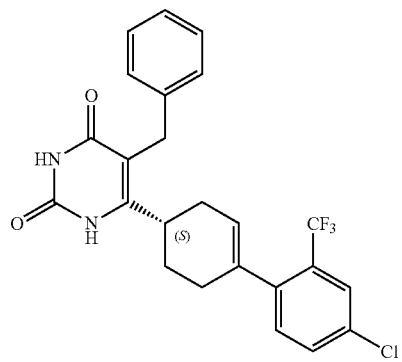

A sample of Example 10 (300 mg, 0.65 mmol) was dissolved to a concentration of 5 mg/mL in DCM and was then purified by Supercritical fluid chromatography (SFC) chiral separation (Lux 3 um (Cellulose-4 4.6*100 mm, 3 um), 35° C., 4 mL/min, 50:50 MeOH (0.1% DEA):CO$_2$). Combined fractions were then concentrated in vacuo to give (R)-5-benzyl-6-(4'-chloro-2'-(trifluoromethyl)-2,3,4,5-tetrahydro-[1,1'-biphenyl]-4-yl)pyrimidine-2,4(1H,3H)-dione (120 mg, X mmol) and (S)-5-benzyl-6-(4'-chloro-2'-(trifluoromethyl)-2,3,4,5-tetrahydro-[1,1'-biphenyl]-4-yl)pyrimidine-2,4(1H,3H)-dione (90 mg, 0.20 mmol) as white solids. Analytical data: R$^t$ 2.67 min (Method 1); m/z 461 (M+H)$^+$ (ES$^+$); and R$^t$ 2.67 min (Method 1); m/z 461 (M+H)$^+$ (ES$^+$). Stereochemistry was assigned arbitrarily Example 111: 5-benzyl-6-(4'-cyclopropyl-2'-fluoro-2,3,4,5-tetrahydro-[1,1'-biphenyl]-4-yl)pyrimidine-2,4(1H,3H)-dione Intermediate K-1 g: 5-benzyl-4-(4'-bromo-2'-fluoro-2,3,4,5-tetrahydro-[1,1'-biphenyl]-4-yl)-2,6-dimethoxypyrimidine

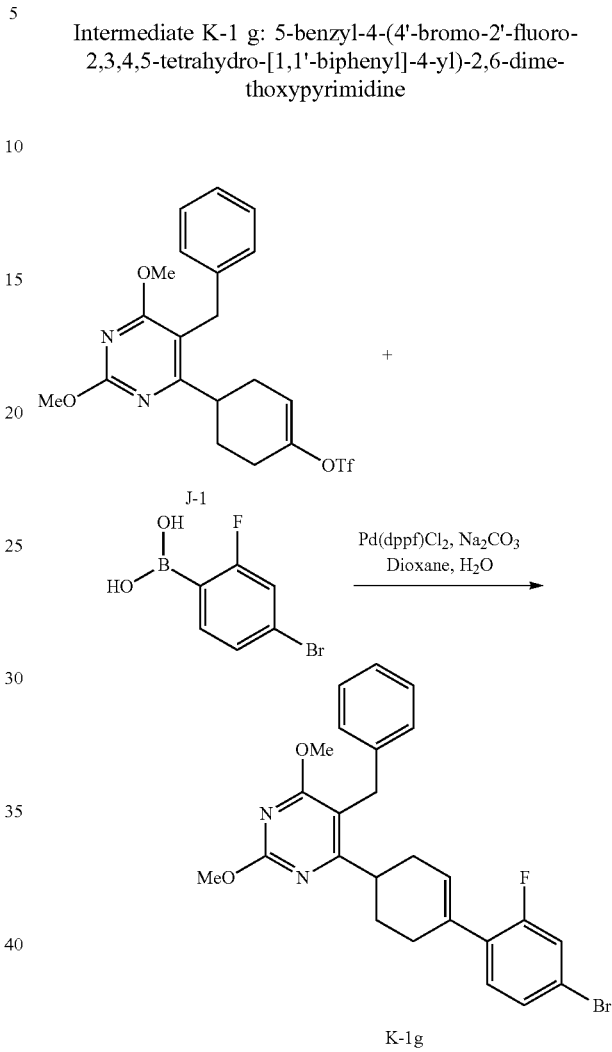

K-1g

A solution of sodium carbonate (76 mg, 0.720 mmol) in H$_2$O (1.2 mL) was added to a suspension of 4-(5-benzyl-2,6-dimethoxypyrimidin-4-yl)cyclohex-1-en-1-yl trifluoromethanesulfonate (Intermediate J-1) (150 mg, 0.327 mmol) and (4-bromo-2-fluorophenyl)boronic acid (75 mg, 0.344 mmol) in dioxane (4.8 ml) and the mixture degassed with bubbling N$_2$ for 5 min. Bis(diphenylphosphino)ferrocene-palladium(II)dichloride dichloromethane complex (26.7 mg, 0.033 mmol) was added and the mixture was heated at 80° C. for 45 minutes. The reaction was cooled to room temperature and partitioned between aqueous NH$_4$Cl solution (5 ml) and EtOAc (10 ml) and the aqueous phase was extracted with EtOAc (2×10 mL). The organic extracts were combined, dried over MgSO$_4$, filtered and concentrated in vacuo to afford a brown solid. The crude product was purified by chromatography on silica gel (12 g cartridge, 0-20% EtOAc/isohexane) to afford 5-benzyl-4-(4'-bromo-2'-fluoro-2,3,4,5-tetrahydro-[1,1'-biphenyl]-4-yl)-2,6-dimethoxypyrimidine (95 mg, 0.183 mmol, 55.9% yield) as a colourless oil. Analytical data: R$^t$ 2.33 min (Method 3); m/z 484 (M+H)$^+$ (ES$^+$);

Intermediate K-1h: 5-benzyl-4-(4'-cyclopropyl-2'-fluoro-2,3,4,5-tetrahydro-[1,1'-biphenyl]-4-yl)-2,6-dimethoxypyrimidine 5-benzyl-6-(4'-cyclopropyl-2'-fluoro-2,3,4,5-tetrahydro-[1,1'-biphenyl]-4-yl)pyrimidine-2,4(1H,3H)-dione

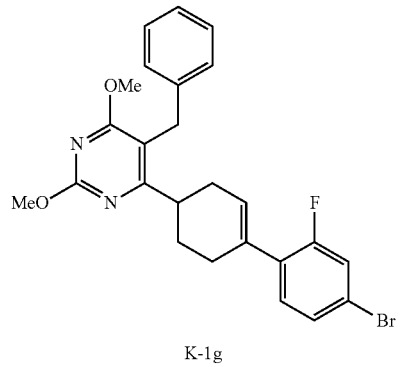
K-1g

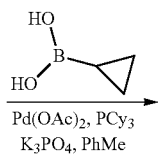

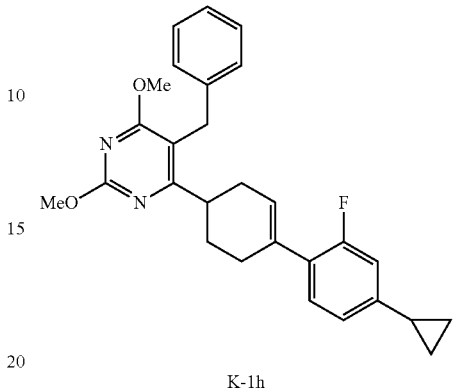
K-1h

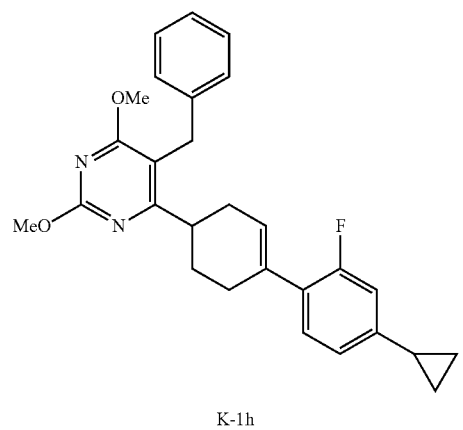
K-1h

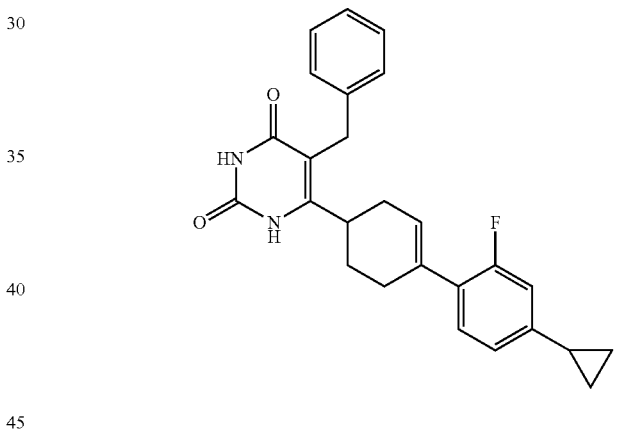

A solution of potassium phosphate (30.7 mg, 0.145 mmol) in H₂O (1.2 mL) was added to a suspension of 5-benzyl-4-(4'-bromo-2'-fluoro-2,3,4,5-tetrahydro-[1,1'-biphenyl]-4-yl)-2,6-dimethoxypyrimidine (Intermediate K1-g) (35 mg, 0.072 mmol), tricyclohexylphosphine (2.031 mg, 7.24 μmol) and cyclopropylboronic acid (9.33 mg, 0.109 mmol) in dioxane (4.8 ml) and the mixture degassed with bubbling N₂ for 5 minutes. Palladium (II) acetate (0.813 mg, 3.62 μmol) was added and the mixture was heated at 80° C. for 45 minutes. The reaction was cooled to room temperature and partitioned between aqueous NH₄Cl solution (5 ml) and EtOAc (10 ml) and the aqueous extracted with EtOAc (2×10 mL). The organic extracts were combined, dried over MgSO₄, filtered and concentrated in vacuo to afford a brown solid. The crude product was purified by chromatography on silica gel (12 g cartridge, 0-20% EtOAc/isohexane) to afford 5-benzyl-4-(4'-cyclopropyl-2'-fluoro-2,3,4,5-tetrahydro-[1,1'-biphenyl]-4-yl)-2,6-dimethoxypyrimidine (33 mg, 0.065 mmol, 90% yield) as a colourless oil. Analytical data: R$^r$ 2.33 min (Method 3); m/z 445 (M+H)⁺ (ES⁺);

To a solution of 5-benzyl-4-(4'-cyclopropyl-2'-fluoro-2,3,4,5-tetrahydro-[1,1'-biphenyl]-4-yl)-2,6-dimethoxypyrimidine (Intermediate K-1h) (32 mg, 0.072 mmol) in DMSO (0.2 mL) was added pyridine hydrochloride (83 mg, 0.720 mmol) and the reaction was heated to 100° C. for 1 hour. The mixture was allowed to cool to room temperature and then water (5 mL) was added. The suspension was cooled in an ice bath and filtered, the solid was washed with ice cold iso-hexane (5 mL) and dried in the desiccator. The crude product was purified by chromatography on silica gel (12 g cartridge, 0-100% EtOAc/isohexane) to afford 5-benzyl-6-(4'-cyclopropyl-2'-fluoro-2,3,4,5-tetrahydro-[1,1'-biphenyl]-4-yl)pyrimidine-2,4(1H,3H)-dione (15 mg, 0.034 mmol, 47.0% yield) as a white solid. Analytical data: R$^r$ 1.72 min (Method 3); m/z 417 (M+H)⁺ (ES⁺); ¹H NMR (500 MHz, DMSO-d₆) δ: 11.13 (s, 1H), 10.46 (s, 1H), 7.26 (dd, J 8.4, 6.9, 2H), 7.15 (m, 4H), 6.88 (dd, J 8.0, 1.8, 1H), 6.85 (dd, J 12.9, 1.8, 1H), 5.87 (s, 1H), 3.79 (d, J 15.8, 1H), 3.69 (d, J 15.7, 1H), 2.97 (m, 1H), 2.45 (obs m, 1H), 2.40-2.30 (m, 1H), 2.26 (m, 1H), 2.06-1.96 (m, 2H), 1.91 (td, J 8.5, 4.3, 1H), 1.50 (m, 1H), 0.99-0.93 (m, 2H), 0.71-0.65 (m, 2H).

Example 112: 5-benzyl-6-(4'-cyclopropyl-2'-(trifluoromethyl)-2,3,4,5-tetrahydro-[1,1'-biphenyl]-4-yl) pyrimidine-2,4(1H,3H)-dione

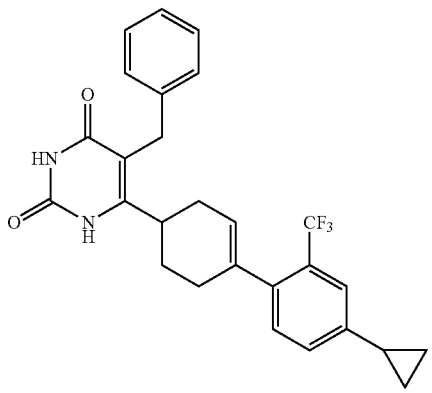 [SMILES: O=c1[nH]c(C2CC=C(c3ccc(C4CC4)cc3C(F)(F)F)CC2)c(Cc2ccccc2)c(=O)[nH]1]

The above compound was prepared from Intermediate J-1 with (4-bromo-2-(trifluoromethyl)phenyl)boronic acid according to the procedures as described in Example 111. Analytical data: $R^r$ 1.82 min (Method 3); m/z 467 (M+H)$^+$ (ES$^+$).

Example 114: 6-(4'-chloro-2'-(trifluoromethyl)-2,3,4,5-tetrahydro-[1,1'-biphenyl]-4-yl)-5-(3-(trifluoromethyl)benzyl)pyrimidine-2,4(1H,3H)-dione Intermediate U-1: 2-amino-6-(4'-chloro-2'-(trifluoromethyl)-2,3,4,5-tetrahydro-[1,1'-biphenyl]-4-yl)-5-(3-(trifluoromethyl)benzyl)pyrimidin-4(3H)-one

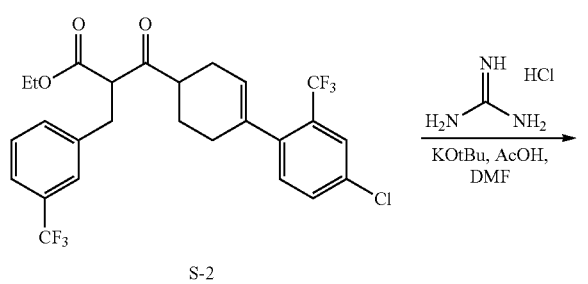

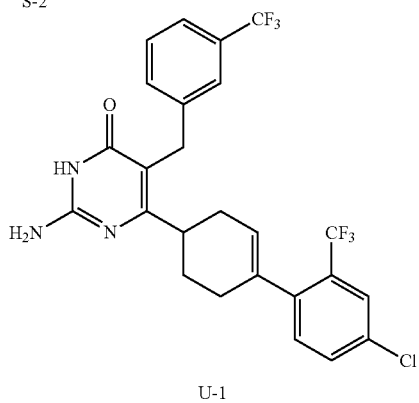

To a solution of ethyl 3-(4'-chloro-2'-(trifluoromethyl)-2,3,4,5-tetrahydro-[1,1'-biphenyl]-4-yl)-3-oxo-2-(3-(trifluoromethyl)benzyl)propanoate (Intermediate S-2, prepared in a similar method to Intermediate S-1) (284 mg, 0.533 mmol) in DMF (3 mL) was added guanidine·HCl (255 mg, 2.66 mmol) and potassium tert-butoxide (269 mg, 2.398 mmol). The mixture was heated to 80° C. overnight then cooled to ~50° C., Acetic acid (122 µl, 2.132 mmol) was then added in small portions over 15 minutes, followed by water (5 mL) over 15 minutes. The mixture was diluted with EtOAc (20 mL) and the organic phase was separated, washed with brine (5 mL) then dried by passing through a hydrophobic frit and concentrated in vacuo. The crude product was purified by chromatography on silica (24 g column, 0-100% EtOAc/isohexane) to afford 2-amino-6-(4'-chloro-2'-(trifluoromethyl)-2,3,4,5-tetrahydro-[1,1'-biphenyl]-4-yl)-5-(3-(trifluoromethyl)benzyl)pyrimidin-4(1H)-one (60 mg, 0.111 mmol, 20.90% yield) as a colourless crystalline solid. Analytical data: $R^r$ 0.73 min (Method 4); m/z 528 (M+H)$^+$ (ES$^+$).

6-(4'-chloro-2'-(trifluoromethyl)-2,3,4,5-tetrahydro-[1,1'-biphenyl]-4-yl)-5-(3-(trifluoromethyl)benzyl)pyrimidine-2,4(1H,3H)-dione

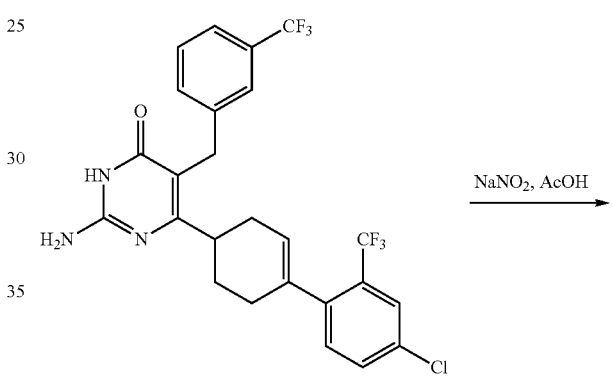

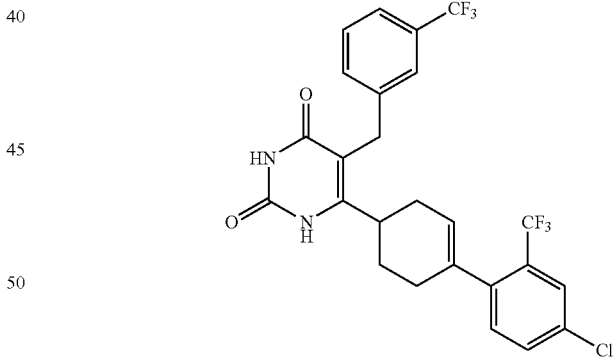

A solution of 2-amino-6-(4'-chloro-2'-(trifluoromethyl)-2,3,4,5-tetrahydro-[1,1'-biphenyl]-4-yl)-5-(3-(trifluoromethyl)benzyl)pyrimidin-4(1H)-one (Intermediate U-1) (60 mg, 0.114 mmol) in 90% aqueous AcOH (2 mL) was stirred at room temperature for 5 minutes. A solution of sodium nitrite (78 mg, 1.137 mmol) in water (0.3 mL) was then added and the mixture was heated to 90° C. for 18 hours. The mixture was cooled to room temperature, a further portion of sodium nitrite (78 mg, 1.137 mmol) in water (0.3 mL) was added and the mixture was heated to 90° C. for a further 18 hours. The mixture was cooled to room temperature, diluted with methanol (3 mL) and left to stand over the weekend. The solid formed was isolated by filtration and washed with ethanol (2 mL) to give 6-(4'-chloro-2'-(trifluoromethyl)-2,3,4,5-tetrahydro-[1,1'-biphenyl]-4-yl)-5-(3-(trifluoromethyl)benzyl)pyrimidine-2,4(1H,3H)-dione (18 mg, 0.034 mmol, 29.9% yield) as a colourless solid. Analytical data: R$^t$ 1.87 min (Method 3); m/z 529 (M+H)$^+$ (ES$^+$). $^1$H NMR 2400-34-1 in DMSO-d6 was consistent with product structure at 99% purity. $^1$H NMR (500 MHz, DMSO-d$_6$) δ: 11.18 (s, 1H), 10.63 (s, 1H), 7.76 (d, J=2.2 Hz, 1H), 7.72 (dd, J=8.3, 2.3 Hz, 1H), 7.59-7.46 (m, 4H), 7.34 (d, J=8.3 Hz, 1H), 5.51 (d, J=5.2 Hz, 1H), 3.88 (d, J=15.7 Hz, 1H), 3.81 (d, J=15.7 Hz, 1H), 3.04-2.94 (m, 1H), 2.48-2.41 (m, 1H), 2.31-2.18 (m, 1H), 2.18-2.02 (m, 2H), 1.96-1.82 (m, 1H), 1.51-1.38 (m, 1H).

Example 115: 5-(2,3-difluorobenzyl)-6-(2'-fluoro-4'-(methylsulfonyl)-2,3,4,5-tetrahydro-[1,1'-biphenyl]-4-yl)pyrimidine-2,4(1H,3H)-dione

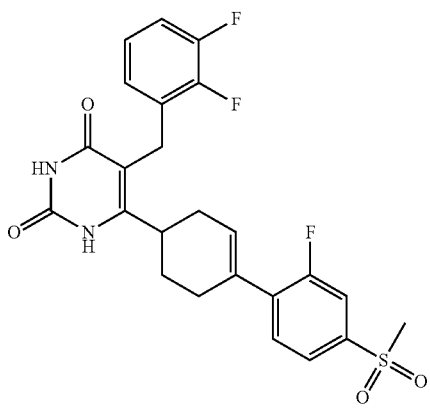 [SMILES: CS(=O)(=O)c1ccc(C2=CCC(c3[nH]c(=O)[nH]c(=O)c3Cc3cccc(F)c3F)CC2)c(F)c1]

Intermediate W: diethyl 2-(2,3-difluorobenzyl)malonate

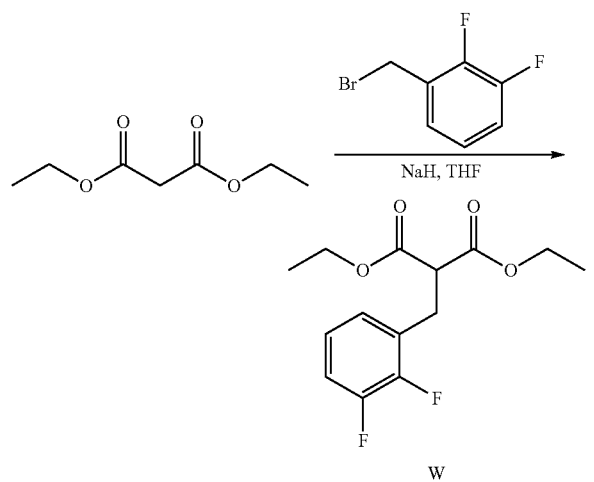

Sodium hydride (0.549 g, 13.74 mmol) was added to a solution of diethyl malonate (1.896 ml, 12.49 mmol) in THF (20 mL) at 0° C. and stirred for 30 minutes. A solution of 1-(bromomethyl)-2,3-difluorobenzene (1.667 ml, 13.11 mmol) in THF (20 mL) was added dropwise and the reaction mixture allowed to warm to room temperature and stirred overnight. The reaction was quenched by the addition of H$_2$O (100 mL) and extracted with EtOAc (3×50 mL). The organics were combined, dried over MgSO$_4$, filtered and concentrated in vacuo and crude product was purified by chromatography on silica gel (80 g cartridge, 0-10% EtOAc/isohexane) to afford diethyl 2-(2,3-difluorobenzyl)malonate (2.4 g, 8.05 mmol, 64.5% yield) as a colourless oil. Analytical data: R$^t$ 0.71 min (Method 4); m/z 287 (M+H)$^+$ (ES$^+$).

Intermediate X: 2-(2,3-difluorobenzyl)-3-ethoxy-3-oxopropanoic acid

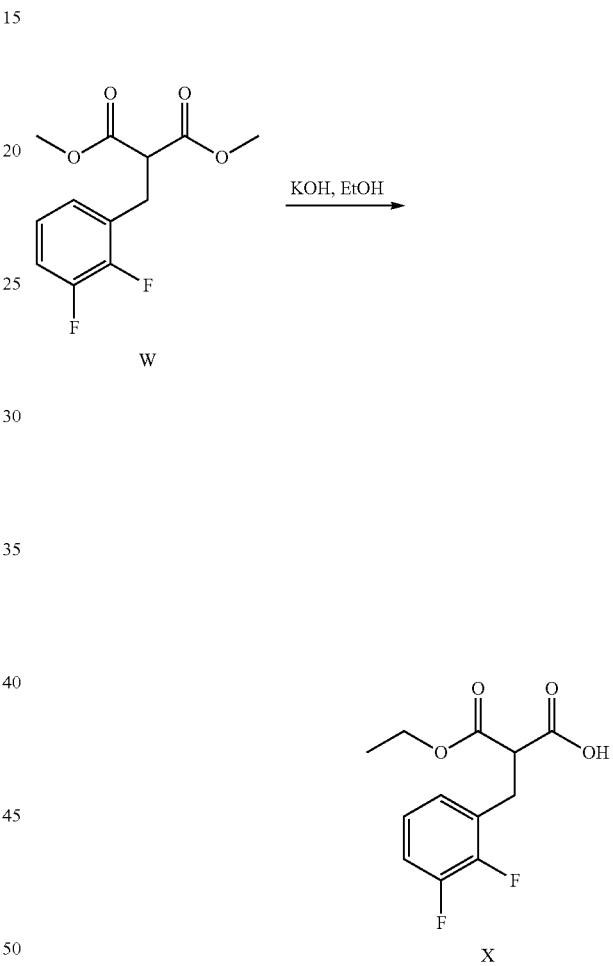

To a solution of diethyl 2-(2,3-difluorobenzyl)malonate (Intermediate W) (1.655 g, 5.78 mmol) in ethanol (5 mL) was added a solution of KOH (0.38 g, 6.10 mmol) in ethanol (5 mL). The mixture was stirred at room temperature for 24 hours. The solvent was removed in vacuo and the colourless solid residue was dissolved in saturated aqueous NaHCO$_3$ (100 mL). The mixture was extracted with EtOAc (1×20 mL), which was then discarded. The aqueous phase was acidified to pH 1 with conc. HCl and extracted with EtOAc (3×60 mL). The combined organics were washed with brine (30 mL) then dried by passing through a hydrophobic frit and concentrated in vacuo to give 2-(2,3-difluorobenzyl)-3-ethoxy-3-oxopropanoic acid (1.405 g, 5.33 mmol, 92% yield) as a colourless oil. Analytical data: Rr 1.26 min (Method 3); m/z no mass observed.

Intermediate S-3: ethyl 2-(2,3-difluorobenzyl)-3-(2'-fluoro-4'-(methylsulfonyl)-2,3,4,5-tetrahydro-[1,1'-biphenyl]-4-yl)-3-oxopropanoate

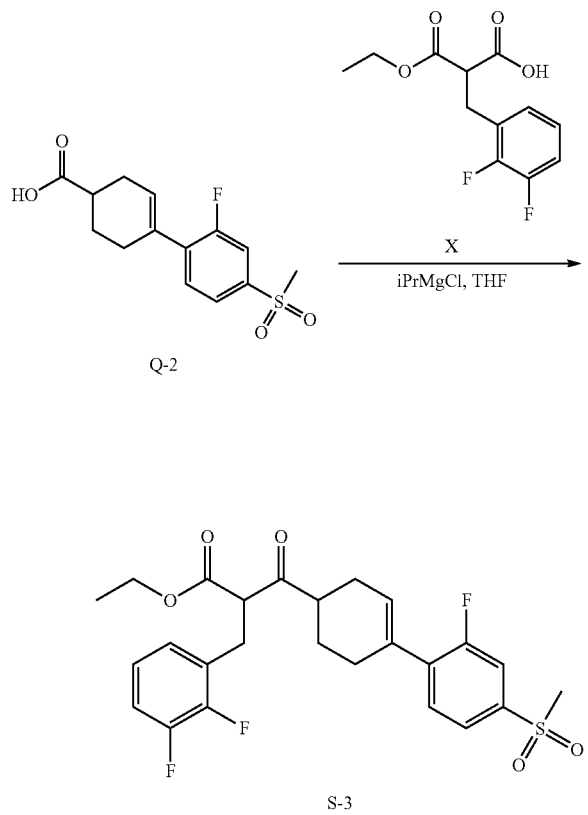

CDI (285 mg, 1.760 mmol) was added to a suspension of 2'-fluoro-4'-(methylsulfonyl)-2,3,4,5-tetrahydro-[1,1'-biphenyl]-4-carboxylic acid (Intermediate Q-2) (500 mg, 1.676 mmol) in MeCN (7 mL) and stirred for 3 hours at room temperature. Isopropylmagnesium chloride (1257 µl, 2.51 mmol) was added dropwise to a solution of 2-(2,3-difluorobenzyl)-3-ethoxy-3-oxopropanoic acid (Intermediate X) (649 mg, 2.51 mmol) in THF (5 mL) −10° C. and stirred for 5 minutes. The solution was allowed to warm to room temperature and added dropwise via syringe to the previously formed CDI adduct. The reaction mixture was heated to 75° C. and stirred overnight. The mixture was allowed to cool to room temperature and 1 M HCl$_{(aq)}$ (20 mL), MTBE (15 mL) and isohexane (15 mL) were added. The layers were separated and organic layer washed with a 10 weight % aqueous solution of $K_2CO_3$ (2×20 mL), dried over $MgSO_4$, filtered and concentrated in vacuo. The crude product was purified by chromatography on silica gel (40 g cartridge, 0-40% EtOAc/isohexane) to afford ethyl 2-(2,3-difluorobenzyl)-3-(2'-fluoro-4'-(methylsulfonyl)-2,3,4,5-tetrahydro-[1,1'-biphenyl]-4-yl)-3-oxopropanoate (440 mg, 0.854 mmol, 51.0% yield) as a colourless glass. Analytical data: $R^t$ 1.75 min (Method 3); m/z 495 (M+H)$^+$ (ES$^+$).

The title compound was prepared from Intermediate S-3 following the procedure outlined for Example 108. Analytical data: $R^t$ 1.31 min (Method 3); m/z 491 (M+H)$^+$ (ES$^+$).

Example 116 & Example 117: 5-substituted 6-(2'-fluoro-4'-(methylsulfonyl)-2,3,4,5-tetrahydro-[1,1'-biphenyl]-4-yl)pyrimidine-2,4(1H,3H)-dione The following compounds as shown in Table 5 were prepared by similar methods to those described in Example 115.

TABLE 5

| Example 116 & Example 117 | | |
|---|---|---|
| EXAMPLE | STRUCTURE | ANALYTICAL DATA |
| 116 | 6-(2'-fluoro-4'-(methylsulfonyl)-2,3,4,5-tetrahydro-[1,1'-biphenyl]-4-yl)-5-(3-(trifluoromethyl)benzyl)pyrimidine-2,4(1H,3H)-dione | $R^t$ 1.40 min (Method 3); m/z 523 (M + H)$^+$ (ES$^+$) |

TABLE 5-continued

Example 116 & Example 117

| EXAMPLE | STRUCTURE | ANALYTICAL DATA |
|---|---|---|
| 117 | 6-(2'-fluoro-4'-(methylsulfonyl)-2,3,4,5-tetrahydro-[1,1'-biphenyl]-4-yl)-5-((6-(pyrrolidin-1-yl)pyridin-2-yl)methyl)pyrimidine-2,4(1H,3H)-dione | $R^t$ 0.77 min (Method 3); m/z 525 (M + H)$^+$ (ES$^+$) |

Example 119: Hey G2 TAT Ki

Glucocorticoid mediated activation of TAT occurs by transactivation of glucocorticoid response elements in the TAT promoter by glucocorticoid receptor-agonist complex. The following protocol describes an assay for measuring induction of TAT by dexamethasone in HepG2 cells (a human liver hepatocellular carcinoma cell line; ECACC, UK).

TAT activity was measured as outlined in the literature by A. Ali et al., J. Med. Chem., 2004, 47, 2441-2452. Dexamethasone induced TAT production with an average $EC_{50}$ value (half-maximal effect) of 20 nM.

HepG2 cells were cultured using MEME media supplemented with 10% (v/v) foetal bovine serum; 2 mM L-glutamine and 1% (v/v) NEAA at 37° C., 5%/95% (v/v) $CO_2$/air. The HepG2 cells were counted and adjusted to yield a density of 0.125×10$^6$ cells/ml in RPMI 1640 without phenol red, 10% (v/v) charcoal stripped FBS, 2 mM L-glutamine and seeded at 25,000 cells/well in 200 µl into 96 well, sterile, tissue culture micro titre plates, and incubated at 37° C., 5% $CO_2$ for 24 hours Growth media was removed and replaced with assay media {RPMI 1640 without phenol red, 2 mM L-glutamine+ 10 µM forskolin}. Test compounds were screened against a challenge of 100 nM dexamethasone. Compounds were serially half log diluted in 100% (v/v) dimethylsulphoxide from a 10 mM stock. Then an 8-point half-log dilution curve was generated followed by a 1:100 dilution into assay media to give a 10× final assay [compound]: this resulted in final assay [compound] that ranged 10 to 0.003 µM in 0.1% (v/v) dimethylsulfoxide.

Test compounds were pre-incubated with cells in microtitre plates for 30 minutes at 37° C., 5/95 (v/v) $CO_2$/air, before the addition of 100 nM dexamethasone and then subsequently for 20 hours to allow optimal TAT induction.

HepG2 cells were then lysed with 30 µl of cell lysis buffer containing a protease inhibitor cocktail for 15 minutes at 4° C. 155 µl of substrate mixture was then added containing 5.4 mM Tyrosine sodium salt, 10.8 mM alpha ketoglutarate and 0.06 mM pyridoxal 5' phosphate in 0.1 M potassium phosphate buffer (pH 7.4). After 2 hours incubation at 37° C. the reaction was terminated by the addition of 15 µl of 10 M aqueous potassium hydroxide solution, and the plates incubated for a further 30 minutes at 37° C. The TAT activity product was measured by absorbance at λ 340 nm.

$IC_{50}$ values were calculated by plotting % inhibition (normalised to 100 nM dexamethasone TAT stimulation) v. [compound] and fitting the data to a 4 parameter logistic equation. $IC_{50}$ values were converted to Ki (equilibrium dissociation constant) using the Cheng and Prusoff equation, assuming the antagonists were competitive inhibitors with respect to dexamethasone.

TABLE 6

Hep G2 TAT Data

| EXAMPLE | Mean GR Binding $IC_{50}$ (nM) | Hep G2 TAT Ki (nM) |
|---|---|---|
| 1 | | 28 |
| 2 | | 99 |
| 3 | | 460 |
| 4 | | 1300 |
| 5 | | 120 |
| 6 | | 65 |
| 7 | | 38 |
| 8 | | 52 |
| 9 | | 26 |
| 10 | | 38 |
| 11 | | 14 |
| 12 | | 350 |
| 13 | | 83 |
| 14 | | 41 |
| 15 | | 520 |
| 16 | | 640 |
| 17 | | 280 |
| 18 | | 260 |
| 19 | | 32 |
| 20 | | 33 |
| 21 | | 270 |
| 22 | | 330 |

TABLE 6-continued

Hep G2 TAT Data

| EXAMPLE | Mean GR Binding IC$_{50}$ (nM) | Hep G2 TAT Ki (nM) |
|---|---|---|
| 23 |  | 330 |
| 24 |  | 33 |
| 25 |  | 100 |
| 26 |  | 50 |
| 27 |  | 210 |
| 28 |  | 150 |
| 29 |  | 12 |
| 30 |  | 50 |
| 31 |  | 120 |
| 32 |  | 66 |
| 33 |  | 740 |
| 34 |  | 23 |
| 35 |  | 59 |
| 36 |  | 110 |
| 37 |  | 140 |
| 38 |  | 75 |
| 39 |  | 69 |
| 40 |  | 42 |
| 41 |  | 480 |
| 42 |  | 33 |
| 43 |  | 150 |
| 44 |  | 45 |
| 45 |  | 970 |
| 46 |  | 300 |
| 47 |  | 400 |
| 48 |  | 130 |
| 49 |  | 280 |
| 50 |  | 14 |
| 51 |  | 400 |
| 52 |  | 568 |
| 53 |  | 51 |
| 54 |  | 1360 |
| 55 |  | 1485 |
| 56 | 459 |  |
| 57 | 266 |  |
| 58 |  | 520 |
| 59 | 134 |  |
| 60 |  | 41 |
| 61 |  | 485 |
| 62 |  | 884 |
| 63 |  | 632 |
| 64 | 142 |  |
| 65 | 103 |  |
| 66 | 3521 |  |
| 67 |  | 120 |
| 68 |  | 497 |
| 69 | 3421 |  |
| 70 | 142 |  |
| 71 |  | 148 |
| 72 | 1915 |  |
| 73 |  | 70 |
| 74 |  | 264 |
| 75 |  | 223 |
| 76 |  | 141 |
| 77 |  | 170 |
| 78 |  | 175 |
| 79 |  | 530 |
| 80 | 295 |  |
| 81 |  | 400 |
| 82 | 4.4 |  |
| 83 | 38.3 |  |
| 84 |  | 259.2 |
| 85 |  | 1396 |
| 86 |  | 1159 |
| 87 |  | 453 |
| 88 | 483 |  |
| 89 |  | 433 |
| 90 |  | 746 |
| 91 |  | 247 |
| 92 |  | 803 |
| 93 | 10 |  |
| 94 |  | 200 |
| 95 | 23 |  |
| 96 | 5093 |  |
| 97 | 2562 |  |

TABLE 6-continued

Hep G2 TAT Data

| EXAMPLE | Mean GR Binding IC$_{50}$ (nM) | Hep G2 TAT Ki (nM) |
|---|---|---|
| 98 |  | 110 |
| 99 |  | 730 |
| 100 |  | 1600 |
| 101 |  | 65 |
| 102 |  | 270 |
| 103 |  | 258 |
| 104 | 3160 |  |
| 105 | 71.6 |  |
| 106 | 2.1 |  |
| 107 | 2.8 |  |
| 108 | 5.4 |  |
| 109 |  | 30 |
| 110 |  | 38 |
| 111 |  | 113 |
| 112 |  | 333 |
| 113 |  | 75 |
| 114 |  | 121 |
| 115 |  | 85 |
| 116 |  | 170 |
| 117 |  | 559 |
| 118 | 0.76 |  |

Example 120: Rat Pharmacokinetics (PK) Studies

Rat PK studies were conducted in male Sprague Dawley rats (or equivalent) with 3 rats per group. Compounds were evaluated in cassettes of 4 compounds per cassette, with each cassette containing 3 test compounds and one comparator compound with known PK parameters. Rats were cannulated in the jugular vein. The compounds were administered by oral gavage using a suitable vehicle, such as 10% DMSO and 90% methyl cellulose. Compounds of Example 1, Example 10, Example 14, and Example 20 were evaluated with a nominal dose of 1.25 mg/kg and the compound of Example 32 was evaluated with a nominal dose of 3 mg/kg. Blood samples were collected at various timepoints out to 24 hours post-dose and processed to provide plasma. Compound concentrations in the plasma samples were determined by LC/MS analysis. $C_{max}$ and AUC were calculated using WinNonlin. The $C_{max}$ concentration of each compound studied was listed in Table 7.

TABLE 7

Rat PK Studies

| Example | $C_{max}$ ng/mL | AUC$_{0-24}$ ng · h/mL |
|---|---|---|
| 1 | 114 | 991 |
| 10 | 196 | 3043 |
| 14 | 63 | 188 |
| 20 | 83.6 | 375 |
| 32 | 453 | 988 |

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of formula Ic-1:

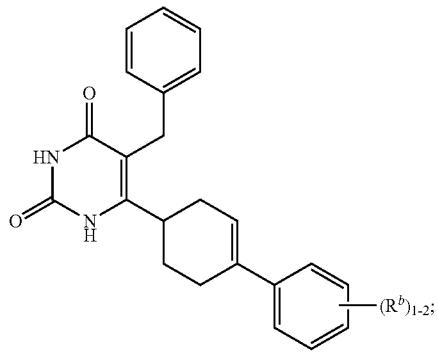

or a pharmaceutically acceptable salt thereof, or an isomer thereof,
wherein
each $R^b$ is independently H, halogen, CN, $C_{1-4}$ alkyl, $C_{1-4}$ alkoxy, $C_{1-4}$ hydroxyalkyl, $C_{1-4}$ haloalkyl, $C_{1-4}$ haloalkoxy, —$OR^{b4}$, —$NR^{b1}R^{b2}$, —$C(O)NR^{b1}R^{b2}$, —$SO_2R^{b1}$, —$SO_2NR^{b1}R^{b2}$, or $C_{3-6}$ cycloalkyl;
$R^{b1}$ and $R^{b2}$ are each independently H or $C_{1-4}$ alkyl; or $R^{b1}$ and $R^{b2}$ when attached to a nitrogen atom are combined to form a 4-6 membered heterocycle having 1-2 nitrogen atoms, which is optionally substituted with 1-2 $R^{b3}$;
each $R^{b3}$ is independently H, halogen, $C_{1-4}$ alkyl, or $C_{1-4}$ alkoxy; and
each $R^{b4}$ is independently $C_{1-4}$ hydroxyalkyl, $C_{3-6}$ cycloalkyl or $C_{3-6}$ cycloalkyl-$C_{1-4}$ alkyl.

2. The compound of claim 1, wherein
each $R^b$ is independently H, halogen, CN, $C_{1-4}$ alkyl, $C_{1-4}$ alkoxy, $C_{1-4}$ hydroxyalkyl, $C_{1-4}$ haloalkyl, or $C_{1-4}$ haloalkoxy.

3. The compound of claim 1, wherein
each $R^b$ is independently H, F, Cl, CN, Me, Et, nPr, iPr, nBu, iBu, sBu, tBu, OMe, OEt, OnPr, OiPr, $CH_2F$, $CHF_2$, $CF_3$, $CH_2CF_3$, $OCH_2F$, $OCHF_2$, $OCF_3$, $OCH_2CF_3$, —$CH_2OH$, —$OCH_2CH_2OH$, —O-cyclopropyl, —O-cyclobutyl, —O-cyclopentyl, —O-cyclohexyl, —O-cyclopropylmethyl, —O-cyclobutylmethyl, —O-cyclopentylmethyl, —O-cyclohexylmethyl, —$NH_2$, —NHMe, —$NMe_2$, —$SO_2Me$, —$SO_2Et$, —$S(O)_2iPr$, —$S(O)_2NHMe$, —$S(O)_2NMe_2$, 1-pyrrolidinyl, 1-piperidinyl, 1-piperazinyl, —C(O)-1-pyrrolidinyl, —C(O)-1-piperidinyl, —C(O)-1-piperazinyl, cyclopropyl, cyclobutyl, cyclopentyl or cyclohexyl, wherein
each of 1-pyrrolidinyl, 1-piperidinyl, and 1-piperazinyl is optionally substituted with 1-2 $R^{b3}$; and
each $R^{b3}$ is independently H, F, Me, or OMe.

4. The compound of claim 1, wherein
each $R^b$ is independently H, F, Cl, CN, Me, Et, iBu, OMe, OEt, OiPr, $CF_3$, $OCHF_2$, $OCF_3$, $OCH_2CF_3$, —$CH_2OH$, —$OCH_2CH_2OH$, —O-cyclopropyl, —O— cyclopropylmethyl, —$NMe_2$, —$S(O)_2Me$, —$S(O)_2Et$, —$S(O)_2iPr$, —$S(O)_2NHMe$, —$S(O)_2NMe_2$, 1-pyrrolidinyl, 1-piperidinyl, 4,4-difluoro-1-piperidinyl, 3,3-dimethyl-1-piperidinyl, 3-methyl-1-piperidinyl, 3-methoxy-1-piperidinyl, —C(O)-1-pyrrolidinyl, —C(O)-4-methyl-1-piperazinyl, or cyclopropyl.

5. The compound of claim 1, wherein each $R^b$ is independently H, F, Cl, CN, Me, $CF_3$, $OCF_3$, or —$CH_2OH$.

6. The compound of claim 1, wherein $R^1$ is H.

7. The compound of claim 1, selected from the group consisting of:

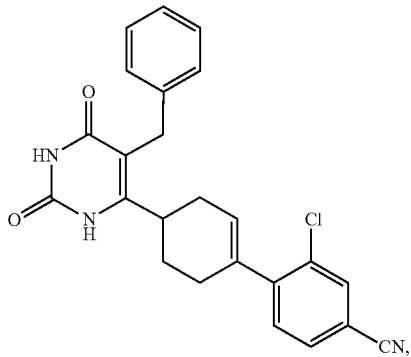

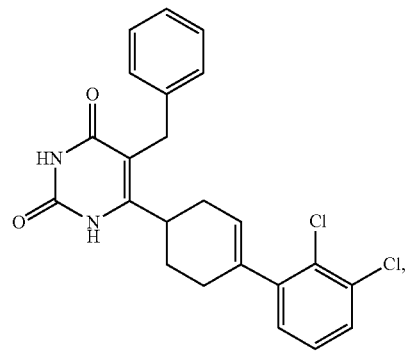

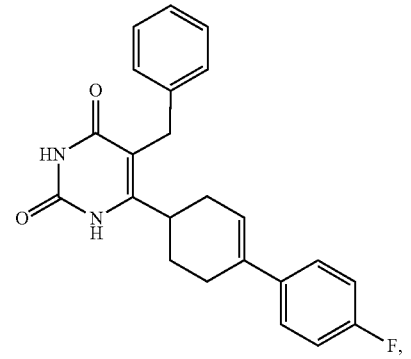

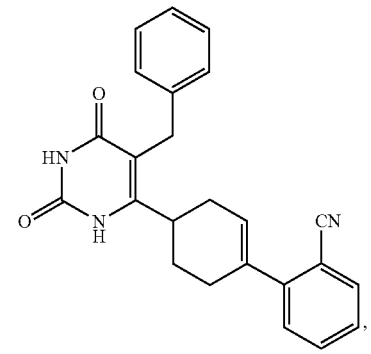

199
-continued
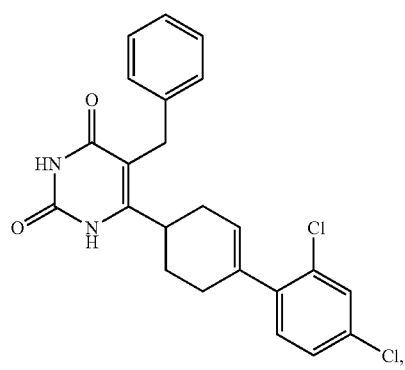
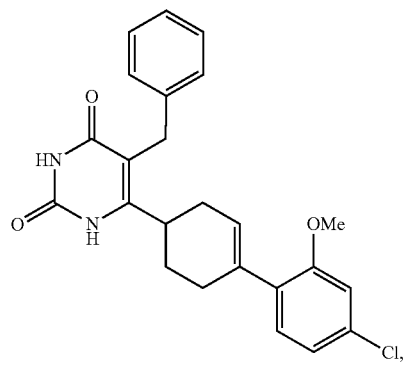
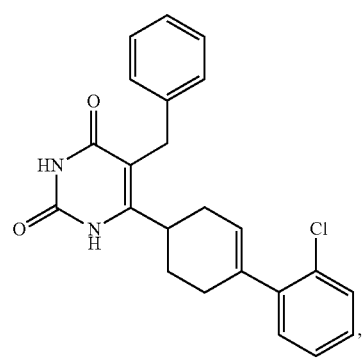
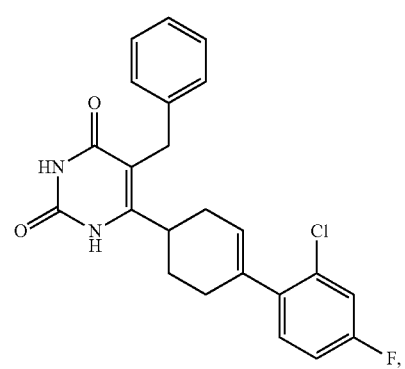
200
-continued
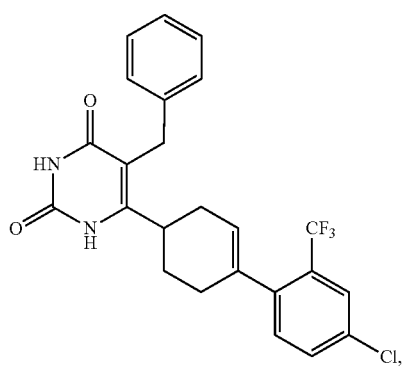
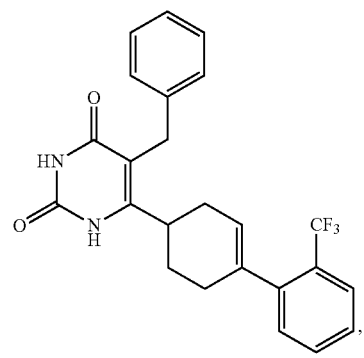
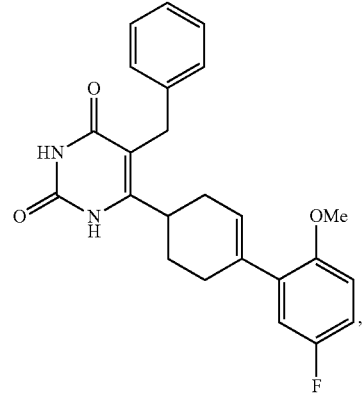
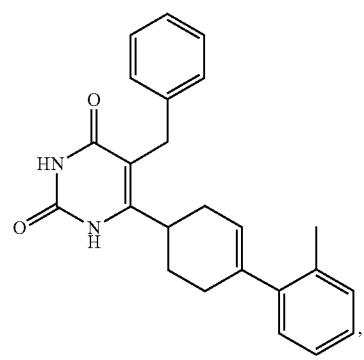

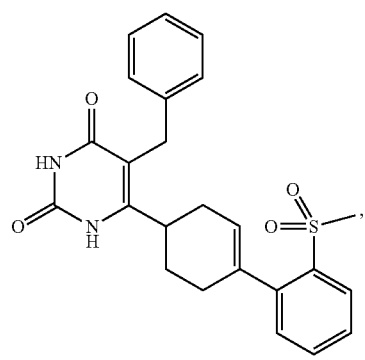
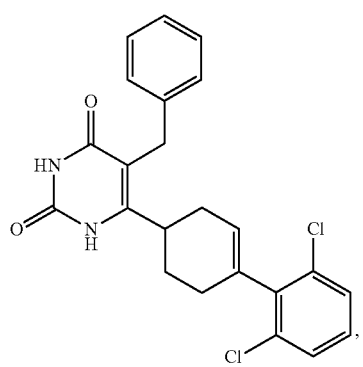
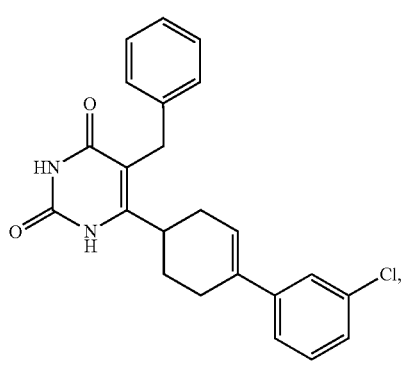
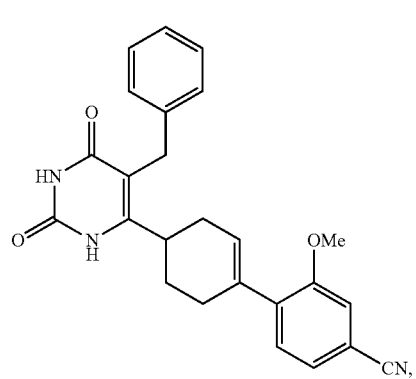
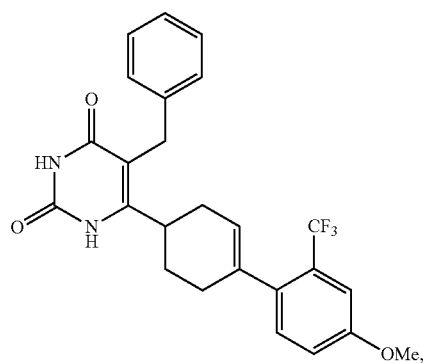
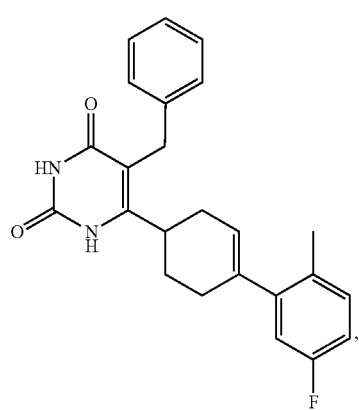
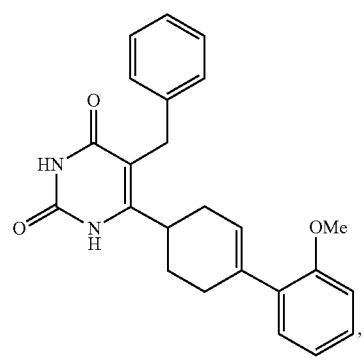 [SMILES: COc1ccccc1C1=CCC(c2[nH]c(=O)[nH]c(=O)c2Cc2ccccc2)CC1]
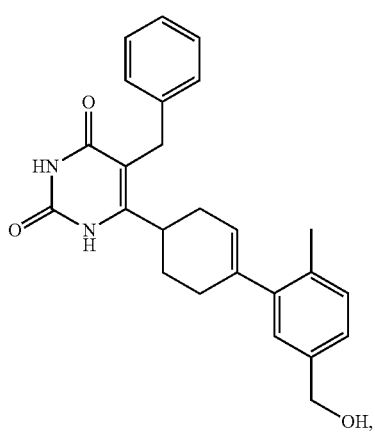

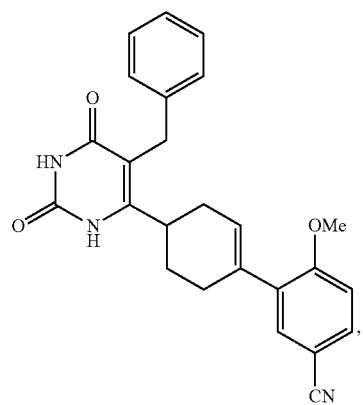
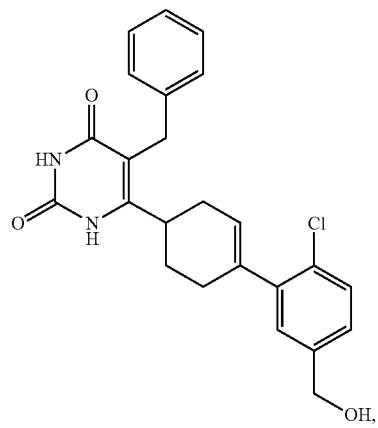
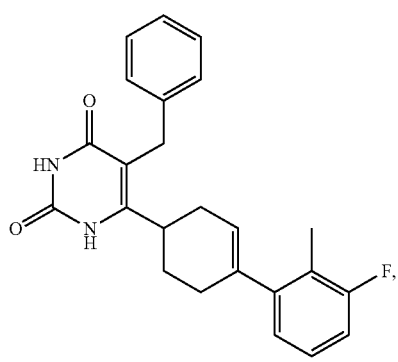
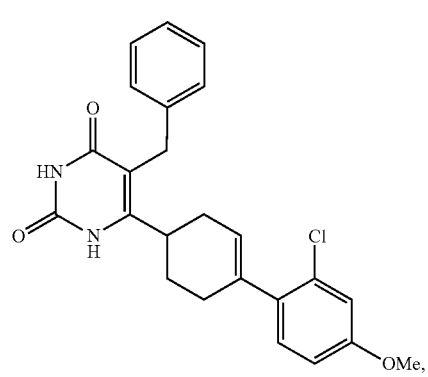
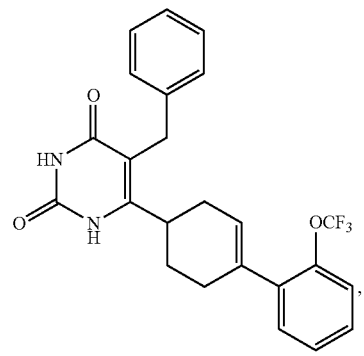
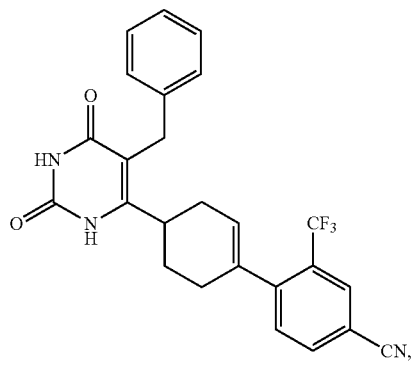
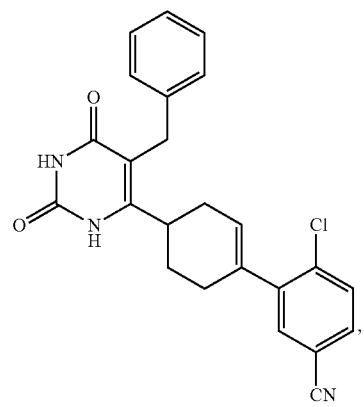
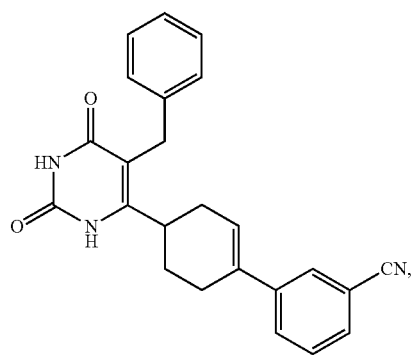

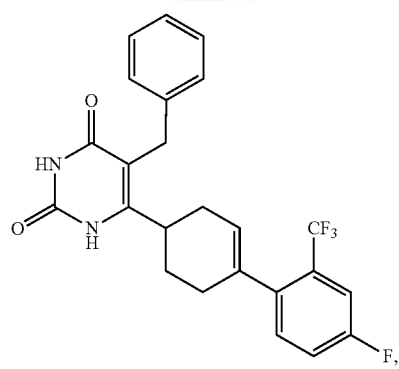
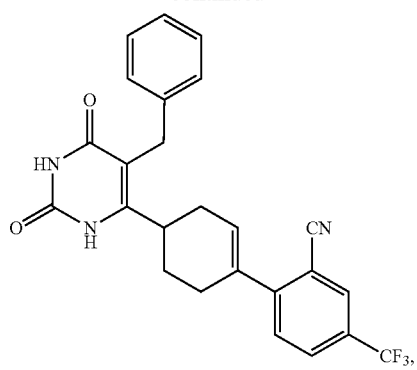
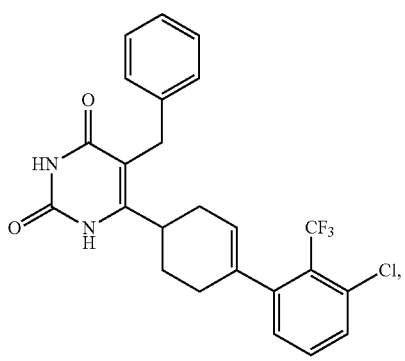
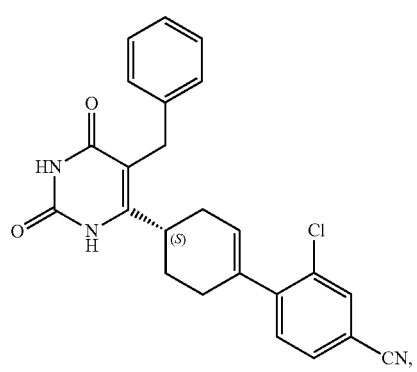
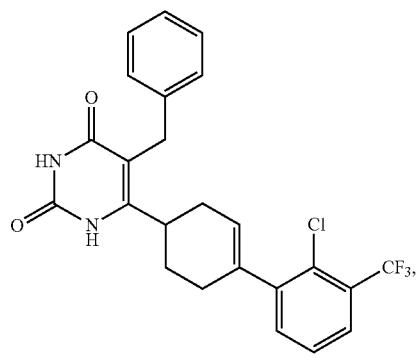
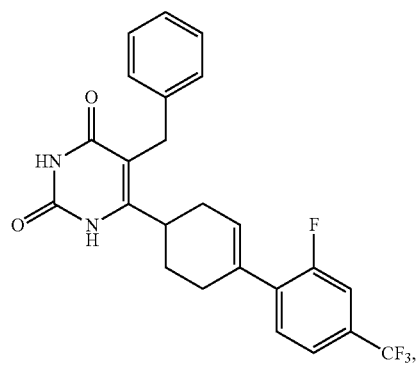

-continued
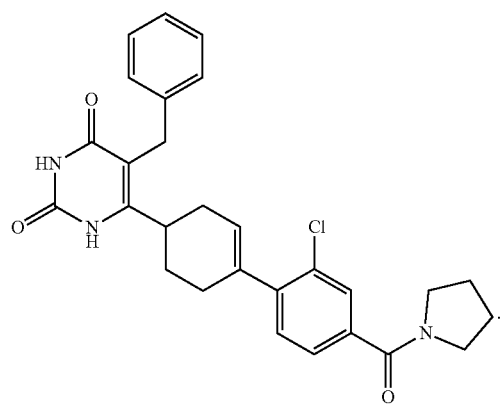
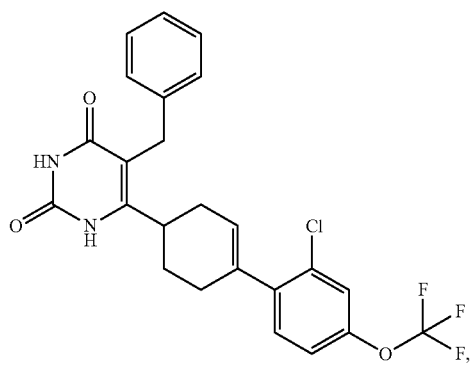
8. The compound of claim 1, selected from the group consisting of:
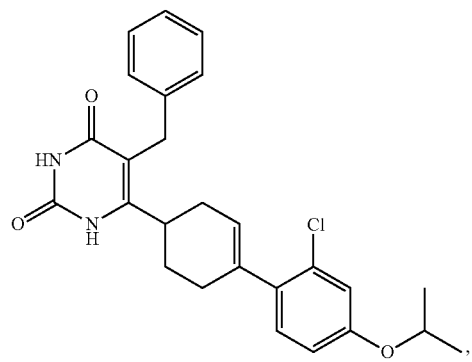
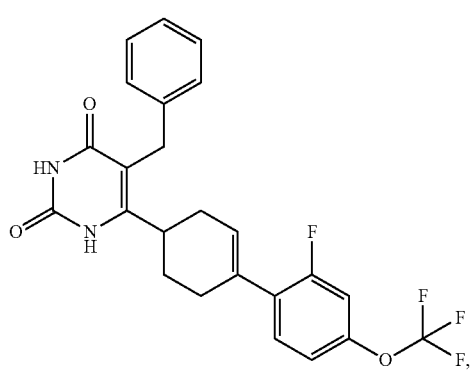
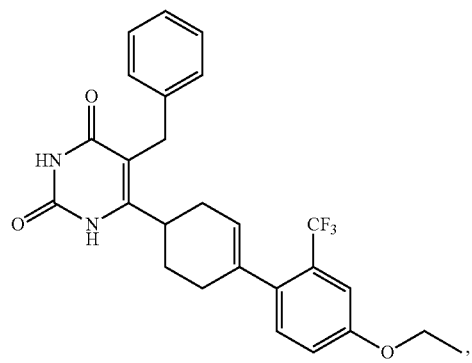
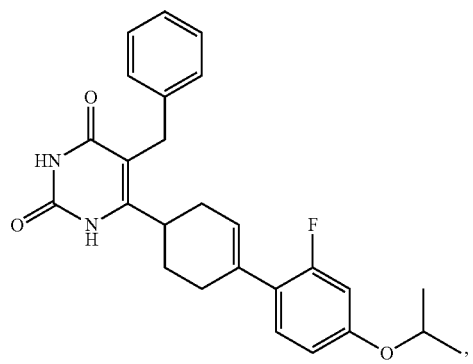
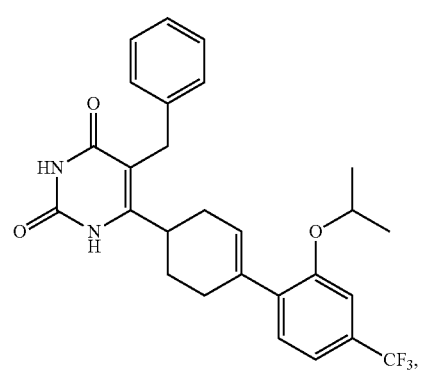
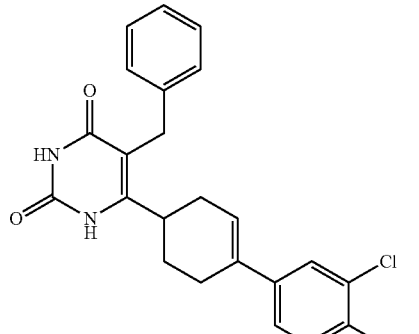

209
-continued
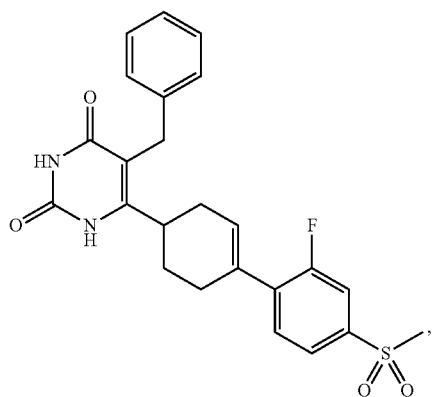
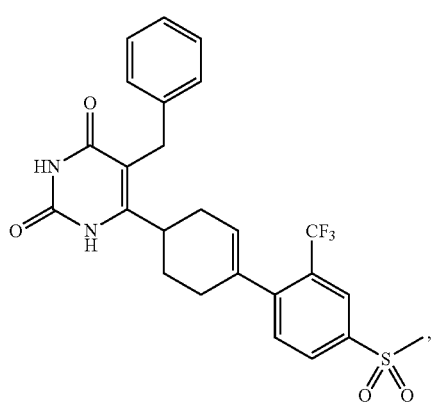
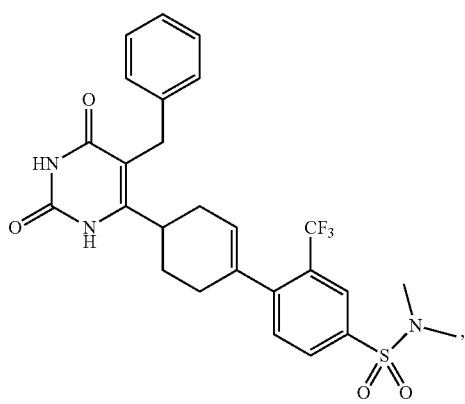
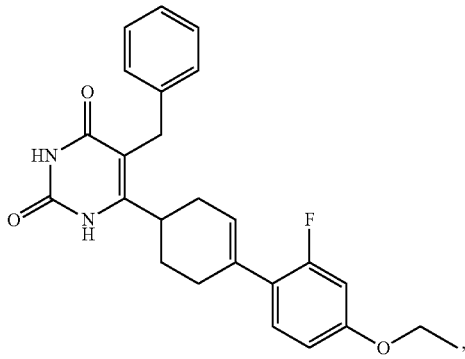
210
-continued
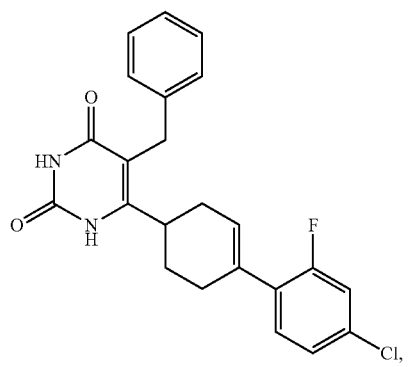
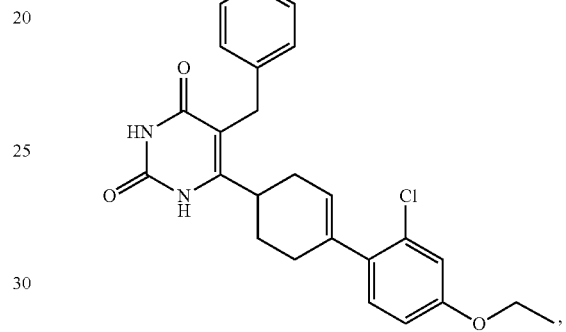
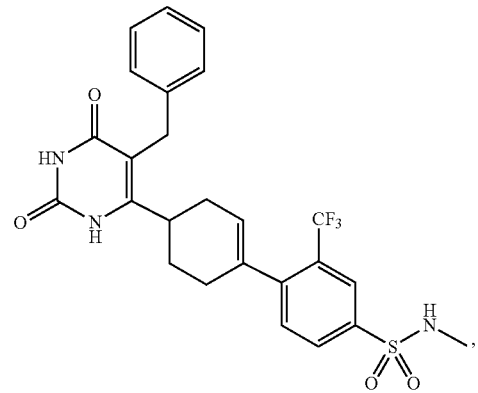
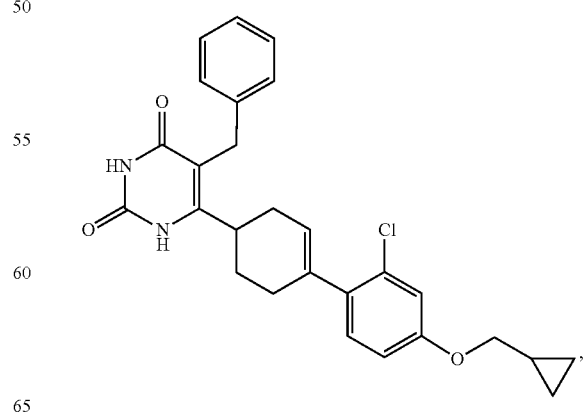

211
-continued
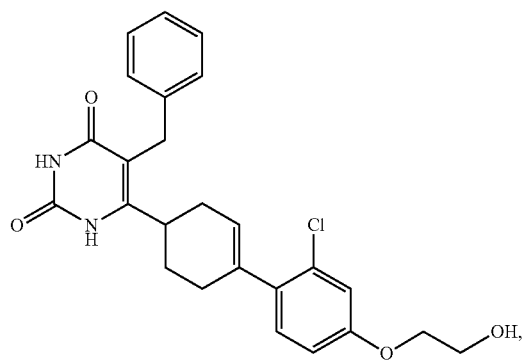
212
-continued
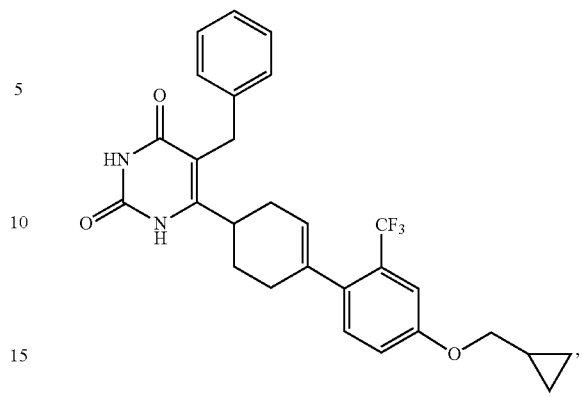
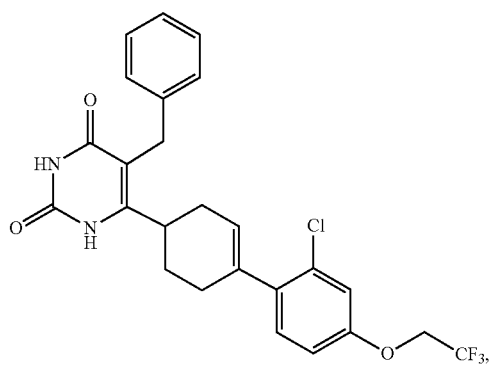
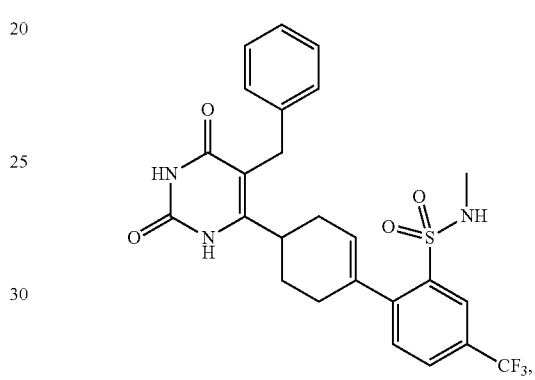
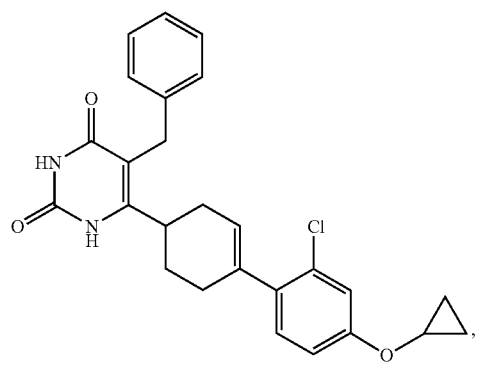
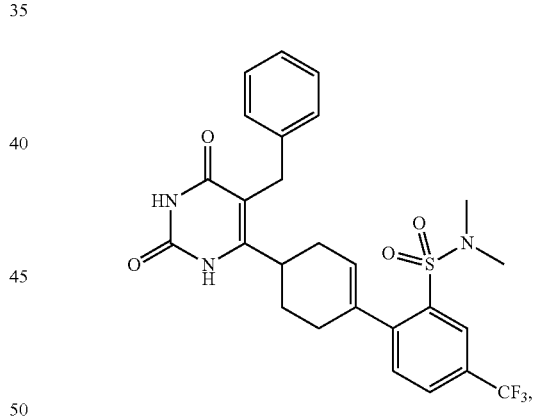
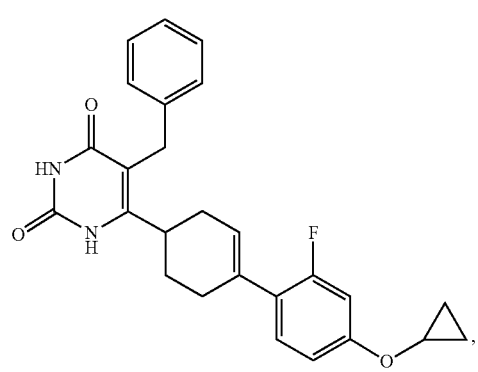
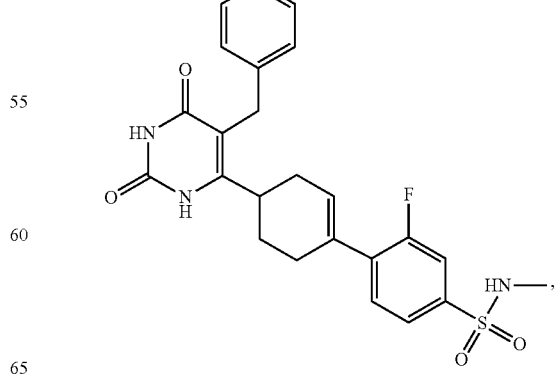

213
-continued
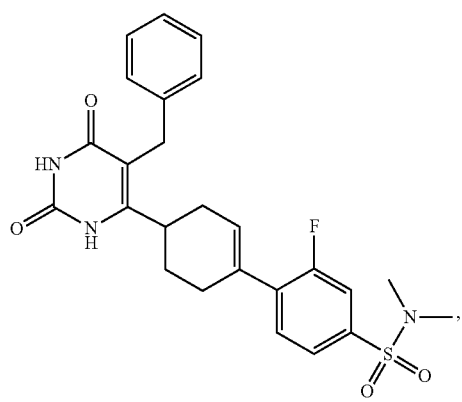
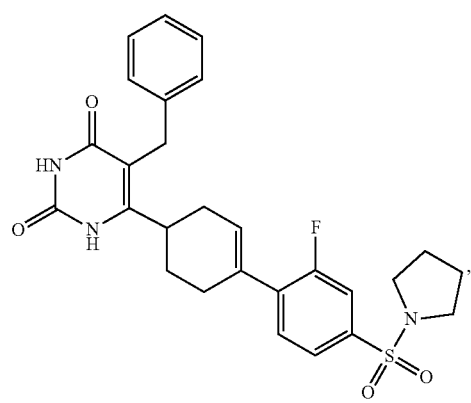
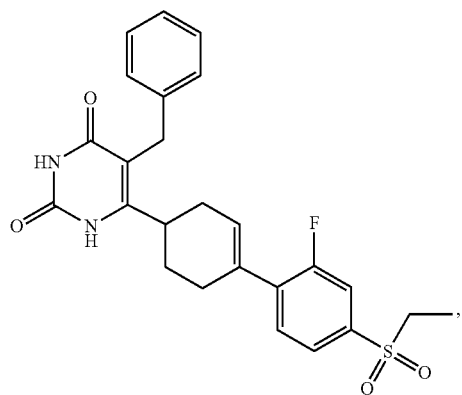
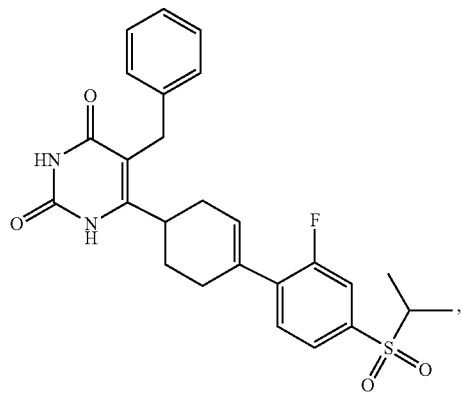
214
-continued
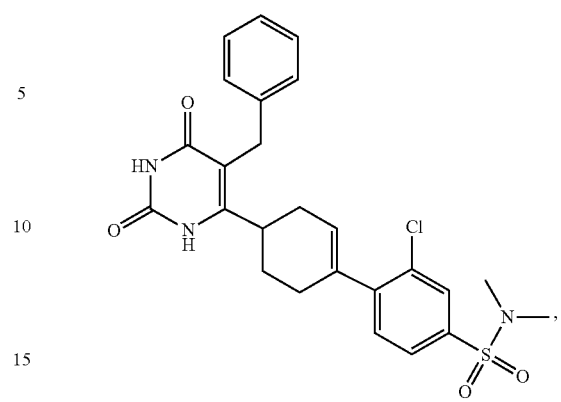
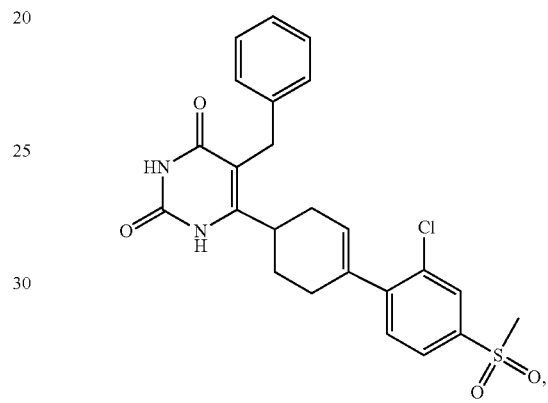
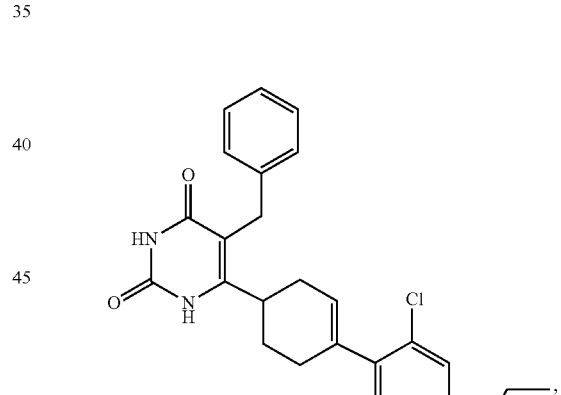
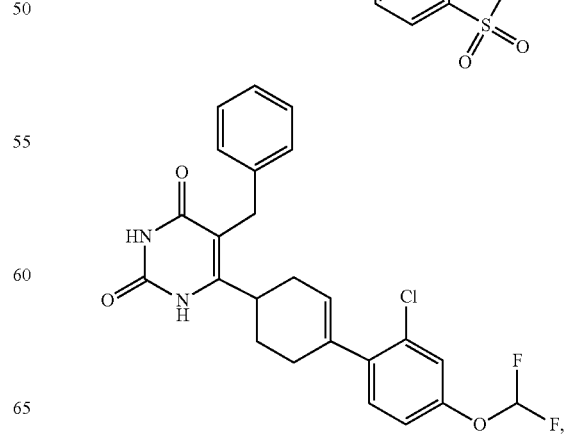

215
-continued
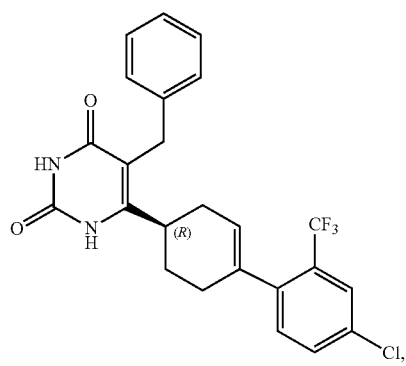
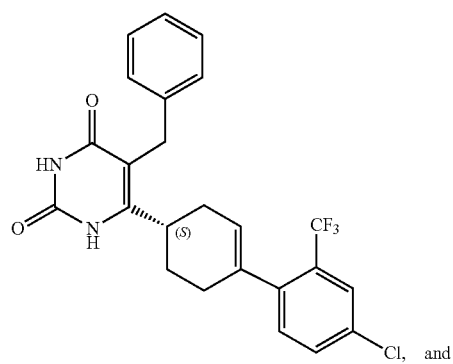
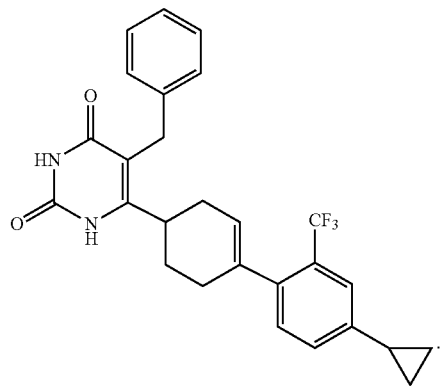
9. The compound of claim 1, selected from the group consisting of:
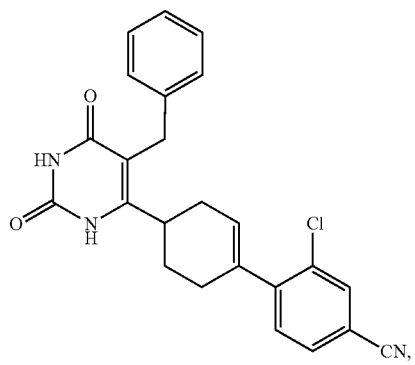 [SMILES: N#Cc1ccc(C2=CCC(c3[nH]c(=O)[nH]c(=O)c3Cc3ccccc3)CC2)c(Cl)c1]
216
-continued
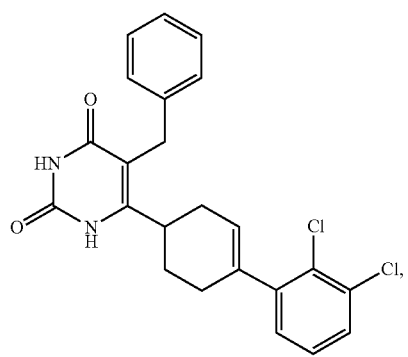
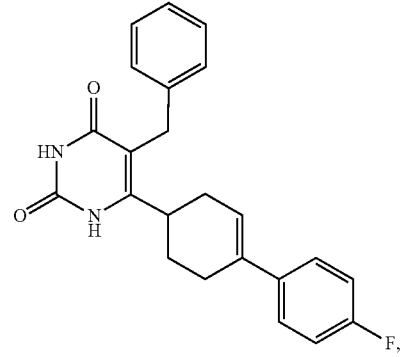
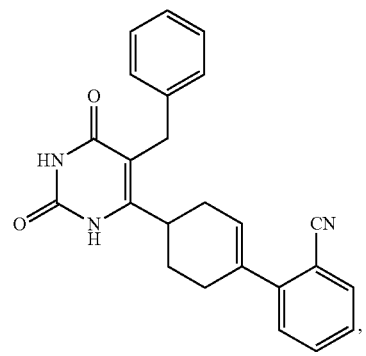
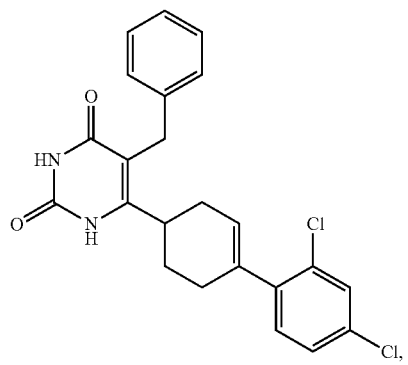

217
-continued
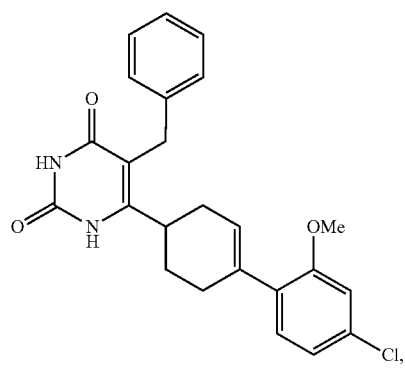
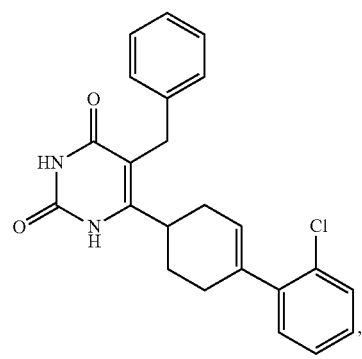
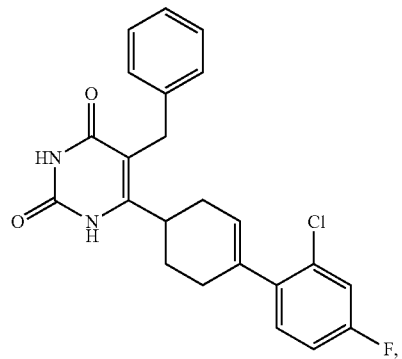
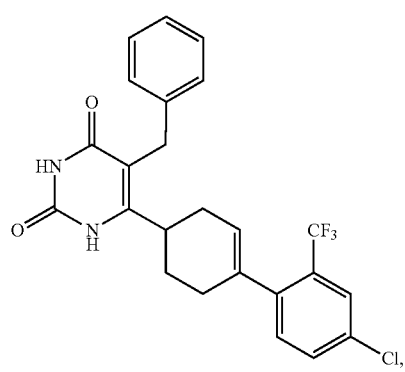
218
-continued
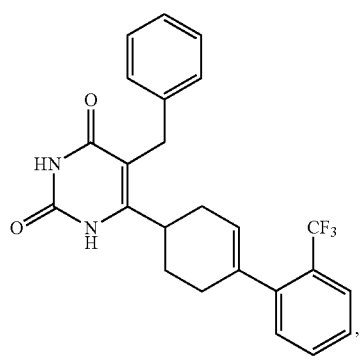
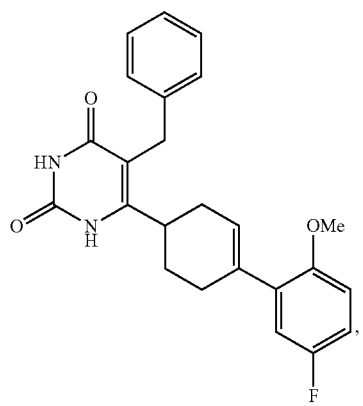
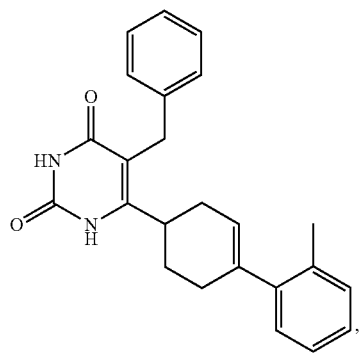
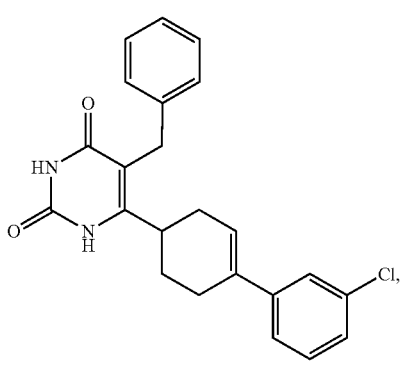

219
-continued
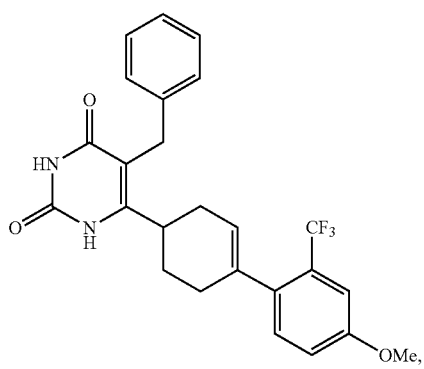
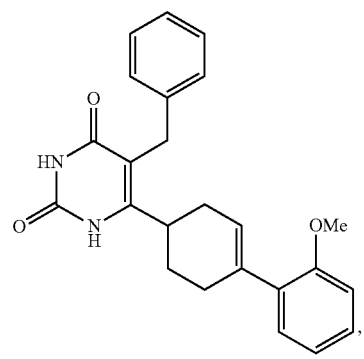
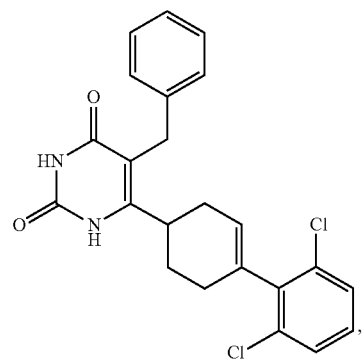
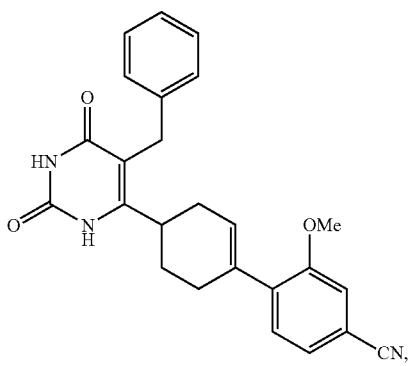
220
-continued
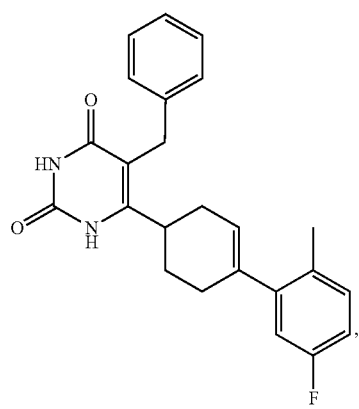
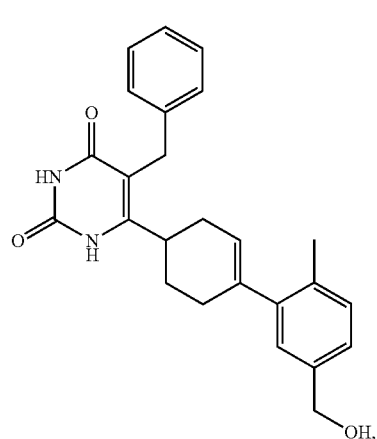
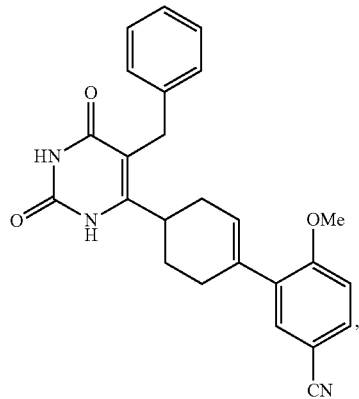
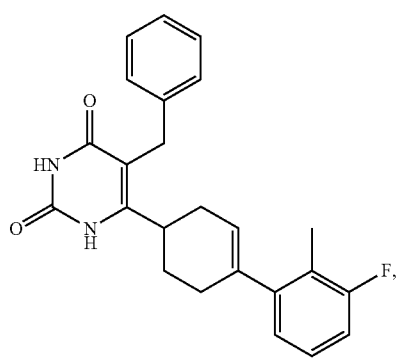

221
-continued
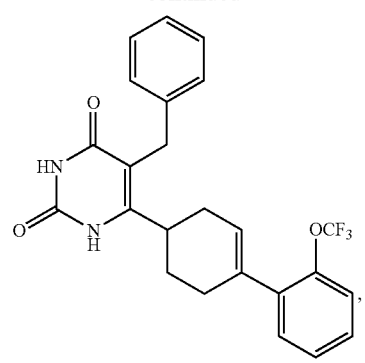
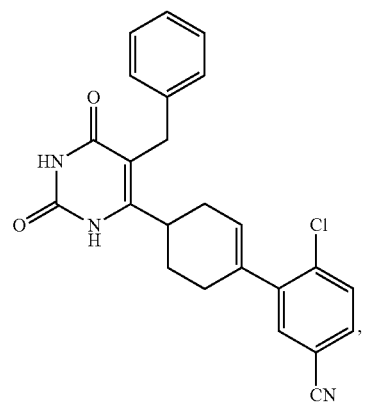
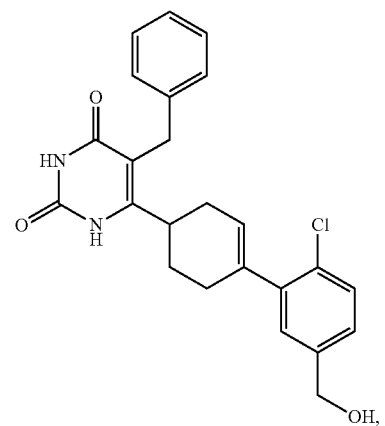
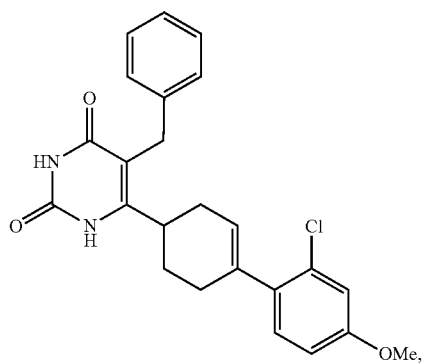
222
-continued
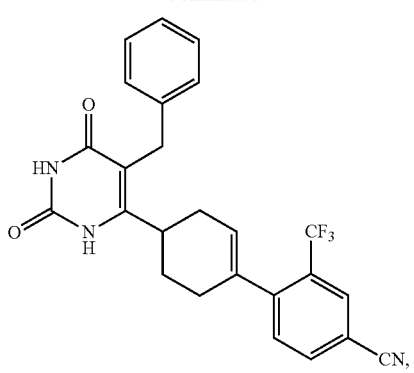
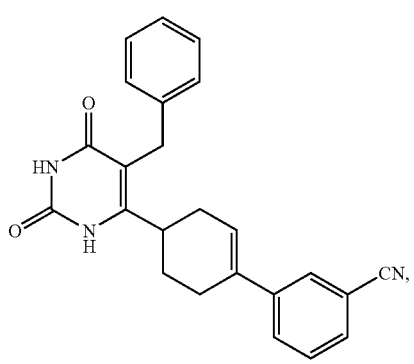
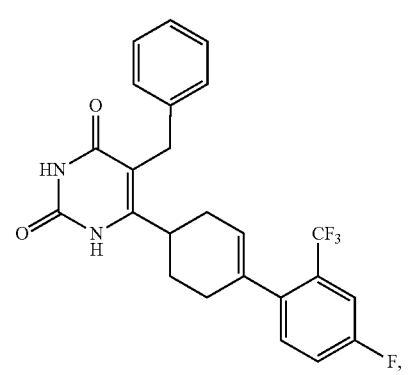
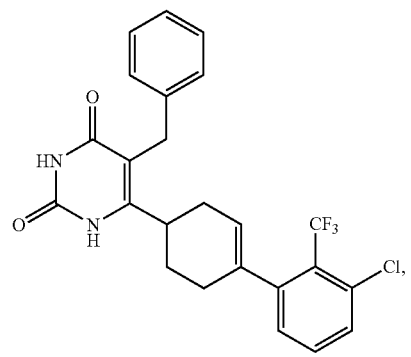

-continued
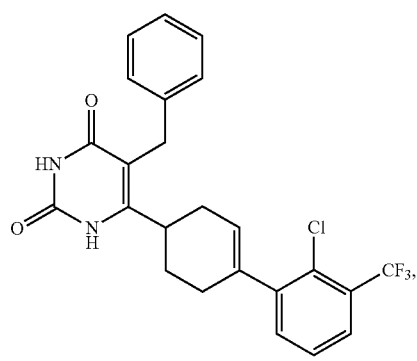
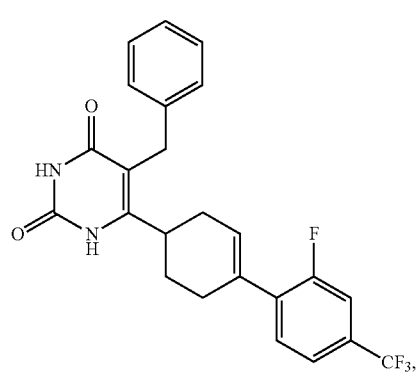
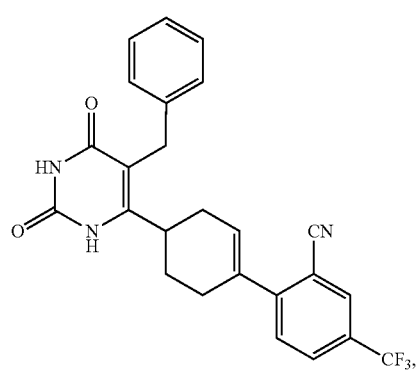
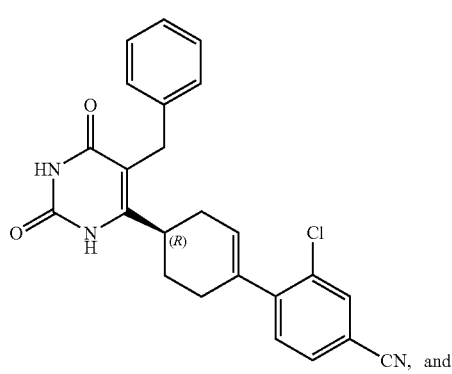
-continued
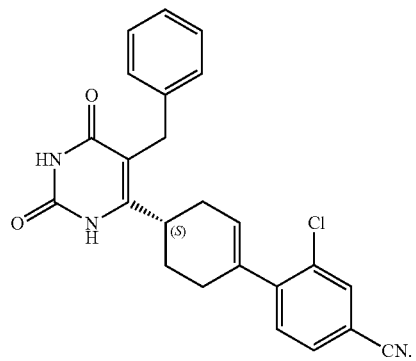
10. The compound of claim 7, selected from the group consisting of:
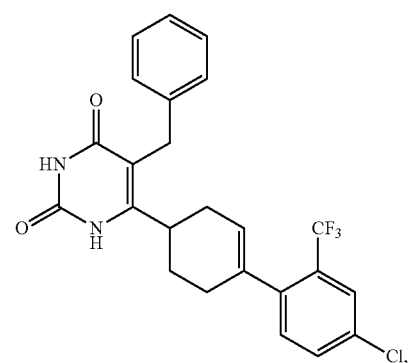
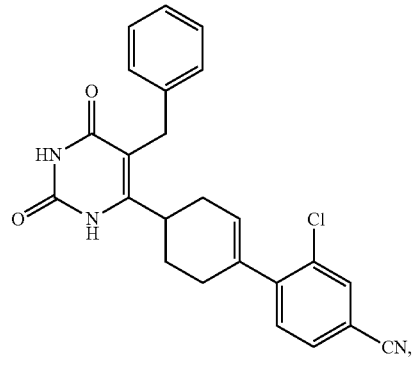

-continued
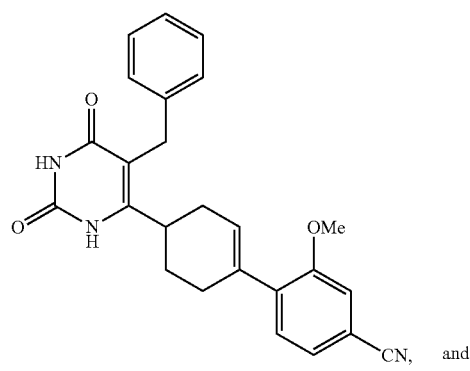
and
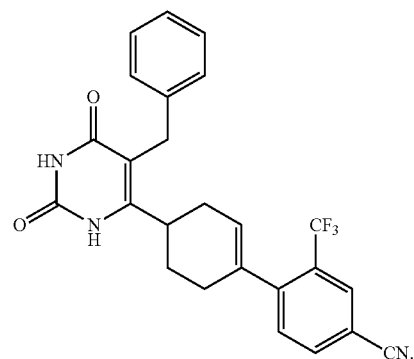
11. The compound of claim 10, wherein the compound is:
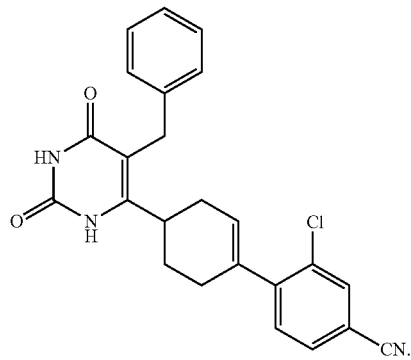
12. The compound of claim 10, wherein the compound is:
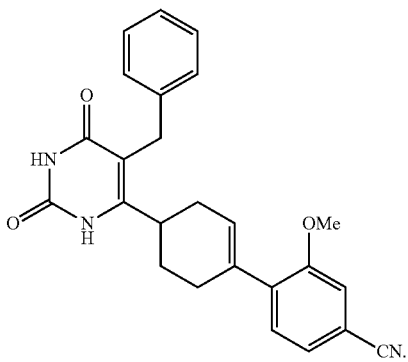 [SMILES: COc1cc(C#N)ccc1C1=CCC(c2[nH]c(=O)[nH]c(=O)c2Cc2ccccc2)CC1]
13. The compound of claim 10, wherein the compound is:
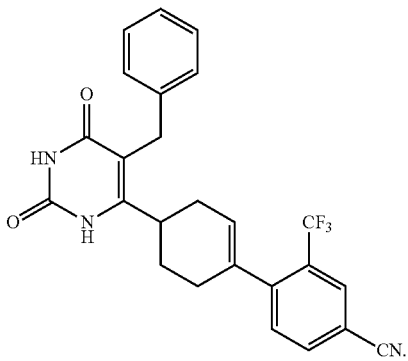
14. A pharmaceutical composition comprising one or more pharmaceutically acceptable excipients and a compound of claim 1.
* * * * *